(12) United States Patent
Li

(10) Patent No.: US 11,013,799 B2
(45) Date of Patent: May 25, 2021

(54) COMPOSITIONS AND METHODS OF ENHANCING IMMUNOGENICITY OF POLYSACCHARIDE PROTEIN CONJUGATES

(71) Applicant: KANVAX BIOPHARMACEUTICALS LTD, Jiangsu (CN)

(72) Inventor: Jianping Li, Gaithersburg, MD (US)

(73) Assignee: KANVAX BIOPHARMACEUTICALS LTD, Jiangsu (CN)

(*) Notice: Subject to any disclaimer, the term of this patent is extended or adjusted under 35 U.S.C. 154(b) by 245 days.

(21) Appl. No.: 15/310,055

(22) PCT Filed: May 8, 2015

(86) PCT No.: PCT/US2015/030037
§ 371 (c)(1),
(2) Date: Nov. 9, 2016

(87) PCT Pub. No.: WO2015/175355
PCT Pub. Date: Nov. 19, 2015

(65) Prior Publication Data
US 2017/0157241 A1    Jun. 8, 2017

(30) Foreign Application Priority Data

May 11, 2014 (CN) .......................... 201410198533.5

(51) Int. Cl.
| | | |
|---|---|---|
| *A61K 39/385* | (2006.01) | |
| *A61K 39/09* | (2006.01) | |
| *A61K 39/095* | (2006.01) | |
| *A61K 39/102* | (2006.01) | |
| *A61K 39/39* | (2006.01) | |
| *A61K 39/00* | (2006.01) | |

(52) U.S. Cl.
CPC .......... *A61K 39/385* (2013.01); *A61K 39/092* (2013.01); *A61K 39/095* (2013.01); *A61K 39/102* (2013.01); *A61K 39/39* (2013.01); *A61K 2039/6031* (2013.01); *A61K 2039/6037* (2013.01); *A61K 2039/64* (2013.01); *A61K 2039/70* (2013.01); *C12N 2720/12333* (2013.01)

(58) Field of Classification Search
None
See application file for complete search history.

(56) References Cited

U.S. PATENT DOCUMENTS

2012/0052090 A1    3/2012    Tamamura et al.

FOREIGN PATENT DOCUMENTS

| | | |
|---|---|---|
| CN | 1425465 A | 6/2003 |
| CN | 1899609 A | 1/2007 |
| CN | 101024079 A | 8/2007 |
| CN | 101972475 A | 2/2011 |
| CN | 103495161 A | 1/2014 |
| CN | 103599529 A | 2/2014 |
| CN | 103690944 A | 4/2014 |
| CN | 104069504 A | 10/2014 |
| CN | 104096223 A | 10/2014 |
| CN | 104096224 A | 10/2014 |
| CN | 104096225 A | 10/2014 |
| CN | 104096226 A | 10/2014 |
| CN | 104096227 A | 10/2014 |
| CN | 104096228 A | 10/2014 |
| CN | 104107428 A | 10/2014 |
| EP | 1027078 A1 | 8/2000 |
| EP | 2 460 813 A1 | 6/2012 |
| WO | WO-1999/15205 A1 | 4/1999 |
| WO | WO-2006/067632 A2 | 6/2006 |
| WO | WO-2008/143709 A2 | 11/2008 |
| WO | WO-2008/143709 A3 | 11/2008 |
| WO | WO-2015/175355 A1 | 11/2015 |
| WO | WO-2015/175355 A8 | 11/2015 |

OTHER PUBLICATIONS

Ellis (Vaccines, W.B. Saunders Company, Chapter 29, 1988, pp. 568-574).*
Boslego et al (Vaccines and Immunotherapy, 1991, Chapter 17).*
Skolnick et al. (Trends in Biotechnology 18: 34-39, 2000).*
Baraldo, K. et al. (Sep. 2005). "Combined Conjugate Vaccines: Enhanced Immunogenicity With the N19 Polyepitope as a Carrier Protein," *Infection and Immunity* 73(9):5835-5841.
Giannini, G. (1984). "The Amino-Acid Sequence of Two Non-Toxic Mutants of Diphtheria Toxin: CRM45 and CRM197," *Nucleic Acid Research* 12(10):4063-4069.
Panina-Bordignon, P. et al. (Dec. 1989). "Universally Immunogenic T Cell Epitopes: Promiscuous Binding to Human MHC Class II and Promiscuous Recognition by T Cells," *Eur. J. Immunol.* 19(12):2237-2242.
Priyanka, V. et al. (2013; e-published on Dec. 6, 2012). "Linkers in the Structural Biology of Protein-Protein Interactions," *Protein Science* 22:153-167.
International Preliminary Report on Patentability for PCT/US2015/030037 dated Nov. 15, 2016, filed on May 8, 2015. 6 pages.
International Search Report for PCT/US2015/030037 dated Jul. 3, 2015, filed on May 8, 2015, 6 pages.

(Continued)

*Primary Examiner* — Robert A Zeman
(74) *Attorney, Agent, or Firm* — Morrison & Foerster LLP

(57) ABSTRACT

The present invention provides compositions and methods for enhancing immunogenicity of polysaccharide antigens. Immunogenic compositions and vaccines comprising polysaccharide-protein conjugates comprising a chimeric carrier protein having a universal epitope are provided. Methods of preparing the compositions, and methods for treating or preventing bacterial infections are further provided. The compositions and methods are useful for enhancing immune response in young children, elderly and immunocompromised individuals.

19 Claims, No Drawings
Specification includes a Sequence Listing.

(56) References Cited

OTHER PUBLICATIONS

Written Opinion International Searching Authority for PCT/US2015/030037 dated Jul. 3, 2015, filed on May 8, 2015, 5 pages.
Avci, F.Y. et al. (Dec. 2011; e-pub. Nov. 20, 2011). "A Mechanism for Glycoconjugate Vaccine Activation of the Adaptive Immune System and Its Implications for Vaccine Design," *Nature Medicine* 17(12):1602-1609.
Dagan, R. et al. (Aug. 1, 2010; e-pub. Jun. 25, 2010). "Glycoconjugate Vaccines and Immune Interference: A Review," *Vaccine* 28(34):5513-5523.
European Supplementary Search Report dated Dec. 13, 2017, for EP Application No. 15792765.8 filed on Dec. 5, 2016, 10 pages.
Eidem, J.K. et al. (Nov. 2000). "Recombinant Antibodies as Carrier Proteins for Sub-Unit Vaccines: Influence of Mode of Fusion on Protein Production and T Cell Activation," *Journal of Immunological Methods* 245(1-2):119-131.
Johnson, V.G. et al. (Feb. 11, 1994). "Histidine 21 Does Not Play a Major Role in Diphtheria Toxin Catalysis," *J Bio Chem.* 269(6):4349-4354.
Su, Y. et al. (Aug. 2013, e-pub. May 31, 2013). "Regulatory T Cell (Tregitopes) in IgG Induce Tolerance in Vivo and Lack Immunogenicity Per Se," *J Leukoc Biol.* 94(2):377-383, 16 pages.

* cited by examiner

COMPOSITIONS AND METHODS OF ENHANCING IMMUNOGENICITY OF POLYSACCHARIDE PROTEIN CONJUGATES

CROSS-REFERENCE TO RELATED APPLICATIONS

This application is a National Phase application under 35 U.S.C. § 371 of International Application No. PCT/US2015/030037, filed May 8, 2015, which claims the priority benefit of Chinese Patent Application No. 201410198533.5, filed on May 11, 2014, the disclosures of which are hereby incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 750342000100SEQLIST.txt, date recorded: Oct. 31, 2016, size: 108 KB).

FIELD OF THE INVENTION

The present invention relates to the fields of immunology and vaccinology, and in particular, methods and compositions for enhancing immunogenicity of polysaccharide-protein conjugates.

BACKGROUND OF THE INVENTION

Covalent conjugation of a polysaccharide to a carrier protein can transform the polysaccharide from a hapten to an immunogen (for example, in children), enhancing the immunogenicity of the polysaccharide. Vaccines based on such polysaccharide-protein conjugates have been widely used among children to prevent bacterial infections by *Streptococcus pneumoniae* (Pn), *Neisseria meningitidis* (Men), and *Haemophilus influenzae* type b (Hib).

Various types of carrier proteins have been used in preparing polysaccharide-protein conjugates, including tetanus toxoid, diphtheria toxoid, a nontoxic mutant of diphtheria toxin CRM197, and recombinant surface protein D of Hib. However, due to the diverse immunological properties of different carrier proteins, the same polysaccharide conjugated to different carrier proteins may show varying degrees of immunogenicity in immunized animals. Therefore, carrier proteins produced using different technologies may give rise to polysaccharide-protein conjugate vaccines of varying immunogenic properties.

It has been well established in immunology that upon entering the body of an animal, an immunogen is processed by Antigen Presenting Cells (APC) into epitopes inside the APCs, which are incorporated in the Major Histocompatibility Complexes (MHC) and displayed on the surface of the APCs to be recognized by T lymphocytes. Three factors contribute to the immunogenicity of a given epitope: (1) production of the proper epitope; (2) expression of the MHC molecules to be bound to the epitope; (3) expression of the T cell receptor to recognize the MHC-epitope complex. Absence of any one of these three factors results in deficiency or loss of immune response to the immunogen.

Experiments in mice have revealed that lack of a proper MHC-epitope complex is the most common reason for loss of immune response to an immunogen. MHC molecules exhibit a high degree of polymorphism. Each epitope may be capable of forming a complex with one or a few alleles of an MHC molecule, but an epitope can seldom form a complex with all alleles of an MHC molecule. Additionally, improper processing of immunogens or lack of T cell tolerance can result in loss of immune response.

Experiments have shown that two out of the three epitopes in tetanus toxoid, namely the QYIKANSKFIGITEL (referred to as P2 (SEQ ID NO:1)) and FNNFTVSFWLRVPKVSASHLE (referred to as P30 (SEQ ID NO:2)) epitopes, as well as the ISQAVHAAHAEINEAGR (referred to as OVAp (SEQ ID NO:3)) epitope of ovalbumin, can bind to a multitude of different MHC class II molecules (Panina-Bordignono P et al. (1989) "Universally immunogenic T cell epitopes promiscuous binding to human MHC class II and promiscuous recognition by T cells." Eur. J. Immunol. 19: 2237-2242). These epitopes can be recognized by T cells, and they demonstrate ubiquitous immunogenic properties. Therefore, these epitopes are referred to as universal epitopes.

Universal epitopes can bind to many human MHC class II molecule isotypes and allelotypes. The ubiquitous MHC binding properties of such universal epitopes can be exploited to develop vaccines that are capable of inducing immune response in majority of individuals in a population.

Research has demonstrated that the P2 epitope consists of amino acids 830-844 of tetanus toxoid (QYIKANSKFIGITE (SEQ ID NO:1)). The P30 epitope consists of amino acids 947-967 of tetanus toxoid (FNNFTVSFWLRVPKVSASHLE (SEQ ID NO:2)). The OVAp epitope consists of amino acids 323-339 of ovalbumin (ISQAVHAAHAEINEAGR (SEQ ID NO:3)). Upon intake by the APCs, proteins having these epitope sequences are degraded, but the epitopes are preserved and bound to the MHC molecules to be displayed on the surface of the APCs and recognized by T cells. These universal epitopes can interact with multiple types of HLA-DRs through the same mechanism.

MHC molecules are receptors for processed immunogens, and their main function is to display epitopes derived from immunogens during the induction of immune tolerance and peripheral immune response against exogenous immunogens in the thymus. On one hand, if MHC molecules display a large number of a certain epitope, an increased level of T cell recognition of the immunogen is expected, but at the expense of depleting a large fraction of the T cell reservoir, leading to immune tolerance. On the other hand, if MHC molecules only display a small number of a certain epitope, the T cell reservoir is conserved, but only a small amount of the exogenous immunogen can be effectively represented to trigger a peripheral immune response. Therefore, an effective epitope from an exogenous immunogen must allow MHC molecules to strike a balance in the number of epitopes being displayed. There exists immunogens having a small number of representative epitopes, which after processing by the APCs, preserve high sequence integrity, and can trigger a certain amount of T cells to establish immune memory without depleting too many T cells to result in immune tolerance. Immunogens having such epitopes have strong immunogenicity, and this phenomenon explains why tetanus toxoid has very strong immunogenicity.

Most currently known T-cell epitopes have limited immunogenic functions with nonspecific MHC class II haplotypes. Different individuals conserve and display different epitope sequences within the same immunogens to trigger their T cells. Such genetic limitation of most epitopes for inducing T cells in a population with diverse MHC class II haplotypes severely hinders the development of synthetic vaccines. The discovery of epitopes that can trigger individuals with diverse MHC class II haplotypes (such as in mice and/or humans) promises a universal strategy to activate T cells. Universal epitopes, such as P2, P30, OVAp etc., can be incorporated in natural protein immunogens. The fused entity is known as a T cell antigen cluster, which can be recognized by MHC class II molecules in most individuals. Such T cell antigen clusters can be used directly to induce T cells, or to facilitate antibody production by B cells against weak immunogens, thereby enhancing the immune response.

Pathogenic bacteria usually express high-molecular weight capsular polysaccharides (CPs) that encapsulate the bacterial cell surface. Capsular polysaccharides are excellent immunogens for adults, and can be used to prepare effective vaccines. However, for children, especially young children under 2 years of age, CPs are considered as T-cell independent antigens. Experiments have revealed that CPs can induce the production of CP-specific IgM antibodies in wildtype and T-cell deficient mice. However, CPs cannot induce the conversion of IgM antibodies to IgG antibodies. Data from humans also demonstrate that CPs can induce production of protective antibodies in adults, but CPs cannot induce immune response in babies and young children. Specifically, after repeated vaccination of children with CP antigens, there is no enhanced response to the second vaccination, nor is persistent T-cell memory induced by such vaccination.

Immunological experiments have established that vaccines based on polysaccharide-protein conjugates have advantages over vaccines based on pure polysaccharides owing to induced humoral immune response associated with polysaccharide-protein conjugates. T-cell independent CP antigens can be covalently linked to a carrier protein to obtain a polysaccharide-protein conjugate. Immunization of mammals using such polysaccharide-protein conjugate can induce T cells to facilitate production of CP-specific IgG antibodies by B cells. The polysaccharide-protein conjugate can thereby induce conversion of CP-specific IgM into IgG, differentiation of memory B cells, and establishment of long-standing T-cell memory.

Vaccines based on polysaccharide conjugates have played significant roles in preventing severe infections, such as *Haemophilus influenzae* type b, *Streptococcus pneumoniae*, and *Neisseria meningitidis*. However, the current vaccines based on polysaccharide-protein conjugates are subject to a high degree of variability in their immunogenicity because of variations in the structures of the specific polysaccharides and the immunogenic carrier proteins. In certain high-risk populations, such as children, elderly, and immunocompromised individuals, protein conjugates of polysaccharides with weak immunogenicity are typically not effective, and their protective effects are rather limited. Therefore, development of vaccines based on polysaccharide-protein conjugates that have stronger immunogenicity is still a much needed area in the field.

All references, publications, and patent applications disclosed herein are hereby incorporated by reference in their entirety.

BRIEF SUMMARY OF THE INVENTION

The present invention provides compositions and methods for enhancing immunogenicity of polysaccharide antigens using chimeric carrier proteins comprising a universal epitope. Immunogenic compositions and vaccines based on the polysaccharide-chimeric carrier protein conjugates, methods of treating bacterial infections, and methods of preparing the polysaccharide-chimeric carrier protein conjugates are further provided.

In one aspect of the present application, there is provided a polysaccharide-protein conjugate comprising a chimeric carrier protein and a polysaccharide antigen, wherein the chimeric carrier protein comprises a carrier protein and a universal epitope, and wherein the polysaccharide antigen is covalently conjugated to the chimeric carrier protein. In some embodiments, the chimeric carrier protein comprises about 1 to about 3 copies of the universal epitope.

In some embodiments according to any one of the polysaccharide-protein conjugates described above, the chimeric carrier protein comprises at least two universal epitopes of different amino acid sequences.

In some embodiments according to any one of the polysaccharide-protein conjugates described above, the universal epitope is about 8 to about 20 amino acids long.

In some embodiments according to any one of the polysaccharide-protein conjugates described above, the universal epitope is covalently fused to the N-terminus, the C-terminus, or both the N-terminus and the C-terminus of the carrier protein.

In some embodiments according to any one of the polysaccharide-protein conjugates described above, the universal epitope comprises the amino acid sequence of any one selected from the group consisting of SEQ ID NOs: 1-3.

In some embodiments according to any one of the polysaccharide-protein conjugates described above, the carrier protein is derived from tetanus toxoid, diphtheria toxoid, cross reacting materials (CRM) of diphtheria toxin, rotavirus capsid protein VP8, meningococcal outer membrane complex, or *Haemophilus influenzae* protein D. In some embodiments, the carrier protein is derived from chain A of CRM197 of diphtheria toxin. In some embodiments, the carrier protein comprises the amino acid sequence of any one selected from the group consisting of SEQ ID NOs: 4-6.

In some embodiments according to any one of the polysaccharide-protein conjugates described above, the universal epitope is covalently fused to the carrier protein by a peptide linker disposed therebetween. In some embodiments, the peptide linker is a flexible linker selected from the group consisting of a glycine polymer, a glycine-serine polymer, a glycine-alanine polymer, or an alanine-serine polymer. In some embodiments, the peptide linker is between 1 to 20 amino acid residues long. In some embodiments, the peptide linker comprises the amino acid sequence of SEQ ID NO:7.

In some embodiments according to any one of the polysaccharide-protein conjugates described above, the chimeric carrier protein comprises the amino acid sequence of any one selected from the group consisting of SEQ ID NOs: 8-32.

In some embodiments according to any one of the polysaccharide-protein conjugates described above, the chimeric carrier protein comprises the amino acid sequence of any one selected from the group consisting of SEQ ID NOs: 39-44.

In some embodiments according to any one of the polysaccharide-protein conjugates described above, the chimeric carrier protein comprises the amino acid sequence of any one selected from the group consisting of SEQ ID NOs: 51-56.

In some embodiments according to any one of the polysaccharide-protein conjugates described above, the weight to weight ratio of the polysaccharide antigen to the chimeric carrier protein is about 0.8 to about 1.2 (such as about any one of 0.8-0.9, 0.9-1.0, 1.0-1.1, or 1.1-1.2).

In some embodiments according to any one of the polysaccharide-protein conjugates described above, the polysaccharide antigen has an average molecular weight between about 10 kDa to about 1000 kDa (such as about any one of 10 kDa-100 kDa, 100 kDa-500 kDa, or 500 kDa-1000 kDa).

In some embodiments according to any one of the polysaccharide-protein conjugates described above, the polysaccharide antigen is derived from a capsular polysaccharide.

In some embodiments according to any one of the polysaccharide-protein conjugates described above, the polysaccharide antigen is derived from *Haemophilus influenzae* type b (Hib), *Streptococcus pneumoniae* (Pn), or *Neisseria meningitidis* (Men). In some embodiments, the capsular polysaccharide is derived from *Streptococcus pneumoniae* of a serotype selected from the group consisting of 1, 2, 3, 4, 5, 6A, 6B, 7F, 8, 9N, 9V, 10A, 1A, 12F, 14, 15B, 17F, 18C, 19A, 19F, 20, 22F, 23F and 33F. In some embodiments, the capsular polysaccharide is derived from *Haemophilus influenzae* type b (Hib). In some embodiments, the capsular polysaccharide is derived from *Neisseria meningitidis* of a serotype selected from the group consisting of A, C, Y, and W-135.

In one aspect of the present application, there is provided an immunogenic composition comprising any one or any combinations of the polysaccharide-protein conjugates described above. In some embodiments, the immunogenic composition comprises a plurality of the polysaccharide-protein conjugates, wherein at least two of the polysaccharide-protein conjugates comprise a carrier protein that is different from each other.

In some embodiments according to any one of the immunogenic compositions described herein, the immunogenic composition comprises a plurality of the polysaccharide-protein conjugates, wherein at least two of the polysaccharide-protein conjugates comprise a polysaccharide antigen that is derived from a bacterial species that is different from each other.

In some embodiments according to any one of the immunogenic compositions described herein, the immunogenic composition comprises a plurality of the polysaccharide-protein conjugates, wherein each polysaccharide-protein conjugate comprises a polysaccharide antigen derived from a bacterium of a distinct serotype of the same species. In some embodiments, the immunogenic composition comprises 13 polysaccharide-protein conjugates, wherein each polysaccharide-protein conjugate comprises a capsular polysaccharide derived from *Streptococcus pneumoniae* of a different serotype selected from the group consisting of 1, 3, 4, 5, 6A, 6B, 7F, 9V, 14, 18C, 19A, 19F, and 23F. In some embodiments, the immunogenic composition comprises 24 polysaccharide-protein conjugates, wherein each polysaccharide-protein conjugate comprises a capsular polysaccharide derived from *Streptococcus pneumoniae* of a different serotype selected from the group consisting of 1, 2, 3, 4, 5, 6A, 6B, 7F, 8, 9N, 9V, 10A, 11A, 12F, 14, 15B, 17F, 18C, 19A, 19F, 20, 22F, 23F and 33F. In some embodiments, the immunogenic composition comprises 4 polysaccharide-protein conjugates, wherein each polysaccharide-protein conjugate comprises a capsular polysaccharide derived from *Neisseria meningitidis* of a different serotype selected from the group consisting of A, C, Y, and W-135.

In some embodiments according to any one of the immunogenic compositions described above, the immunogenic composition further comprises an adjuvant. In some embodiments, the adjuvant is aluminum phosphate or aluminum hydroxide.

In one aspect of the present application, there is provided a vaccine comprising any one of the immunogenic compositions described above and a pharmaceutically acceptable carrier.

In one aspect of the present application, there is provided a method of immunizing an individual against a disease caused by a bacterium comprising administering to the individual an effective amount of any one of the immunogenic compositions described above or any one of the vaccines described above, wherein the polysaccharide antigen is a polysaccharide expressed on the surface of the bacterium or a derivative thereof. In some embodiments, the immunogenic composition or the vaccine is administered to the individual in at least two doses. In some embodiments, the disease is pneumonia, ear infection, sinus infection, meningitis, or bacteremia caused by *Streptococcus pneumoniae*. In some embodiments, the disease is meningitis, pneumonia, epiglottitis, cellulitis, arthritis, or ear infection caused by *Haemophilus influenzae* type b. In some embodiments, the disease is meningitis or meningococcemia caused by *Neisseria meningitidis*.

In some embodiments according to any one of the methods of immunization described above, the individual has poor immune response to the polysaccharide antigen.

In some embodiments according to any one of the methods of immunization described above, the individual is a child below about 2 years of age, an elderly (such as an individual more than about 65 years old), or an immunocompromised individual.

In one aspect of the present application, there is provided use of any one of the immunogenic compositions described above or any one of the vaccines described above in the manufacture of a medicament for the treatment or prevention of a disease caused by a bacterium, wherein the polysaccharide antigen is a polysaccharide expressed on the surface of the bacterium or a derivative thereof.

Further provided in one aspect of the present application is a method of preparing any one of the polysaccharide-protein conjugates described above, comprising conjugating the polysaccharide antigen to the chimeric carrier protein. In some embodiments, the polysaccharide antigen is prepared by culturing a bacterium comprising the polysaccharide antigen, and recovering the polysaccharide antigen from the culture.

In some embodiments according to any one of the methods of preparation described above, the method further comprises preparing the polysaccharide antigen prior to conjugating the polysaccharide antigen to the chimeric carrier protein.

In some embodiments according to any one of the methods of preparation described above, the chimeric carrier protein is prepared by culturing a host cell transformed with a vector comprising the nucleic acid sequence encoding the chimeric carrier protein under conditions allowing the expression of the chimeric carrier protein, and recovering the expressed chimeric carrier protein from the culture. In some embodiments, the vector comprises the nucleic acid sequence of any one selected from the group consisting of SEQ ID NOs: 34-38. In some embodiments, the vector comprises the nucleic acid sequence of any one selected from the group consisting of SEQ ID NOs: 46-50. In some embodiments, the vector comprises the nucleic acid sequence of any one selected from the group consisting of SEQ ID NOs: 58-63.

In some embodiments according to any one of the methods of preparation described above, the host cell is *Escherichia coli* or yeast.

In some embodiments according to any one of the methods of preparation described above, the method further comprises preparing the chimeric carrier protein prior to conjugating the polysaccharide antigen to the chimeric carrier protein.

In some embodiments according to any one of the methods of preparation described above, the polysaccharide antigen is conjugated to the chimeric carrier protein by reductive amination, cyanylation conjugation, or a carbodiimide reaction. In some embodiments, the polysaccharide antigen is activated by 1-cyano-4-dimethylammoniumpyridinium tetrafluoroborate (CDAP). In some embodiments, the polysaccharide antigen is conjugated to the chimeric carrier protein through an adipic acid dihydrazide (ADH) linker.

In some embodiments according to any one of the methods of preparation described above, the method further comprises isolating the conjugated chimeric carrier protein and polysaccharide antigen to obtain the polysaccharide-protein conjugate.

Further provided are pharmaceutical compositions, kits and articles of manufacture of any one of the polysaccharide-protein conjugates, or any one of the immunogenic compositions, or any one of the vaccines described above.

These and other aspects and advantages of the present invention will become apparent from the subsequent detailed description and the appended claims. It is to be understood that one, some, or all of the properties of the various embodiments described herein may be combined to form other embodiments of the present invention.

Terms are used herein as generally used in the art, unless otherwise defined.

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

As used herein and in the appended claims, the singular forms "a," "or," and "the" include plural referents unless the context clearly dictates otherwise.

DETAILED DESCRIPTION OF THE INVENTION

The present invention provides chimeric carrier proteins, as well as polysaccharide-protein conjugates comprising a chimeric carrier protein and a polysaccharide antigen. The chimeric carrier protein comprises an immunogenic carrier protein and a universal epitope.

Immunogenic compositions and vaccines comprising the polysaccharide-protein conjugates and methods of producing the polysaccharide-protein conjugates are further provided.

Compared to corresponding conjugates of the same polysaccharide antigen to carrier proteins without the universal epitopes, the polysaccharide-protein conjugates described herein have at least about 3 to 5 fold increased immunogenicity. The polysaccharide-protein conjugates are useful as vaccines for providing protection against bacterial infections among individuals, especially young children, elderly and other individuals with a compromised immune system.

Thus, in one aspect, there is provided a chimeric carrier protein comprising a carrier protein and a universal epitope. In some embodiments, the universal epitope comprises the amino acid sequence of any one selected from the group consisting of SEQ ID NOs: 1-3.

In another aspect, there is provided a polysaccharide-protein conjugate comprising a chimeric carrier protein and a polysaccharide antigen, wherein the chimeric carrier protein comprises a carrier protein and a universal epitope, and wherein the polysaccharide antigen is covalently conjugated to the chimeric carrier protein. In some embodiments, the universal epitope comprises the amino acid sequence of any one selected from the group consisting of SEQ ID NOs: 1-3.

Polysaccharide-Protein Conjugates

The present invention in one aspect provides a polysaccharide-protein conjugate with enhanced immunogenicity comprising a chimeric carrier protein comprising one or more universal epitopes.

Accordingly, one aspect of the present invention provides a polysaccharide-protein conjugate comprising a chimeric carrier protein and a polysaccharide antigen, wherein the chimeric carrier protein comprises a carrier protein and a universal epitope, and wherein the polysaccharide antigen is conjugated (e.g. covalently conjugated) to the chimeric carrier protein. In some embodiments, the universal epitope comprises (including consisting essentially of or consisting of) the amino acid sequence of any one selected from the group consisting of SEQ ID NOs: 1-3. In some embodiments, the carrier protein is derived from tetanus toxoid, diphtheria toxoid, cross reacting materials (CRM) of diphtheria toxin, rotavirus capsid protein VP8, meningococcal outer membrane complex, or *Haemophilus influenzae* protein D. In some embodiments, the polysaccharide antigen is derived from a capsular polysaccharide. In some embodiments, the polysaccharide antigen is derived from *Haemophilus influenzae* type b (Hib), *Streptococcus pneumoniae* (Pn), or *Neisseria meningitidis* (Men). In some embodiments, the weight to weight ratio of the polysaccharide antigen to the chimeric carrier protein is about 0.8 to about 1.2 (such as about any one of 0.8-0.9, 0.9-1.0, 1.0-1.1, or 1.1-1.2).

In some embodiments, there is provided a polysaccharide-protein conjugate comprising a chimeric carrier protein and a polysaccharide antigen, wherein the chimeric carrier protein comprises a carrier protein and a universal epitope, wherein the universal epitope comprises (including consisting essentially of or consisting of) the amino acid sequence of any one selected from the group consisting of SEQ ID NOs: 1-3, and wherein the polysaccharide antigen is conjugated (e.g. covalently conjugated) to the chimeric carrier protein. In some embodiments, the carrier protein is derived from tetanus toxoid, diphtheria toxoid, cross reacting materials (CRM) of diphtheria toxin, rotavirus capsid protein VP8, meningococcal outer membrane complex, or *Haemophilus influenzae* protein D. In some embodiments, the polysaccharide antigen is derived from a capsular polysaccharide. In some embodiments, the polysaccharide antigen is derived from *Haemophilus influenzae* type b (Hib), *Streptococcus pneumoniae* (Pn), or *Neisseria meningitidis* (Men). In some embodiments, the weight to weight ratio of the polysaccharide antigen to the chimeric carrier protein is about 0.8 to about 1.2 (such as about any one of 0.8-0.9, 0.9-1.0, 1.0-1.1, or 1.1-1.2).

In some embodiments, there is provided a polysaccharide-protein conjugate comprising a chimeric carrier protein and a polysaccharide antigen, wherein the chimeric carrier protein comprises a carrier protein and a universal epitope, wherein the universal epitope comprises (including consisting essentially of or consisting of) the amino acid sequence of any one selected from the group consisting of SEQ ID NOs: 1-3, wherein the carrier protein is derived from tetanus toxoid, diphtheria toxoid, cross reacting materials (CRM) of diphtheria toxin, rotavirus capsid protein VP8, meningococcal outer membrane complex, or *Haemophilus influenzae* protein D, and wherein the polysaccharide antigen is conjugated (e.g. covalently conjugated) to the chimeric carrier protein. In some embodiments, the polysaccharide antigen is derived from a capsular polysaccharide. In some embodiments, the polysaccharide antigen is derived from *Haemophilus influenzae* type b (Hib), *Streptococcus pneumoniae* (Pn), or *Neisseria meningitidis* (Men). In some embodiments, the weight to weight ratio of the polysaccharide antigen to the chimeric carrier protein is about 0.8 to about 1.2 (such as about any one of 0.8-0.9, 0.9-1.0, 1.0-1.1, or 1.1-1.2).

In some embodiments, there is provided a polysaccharide-protein conjugate comprising a chimeric carrier protein and a polysaccharide antigen, wherein the chimeric carrier protein comprises a carrier protein and a universal epitope, wherein the universal epitope comprises (including consisting essentially of or consisting of) the amino acid sequence of any one selected from the group consisting of SEQ ID NOs: 1-3, wherein the carrier protein comprises any one of the amino acid sequences selected from the group consisting of SEQ ID NOs: 4-6, and wherein the polysaccharide antigen is conjugated (e.g. covalently conjugated) to the chimeric carrier protein. In some embodiments, the polysaccharide antigen is derived from a capsular polysaccharide. In some embodiments, the polysaccharide antigen is derived from *Haemophilus influenzae* type b (Hib), *Streptococcus pneumoniae* (Pn), or *Neisseria meningitidis* (Men). In some embodiments, the weight to weight ratio of the polysaccharide antigen to the chimeric carrier protein is about 0.8 to about 1.2 (such as about any one of 0.8-0.9, 0.9-1.0, 1.0-1.1, or 1.1-1.2).

In some embodiments, there is provided a polysaccharide-protein conjugate comprising a chimeric carrier protein and a polysaccharide antigen, wherein the chimeric carrier protein comprises a carrier protein and a universal epitope, wherein the chimeric carrier protein comprises any one of the amino acid sequences selected from the group consisting of SEQ ID NOs: 8-32, 39-44, and 51-56, and wherein the polysaccharide antigen is conjugated (e.g. covalently conjugated) to the chimeric carrier protein. In some embodiments, the polysaccharide antigen is derived from a capsular polysaccharide. In some embodiments, the polysaccharide antigen is derived from *Haemophilus influenzae* type b (Hib), *Streptococcus pneumoniae* (Pn), or *Neisseria meningitidis* (Men). In some embodiments, the weight to weight ratio of the polysaccharide antigen to the chimeric carrier protein is about 0.8 to about 1.2 (such as about any one of 0.8-0.9, 0.9-1.0, 1.0-1.1, or 1.1-1.2).

The polysaccharide-protein conjugates described herein comprises a polysaccharide antigen. The term "polysaccharide" refers to a polymeric carbohydrate molecule composed of a large number (e.g. more than about 9) of monosaccharide (e.g. repeating) units that are covalently linked together by glycosidic linkages. Hydrolysis of the glycosidic linkages in a polysaccharide by chemical or biochemical (e.g. enzymatic digestion) reactions can produce the constituent monosaccharides or oligosaccharides. Monosaccharides are simple sugar molecules, including molecules with a chemical formula of $C_x(H_2O)_y$, wherein in x and y are integers that are typically at least about 3 and no more than about 10, as well as modified molecules thereof, such as amino sugars (e.g. galactosamine, glucosamine, N-acetylglucosamine). Oligosaccharides are polymers containing a small number (e.g. about 3 to about 9) of monosaccharides. As used herein, "polysaccharide", "PS" may refer to a naturally occurring full length polysaccharide molecule, a mixture of any combinations of hydrolysis products (including monosaccharide, oligosaccharide and polysaccharide species) of a full length polysaccharide molecule, any chemically modified or functionalized derivative of the full-length polysaccharide molecule or its hydrolysis product, or any combinations thereof. The polysaccharide may be linear or branched, a single chemical species or a mixture of related chemical species (such as molecules with the same basic monosaccharide units, but different number of repeats).

The term "polysaccharide antigen", or "PS antigen" refers to a polysaccharide (including a mixture of related polysaccharide species derived from the same polysaccharide molecule) that can trigger an immune response, such as PS-specific antibody production. In some embodiments, the polysaccharide antigen alone can trigger a T-cell independent immune response, or an immune response without immune memory. In some embodiments, the polysaccharide antigen alone does not trigger a strong (with high anti-PS antibody titer, and/or high antibody affinity to the PS antigen) or long-lasting immune response in individuals (such as immunocompromised individuals, young children, or elderly) immunized with the PS antigen. "Strong", "high", and "long-lasting" refer to a level or an amount that is enough to provide protection to some extent in the individual to prevent, ameliorate, slow, or delay an infection and/or one or more symptoms associated with the infection caused by an agent (such as a bacterium) bearing the PS antigen. In some embodiments, the polysaccharide antigen has an average molecular weight of at least about any of 10 kDa, 50 kDa, 100 kDa, 150 kDa, 200 kDa, 250 kDa, 300 kDa, 400 kDa, 500 kDa, 600 kDa, 700 kDa, 800 kDa, 900 kDa, 1000 kDa or more. In some embodiments, the polysaccharide antigen has an average molecular weight of about any one of 10 kDa-50 kDa, 50 kDa-100 kDa, 100 kDa-150 kDa, 150 kDa-200 kDa, 200 kDa-250 kDa, 250 kDa-300 kDa, 300 kDa-400 kDa, 400 kDa-500 kDa, 500 kDa-600 kDa, 600 kDa-700 kDa, 700 kDa-800 kDa, 800 kDa-900 kDa, 900 kDa-1000 kDa, 10 kDa-100 kDa, 10 kDa-250 kDa, 10 kDa-500 kDa, 100 kDa-250 kDa, 100 kDa-500 kDa, 10 kDa-750 kDa, 500 kDa-750 kDa, 500 kDa-1000 kDa, 250 kDa-750 kDa, or 10 kDa-1000 kDa. In some embodiments, the polysaccharide antigen has an average molecular weight of between about 10 kDa to about 10000 kDa (such as about any one of 10 kDa-100 kDa, 100 kDa-500 kDa, or 500 kDa-1000 kDa).

In some embodiments, the polysaccharide antigen is a capsular polysaccharide. "Capsular polysaccharide" or "CP" as used herein refers to polysaccharide molecules produced by a bacterium species or another microbe (such as a fungus or an alga) that enwrap the surface of the bacterium or microbe. Each bacterial or microbial species may include subspecies, each of which can produce a CP of a unique chemical structure and/or composition (such as monosaccharides, and/or linkages between monosaccharides), which may trigger specific immune response. In the present disclosure, "polysaccharide" or "PS" may be used to refer to "capsular polysaccharide" or "CP", but the polysaccharide or polysaccharide derivatives (such as polysaccharide-protein conjugates) described herein are not limited to capsular polysaccharide or CP derivatives thereof. In some embodiments, the polysaccharide antigen comprises repeating monosaccharide or oligosaccharide units derived from a capsular polysaccharide. In some embodiments, the polysaccharide antigen comprises chemically modified CP or fragments (such as repeating monosaccharide or oligosaccharide units) thereof.

In some embodiments, the polysaccharide antigen is a capsular polysaccharide derived from a pathogenic bacterium. The pathogenic bacteria contemplated by the present invention include, but are not limited to, *Haemophilus influenzae* type b (Hib), *Streptococcus pneumoniae* (Pn), and *Neisseria meningitidis* (Men), including all subspecies, serotypes, types, groups, strains, and variations thereof. For example, more than 90 serotypes of *Streptococcus pneumoniae* and at least 12 serotypes of *Neisseria meningitidis* have been identified, and each serotype is associated with a unique capsular polysaccharide. In some embodiments, the polysaccharide antigen is a capsular polysaccharide derived from *Streptococcus pneumoniae* of a serotype selected from the group consisting of 1, 2, 3, 4, 5, 6A, 6B, 7F, 8, 9N, 9V, 10A, 11A, 12F, 14, 15B, 17F, 18C, 19A, 19F, 20, 22F, 23F and 33F. In some embodiments, the polysaccharide antigen is a capsular polysaccharide derived from *Haemophilus influenzae* type b (Hib). In some embodiments, the polysaccharide antigen is a capsular polysaccharide derived from *Neisseria meningitidis* of a serotype selected from the group consisting of A, C, Y, and W-135. In some embodiments, the polysaccharide-protein conjugate comprise more than one (such as at least any of 1, 2, 3, 4, 5, 6, 7, 8, 9, 10, or more) different polysaccharide antigens, such as polysaccharide antigens of different serotypes of the same bacterium species.

The polysaccharide antigen may be covalently conjugated or linked to any amino acid residue of the chimeric carrier protein. In some embodiments, the polysaccharide antigen is covalently linked to the amino groups (such as the side chains of lysines) or sulfhydryl groups (such as the side chains of cysteine residues). In some embodiments, a flexible organic linker is disposed between the polysaccharide antigen and the chimeric carrier protein. In some embodiments, one or more residues (such as any of 1, 2, 3, 4, 5, or more) of the chimeric carrier protein are covalently linked to a polysaccharide antigen molecule. The relative ratio (weight by weight) of the polysaccharide antigen (i.e. the total polysaccharide antigen molecules) to the chimeric carrier protein may be important for achieving desirable immunogenic efficacy. In some embodiments, the weight to weight ratio of the polysaccharide antigen to the chimeric carrier protein is about any of 0.2, 0.4, 0.5, 0.6, 0.7, 0.8, 0.9, 1.0, 1.1, 1.2, 1.2, 1.4, 1.5, 1.75, 2, or more. In some embodiments, the weight to weight ratio of the polysaccharide antigen to the chimeric carrier protein is about any of 0.2-0.5, 0.5-0.8, 0.8-0.9, 0.9-1.0, 1.0-1.1, 1.1-1.2, 0.6-1.0, 1.0-1.2, 1.2-1.5, 1.5-2, 1.0-1.4, 0.8-1.2, 0.6-1.5, 0.2-1.0, or 1.0-2.0. In some embodiments, the weight to weight ratio of the polysaccharide antigen to the chimeric carrier protein is about 0.8-1.0. In some embodiments, the percentage of weight of the polysaccharide antigen in the polysaccharide-protein conjugate is about any of 10%, 20%, 30%, 40%, 42%, 44%, 46%, 48%, 50%, 52%, 54%, 56%, 58%, 60%, 70%, 80%, or more. In some embodiments, the percentage of weight of the polysaccharide antigen in the polysaccharide-protein conjugate is about any of 10%-30%, 30%-40%, 40%-44%, 44%-46%, 46%-48%, 48%-50%, 50%-52%, 52%-54%, 54%-60%, 60%-80%, 44%-49%, 49%-54%, or 44%-54%. In some embodiments, the percentage of weight of the chimeric carrier protein in the polysaccharide-protein conjugate is about any of 10%, 20%, 30%, 40%, 42%, 44%, 46%, 48%, 50%, 52%, 54%, 56%, 58%, 60%, 70%, 80%, or more. In some embodiments, the percentage of weight of the chimeric carrier protein in the polysaccharide-protein conjugate is about any of 10%-30%, 30%-40%, 40%-46%, 46%-48%, 48%-50%, 50%-52%, 52%-54%, 54%-56%, 56%-60%, 60%-80%, 46%-51%, 51%-56%, or 46%-56%.

The polysaccharide-protein conjugate describe herein may include a single species of polysaccharide-protein conjugate molecule, or a mixture of related polysaccharide-protein conjugate molecule species, wherein the related PS-protein conjugate species comprise the same chimeric carrier protein, and PS antigen derived from the same source (such as the same bacterium species, the same capsular polysaccharide, etc.), but the exact chemical structure of the PS antigen (including length, chemical nature of the repeating unit, number of repeating units in each PS antigen molecule, etc.), the position(s) of linkage in the chimeric carrier protein, and/or the number of PS antigen molecules on the chimeric carrier protein may differ between different molecules of the polysaccharide-protein conjugate. Therefore, the properties of the polysaccharide-protein conjugate described above may refer to the average value of the PS-protein conjugate molecules.

Chimeric Carrier Protein

The polysaccharide-protein conjugates described herein comprise a chimeric carrier protein, comprising a carrier protein and a universal epitope.

Further provided by the present application are chimeric carrier proteins, which may be conjugated to an antigen (such as a polysaccharide antigen) to form an antigen-protein conjugate with enhanced immunogenicity.

In one aspect, there is provided a chimeric carrier protein for enhancing immune response of a polysaccharide antigen, comprising a carrier protein and a universal epitope. In some embodiments, the chimeric carrier protein comprises about 1 to about 3 copies of the universal epitope. In some embodiments, the chimeric carrier protein comprises at least two universal epitopes of different amino acid sequences. In some embodiments, the universal epitope is covalently fused to the N-terminus, the C-terminus, or both the N-terminus and the C-terminus of the carrier protein. In some embodiments, the universal epitope comprises (including consisting essentially of or consisting of) the amino acid sequence of any one selected from the group consisting of SEQ ID NOs: 1-3. In some embodiments, the carrier protein is derived from tetanus toxoid, diphtheria toxoid, cross reacting materials (CRM) of diphtheria toxin, rotavirus capsid protein VP8, meningococcal outer membrane complex, or *Haemophilus influenzae* protein D. In some embodiments, the carrier protein comprises the amino acid sequence of any one selected from the group consisting of SEQ ID NOs: 4-6. In some embodiments, the universal epitope is covalently fused to the carrier protein by a peptide linker disposed therebetween.

In some embodiments, there is provided a chimeric carrier protein for enhancing immune response of a polysaccharide antigen, comprising a carrier protein and a universal epitope, wherein the universal epitope comprises (including consisting essentially of or consisting of) the amino acid sequence of any one selected from the group consisting of SEQ ID NOs: 1-3. In some embodiments, the chimeric carrier protein comprises about 1 to about 3 copies of the universal epitope. In some embodiments, the chimeric carrier protein comprises at least two universal epitopes of different amino acid sequences. In some embodiments, the universal epitope is covalently fused to the N-terminus, the C-terminus, or both the N-terminus and the C-terminus of the carrier protein. In some embodiments, the carrier protein is derived from tetanus toxoid, diphtheria toxoid, cross reacting materials (CRM) of diphtheria toxin, rotavirus capsid protein VP8, meningococcal outer membrane complex, or *Haemophilus influenzae* protein D. In some embodiments, the carrier protein comprises the amino acid sequence of any one selected from the group consisting of SEQ ID NOs: 4-6. In some embodiments, the universal epitope is covalently fused to the carrier protein by a peptide linker disposed therebetween.

In some embodiments, there is provided a chimeric carrier protein for enhancing immune response of a polysaccharide antigen, comprising a carrier protein and a universal epitope, wherein the universal epitope comprises (including consisting essentially of or consisting of) the amino acid sequence of any one selected from the group consisting of SEQ ID NOs: 1-3, and wherein the carrier protein is derived from tetanus toxoid, diphtheria toxoid, cross reacting materials (CRM) of diphtheria toxin, rotavirus capsid protein VP8, meningococcal outer membrane complex, or *Haemophilus influenzae* protein D. In some embodiments, the chimeric carrier protein comprises about 1 to about 3 copies of the universal epitope. In some embodiments, the chimeric carrier protein comprises at least two universal epitopes of different amino acid sequences. In some embodiments, the universal epitope is covalently fused to the N-terminus, the C-terminus, or both the N-terminus and the C-terminus of the carrier protein. In some embodiments, the carrier protein comprises the amino acid sequence of any one selected from the group consisting of SEQ ID NOs: 4-6. In some embodiments, the universal epitope is covalently fused to the carrier protein by a peptide linker disposed therebetween.

In some embodiments, there is provided a chimeric carrier protein for enhancing immune response of a polysaccharide antigen, comprising a carrier protein and a universal epitope, wherein the universal epitope comprises (including consisting essentially of or consisting of) the amino acid sequence of any one selected from the group consisting of SEQ ID NOs: 1-3, and wherein the carrier protein comprises the amino acid sequence of any one selected from the group consisting of SEQ ID NOs: 4-6. In some embodiments, the chimeric carrier protein comprises about 1 to about 3 copies of the universal epitope. In some embodiments, the chimeric carrier protein comprises at least two universal epitopes of different amino acid sequences. In some embodiments, the universal epitope is covalently fused to the N-terminus, the C-terminus, or both the N-terminus and the C-terminus of the carrier protein. In some embodiments, the universal epitope is covalently fused to the carrier protein by a peptide linker disposed therebetween.

As used herein, the chimeric carrier protein comprises a fusion molecule, i.e. a polymer of amino acids made by fusing at least two constituent polypeptide molecules or amino acid sequences that are not naturally derived from the same polypeptide molecule or protein. The chimeric carrier protein contemplated herein may have a single long chain of amino acids (e.g. at least 30 amino acids long), or may have multiple long chains of amino acids that may have the same sequence or different sequences. The chain(s) of the chimeric carrier protein may be able to fold into a single structural entity. At least one of the chain(s) in the chimeric carrier protein comprises the fusion molecule, wherein the at least two constituent polypeptide molecules may be covalently linked to each other through a peptide bond, a linkage involving the side chain groups (such as a disulfide bond), and/or a linkage mediated by an organic linker (such as a linker without significant steric hindrance). In some embodiments, a linker may be disposed between two adjacent constituent polypeptide molecules or amino acid sequences within the chimeric protein, thereby linking the adjacent constituent polypeptide molecules or amino acid sequences. "Linker" as used herein may refer to a short peptide (such as comprising 1-30 amino acids) that joins or links by peptide bonds two constituent amino acid sequences or polypeptide molecules within the chimeric protein. In some embodiments, the linker does not affect or significantly affect the fold, conformation, and/or bioactivity of the constituent polypeptide molecules. The chimeric protein may be produced by recombinant DNA techniques, produced by chemical synthesis, or by covalently joining (such as via a chemical reaction) at least two polypeptide molecules, which may be derived from natural sources or prepared by recombinant DNA techniques or chemical synthesis. The chimeric protein referred herein may also include amino acid polymer(s) that has been modified naturally or by intervention, such as disulfide bond formation, glycosylation, lipidation, acetylation, phosphorylation, or any other manipulation or modification. Also included within this term are, for example, polypeptides containing one or more analogs of an amino acid (including, for example, unnatural amino acids, etc.), as well as other modifications known in the art. The term "chimeric carrier protein" and "chimeric protein" may be used interchangeably herein.

In some embodiments, the chimeric carrier protein comprises a carrier protein and a universal epitope. As used herein, "carrier protein" refers to a naturally occurring protein or derivative thereof (such as mutant, chemically or naturally modified protein, or the like) that can provide antigenic epitopes for recognition by T cells (such as helper T cells), and can be conjugated to an unrelated antigen (such as polysaccharide antigen) to enhance the immunogenicity of the unrelated antigen. Many carrier proteins are known in the art, including, but are not limited to, cross-reacting materials (CRM) of diphtheria toxin, tetanus toxoid, meningococcal outer membrane protein complex (OMPC), diphtheria toxoid, *Haemophilus* influenza protein D, as well as fragments, mutants, and other variations thereof. For example, cross reacting materials (CRMs, such as CRM197) are variant of the diphtheria toxin isolated from Cornebacterium diphtheria C7 (0197) cultures, which have low or no cellular toxicity, but preserve the immunogenic properties of the diphtheria toxin. Any of the CRMs or genetically modified version thereof (such as CRM197) may be a suitable carrier protein in the chimeric protein of the present invention. Chain A of CRM197 has previously been used as a carrier protein in polysaccharide-protein conjugate vaccines (see Chinese patent application publication No. CN103495161A, incorporated herein by reference). Any of chain A of CRM197 and its derivatives (such as fragments, mutants, or modified variants, including CRM197A with SEQ ID NO: 4) may be used as the carrier protein in the chimeric carrier protein of the present application. Any of the nontoxic mutant of diphtheria toxin having its histidine of amino acid residue 21 replaced by a glycine and its derivatives (such as fragments, mutants, or modified variants, including CRM197A with SEQ ID NO: 6) may also be used in chimeric carrier proteins of the present invention.

Additionally, bacterial or viral proteins (including surface proteins, capsid proteins and the like) and derivatives thereof (such as fragments, mutants, or modified variants) that may trigger T-cell response without inducing cellular toxicity may be used as the carrier protein in the present invention. For example, any of the rotavirus capsid protein VP8 or its derivatives (such as fragments, mutants, or modified variants, including the fragment CoreVP8 with SEQ ID NO: 5) may be used as the carrier protein in the chimeric carrier protein of the present invention. In some embodiments, the carrier protein is derived from tetanus toxoid, diphtheria toxoid, cross reacting materials (CRM) of diphtheria toxin, rotavirus capsid protein VP8, meningococcal outer membrane complex, or *Haemophilus influenzae* protein D. In some embodiments, the carrier protein is derived from chain A of CRM197 of diphtheria toxin. In some embodiments, the carrier protein comprises the amino acid sequence of any one selected from the group consisting of SEQ ID NOs: 4-6. In some embodiments, the carrier protein comprises the amino acid sequence of SEQ ID NO: 4. In some embodiments, the carrier protein comprises the amino acid sequence of SEQ ID NO: 5. In some embodiments, the carrier protein comprises the amino acid sequence of SEQ ID NO: 6.

As used herein, "universal epitope" refers to a polymer of amino acids no more than about 30 amino acids long, which comprises an epitope that can be bound and represented by an MHC class I and/or an MHC class II molecule and recognized by a T cell receptor. The universal epitope described herein may have the following properties when incorporated as part of a chimeric protein: (1) upon exposure to and uptaken by an Antigen Presenting Cell (APC), the integrity of at least the epitope portion of the universal epitope is preserved, i.e. the APC does not cleave or degrade the epitope portion of the universal epitope within a chimeric protein; and (2) the epitope can enhance the immune response against the carrier protein in the chimeric protein, as compared to the carrier protein portion of the chimeric protein without the universal epitope. A variety of techniques known in the art may be used to measure the immune response, including, but are not limited to, ELISA assays that determine antibody titers. The universal epitope may exhibit the above properties in multiple chimeric protein constructs (such as when fused to different protein sequences), in one or a variety of APC cell types, and/or in APCs from different individuals (including individuals having different polymorphic alleles of MHC molecules). The amino acid sequence of the universal epitope may be derived from a naturally occurring protein or polypeptide, artificially designed, or identified through a screen of a random peptide library. The universal epitope may be derived from a natural source, produced by recombinant DNA techniques, or produced by chemical synthesis. The universal epitope contemplated herein may include linear or branched peptides, peptides with modified amino acids, and/or peptides interrupted by non-amino acids. For example, the universal epitope may encompass an amino acid polymer that has been modified naturally or by intervention, such as disulfide bond formation, glycosylation, lipidation, acetylation, phosphorylation, or any other manipulation or modification. Also included within this term are, for example, polypeptides containing one or more analogs of an amino acid (including, for example, unnatural amino acids, etc.), as well as other modifications known in the art.

In some embodiments, the chimeric carrier protein comprises at least about any of 1, 2, 3, 4, 5, or more universal epitopes. In some embodiments, the chimeric carrier protein comprises a single type of universal epitope having the same amino acid sequences. In some embodiments, the chimeric carrier protein comprises about any of 1, 2, 3, 4, 5, or more copies of the universal epitope. In some embodiments, the chimeric carrier protein comprises about 1 to about 3 copies of the universal epitope. In some embodiments, the chimeric carrier protein comprises at least about any of 1, 2 or 3 types of universal epitopes, wherein each type of universal epitopes has a unique amino acid sequence. In some embodiments, the chimeric carrier protein comprises about any one of 1, 2, 3, 4, or 5 copies of the same universal epitope. In some embodiments, the chimeric carrier protein comprises at least two universal epitopes of different amino acid sequences. In some embodiments, the chimeric carrier protein comprises about 1 to about 3 copies of each type of universal epitope. In some embodiments, the universal epitope comprises about any of 7, 8, 9, 10, 11, 12, 13, 14, 15, 16, 17, 18, 19, 20, 21, 22, 23, 24, 25, or more amino acids. In some embodiments, the universal epitope is about 8 to about 20 amino acids long (such as about any one of 8-10, 10-12, 12-14, 14-16, 16-18, 18-20, 8-12, 12-15, 10-15, or 15-20). In some embodiments, the universal epitope is derived from tetanus toxoid, ovalbumin, or other naturally occurring immunogenic proteins (for example, see Panina-Bordignono P et al. (1989) "Universally immunogenic T cell epitopes promiscuous binding to human MHC class II and promiscuous recognition by T cells." Eur. J. Immunol. 19: 2237-2242, incorporated herein by reference). In some embodiments, the universal epitope binds to a plurality (such as at least any of 2, 3, 4, 5, 10, 20, 30, 40, 50, or more) of MHC class II molecules encoded by different polymorphic alleles. In some embodiments, the universal epitope is selected from P2 (SEQ ID NO: 1), P30 (SEQ ID NO: 2), and OVAp (SEQ ID NO: 3). In some embodiments, the universal epitope comprises the amino acid sequence of any one selected from the group consisting of SEQ ID NOs: 1-3. In some embodiments, the universal epitope comprises the amino acid sequence of SEQ ID NO: 1. In some embodiments, the universal epitope comprises the amino acid sequence of SEQ ID NO: 2. In some embodiments, the universal epitope comprises the amino acid sequence of SEQ ID NO: 3.

The universal epitope may be fused to any position in the carrier protein, which does not affect or significantly affect the folding, conformation, and/or immunogenicity of the carrier protein. In some embodiments, the universal epitope is covalently fused to the N-terminus, or the C terminus of the carrier protein. In some embodiments, a first universal epitope is covalently fused to the N-terminus of the carrier protein, and a second universal epitope is covalently fused to the C-terminus of the carrier protein, wherein the first universal epitope and the second universal epitope may have the same amino acid sequence, or different amino acid sequences. In some embodiments, the universal epitope is inserted within an internal position of the carrier protein, such as within a flexible loop of the carrier protein. In some embodiments, a first universal epitope is fused to a second universal epitope to provide a fusion universal epitope, and the fusion universal epitope is covalently fused to the N-terminus, C-terminus, or an internal position in the carrier protein, wherein the first universal epitope and the second universal epitope may have the same amino acid sequence or different amino acid sequences, and the first universal epitope or the second universal epitope may be a fusion universal epitope having at least two universal epitope sequences fused to each other with or without a linker disposed therebetween.

For example, in some embodiments, the chimeric carrier protein comprises about any of 1, 2 or 3 copies of a universal epitope fused to the N-terminus of a carrier protein. In some embodiments, the chimeric carrier protein comprises at least 1 copy (such as any of 1, 2, or 3) of a universal epitope comprising SEQ ID NO:1 fused to the N-terminus of a carrier protein comprising SEQ ID NO:4. In some embodiments, the chimeric carrier protein comprises at least 1 copy (such as any of 1, 2, or 3) of a universal epitope comprising SEQ ID NO:2 fused to the N-terminus of a carrier protein comprising SEQ ID NO:4. In some embodiments, the chimeric carrier protein comprises at least 1 copy (such as any of 1, 2, or 3) of a universal epitope comprising SEQ ID NO:3 fused to the N-terminus of a carrier protein comprising SEQ ID NO:4. In some embodiments, the chimeric carrier protein comprises at least 1 copy (such as any of 1, 2, or 3) of a universal epitope comprising SEQ ID NO:1 fused to the N-terminus of a carrier protein comprising SEQ ID NO:5. In some embodiments, the chimeric carrier protein comprises at least 1 copy (such as any of 1, 2, or 3) of a universal epitope comprising SEQ ID NO:2 fused to the N-terminus of a carrier protein comprising SEQ ID NO:5. In some embodiments, the chimeric carrier protein comprises at least 1 copy (such as any of 1, 2, or 3) of a universal epitope comprising SEQ ID NO:3 fused to the N-terminus of a carrier protein comprising SEQ ID NO:5. In some embodiments, the chimeric carrier protein comprises at least 1 copy (such as any of 1, 2, or 3) of a universal epitope comprising SEQ ID NO:1 fused to the N-terminus of a carrier protein comprising SEQ ID NO:6. In some embodiments, the chimeric carrier protein comprises at least 1 copy (such as any of 1, 2, or 3) of a universal epitope comprising SEQ ID NO:2 fused to the N-terminus of a carrier protein comprising SEQ ID NO:6. In some embodiments, the chimeric carrier protein comprises at least 1 copy (such as any of 1, 2, or 3) of a universal epitope comprising SEQ ID NO:3 fused to the N-terminus of a carrier protein comprising SEQ ID NO:6.

In some embodiments, the chimeric carrier protein comprises about any of 1, 2 or 3 copies of a universal epitope fused to the C-terminus of the carrier protein. In some embodiments, the chimeric carrier protein comprises at least 1 copy (such as any of 1, 2, or 3) of a universal epitope comprising SEQ ID NO:1 fused to the C-terminus of a carrier protein comprising SEQ ID NO:4. In some embodiments, the chimeric carrier protein comprises at least 1 copy (such as any of 1, 2, or 3) of a universal epitope comprising SEQ ID NO:2 fused to the C-terminus of a carrier protein comprising SEQ ID NO:4. In some embodiments, the chimeric carrier protein comprises at least 1 copy (such as any of 1, 2, or 3) of a universal epitope comprising SEQ ID NO:3 fused to the C-terminus of a carrier protein comprising SEQ ID NO:4. In some embodiments, the chimeric carrier protein comprises at least 1 copy (such as any of 1, 2, or 3) of a universal epitope comprising SEQ ID NO:1 fused to the C-terminus of a carrier protein comprising SEQ ID NO:5. In some embodiments, the chimeric carrier protein comprises at least 1 copy (such as any of 1, 2, or 3) of a universal epitope comprising SEQ ID NO:2 fused to the C-terminus of a carrier protein comprising SEQ ID NO:5. In some embodiments, the chimeric carrier protein comprises at least 1 copy (such as any of 1, 2, or 3) of a universal epitope comprising SEQ ID NO:3 fused to the C-terminus of a carrier protein comprising SEQ ID NO:5. In some embodiments, the chimeric carrier protein comprises at least 1 copy (such as any of 1, 2, or 3) of a universal epitope comprising SEQ ID NO:1 fused to the C-terminus of a carrier protein comprising SEQ ID NO:6. In some embodiments, the chimeric carrier protein comprises at least 1 copy (such as any of 1, 2, or 3) of a universal epitope comprising SEQ ID NO:2 fused to the C-terminus of a carrier protein comprising SEQ ID NO:6. In some embodiments, the chimeric carrier protein comprises at least 1 copy (such as any of 1, 2, or 3) of a universal epitope comprising SEQ ID NO:3 fused to the C-terminus of a carrier protein comprising SEQ ID NO:6.

In some embodiments, the chimeric carrier protein comprises a first universal epitope fused to the N-terminus of the carrier protein, wherein the C-terminus of the carrier protein is fused to a second universal epitope, and wherein the first universal epitope and the second universal epitope have the same amino acid sequence. In some embodiments, the chimeric carrier protein comprises at least 1 copy (such as any of 1, 2, or 3) of a universal epitope comprising SEQ ID NO:1 fused to the N-terminus of a carrier protein comprising SEQ ID NO:4, wherein the C-terminus of the carrier protein is further fused to at least 1 copy (such as any of 1, 2, or 3) of the universal epitope. In some embodiments, the chimeric carrier protein comprises at least 1 copy (such as any of 1, 2, or 3) of a universal epitope comprising SEQ ID NO:2 fused to the N-terminus of a carrier protein comprising SEQ ID NO:4, wherein the C-terminus of the carrier protein is further fused to at least 1 copy (such as any of 1, 2, or 3) of the universal epitope. In some embodiments, the chimeric carrier protein comprises at least 1 copy (such as any of 1, 2, or 3) of a universal epitope comprising SEQ ID NO:3 fused to the N-terminus of a carrier protein comprising SEQ ID NO:4, wherein the C-terminus of the carrier protein is further fused to at least 1 copy (such as any of 1, 2, or 3) of the universal epitope. In some embodiments, the chimeric carrier protein comprises at least 1 copy (such as any of 1, 2, or 3) of a universal epitope comprising SEQ ID NO:1 fused to the N-terminus of a carrier protein comprising SEQ ID NO:5, wherein the C-terminus of the carrier protein is further fused to at least 1 copy (such as any of 1, 2, or 3) of the universal epitope. In some embodiments, the chimeric carrier protein comprises at least 1 copy (such as any of 1, 2, or 3) of a universal epitope comprising SEQ ID NO:2 fused to the N-terminus of a carrier protein comprising SEQ ID NO:5, wherein the C-terminus of the carrier protein is further fused to at least 1 copy (such as any of 1, 2, or 3) of the universal epitope. In some embodiments, the chimeric carrier protein comprises at least 1 copy (such as any of 1, 2, or 3) of a universal epitope comprising SEQ ID NO:3 fused to the N-terminus of a carrier protein comprising SEQ ID NO:5, wherein the C-terminus of the carrier protein is further fused to at least 1 copy (such as any of 1, 2, or 3) of the universal epitope. In some embodiments, the chimeric carrier protein comprises at least 1 copy (such as any of 1, 2, or 3) of a universal epitope comprising SEQ ID NO:1 fused to the N-terminus of a carrier protein comprising SEQ ID NO:6, wherein the C-terminus of the carrier protein is further fused to at least 1 copy (such as any of 1, 2, or 3) of the universal epitope. In some embodiments, the chimeric carrier protein comprises at least 1 copy (such as any of 1, 2, or 3) of a universal epitope comprising SEQ ID NO:2 fused to the N-terminus of a carrier protein comprising SEQ ID NO:6, wherein the C-terminus of the carrier protein is further fused to at least 1 copy (such as any of 1, 2, or 3) of the universal epitope. In some embodiments, the chimeric carrier protein comprises at least 1 copy (such as any of 1, 2, or 3) of a universal epitope comprising SEQ ID NO:3 fused to the N-terminus of a carrier protein comprising SEQ ID NO:6, wherein the C-terminus of the carrier protein is further fused to at least 1 copy (such as any of 1, 2, or 3) of the universal epitope.

In some embodiments, the chimeric carrier protein comprises a first universal epitope fused to the N-terminus of the carrier protein, wherein the C-terminus of the carrier protein is fused to a second universal epitope, and wherein the first universal epitope and the second universal epitope have different amino acid sequences. In some embodiments, the chimeric carrier protein comprises at least 1 copy (such as any of 1, 2, or 3) of a first universal epitope comprising SEQ ID NO:1 fused to the N-terminus of a carrier protein comprising SEQ ID NO:4, wherein the C-terminus of the carrier protein is further fused to at least 1 copy (such as any of 1, 2, or 3) of a second universal epitope comprising SEQ ID NO:2. In some embodiments, the chimeric carrier protein comprises at least 1 copy (such as any of 1, 2, or 3) of a first universal epitope comprising SEQ ID NO:2 fused to the N-terminus of a carrier protein comprising SEQ ID NO:4, wherein the C-terminus of the carrier protein is further fused to at least 1 copy (such as any of 1, 2, or 3) of a second universal epitope comprising SEQ ID NO:1. In some embodiments, the chimeric carrier protein comprises at least 1 copy (such as any of 1, 2, or 3) of a first universal epitope comprising SEQ ID NO:1 fused to the N-terminus of a carrier protein comprising SEQ ID NO:4, wherein the C-terminus of the carrier protein is further fused to at least 1 copy (such as any of 1, 2, or 3) of a second universal epitope comprising SEQ ID NO:3. In some embodiments, the chimeric carrier protein comprises at least 1 copy (such as any of 1, 2, or 3) of a first universal epitope comprising SEQ ID NO:3 fused to the N-terminus of a carrier protein comprising SEQ ID NO:4, wherein the C-terminus of the carrier protein is further fused to at least 1 copy (such as any of 1, 2, or 3) of a second universal epitope comprising SEQ ID NO:1. In some embodiments, the chimeric carrier protein comprises at least 1 copy (such as any of 1, 2, or 3) of a first universal epitope comprising SEQ ID NO:2 fused to the N-terminus of a carrier protein comprising SEQ ID NO:4, wherein the C-terminus of the carrier protein is further fused to at least 1 copy (such as any of 1, 2, or 3) of a second universal epitope comprising SEQ ID NO:3. In some embodiments, the chimeric carrier protein comprises at least 1 copy (such as any of 1, 2, or 3) of a first universal epitope comprising SEQ ID NO:3 fused to the N-terminus of a carrier protein comprising SEQ ID NO:4, wherein the C-terminus of the carrier protein is further fused to at least 1 copy (such as any of 1, 2, or 3) of a second universal epitope comprising SEQ ID NO:2. In some embodiments, the chimeric carrier protein comprises at least 1 copy (such as any of 1, 2, or 3) of a first universal epitope comprising SEQ ID NO:1 fused to the N-terminus of a carrier protein comprising SEQ ID NO:5, wherein the C-terminus of the carrier protein is further fused to at least 1 copy (such as any of 1, 2, or 3) of a second universal epitope comprising SEQ ID NO:2. In some embodiments, the chimeric carrier protein comprises at least 1 copy (such as any of 1, 2, or 3) of a first universal epitope comprising SEQ ID NO:2 fused to the N-terminus of a carrier protein comprising SEQ ID NO:5, wherein the C-terminus of the carrier protein is further fused to at least 1 copy (such as any of 1, 2, or 3) of a second universal epitope comprising SEQ ID NO:1. In some embodiments, the chimeric carrier protein comprises at least 1 copy (such as any of 1, 2, or 3) of a first universal epitope comprising SEQ ID NO:1 fused to the N-terminus of a carrier protein comprising SEQ ID NO:5, wherein the C-terminus of the carrier protein is further fused to at least 1 copy (such as any of 1, 2, or 3) of a second universal epitope comprising SEQ ID NO:3. In some embodiments, the chimeric carrier protein comprises at least 1 copy (such as any of 1, 2, or 3) of a first universal epitope comprising SEQ ID NO:3 fused to the N-terminus of a carrier protein comprising SEQ ID NO:5, wherein the C-terminus of the carrier protein is further fused to at least 1 copy (such as any of 1, 2, or 3) of a second universal epitope comprising SEQ ID NO:1. In some embodiments, the chimeric carrier protein comprises at least 1 copy (such as any of 1, 2, or 3) of a first universal epitope comprising SEQ ID NO:2 fused to the N-terminus of a carrier protein comprising SEQ ID NO:5, wherein the C-terminus of the carrier protein is further fused to at least 1 copy (such as any of 1, 2, or 3) of a second universal epitope comprising SEQ ID NO:3. In some embodiments, the chimeric carrier protein comprises at least 1 copy (such as any of 1, 2, or 3) of a first universal epitope comprising SEQ ID NO:3 fused to the N-terminus of a carrier protein comprising SEQ ID NO:5, wherein the C-terminus of the carrier protein is further fused to at least 1 copy (such as any of 1, 2, or 3) of a second universal epitope comprising SEQ ID NO:2. In some embodiments, the chimeric carrier protein comprises at least 1 copy (such as any of 1, 2, or 3) of a first universal epitope comprising SEQ ID NO:1 fused to the N-terminus of a carrier protein comprising SEQ ID NO:6, wherein the C-terminus of the carrier protein is further fused to at least 1 copy (such as any of 1, 2, or 3) of a second universal epitope comprising SEQ ID NO:2. In some embodiments, the chimeric carrier protein comprises at least 1 copy (such as any of 1, 2, or 3) of a first universal epitope comprising SEQ ID NO:2 fused to the N-terminus of a carrier protein comprising SEQ ID NO:6, wherein the C-terminus of the carrier protein is further fused to at least 1 copy (such as any of 1, 2, or 3) of a second universal epitope comprising SEQ ID NO:1. In some embodiments, the chimeric carrier protein comprises at least 1 copy (such as any of 1, 2, or 3) of a first universal epitope comprising SEQ ID NO:1 fused to the N-terminus of a carrier protein comprising SEQ ID NO:6, wherein the C-terminus of the carrier protein is further fused to at least 1 copy (such as any of 1, 2, or 3) of a second universal epitope comprising SEQ ID NO:3. In some embodiments, the chimeric carrier protein comprises at least 1 copy (such as any of 1, 2, or 3) of a first universal epitope comprising SEQ ID NO:3 fused to the N-terminus of a carrier protein comprising SEQ ID NO:6, wherein the C-terminus of the carrier protein is further fused to at least 1 copy (such as any of 1, 2, or 3) of a second universal epitope comprising SEQ ID NO:1. In some embodiments, the chimeric carrier protein comprises at least 1 copy (such as any of 1, 2, or 3) of a first universal epitope comprising SEQ ID NO:2 fused to the N-terminus of a carrier protein comprising SEQ ID NO:6, wherein the C-terminus of the carrier protein is further fused to at least 1 copy (such as any of 1, 2, or 3) of a second universal epitope comprising SEQ ID NO:3. In some embodiments, the chimeric carrier protein comprises at least 1 copy (such as any of 1, 2, or 3) of a first universal epitope comprising SEQ ID NO:3 fused to the N-terminus of a carrier protein comprising SEQ ID NO:6, wherein the C-terminus of the carrier protein is further fused to at least 1 copy (such as any of 1, 2, or 3) of a second universal epitope comprising SEQ ID NO:2.

In some embodiments, the chimeric carrier protein comprises a fusion universal epitope fused to the N-terminus of a carrier protein, wherein the fusion universal epitope comprises one or two copies of a first universal epitope covalently fused to one or two copies of a second universal epitope, wherein the first universal epitope and the second universal epitope have different amino acid sequences. In some embodiments, the chimeric carrier protein comprises a fusion universal epitope fused to the N-terminus of a chimeric carrier protein, wherein the fusion universal epitope comprises SEQ ID NO:1 and SEQ ID NO:2, and wherein the carrier protein comprises SEQ ID NO:4. In some embodiments, the chimeric carrier protein comprises a fusion universal epitope fused to the N-terminus of a chimeric carrier protein, wherein the fusion universal epitope comprises SEQ ID NO:1 and SEQ ID NO:3, and wherein the carrier protein comprises SEQ ID NO:4. In some embodiments, the chimeric carrier protein comprises a fusion universal epitope fused to the N-terminus of a chimeric carrier protein, wherein the fusion universal epitope comprises SEQ ID NO:2 and SEQ ID NO:3, and wherein the carrier protein comprises SEQ ID NO:4. In some embodiments, the chimeric carrier protein comprises a fusion universal epitope fused to the N-terminus of a chimeric carrier protein, wherein the fusion universal epitope comprises SEQ ID NO:1 and SEQ ID NO:2, and wherein the carrier protein comprises SEQ ID NO:5. In some embodiments, the chimeric carrier protein comprises a fusion universal epitope fused to the N-terminus of a chimeric carrier protein, wherein the fusion universal epitope comprises SEQ ID NO:1 and SEQ ID NO:3, and wherein the carrier protein comprises SEQ ID NO:5. In some embodiments, the chimeric carrier protein comprises a fusion universal epitope fused to the N-terminus of a chimeric carrier protein, wherein the fusion universal epitope comprises SEQ ID NO:2 and SEQ ID NO:3, and wherein the carrier protein comprises SEQ ID NO:5. In some embodiments, the chimeric carrier protein comprises a fusion universal epitope fused to the N-terminus of a chimeric carrier protein, wherein the fusion universal epitope comprises SEQ ID NO:1 and SEQ ID NO:2, and wherein the carrier protein comprises SEQ ID NO:6. In some embodiments, the chimeric carrier protein comprises a fusion universal epitope fused to the N-terminus of a chimeric carrier protein, wherein the fusion universal epitope comprises SEQ ID NO:1 and SEQ ID NO:3, and wherein the carrier protein comprises SEQ ID NO:6. In some embodiments, the chimeric carrier protein comprises a fusion universal epitope fused to the N-terminus of a chimeric carrier protein, wherein the fusion universal epitope comprises SEQ ID NO:2 and SEQ ID NO:3, and wherein the carrier protein comprises SEQ ID NO:6.

In some embodiments, the chimeric carrier protein comprises a fusion universal epitope fused to the C-terminus of a carrier protein, wherein the fusion universal epitope comprises one or two copies of a first universal epitope covalently fused to one or two copies of a second universal epitope, wherein the first universal epitope and the second universal epitope have different amino acid sequences. In some embodiments, the chimeric carrier protein comprises a fusion universal epitope fused to the C-terminus of a chimeric carrier protein, wherein the fusion universal epitope comprises SEQ ID NO:1 and SEQ ID NO:2, and wherein the carrier protein comprises SEQ ID NO:4. In some embodiments, the chimeric carrier protein comprises a fusion universal epitope fused to the C-terminus of a chimeric carrier protein, wherein the fusion universal epitope comprises SEQ ID NO:1 and SEQ ID NO:3, and wherein the carrier protein comprises SEQ ID NO:4. In some embodiments, the chimeric carrier protein comprises a fusion universal epitope fused to the C-terminus of a chimeric carrier protein, wherein the fusion universal epitope comprises SEQ ID NO:2 and SEQ ID NO:3, and wherein the carrier protein comprises SEQ ID NO:4. In some embodiments, the chimeric carrier protein comprises a fusion universal epitope fused to the C-terminus of a chimeric carrier protein, wherein the fusion universal epitope comprises SEQ ID NO:1 and SEQ ID NO:2, and wherein the carrier protein comprises SEQ ID NO:5. In some embodiments, the chimeric carrier protein comprises a fusion universal epitope fused to the C-terminus of a chimeric carrier protein, wherein the fusion universal epitope comprises SEQ ID NO:1 and SEQ ID NO:3, and wherein the carrier protein comprises SEQ ID NO:5. In some embodiments, the chimeric carrier protein comprises a fusion universal epitope fused to the C-terminus of a chimeric carrier protein, wherein the fusion universal epitope comprises SEQ ID NO:2 and SEQ ID NO:3, and wherein the carrier protein comprises SEQ ID NO:5. In some embodiments, the chimeric carrier protein comprises a fusion universal epitope fused to the C-terminus of a chimeric carrier protein, wherein the fusion universal epitope comprises SEQ ID NO:1 and SEQ ID NO:2, and wherein the carrier protein comprises SEQ ID NO:6. In some embodiments, the chimeric carrier protein comprises a fusion universal epitope fused to the C-terminus of a chimeric carrier protein, wherein the fusion universal epitope comprises SEQ ID NO:1 and SEQ ID NO:3, and wherein the carrier protein comprises SEQ ID NO:6. In some embodiments, the chimeric carrier protein comprises a fusion universal epitope fused to the C-terminus of a chimeric carrier protein, wherein the fusion universal epitope comprises SEQ ID NO:2 and SEQ ID NO:3, and wherein the carrier protein comprises SEQ ID NO:6.

In some embodiments, the chimeric carrier protein comprises a first universal epitope fused to the C-terminus of a carrier protein, wherein the N-terminus of the carrier protein is fused to a fusion universal epitope. In some embodiments, the chimeric carrier protein comprises a first universal epitope fused to the N-terminus of a carrier protein, wherein the C-terminus of the carrier protein is fused to a fusion universal epitope. The fusion universal epitope comprises at least two universal epitopes of the same amino acid sequence or different amino acid sequences. For example, the fusion universal epitope may comprises SEQ ID NO:1 and SEQ ID NO:2, SEQ ID NO:2 and SEQ ID NO:3, SEQ ID NO:1 and SEQ ID NO:3.

In some embodiments, the chimeric carrier protein comprises a fusion universal epitope fused to the N-terminus of a carrier protein, wherein the C-terminus of the carrier protein is fused to a universal epitope, wherein the fusion universal epitope comprises SEQ ID NO:1 and SEQ ID NO:2, the carrier protein comprises SEQ ID NO:4, and the universal epitope comprises SEQ ID NO:3. In some embodiments, the chimeric carrier protein comprises a fusion universal epitope fused to the N-terminus of a carrier protein, wherein the C-terminus of the carrier protein is fused to a universal epitope, wherein the fusion universal epitope comprises SEQ ID NO:1 and SEQ ID NO:3, the carrier protein comprises SEQ ID NO:4, and the universal epitope comprises SEQ ID NO:2. In some embodiments, the chimeric carrier protein comprises a fusion universal epitope fused to the N-terminus of a carrier protein, wherein the C-terminus of the carrier protein is fused to a universal epitope, wherein the fusion universal epitope comprises SEQ ID NO:2 and SEQ ID NO:3, the carrier protein comprises SEQ ID NO:4, and the universal epitope comprises SEQ ID NO:1. In some embodiments, the chimeric carrier protein comprises a fusion universal epitope fused to the N-terminus of a carrier protein, wherein the C-terminus of the carrier protein is fused to a universal epitope, wherein the fusion universal epitope comprises SEQ ID NO:1 and SEQ ID NO:2, the carrier protein comprises SEQ ID NO:5, and the universal epitope comprises SEQ ID NO:3. In some embodiments, the chimeric carrier protein comprises a fusion universal epitope fused to the N-terminus of a carrier protein, wherein the C-terminus of the carrier protein is fused to a universal epitope, wherein the fusion universal epitope comprises SEQ ID NO:1 and SEQ ID NO:3, the carrier protein comprises SEQ ID NO:5, and the universal epitope comprises SEQ ID NO:2. In some embodiments, the chimeric carrier protein comprises a fusion universal epitope fused to the N-terminus of a carrier protein, wherein the C-terminus of the carrier protein is fused to a universal epitope, wherein the fusion universal epitope comprises SEQ ID NO:2 and SEQ ID NO:3, the carrier protein comprises SEQ ID NO:5, and the universal epitope comprises SEQ ID NO:1. In some embodiments, the chimeric carrier protein comprises a fusion universal epitope fused to the N-terminus of a carrier protein, wherein the C-terminus of the carrier protein is fused to a universal epitope, wherein the fusion universal epitope comprises SEQ ID NO:1 and SEQ ID NO:2, the carrier protein comprises SEQ ID NO:6, and the universal epitope comprises SEQ ID NO:3. In some embodiments, the chimeric carrier protein comprises a fusion universal epitope fused to the N-terminus of a carrier protein, wherein the C-terminus of the carrier protein is fused to a universal epitope, wherein the fusion universal epitope comprises SEQ ID NO:1 and SEQ ID NO:3, the carrier protein comprises SEQ ID NO:6, and the universal epitope comprises SEQ ID NO:2. In some embodiments, the chimeric carrier protein comprises a fusion universal epitope fused to the N-terminus of a carrier protein, wherein the C-terminus of the carrier protein is fused to a universal epitope, wherein the fusion universal epitope comprises SEQ ID NO:2 and SEQ ID NO:3, the carrier protein comprises SEQ ID NO:6, and the universal epitope comprises SEQ ID NO:1.

Any of the chimeric carrier proteins described above may or may not comprise additional sequences between adjacent universal epitopes, and/or between each universal epitope and the carrier protein. In some embodiments, the universal epitope (including fusion universal epitope) is covalently fused to a second universal epitope (including fusion universal epitope) or the carrier protein by a peptide linker disposed therebetween. In some embodiments, the universal epitope is directly fused to the carrier protein without having a peptide linker disposed therebetween. In some embodiments, the chimeric carrier protein comprises a fusion universal epitope comprising a first universal epitope to a second universal epitope with a peptide linker disposed therebetween, wherein the first universal epitope and the second universal epitope may have the same amino acid sequence, or different amino acid sequences. Suitable linkers can be readily selected and can be of any suitable of length, such as about any of from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be about any of 1, 2, 3, 4, 5, 6, or 7 amino acids. Exemplary flexible linkers include glycine polymers (G)n, glycine-serine polymers (including, for example, (GS)n (SEQ ID NO:68), (GSGSG)n (SEQ ID NO:7), (GSGGS)n (SEQ ID NO:69) and (GGGS)n (SEQ ID NO:70), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Exemplary flexible linkers include, but are not limited to GGSG (SEQ ID NO:71), GSGSG (SEQ ID NO: 7), GGGGSGGGGSGGGGS (SEQ ID NO:72), GGGGSG (SEQ ID NO:73), GGSGG (SEQ ID NO:74), GSGGG (SEQ ID NO:75), GGGSG (SEQ ID NO:76), GSSSG (SEQ ID NO:77), and the like. In some embodiments, the peptide linker is between about 1 to 20 amino acid residues long. In some embodiments, the peptide linker comprises the amino acid sequence of SEQ ID NO: 7.

Any one of the carrier proteins described above can be combined with one or more copies (such as 1, 2, 3, or more) of any one or combinations of the universal epitopes described above, and optionally combined with any one of the linkers described above to provide the chimeric carrier protein of the present application. In some embodiments, the chimeric carrier protein comprises a carrier protein and one or more universal epitopes selected from the group consisting of SEQ ID NOs: 1-3. In some embodiments, the chimeric carrier protein comprises a carrier protein comprising any one of the amino acid sequences selected from the group consisting of SEQ ID NOs: 4-6. In some embodiments, the chimeric carrier protein comprises a carrier protein comprising any one of the amino acid sequences selected from the group consisting of SEQ ID NOs: 4-6, and one or more universal epitopes selected from the group consisting of SEQ ID NOs: 1-3. In some embodiments, the chimeric carrier protein comprises the amino acid sequence of any one selected from the group consisting of SEQ ID NOs: 8-32. In some embodiments, the chimeric carrier protein comprises the amino acid sequence of any one selected from the group consisting of SEQ ID NOs: 39-44. In some embodiments, the chimeric carrier protein comprises the amino acid sequence of any one selected from the group consisting of SEQ ID NOs:51-56.

The polysaccharide-protein conjugates described in the previous section may comprise any one of the chimeric carrier proteins described above in this section in combination with any of the polysaccharide antigens described in the previous section. Any of the polysaccharide antigens and any of the chimeric carrier proteins may also be used in the methods of preparation described in the section below.

Methods of Preparation

The present invention further provides methods for preparing any of the chimeric carrier proteins and the polysaccharide-protein conjugates described herein.

In one aspect of the present invention, there is provided a method of preparing the polysaccharide-protein conjugate, comprising conjugating the polysaccharide antigen to the chimeric carrier protein. In some embodiments, the method further comprises preparing the polysaccharide antigen prior to conjugating the polysaccharide antigen to the chimeric carrier protein. In some embodiments, the method further comprises preparing the chimeric carrier protein prior to conjugating the polysaccharide antigen to the chimeric carrier protein. In some embodiments, the polysaccharide antigen is prepared by culturing a bacterium comprising the polysaccharide antigen, and recovering the polysaccharide antigen from the culture. In some embodiments, the chimeric carrier protein is prepared by culturing a host cell transformed with a vector comprising the nucleic acid sequence encoding the chimeric carrier protein under conditions allowing the expression of the chimeric carrier protein, and recovering the expressed chimeric carrier protein from the culture.

In some embodiments, there is provided a method of preparing the polysaccharide-protein conjugate, comprising preparing the polysaccharide antigen, and conjugating the polysaccharide antigen to the chimeric carrier protein. In some embodiments, the polysaccharide antigen is prepared by culturing a bacterium comprising the polysaccharide antigen, and recovering the polysaccharide antigen from the culture. In some embodiments, the chimeric carrier protein is prepared by culturing a host cell transformed with a vector comprising the nucleic acid sequence encoding the chimeric carrier protein under conditions allowing the expression of the chimeric carrier protein, and recovering the expressed chimeric carrier protein from the culture.

In some embodiments, there is provided a method of preparing the polysaccharide-protein conjugate, comprising preparing the chimeric carrier protein, and conjugating the polysaccharide antigen to the chimeric carrier protein. In some embodiments, the polysaccharide antigen is prepared by culturing a bacterium comprising the polysaccharide antigen, and recovering the polysaccharide antigen from the culture. In some embodiments, the chimeric carrier protein is prepared by culturing a host cell transformed with a vector comprising the nucleic acid sequence encoding the chimeric carrier protein under conditions allowing the expression of the chimeric carrier protein, and recovering the expressed chimeric carrier protein from the culture.

In some embodiments, there is provided a method of preparing the polysaccharide-protein conjugate, comprising preparing the polysaccharide antigen, preparing the chimeric carrier protein, and conjugating the polysaccharide antigen to the chimeric carrier protein. In some embodiments, the polysaccharide antigen is prepared by culturing a bacterium comprising the polysaccharide antigen, and recovering the polysaccharide antigen from the culture. In some embodiments, the chimeric carrier protein is prepared by culturing a host cell transformed with a vector comprising the nucleic acid sequence encoding the chimeric carrier protein under conditions allowing the expression of the chimeric carrier protein, and recovering the expressed chimeric carrier protein from the culture.

In some embodiments, there is provided a method of preparing the polysaccharide-protein conjugate, comprising:
i) culturing a bacterium comprising a polysaccharide antigen;
ii) recovering the polysaccharide antigen from the culture;
iii) culturing a host cell transformed with a vector comprising the nucleic acid sequence encoding a chimeric carrier protein under conditions allowing the expression of the chimeric carrier protein;
iv) recovering the expressed chimeric carrier protein from the culture; and
v) conjugating the polysaccharide antigen to the chimeric carrier protein.

In one aspect of the present application, there is provided a method of preparing a chimeric carrier protein, comprising culturing a host cell transformed with a vector comprising the nucleic acid sequence encoding the chimeric carrier protein under conditions allowing the expression of the chimeric carrier protein, and recovering the expressed chimeric carrier protein from the culture. In some embodiments, the vector comprises the nucleic acid sequence of any one selected from the group consisting of SEQ ID NOs:34-38. In some embodiments, the vector comprises the nucleic acid sequence of any one selected from the group consisting of SEQ ID NOs:46-50. In some embodiments, the vector comprises the nucleic acid sequence of any one selected from the group consisting of SEQ ID NOs:58-63.

The present invention contemplates use of any one of the many methods known in the art for conjugating or covalently linking polysaccharides to proteins, for example, see Hermanson, Greg T. "Bioconjugate techniques." Academic press, 2013, incorporated herein by reference. For example, three methods are commonly applied for conjugating polysaccharides to proteins, including: 1) reductive amination, wherein the aldehyde or ketone group on one component of the reaction reacts with the amino or hydrazide group on the other component, and the C=N double bond formed is subsequently reduced to C—N single bond by a reducing agent; 2) cyanylation conjugation, wherein the polysaccharide is activated either by cyanogens bromide (CNBr) or by 1-cyano-4-dimethylammoniumpyridinium tetrafluoroborate (CDAP) to introduce a cyanate group to the hydroxyl group, which forms a covalent bond to the amino or hydrazide group upon addition of the protein component; and 3) a carbodiimide reaction, wherein carbodiimide (such as 1-ethyl-3-(3-dimethylaminopropyl)carbodiimide or EDC) activates the carboxyl group on one component of the conjugation reaction, and the activated carbonyl group reacts with the amino or hydrazide group on the other component. These reactions are also frequently employed to activate the components of the conjugate prior to the conjugation reaction. In some embodiments, the polysaccharide antigen is conjugated to the chimeric carrier protein by reductive amination, cyanylation conjugation, or a carbodiimide reaction. In some embodiments, the polysaccharide antigen is activated by 1-cyano-4-dimethylammoniumpyridinium tetrafluoroborate (CDAP). In some embodiments, the polysaccharide antigen is conjugated to the chimeric carrier protein through an adipic acid dihydrazide (ADH) linker. In some embodiments, the synthesized polysaccharide-protein conjugate is further purified by any of the methods known in the art, such as chromatography, electrophoresis, ultrafiltration, dialysis, etc. The polysaccharide-protein conjugated may be characterized and quantified using methods known in the art, such as chromatography, mass spectroscopy, etc. In some embodiments, the polysaccharide-protein conjugate has a purity of about any of more than 70%, 80%, 90%, 95%, 99% or more.

The polysaccharide antigen may be prepared by any of the methods known in the art, including, but not limited to, chemical synthesis, and isolation from natural sources, such as isolation from a bacteria culture. In some embodiments, the polysaccharide antigen is prepared by culturing the bacterium comprising the polysaccharide antigen, and recovering the polysaccharide antigen from the culture. In some embodiments, the polysaccharide antigen is extracted from soluble fraction of lysed bacteria in a bacteria culture. In some embodiments, the extracted polysaccharide antigen is further purified, for example, by removing nucleic acids and proteins respectively. In some embodiments, the extracted and optionally purified polysaccharide antigen is further processed (such as biochemically or chemically hydrolyzed, cleaved, or digested) to obtain a polysaccharide antigen of an appropriate molecular weight range and/or median molecular weight. Additional purification steps, such as chromatography, dialysis, ultrafiltration, electrophoresis, differential precipitation, etc., may be used to prepare the polysaccharide antigen. The prepared polysaccharide antigen may be characterized using a variety of methods known in the art, such as mass spectroscopy, FTIR, colorimetric assays, electrophoresis, etc., in order to quantify and/or to confirm chemical, physical and/or structural properties of the polysaccharide antigen. In some embodiments, the polysaccharide antigen is further activated and/or oxidized to obtain a polysaccharide antigen derivative that can readily be conjugated to the chimeric carrier protein. In some embodiments, the polysaccharide antigen derivative has an aldehyde group that can be covalently linked to an amino acid residue in the chimeric carrier protein, such as via an organic linker.

The chimeric carrier protein can be prepared by any method known in the art, including, but not limited to, chemical synthesis, recombinant DNA techniques and protein expression, and conjugation of the universal epitope to the carrier protein by chemical or biochemical methods known in the art, wherein the universal epitope and/or the carrier protein may be prepared by chemical synthesis or recombinant DNA techniques and protein expression. Commonly used recombinant DNA techniques, cell transformation, protein expression and purification techniques, and other techniques related to preparation or characterization of proteins are described in, for example, Sambrook et al., Molecular Cloning: A Laboratory Manual 3d edition (2001) Cold Spring Harbor Laboratory Press, Cold Spring Harbor, N.Y., which is incorporated herein by reference. In some embodiments, the chimeric carrier protein is prepared by culturing a host cell transformed with a vector comprising the nucleic acid sequence encoding the chimeric carrier protein under conditions allowing the expression of the chimeric carrier protein, and recovering the expressed chimeric carrier protein from the culture. The host cell suitable for expressing the chimeric carrier protein includes, but is not limited to, bacteria, yeast, mammalian cells, and insect cells. In some embodiments, the host cell is *Escherichia coli* or *Saccharomyces cerevisiae*. In some embodiments, the host cell is genetically engineered to enhance protein expression. Appropriate parameters for protein expression, such as temperature, media, duration, induction time, etc., can be chosen and optimized by a person skilled in the art based on the nature of the protein expression system (including host cell, size, yield, solubility and other physical properties of the chimeric carrier protein, etc.). In some embodiments, the host cell does not have protein glycosylation pathways. In some embodiments, the vector is a plasmid.

In some embodiments, the vector comprises optimized nucleic acid sequence (e.g. based on native codon frequency of the host cell, and/or with addition regulatory sequences) encoding the chimeric carrier protein, wherein the optimized nucleic acid sequence can be transcribed, and/or translated at high efficiency. In some embodiments, the vector comprises nucleic acid sequence of any one selected from the group consisting of SEQ ID NOs:34-38. In some embodiments, the vector comprises nucleic acid sequence of any one selected from the group consisting of SEQ ID NOs:46-50. In some embodiments, the vector comprises nucleic acid sequence of any one selected from the group consisting of SEQ ID NOs:58-63. In some embodiments, the expressed chimeric carrier protein is isolated from the soluble fraction of the culture. In some embodiments, the expressed chimeric carrier protein is isolated from the inclusion body of the bacteria culture. In some embodiments, the expressed chimeric protein is refolded. In some embodiments, the expressed chimeric protein is further purified using any of the methods known in the art, such as, chromatography and dialysis. In some embodiments, the chimeric carrier protein has a purity of about any of more than 70%, 80%, 90%, 95%, 99% or more.

It is intended that any of the steps and parameters described herein for preparing the chimeric carrier protein, for preparing the polysaccharide antigen, and for conjugating the polysaccharide antigen to the chimeric carrier protein can be combined with each other for preparing the polysaccharide-protein conjugates, as if each and every combination is individually described. Further provided herein are chimeric carrier proteins and polysaccharide-protein conjugates prepared by any one of the methods of preparation as described herein.

Immunogenic Compositions

One aspect of the present invention provides compositions (including immunogenic compositions, pharmaceutical compositions, and vaccines) comprising any one or any combination of the polysaccharide-protein conjugates described above.

Accordingly, in some embodiments, there is provided an immunogenic composition comprising one or more polysaccharide-protein conjugate, wherein each of the one or more polysaccharide-protein conjugate comprises a chimeric carrier protein and a polysaccharide antigen, wherein the chimeric carrier protein comprises a carrier protein and a universal epitope, and wherein the polysaccharide antigen is covalently conjugated to the chimeric carrier protein. In some embodiments, the universal epitope comprises the amino acid sequence of any one selected from the group consisting of SEQ ID NOs: 1-3. In some embodiments, the carrier protein is derived from tetanus toxoid, diphtheria toxoid, cross reacting materials (CRM) of diphtheria toxin, rotavirus capsid protein VP8, meningococcal outer membrane complex, or *Haemophilus influenzae* protein D. In some embodiments, the polysaccharide antigen is derived from a capsular polysaccharide. In some embodiments, the polysaccharide antigen is derived from *Haemophilus influenzae* type b (Hib), *Streptococcus pneumoniae* (Pn), or *Neisseria meningitidis* (Men). In some embodiments, the weight to weight ratio of the polysaccharide antigen to the chimeric carrier protein is about 0.8 to about 1.2 (such as.

In some embodiments, there is provided an immunogenic composition comprising one or more polysaccharide-protein conjugate, wherein each of the one or more polysaccharide-protein conjugate comprises a chimeric carrier protein and a polysaccharide antigen, wherein the chimeric carrier protein comprises a carrier protein and a universal epitope, wherein the universal epitope comprises the amino acid sequence of any one selected from the group consisting of SEQ ID NOs: 1-3, and wherein the polysaccharide antigen is covalently conjugated to the chimeric carrier protein. In some embodiments, the carrier protein is derived from tetanus toxoid, diphtheria toxoid, cross reacting materials (CRM) of diphtheria toxin, rotavirus capsid protein VP8, meningococcal outer membrane complex, or *Haemophilus influenzae* protein D. In some embodiments, the polysaccharide antigen is derived from a capsular polysaccharide. In some embodiments, the polysaccharide antigen is derived from *Haemophilus influenzae* type b (Hib), *Streptococcus pneumoniae* (Pn), or *Neisseria meningitidis* (Men). In some embodiments, the weight to weight ratio of the polysaccharide antigen to the chimeric carrier protein is about 0.8 to about 1.2.

In some embodiments, there is provided an immunogenic composition comprising one or more polysaccharide-protein conjugate, wherein each of the one or more polysaccharide-protein conjugate comprises a chimeric carrier protein and a polysaccharide antigen, wherein the chimeric carrier protein comprises a carrier protein and a universal epitope, and wherein the polysaccharide antigen is conjugated (e.g. covalently conjugated) to the chimeric carrier protein. In some embodiments, the universal epitope comprises (including consisting essentially of or consisting of) the amino acid sequence of any one selected from the group consisting of SEQ ID NOs: 1-3. In some embodiments, the carrier protein is derived from tetanus toxoid, diphtheria toxoid, cross reacting materials (CRM) of diphtheria toxin, rotavirus capsid protein VP8, meningococcal outer membrane complex, or *Haemophilus influenzae* protein D. In some embodiments, the polysaccharide antigen is derived from a capsular polysaccharide. In some embodiments, the polysaccharide antigen is derived from *Haemophilus influenzae* type b (Hib), *Streptococcus pneumoniae* (Pn), or *Neisseria meningitidis* (Men). In some embodiments, the weight to weight ratio of the polysaccharide antigen to the chimeric carrier protein is about 0.8 to about 1.2 (such as about any one of 0.8-0.9, 0.9-1.0, 1.0-1.1, or 1.1-1.2).

In some embodiments, there is provided an immunogenic composition comprising one or more polysaccharide-protein conjugate, wherein each of the one or more polysaccharide-protein conjugate comprises a chimeric carrier protein and a polysaccharide antigen, wherein the chimeric carrier protein comprises a carrier protein and a universal epitope, wherein the universal epitope comprises (including consisting essentially of or consisting of) the amino acid sequence of any one selected from the group consisting of SEQ ID NOs: 1-3, wherein the carrier protein comprises any one of the amino acid sequences selected from the group consisting of SEQ ID NOs: 4-6, and wherein the polysaccharide antigen is (e.g. covalently conjugated) to the chimeric carrier protein. In some embodiments, the polysaccharide antigen is derived from a capsular polysaccharide. In some embodiments, the polysaccharide antigen is derived from *Haemophilus influenzae* type b (Hib), *Streptococcus pneumoniae* (Pn), or *Neisseria meningitidis* (Men). In some embodiments, the weight to weight ratio of the polysaccharide antigen to the chimeric carrier protein is about 0.8 to about 1.2 (such as about any one of 0.8-0.9, 0.9-1.0, 1.0-1.1, or 1.1-1.2).

In some embodiments, there is provided an immunogenic composition comprising one or more polysaccharide-protein conjugate, wherein each of the one or more polysaccharide-protein conjugate comprises a chimeric carrier protein and a polysaccharide antigen, wherein the chimeric carrier protein comprises a carrier protein and a universal epitope, wherein the chimeric carrier protein comprises (including consisting essentially of or consisting of) any one of the amino acid sequences selected from the group consisting of SEQ ID NOs:8-32, 39-44, and 51-56, and wherein the polysaccharide antigen is conjugated (e.g. covalently conjugated) to the chimeric carrier protein. In some embodiments, the polysaccharide antigen is derived from a capsular polysaccharide. In some embodiments, the polysaccharide antigen is derived from *Haemophilus influenzae* type b (Hib), *Streptococcus pneumoniae* (Pn), or *Neisseria meningitidis* (Men). In some embodiments, the weight to weight ratio of the polysaccharide antigen to the chimeric carrier protein is about 0.8 to about 1.2 (such as about any one of 0.8-0.9, 0.9-1.0, 1.0-1.1, or 1.1-1.2).

In some embodiments, the immunogenic composition consists of one polysaccharide-protein conjugate. In some embodiments, the immunogenic composition comprises a plurality (such as about any of 2, 3, 4, 5, 6, 7, 8, 9, 10, 11, 12, 13, 14, 15, 16, 17, 18, 19, 20, 21, 22, 23, 24, or more) of the polysaccharide-protein conjugates. The plurality of polysaccharide-protein conjugates contains different types of polysaccharide-protein conjugates, such as PS-protein conjugates with different chimeric carrier protein, PS-protein conjugates with PS derived from different serotypes of the same bacterium species, PS-protein conjugates with PS derived from different bacteria species, PS-protein conjugates with different PS to chimeric carrier protein ratio, or any combination thereof. In some embodiments, there is no interaction among the different polysaccharide-protein conjugates which substantially impairs the desired efficacy of each polysaccharide-protein conjugate. In some embodiments, the immunogenic composition comprises a plurality of the polysaccharide-protein conjugates, wherein at least two of the polysaccharide-protein conjugates are different. For example, the at least two of the polysaccharide-protein conjugates may differ in the chimeric carrier proteins, types or combinations of types of universal epitopes in the chimeric carrier proteins, copies of universal epitopes in the chimeric carrier proteins, linkers in the chimeric carrier proteins, positions (i.e. N-terminus, C-terminus, or both) of the universal epitopes within the chimeric carrier proteins, or any combination thereof. In some embodiments, the immunogenic composition comprises a plurality of the polysaccharide-protein conjugates comprising polysaccharide antigens derived from at least two different bacterial species (including different serotypes). In some embodiments, the at least two different bacterial species are selected from the group consisting of *Haemophilus influenzae* type b (Hib), *Streptococcus pneumoniae* (Pn), or *Neisseria meningitidis* (Men). In some embodiments, the immunogenic composition comprises a plurality of the polysaccharide-protein conjugates, wherein each polysaccharide-protein conjugate comprises a polysaccharide antigen derived from a bacterium of a distinct serotype of the same species. In some embodiments, the immunogenic composition comprises one or more (such as about any of 1, 2, 3, 4, 5, 6, 7, 8, 9, 10, 11, 12, 13, 14, 15, 16, 17, 18, 19, 20, 21, 22, 23, or 24) of the polysaccharide-protein conjugates, wherein the polysaccharide antigen (such as capsular polysaccharide antigen) is derived from *Streptococcus pneumoniae* of a serotype selected from the group consisting of 1, 2, 3, 4, 5, 6A, 6B, 7F, 8, 9N, 9V, 10A, 11A, 12F, 14, 15B, 17F, 18C, 19A, 19F, 20, 22F, 23F and 33F. In some embodiments, the immunogenic composition comprises one or more (such as about any of 1, 2, 3, 4, 5, 6, 7, 8, 9, 10, 11, 12, or 13) polysaccharide-protein conjugates, wherein each polysaccharide-protein conjugate comprises a capsular polysaccharide derived from *Streptococcus pneumoniae* of a different serotype selected from the group consisting of 1, 3, 4, 5, 6A, 6B, 7F, 9V, 14, 18C, 19A, 19F, and 23F. In some embodiments, the immunogenic composition comprises about 24 polysaccharide-protein conjugates, wherein each polysaccharide-protein conjugate comprises a capsular polysaccharide derived from *Streptococcus pneumoniae* of a different serotype selected from the group consisting of 1, 2, 3, 4, 5, 6A, 6B, 7F, 8, 9N, 9V, 10A, 11A, 12F, 14, 15B, 17F, 18C, 19A, 19F, 20, 22F, 23F and 33F. In some embodiments, the immunogenic composition comprises about 13 polysaccharide-protein conjugates, wherein each polysaccharide-protein conjugate comprises a capsular polysaccharide derived from *Streptococcus pneumoniae* of a different serotype selected from the group consisting of 1, 3, 4, 5, 6A, 6B, 7F, 9V, 14, 18C, 19A, 19F, and 23F. In some embodiments, the immunogenic composition comprises one or more (such as about any of 1, 2, 3, or 4) of the polysaccharide-protein conjugates, wherein the polysaccharide antigen (such as capsular polysaccharide antigen) is derived from *Neisseria meningitidis* of a serotype selected from the group consisting of A, C, Y, and W-135. In some embodiments, the immunogenic composition comprises about 4 polysaccharide-protein conjugates, wherein each polysaccharide-protein conjugate comprises a capsular polysaccharide derived from *Neisseria meningitidis* of a different serotype selected from the group consisting of A, C, Y, and W-135.

The relative ratio (such as weight by weight or mole by mole) among the different polysaccharide-protein conjugates in the immunogenic composition comprising a plurality of polysaccharide-protein conjugates may depend on multiple factors that affect the immunogenicity of each polysaccharide-protein conjugate, as well as the desired immunogenic efficacy against each polysaccharide antigen included in the immunogenic composition. For example, the relative ratio of the polysaccharide antigen to the chimeric carrier protein, the nature of the chimeric carrier protein (such as type and number of universal epitopes), the nature of the PS antigen (such as the molecular weight, length, number of repeating units, chemical nature of the repeating units, the bacterial source etc.), and/or the method for producing the PS antigen, the chimeric carrier protein, and/or conjugating the PS antigen to the chimeric carrier protein may all affect the immunogenic efficacy of each PS-protein conjugate in the immunogenic composition, which may differ from batch to batch of preparing the PS-protein conjugates, and therefore, may have to be determined experimentally for each batch of PS-protein conjugate prior to mixing the PS-protein conjugates to obtain the immunogenic composition. The desired immunogenic efficacy against each polysaccharide antigen depends on the actual application of the immunogenic composition, for example, the frequency of each bacterial serotype among a population of individuals to be immunized, the severity of each bacterial serotype, the individuals to be immunized (such as whether the individual has normal or weak immune response against PS antigens, previous or concurrent exposure to similar PS-protein conjugates, etc.), and the effective PS-specific antibody titer required to achieve desirable protection against the bacterium serotype. Any of the methods known in the art to determine immunogenicity, such as ELISA assays quantifying PS-specific antibody titers in an animal immunized with the immunogenic composition, may be used to determine the relative ratio among the different polysaccharide-protein conjugates in the immunogenic composition. Additionally, analytical methods, such as chromatography, mass spectroscopy, and the like, may be used to determine the chemical and structural properties of each polysaccharide-protein conjugate in the immunogenic composition. In some embodiments, the immunogenic composition comprises a plurality of polysaccharide-protein conjugates at about equal molar ratio.

In some embodiments, the immunogenic composition further comprises one or more adjuvants. As used herein, an adjuvant is an agent that modifies the effect of the other agents in the immunogenic composition or vaccine, such as enhancing the immunogenicity of the immunogenic composition. Adjuvants may be given to boost the immune response, such as yielding a higher titer of antibodies, providing a longer-lasting protection, and/or reducing the number and dosage of injections. Adjuvants are well known in the art. In some embodiments, the adjuvant may stabilize formulations of the immunogenic composition. Suitable adjuvants to enhance effectiveness of the immunogenic composition include, but are not limited to: aluminum salts (alum), such as aluminum hydroxide, aluminum phosphate, aluminum sulfate, etc.; mineral oil, such as paraffin oil; bacterial products, such as bacteria cell wall components, killed bacteria, detoxified mutants of bacterial toxins, etc.; nonbacterial organics, such as squalene, thimerosal, etc.; delivery systems, such as saponin adjuvant systems (e.g. Quil-A®), Ribi™ adjuvant system (RAS), etc.; cytokines, such as interleukins (e.g., IL-1, IL-2, IL-12, etc.), interferons (e.g., gamma interferon), granulocyte macrophage colony stimulating factor (GM-CSF), macrophage colony stimulating factor (M-CSF), tumor necrosis factor (TNF), costimulatory molecules B7-1 and B7-2, etc.; compositions such as Freund's complete adjuvant, Freund's incomplete adjuvant; other substances that act as immunostimulating agents to enhance the effectiveness of the immunogenic composition; and any combination thereof. In some embodiments, the immunogenic composition further comprises aluminum phosphate or aluminum hydroxide.

Further provided by the present invention is a vaccine comprising any one of the immunogenic compositions described above and a pharmaceutically acceptable carrier. The term "pharmaceutically acceptable carrier" as used herein means one or more compatible solid or liquid filler, diluents or encapsulating substances which are suitable for administration into a subject. "Pharmaceutically acceptable" is used to refer to a non-toxic material that is compatible with a biological system such as a cell, cell culture, tissue, or organism. The term "carrier" denotes an organic or inorganic ingredient, natural or synthetic, with which the active ingredient is combined to facilitate the application. The characteristics of the carrier depend on the route of administration. Physiologically and pharmaceutically acceptable carriers include diluents, fillers, salts, buffers, stabilizers, solubilizers, and other materials which are well known in the art.

Any one or combination of the immunogenic compositions described herein may be used in the vaccine, or other pharmaceutical compositions or formulations, by combining the immunogenic composition(s) described with a pharmaceutically acceptable carrier, excipients, stabilizing agents and/or other agents, which are known in the art, for use in the methods of treatment, methods of administration, and dosage regimes described herein.

Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving, stabilizing, wetting, emulsifying agents and the like together with the penetration enhancer. The final form may be sterile and may also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

The pharmaceutical compositions (including vaccines) described herein may include other agents, excipients, or stabilizers to improve properties of the immunogenic composition. Examples of suitable excipients and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. Examples of emulsifying agents include tocopherol esters such as tocopheryl polyethylene glycol succinate and the like, Pluronic®, emulsifiers based on polyoxy ethylene compounds, Span 80 and related compounds and other emulsifiers known in the art and approved for use in animals or human dosage forms. The pharmaceutical compositions (including vaccines) can be formulated so as to provide rapid, sustained or delayed release of the active ingredient after administration to the patient by employing procedures well known in the art.

In some embodiments, the pharmaceutical composition (including vaccine) is formulated to have a pH in the range of about 4.5 to about 9.0, including for example pH ranges of any one of about 5.0 to about 8.0, about 5.5 to about 6.5, or about 5.6 to about 6.0. In some embodiments, the pH of the pharmaceutical composition (including vaccine) is formulated to no less than about 5.6. The pharmaceutical composition (including vaccine) can also be made to be isotonic with blood by the addition of a suitable tonicity modifier, such as glycerol.

"Individual", "subject" or "patient" as used herein refers to a mammal and includes, but is not limited to, human, bovine, horse, feline, canine, rodent, or primate. In some embodiments, the pharmaceutical composition (including vaccine) is suitable for administration to a human. In some embodiments, the pharmaceutical composition (including vaccine) is suitable for administration to a human by parenteral administration. Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizing agents, and preservatives. The formulations can be presented in unit-dose or multi-dose sealed containers, such as syringes and vials, and can be stored in a freeze-dried (lyophilized) condition requiring only the addition of the sterile liquid excipient methods of treatment, methods of administration, and dosage regimes described herein (i.e., water) for injection, immediately prior to use. Extemporaneous injection solutions and suspensions can be prepared from sterile powders, granules, and of the kind previously described. Injectable formulations are preferred. In some embodiments, the pharmaceutical composition (including vaccine) is contained in a single-use syringe, such as a single-use sealed syringe. In some embodiments, each single-use syringe contains a therapeutically or prophylactically effective amount of the polysaccharide conjugate or the plurality of polysaccharide conjugates in a unit of weight or volume suitable for administration to an individual. In some embodiments, the pharmaceutical composition (including vaccine) is contained in a multi-use vial. In some embodiments, the pharmaceutical composition (including vaccine) is contained in bulk in a container.

In some embodiments, the vaccine is a monovalent vaccine, wherein the vaccine comprises an immunogenic composition comprising one or more polysaccharide-protein conjugates, wherein the one or more polysaccharide-protein conjugates comprises a polysaccharide antigen derived from a single bacterium serotype. In some embodiments, there is provided a monovalent *Haemophilus influenzae* type b (Hib) vaccine comprising one or more polysaccharide-protein conjugates, wherein each of the one or more polysaccharide-protein conjugates comprises a chimeric carrier protein and a polysaccharide antigen, wherein the chimeric carrier protein comprises a carrier protein and a universal epitope (such as a universal epitope comprising the amino acid sequence of any one of SEQ ID NOs:1-3), and wherein the polysaccharide antigen is derived from *Haemophilus influenzae* type b (Hib). In some embodiments, the vaccine is a multi-valent vaccine, wherein the vaccine comprises an immunogenic composition comprising a plurality of polysaccharide-protein conjugates, wherein each polysaccharide-protein conjugate comprises a polysaccharide antigen derived from a bacterium of a distinct serotype of the same species. In some embodiments, there is provided a 13-valent *Streptococcus pneumoniae* vaccine comprising about 13 polysaccharide-protein conjugates, wherein each polysaccharide-protein conjugate comprises a chimeric carrier protein and a polysaccharide antigen, wherein the chimeric carrier protein comprises a carrier protein and a universal epitope (such as a universal epitope comprising the amino acid sequence of any one of SEQ ID NOs:1-3), and wherein each polysaccharide-protein conjugate comprises a capsular polysaccharide derived from *Streptococcus pneumoniae* of a different serotype selected from the group consisting of 1, 3, 4, 5, 6A, 6B, 7F, 9V, 14, 18C, 19A, 19F, and 23F. In some embodiments, there is provided a 24-valent *Streptococcus pneumoniae* vaccine comprising about 24 polysaccharide-protein conjugates, wherein each polysaccharide-protein conjugate comprises a chimeric carrier protein and a polysaccharide antigen, wherein the chimeric carrier protein comprises a carrier protein and a universal epitope (such as a universal epitope comprising the amino acid sequence of any one of SEQ ID NOs:1-3), and wherein each polysaccharide-protein conjugate comprises a capsular polysaccharide derived from *Streptococcus pneumoniae* of a different serotype selected from the group consisting of 1, 2, 3, 4, 5, 6A, 6B, 7F, 8, 9N, 9V, 10A, 11A, 12F, 14, 15B, 17F, 18C, 19A, 19F, 20, 22F, 23F and 33F. In some embodiments, there is provided a 4-valent *Neisseria meningitidis* vaccine comprising about 24 polysaccharide-protein conjugates, wherein each polysaccharide-protein conjugate comprises a chimeric carrier protein and a polysaccharide antigen, wherein the chimeric carrier protein comprises a carrier protein and a universal epitope (such as a universal epitope comprising the amino acid sequence of any one of SEQ ID NOs:1-3), and wherein each polysaccharide-protein conjugate comprises a capsular polysaccharide derived from *Neisseria meningitidis* of a different serotype selected from the group consisting of A, C, Y, and W-135. In some embodiments, the vaccine further comprises other antigens (related or unrelated to the PS antigen or the chimeric carrier protein). In some embodiments, the other antigens may be formulated with adjuvants, diluents, excipients, carriers, and other pharmaceutically acceptable substances.

Methods of Treatment

The present invention further provides methods of treating or preventing a disease (such as an infection) caused by a bacterium, comprising administering to an individual an effective amount of any one of the compositions (including polysaccharide-protein conjugates, immunogenic compositions, pharmaceutical compositions, and vaccines) described herein, wherein the bacterium comprises the polysaccharide antigen. In some embodiments, the individual is a child below about 2 years of age, an elderly, or an immunocompromised individual.

In one aspect, there is provided a method of immunizing an individual against a disease caused by a bacterium comprising administering to the individual an effective amount of any one of the immunogenic compositions, pharmaceutical compositions, or vaccines described herein, wherein the bacterium expresses a polysaccharide (such as capsular polysaccharide) comprising the polysaccharide antigen. In another aspect, there is provided use of any one of the immunogenic compositions, pharmaceutical compositions, and vaccines in the manufacture of a medicament for the treatment or prevention of a disease caused by a bacterium, wherein the polysaccharide antigen is a polysaccharide expressed on the surface of the bacterium or a derivative thereof. In some embodiments, the bacterium is *Haemophilus influenzae* type b (Hib), *Streptococcus pneumoniae*, or *Neisseria meningitidis* (Men). In some embodiments, the individual is a child below about 2 years of age, an elderly, or an immunocompromised individual.

The methods of treatment described herein is generally applicable to any disease or condition caused by a bacterium that expresses a polysaccharide (such as a capsular polysaccharide) comprising a polysaccharide antigen, including, but not limited to disease or conditions caused by *Haemophilus influenzae* type b (Hib), *Streptococcus pneumoniae* (Pn), or *Neisseria meningitidis* (Men). For example, in some embodiments, the disease is pneumonia, ear infection, sinus infection, meningitis, bacteremia, any combination thereof, and/or any other disease or condition caused by *Streptococcus pneumoniae*. In some embodiments, the disease is meningitis, pneumonia, epiglottitis, cellulitis, arthritis, ear infection, any combination thereof, and/or any other disease or condition caused by *Haemophilus influenzae* type b. In some embodiments, the disease is meningitis, meningococcemia, combination thereof and/or any other disease or condition caused by *Neisseria meningitidis*.

"Individual", "subject" or "patient" as used herein refers to a mammal and includes, but is not limited to, human, bovine, horse, feline, canine, rodent, or primate. In some embodiments, the individual is a human individual. In some embodiments, the individual has a compromised immune system. In some embodiments, the individual weak immune response to polysaccharide antigens (such as low PS-specific antibody titer, short duration of immune response, and/or low immune memory) compared to a healthy adult. In some embodiments, the individual has a deficient or immature T cell system. In some embodiments, the individual has a deficient or immature immune memory system. In some embodiments, the individual is a young child (such as a child below about 2 years of age, such as a child below about any of 3 months, 6 months, 12 months, 1.5 years, or 2 years of age). In some embodiments, the individual is an elderly, such as an individual above any of 50, 55, 60, 65, 70, 75, 80, 85, 90, 95 or more years of age. In some embodiments, the individual is an immunocompromised individual. In some embodiments, the method provides broad immunoprotection among individuals having different polymorphisms in MHC molecules.

As used herein, "treatment" or "treating" is an approach for obtaining beneficial or desired results including clinical results, including both therapeutic treatment and prophylactic or preventative measures. For purposes of this invention, beneficial or desired clinical results include, but are not limited to, one or more of the following: decreasing one more symptoms resulting from the disease, diminishing the extent of the disease, stabilizing the disease (e.g., preventing or delaying the worsening of the disease), preventing or delaying the spread of the disease, preventing or delaying the occurrence or recurrence of the disease, delay or slowing the progression of the disease, ameliorating the disease state, providing a remission (whether partial or total) of the disease, decreasing the dose of one or more other medications required to treat the disease, increasing the quality of life, and/or prolonging survival. In some embodiments, the composition reduces the severity of one or more symptoms associated with the disease (such as infection by a bacterium) by at least about any of 10%, 20%, 30%, 40%, 50%, 60%, 70%, 80%, 90%, 95% or 100% compared to the corresponding symptom in the same individual prior to treatment or compared to the corresponding symptom in other individuals not receiving the treatment method or composition. The methods of the invention contemplate any one or more of these aspects of treatment.

A treatment capable of "delaying progression" of a disease may include deferring, hindering, slowing, retarding, stabilizing, and/or postponing development of the disease. This delay can be of varying lengths of time, depending on the history of the disease and/or individual being treated. As is evident to one skilled in the art, a sufficient or significant delay can, in effect, encompass prevention, in that the individual, e.g., an individual at risk for developing the disorder or condition, does not develop the disease.

As is understood in the art, an "effective amount" refers to an amount of a composition, or a combination therapy sufficient to produce a desired therapeutic outcome (e.g., reducing the severity or duration of, stabilizing the severity of, eliminating one or more symptoms of, or preventing the onset of the disease). The amount may be in one or more doses, i.e., a single dose or multiple doses. Standard methods can be used to measure the magnitude of the beneficial effect, such as in vitro assays (e.g. ELISA), cell-based assays (e.g. opsonophagocytotic killing assays), animal models, and/or human testing. In some embodiments, the composition (including polysaccharide-protein conjugates, immunogenic compositions, pharmaceutical compositions, and vaccines) is administered at an amount that induces an immunoprotective response without significant, adverse effects. Such amount can vary depending upon the bacteria species, and the serotype of the bacteria. Optimal amounts of components for a particular vaccine can be ascertained by standard studies involving observation of appropriate immune responses in subjects. Following an initial vaccination, subjects can receive one or several booster immunizations adequately spaced. In some embodiments, the composition (including polysaccharide-protein conjugates, immunogenic compositions, pharmaceutical compositions, and vaccines) is administered in one or more (such as 1, 2, 3, or more) doses. In some embodiments, the composition is administered in at least 2 (such as 2, 3, 4, or more) doses. In some embodiments, the polysaccharide-specific antibody titer in the individual increases in response to later doses compared to the initial dose. In some embodiments, the internal between two adjacent doses is about any one of 1 months, 3 months, 6 months, 1 year, 2 years, 3 years, 4 years, 5 years, or more. In some embodiments, each dose comprises 0.1 to 100 μg of the polysaccharide antigen. In some embodiments, each dose comprises 0.1 to 10 μg of the polysaccharide antigen.

The compositions (including polysaccharide-protein conjugates, immunogenic compositions, pharmaceutical compositions, and vaccines) of the present invention can be administered via any suitable route of administration. In some embodiments, the composition is administered parentally, such as injection. In some embodiments, the composition is administered through a systemic or mucosal route. Exemplary routes of administration applicable to the present invention include, but are not limited to injection via the intramuscular, intraperitoneal, intradermal or subcutaneous routes; or injection via mucosal administration to the oral/alimentary, respiratory (e.g. intranasal) or genitourinary tracts.

Kits and Article of Manufacture

The present invention further provides a kit or an article of manufacture comprising any one of the compositions, including the chimeric carrier proteins, the polysaccharide-protein conjugates, the immunogenic compositions, the pharmaceutical compositions, and the vaccines described herein.

In some embodiments, there is provided a kit useful for enhancing immunogenicity of a polysaccharide antigen comprising a chimeric carrier protein comprising a carrier protein and a universal epitope. In some embodiments, the universal epitope comprises the amino acid sequence of any one selected from SEQ ID NOs: 1-3. In some embodiments, the carrier protein is derived from tetanus toxoid, diphtheria toxoid, cross reacting materials (CRM) of diphtheria toxin, rotavirus capsid protein VP8, meningococcal outer membrane complex, or *Haemophilus influenzae* protein D. In some embodiments, the carrier protein comprises the amino acid sequence of any one selected from SEQ ID NOs: 4-6. In some embodiments, the chimeric carrier protein comprises the amino acid sequence of any one selected from SEQ ID NOs: 8-32, 39-44, and 51-56. In some embodiments, the kit further comprises a polysaccharide antigen, and optionally reagents for conjugating the polysaccharide antigen to the chimeric carrier protein, for preparation of a polysaccharide-protein conjugate useful as a vaccine against the bacterium comprising the polysaccharide antigen.

In some embodiments, there is provided a kit useful for treating or preventing a disease (such as infection) caused by a bacterium comprising any one of the compositions (including the polysaccharide-protein conjugates, the immunogenic compositions, the pharmaceutical compositions, and the vaccines described herein), wherein the polysaccharide antigen is a polysaccharide expressed on the surface of the bacterium or a derivative thereof. In some embodiments, there is provided a kit useful for immunizing an individual against a bacterium comprising any one of the compositions (including the polysaccharide-protein conjugates, the immunogenic compositions, the pharmaceutical compositions, and the vaccines described herein), wherein the polysaccharide antigen is a polysaccharide expressed on the surface of the bacterium or a derivative thereof. In some embodiments, the bacterium is *Haemophilus influenzae* type b (Hib), *Streptococcus pneumoniae*, or *Neisseria meningitidis* (Men). In some embodiments, the composition, such as the vaccine, is contained in a syringe.

The article of manufacture or kit may further comprise a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is the chimeric carrier protein, or the polysaccharide-protein conjugate of the present invention. The label or package insert indicates that the composition is used for treating the condition of choice. The article of manufacture in this embodiment of the invention may further comprise a package insert indicating that the compositions can be used to treat a particular condition. Alternatively, or additionally, the article of manufacture or kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

Exemplary Embodiments

Embodiment 1. In some embodiments, there is provided a polysaccharide-protein conjugate comprising a chimeric carrier protein and a polysaccharide antigen, wherein the chimeric carrier protein comprises a carrier protein and a universal epitope, and wherein the polysaccharide antigen is covalently conjugated to the chimeric carrier protein.

Embodiment 2. In some further embodiments of embodiment 1, the chimeric carrier protein comprises about 1 to about 3 copies of the universal epitope.

Embodiment 3. In some further embodiments of embodiment 1 or embodiment 2, the chimeric carrier protein comprises at least two universal epitopes of different amino acid sequences.

Embodiment 4. In some further embodiments according to any one of embodiments 1-3, the universal epitope is about 8 to about 20 amino acids long.

Embodiment 5. In some further embodiments according to any one of embodiments 1-4, the universal epitope is covalently fused to the N-terminus, the C-terminus, or both the N-terminus and the C-terminus of the carrier protein.

Embodiment 6. In some further embodiments according to any one of embodiments 1-5, the universal epitope comprises the amino acid sequence of any one selected from the group consisting of SEQ ID NOs: 1-3.

Embodiment 7. In some further embodiments according to any one of embodiments 1-6, the carrier protein is derived from tetanus toxoid, diphtheria toxoid, cross reacting materials (CRM) of diphtheria toxin, rotavirus capsid protein VP8, meningococcal outer membrane complex, or *Haemophilus influenzae* protein D.

Embodiment 8. In some further embodiments of embodiment 7, the carrier protein is derived from chain A of CRM197 of diphtheria toxin.

Embodiment 9. In some further embodiments of embodiment 7, the carrier protein comprises the amino acid sequence of any one selected from the group consisting of SEQ ID NOs: 4-6.

Embodiment 10. In some further embodiments according to any one of embodiments 1-9, the universal epitope is covalently fused to the carrier protein by a peptide linker disposed therebetween.

Embodiment 11. In some further embodiments of embodiment 10, the peptide linker is a flexible linker selected from the group consisting of a glycine polymer, a glycine-serine polymer, a glycine-alanine polymer, or an alanine-serine polymer.

Embodiment 12. In some further embodiments of embodiment 10 or embodiment 11, the peptide linker is between about 1 to about 20 amino acid residues long.

Embodiment 13. In some further embodiments according to any one of embodiments 10-12, the peptide linker comprises the amino acid sequence of SEQ ID NO:7.

Embodiment 14. In some further embodiments according to any one of embodiments 1-13, the chimeric carrier protein comprises the amino acid sequence of any one selected from the group consisting of SEQ ID NOs: 8-32.

Embodiment 15. In some further embodiments according to any one of embodiments 1-13, the chimeric carrier protein comprises the amino acid sequence of any one selected from the group consisting of SEQ ID NOs: 39-44.

Embodiment 16. In some further embodiments according to any one of embodiments 1-13, the chimeric carrier protein comprises the amino acid sequence of any one selected from the group consisting of SEQ ID NOs: 51-56.

Embodiment 17. In some further embodiments according to any one of embodiments 1-16, the weight to weight ratio of the polysaccharide antigen to the chimeric carrier protein is about 0.8 to about 1.2.

Embodiment 18. In some further embodiments according to any one of embodiments 1-17, the polysaccharide antigen has an average molecular weight between about 10 kDa to about 1000 kDa.

Embodiment 19. In some further embodiments according to any one of embodiments 1-18, the polysaccharide antigen is derived from a capsular polysaccharide.

Embodiment 20. In some further embodiments according to any one of embodiments 1-19, the polysaccharide antigen is derived from *Haemophilus influenzae* type b (Hib), *Streptococcus pneumoniae* (Pn), or *Neisseria meningitidis* (Men).

Embodiment 21. In some further embodiments of embodiment 20, the capsular polysaccharide is derived from *Streptococcus pneumoniae* of a serotype selected from the group consisting of 1, 2, 3, 4, 5, 6A, 6B, 7F, 8, 9N, 9V, 10A, 11A, 12F, 14, 15B, 17F, 18C, 19A, 19F, 20, 22F, 23F and 33F.

Embodiment 22. In some further embodiments of embodiment 20, the capsular polysaccharide is derived from *Haemophilus influenzae* type b (Hib).

Embodiment 23. In some further embodiments of embodiment 20, the capsular polysaccharide is derived from *Neisseria meningitidis* of a serotype selected from the group consisting of A, C, Y, and W-135.

Embodiment 24. In some embodiments, there is provided an immunogenic composition comprising any one or any combinations of the polysaccharide-protein conjugates according to embodiments 1-23.

Embodiment 25. In some further embodiments of embodiment 24, the immunogenic composition comprises a plurality of the polysaccharide-protein conjugates, wherein at least two of the polysaccharide-protein conjugates comprise a carrier protein that is different from each other.

Embodiment 26. In some further embodiments of embodiment 24 or embodiment 25, the immunogenic composition comprises a plurality of the polysaccharide-protein conjugates, wherein at least two of the polysaccharide-protein conjugates comprise a polysaccharide antigen that is derived from a bacterial species that is different from each other.

Embodiment 27. In some further embodiments of embodiment 24 or embodiment 25, the immunogenic composition comprises a plurality of the polysaccharide-protein conjugates, wherein each polysaccharide-protein conjugate comprises a polysaccharide antigen derived from a bacterium of a distinct serotype of the same species.

Embodiment 28. In some further embodiments of embodiment 27, the immunogenic composition comprises about 13 polysaccharide-protein conjugates, wherein each polysaccharide-protein conjugate comprises a capsular polysaccharide derived from *Streptococcus pneumoniae* of a different serotype selected from the group consisting of 1, 3, 4, 5, 6A, 6B, 7F, 9V, 14, 18C, 19A, 19F, and 23F.

Embodiment 29. In some further embodiments of embodiment 27, the immunogenic composition comprises about 24 polysaccharide-protein conjugates, wherein each polysaccharide-protein conjugate comprises a capsular polysaccharide derived from *Streptococcus pneumoniae* of a different serotype selected from the group consisting of 1, 2, 3, 4, 5, 6A, 6B, 7F, 8, 9N, 9V, 10A, 11A, 12F, 14, 15B, 17F, 18C, 19A, 19F, 20, 22F, 23F and 33F.

Embodiment 30. In some further embodiments of embodiment 27, the immunogenic composition comprises about 4 polysaccharide-protein conjugates, wherein each polysaccharide-protein conjugate comprises a capsular polysaccharide derived from *Neisseria meningitidis* of a different serotype selected from the group consisting of A, C, Y, and W-135.

Embodiment 31. In some further embodiments according to any one of embodiments 24-30, the immunogenic composition further comprises an adjuvant.

Embodiment 32. In some further embodiments of embodiment 31, the adjuvant is aluminum phosphate or aluminum hydroxide.

Embodiment 33. In some embodiments, there is provided a vaccine comprising any one of the immunogenic compositions according to embodiments 24-32 and a pharmaceutically acceptable carrier.

Embodiment 34. In some embodiments, there is provided a method of immunizing an individual against a disease caused by a bacterium comprising administering to the individual an effective amount of any one of the immunogenic compositions according to embodiments 24-32 or the vaccine of claim 33, wherein the polysaccharide antigen is a polysaccharide expressed on the surface of the bacterium or a derivative thereof.

Embodiment 35. In some further embodiments of embodiment 34, the immunogenic composition or the vaccine is administered to the individual in at least two doses.

Embodiment 36. In some further embodiments of embodiment 34 or embodiment 35, the disease is pneumonia, ear infection, sinus infection, meningitis, or bacteremia caused by *Streptococcus pneumoniae*.

Embodiment 37. In some further embodiments of embodiment 34 or embodiment 35, the disease is meningitis, pneumonia, epiglottitis, cellulitis, arthritis, or ear infection caused by *Haemophilus influenzae* type b.

Embodiment 38. In some further embodiments of embodiment 34 or embodiment 35, the disease is meningitis or meningococcemia caused by *Neisseria meningitidis*.

Embodiment 39. In some further embodiments according to any one of embodiments 34-38, the individual has poor immune response to the polysaccharide antigen.

Embodiment 40. In some further embodiments according to any one of embodiments 34-39, the individual is a child below about 2 years of age, an elderly, or an immunocompromised individual.

Embodiment 41. In some embodiments, there is provided use of any one of the immunogenic compositions according to embodiments 24-32 or the vaccine according to embodiment 33 in the manufacture of a medicament for the treatment or prevention of a disease caused by a bacterium, wherein the polysaccharide antigen is a polysaccharide expressed on the surface of the bacterium or a derivative thereof.

Embodiment 42. In some embodiments, there is provided a method of preparing any one of the polysaccharide-protein conjugates of embodiments 1-23, comprising conjugating the polysaccharide antigen to the chimeric carrier protein.

Embodiment 43. In some further embodiments of embodiment 42, the polysaccharide antigen is prepared by culturing a bacterium comprising the polysaccharide antigen, and recovering the polysaccharide antigen from the culture.

Embodiment 44. In some further embodiments of embodiment 42 or embodiment 43, the method further comprises preparing the polysaccharide antigen prior to conjugating the polysaccharide antigen to the chimeric carrier protein.

Embodiment 45. In some further embodiments according to any one of embodiments 42-44, the chimeric carrier protein is prepared by culturing a host cell transformed with a vector comprising the nucleic acid sequence encoding the chimeric carrier protein under conditions allowing the expression of the chimeric carrier protein, and recovering the expressed chimeric carrier protein from the culture.

Embodiment 46. In some further embodiments of embodiment 45, the host cell is *Escherichia coli* or yeast.

Embodiment 47. In some further embodiments of embodiment 45 or embodiment 46, the vector comprises the nucleic acid sequence of any one selected from the group consisting of SEQ ID NOs: 34-38.

Embodiment 48. In some further embodiments of embodiment 45 or embodiment 46, the vector comprises the nucleic acid sequence of any one selected from the group consisting of SEQ ID NOs: 46-50.

Embodiment 49. In some further embodiments of embodiment 45 or embodiment 46, the vector comprises the nucleic acid sequence of any one selected from the group consisting of SEQ ID NOs: 58-63.

Embodiment 50. In some further embodiments according to any one of embodiments 42-49, the method further comprises preparing the chimeric carrier protein prior to conjugating the polysaccharide antigen to the chimeric carrier protein.

Embodiment 51. In some further embodiments according to any one of embodiments 42-50, the polysaccharide antigen is conjugated to the chimeric carrier protein by reductive amination, cyanylation conjugation, or a carbodiimide reaction.

Embodiment 52. In some further embodiments of embodiment 51, the polysaccharide antigen is activated by 1-cyano-4-dimethylammoniumpyridinium tetrafluoroborate (CDAP).

Embodiment 53. In some further embodiments of embodiment 51, the polysaccharide antigen is conjugated to the chimeric carrier protein through an adipic acid dihydrazide (ADH) linker.

Embodiment 54. In some further embodiments according to any one of embodiments 42-53, the method further comprises isolating the conjugated chimeric carrier protein and polysaccharide antigen to obtain the polysaccharide-protein conjugate.

EXAMPLES

The examples, which are intended to be purely exemplary of the invention and should therefore not be considered to limit the invention in any way, also describe and detail aspects and embodiments of the invention discussed above. The examples are not intended to represent that the experiments below are all or the only experiments performed. Efforts have been made to ensure accuracy with respect to numbers used (for example, amounts, temperature, etc.), but some experimental errors and deviations should be accounted for. Unless indicated otherwise, parts are parts by weight, molecular weight is average molecular weight, temperature is in degrees Centigrade, and pressure is at or near atmospheric.

The examples below provide a method for enhancing the immunogenicity of polysaccharide-protein conjugates by adding universal epitope(s) to the carrier protein in the conjugate. The chimeric carrier protein comprising the universal epitope is produced using recombinantly engineered bacteria. Then a polysaccharide is covalently conjugated to the chimeric carrier protein comprising the universal epitope. Upon entering the body of an animal, the polysaccharide-protein conjugate can be uptaken and degraded by Antigen Presenting Cells (APCs) to yield universal epitopes and fractions of repeating units of the polysaccharides, which can be bound and displayed by MHC class II molecules for effective T cell induction, leading to enhanced immunogenicity, and production of an increased titer of specific antibodies against bacterial capsular polysaccharides. Compared to a corresponding polysaccharide-protein conjugate without any universal epitopes, the exemplary polysaccharide-protein conjugates having universal epitopes in the carrier protein as described herein have enhanced immunogenicity of about 3-5 fold.

The technical strategy for the exemplary polysaccharide-protein conjugates described herein is as follows:

a) introduce universal epitope(s) to a carrier protein to make a chimeric carrier protein, and produce the chimeric carrier protein using genetically recombinant engineered bacteria;

b) covalently conjugate the chimeric carrier protein in a) having a universal epitope to a polysaccharide to obtain a polysaccharide-protein conjugate.

In some further embodiments, the chimeric carrier protein as described in these examples comprises X number of universal epitopes, wherein X is greater than or equal to 1.

In some further embodiments, the chimeric carrier protein as described in these examples comprises a universal epitope linked to the N-terminus, C-terminus, or simultaneously both the N-terminus and the C-terminus of the carrier protein.

In some further embodiments, the chimeric carrier protein as described in these examples comprises universal epitope linked to the N-terminus and/or C-terminus of the carrier protein via a GSGSG amino acid sequence.

In some further embodiments, the chimeric carrier protein as described in these examples comprises a universal epitope selected from QYIKANSKFIGITEL (referred to as P2 (SEQ ID NO:1)), FNNFTVSFWLRVPKVSASHLE (referred to as P30 (SEQ ID NO:2)), ISQAVHAAHAEINEAGR (referred to as OVAp (SEQ ID NO:3)), and any combinations thereof.

In some further embodiments, the chimeric carrier protein as described in these examples comprises a carrier protein selected from the mutant diphtheria toxin CRM197 chain A (referred to as CRM197A), rotavirus surface protein core VP8 (referred to as CoreVP8), and the mutant diphtheria toxin H21G chain A (referred to as H21G).

In some further embodiments, the genetically recombinant engineered bacteria described in these examples are genetically recombinant *E. coli*.

In some further embodiments, the polysaccharide as described in these examples are capsular polysaccharides prepared by culturing *Haemophilus influenzae* type b (Hib), *Streptococcus pneumoniae* (Pn), or *Neisseria meningitidis* (Men).

In some further embodiments, the method to covalently conjugate the polysaccharide to the chimeric carrier protein comprising the universal epitope as described in these examples is reductive amination, ADH method (using adipic acid dihydrazide), or CDAP method (using 3-(ethyliminomethyleneamino)-N,N-dimethyl-propan-1-amine).

Example 1: Preparation and Immunological Assessment of Polysaccharide-Protein Conjugates Comprising a Chimeric Carrier Protein Comprising CRM197A and a Universal Epitope Part 1. Design of the Amino Acid Sequences of Chimeric Carrier Proteins
1. Sequence Design of the CRM197 Immunogenic Carrier Protein Diphtheria toxin is a cytoplasmic polypeptide expressed by 0 phage carrying the diphtheria toxin gene in the bacteria *Corynebacterium diphtheriae*. The polypeptide has 560 amino acids, and a molecular weight of 62,000 Dalton. The amino acid sequence of wildtype diphtheria toxin is shown below in SEQ ID NO:64.

```
                                        (SEQ ID NO: 64)
MSRKLEASILIGALLGIGAPPSAHAGADDVVDSSKSFVMENFSSYHGTKP

GYVDSIQKGIQKPKSGTQGNYDDDWKGFYSTDNKYDAAGYSVDNENPLSG

KAGGVVKVTYPGLTKVLALKVDNAETIKKELGLSLTEPLMEQVGTEEFIK

REGDGASRVVLSLPFAEGSSSVEYINNWEQAKALSVELEINFETRGKRGQ

DAMYEYMAQACAGNRVRRSVGSSLSCINLDWDVIRDKTKTKIESLKEHGP

IKNKMSESPNKTVSEEKAKQYLEEFHQTALEHPELSELKTVTGTNPVFAG

ANYAAWAVNVAQVIDSETADNLEKTTAALSILPGIGSVMGIADGAVHHNT

EEIVAQSIALSSLMVAQAIPLVGELVDIGFAAYNFVESIINLFQVVHNSY

NRPAYSPGHKTQPFLHDGYAVSWNTVEDSIIRTGFQGESGHDIKITAENT

PLPIAGVILPTIPGKLDVNKSKTHISVNGRKIRMRCRAIDGDVTFCRPKS

PVYVGNGVHANLHVAFHRSSSEKIHSNEISSDSIGVLGYQKTVDHTKVNS

KLSLFFEIKS
```

The N-terminal 25-residue leader sequence is removed upon secretion of the polypeptide outside of the bacteria, resulting in a secreted single-chain polypeptide having 535 amino acids and a molecular weight of 58 kDa, with an amino acid sequence of SEQ ID No:65 shown below.

```
                                        (SEQ ID NO: 65)
GADDVVDSSKSFVMENFSSYHGTKPGYVDSIQKGIQKFKSGTQGNYDDDW

KGFYSTDNKYDAAGYSVDNENPLSGKAGGVVKVTYPGLTKVLALKVDNAE

TIKKELGLSLTEPLMEQVGTEEFIKRFGDGASRVVLSLPFAEGSSSVEYI

NNWEQAKALSVELEINFETRGKRGQDAMYEYMAQACAGNRVRRSVGSSLS

CINLDWDVIRDKTKTKIESLKEHGPIKNKMSESPNKTVSEEKAKQYLEEF

HQTALEHPELSELKTVTGTNPVFAGANYAAWAVNVAQVIDSETADNLEKT

TAALSILPGIGSVMGIADGAVHHNTEEIVAQSIALSSLMVAQAIPLVGEL

-continued
VDIGFAAYNFVESIINLFQVVHNSYNRPAYSTGHKTQPFLHDGYAVSWNT

VEDSIIRTGFQGESGHDIKITAENTPLPIAGVLLPTIPGKLDVNKSKTHI

SVNGRKIRMRCRAIDGDVTFCRPKSPVYVGNGVHANLHVAFHRSSSEKIH

SNEISSDSIGVLGYQKTVDHTKVNSKLSLFFEIKS
```

The secreted diphtheria toxin is enzymatically cut into chain A and chain B, which are connected via a disulfide bond to form a single protein molecule. Each of the two polypeptide chains has a unique function. Chain A is the N-terminal fragment of the diphtheria toxin protein, having 193 amino acids and a molecular weight of 21 kDa. Chain A is the culprit for the toxicity of diphtheria toxin. In the cytoplasm of eukaryotic cells, Chain A covalently transfers an ADP-ribose moiety of NAD+ to Elongation Factor-2 (EF-2), thereby attenuating protein synthesis in the host cell, which leads to inhibition of cell growth and eventually results in cell death. Chain B is the C-terminal fragment of diphtheria toxin, having 342 amino acids and a molecular weight of 37 kDa. Chain B can recognize specific receptors on the surface of sensitive cells, which allows attachment of the diphtheria toxin to sensitive cells and facilitate entry of Chain A into the cells.

Chain A of diphtheria toxin has excellent solubility in water. Its amino acids is as shown below in SEQ ID NO:66.

```
                                        (SEQ ID NO: 66)
GADDVVDSSKSFVMENFSSYHGTKPGYVDSIQKGIQKPKSGTQGNYDDDW

KGFYSTDNKYDAAGYSVDNENPLSGKAGGVVKVTYPGLTKVLALKVDNAE

TIKKELGLSLTEPLMEQVGTEEFIKRFGDGASRVVLSLPFAEGSSSVEYI

NNWEQAKALSVELEINFETRGKRGQDAMYEYMAQACAGNRVRR
```

Research has shown that mutations in the tox gene encoding the diphtheria toxin in 0 phage have little effect on replication of the phage, but greatly reduce or eliminate toxicity of the expressed diphtheria toxin, which are known as Cross Reacting Material (CRM) (Giannini et al. (1984) "The amino-acid sequence of two non-toxic mutants of diphtheria toxin: CRM45 and CRM197." Nucleic Acid Research 12:4063-4069). The immunogenic properties of the CRM in the serum are still highly correlated with those of the wildtype toxin. In particular, the non-toxic mutant CRM197 has a Gly-Glu point mutation in amino acid 52, and its amino acid sequence is as shown below in SEQ ID NO: 4.

```
                                        (SEQ ID NO: 4)
GADDVVDSSKSFVMENFSSYHGTKPGYVDSIQKGIQKPKSGTQGNYDDDW

KEFYSTDNKYDAAGYSVDNENPLSGKAGGVVKVTYPGLTKVLALKVDNAE

TIKKELGLSLTEPLMEQVGTEEFIKRFGDGASRVVLSLPFAEGSSSVEYI

NNWEQAKALSVELEINFETRGKRGQDAMYEYMAQACAGNRVRR
```

In comparison with other carrier proteins on the market used for vaccines against *Streptococcus pneumonia*, CRM197 Chain A (referred to as CRM197A hereafter) has the following advantages. The immunogenicitic properties of CRM197A and the full length wildtype diphtheria toxin are highly correlated. Having a small molecular weight and high water solubility, CRM197A is easy to produce and to be used in chemical reactions for preparation of high molecular-weight molecules. Long-term clinical applications of vaccines based on diphtheria toxin have proven the safety and efficacy of such vaccines.

Here, recombinantly expressed CRM197A protein was used as a carrier protein in the production of polysaccharide-protein conjugates. CRM197A was covalently linked to capsular polysaccharides (CP) of *Streptococcus pneumoniae* (Pn) to prepare Pn PS-CRM197A conjugates. CRM197A was covalently linked to capsular polysaccharides (CP) of *Haemophila influenzae* type b (Hib) to prepare Hib PS-CRM197A conjugates. CRM197A was covalently linked to capsular polysaccharides (CP) of *Neisseria meningitidis* (Men) to prepare Men CP-CRM197A conjugates. Each of the conjugates was further prepared into a vaccine composition to serve as a control for investigation of immunogenicity of the corresponding conjugates having the same CP but a chimeric carrier protein compring CRM197A and one or more universal epitopes.

2. Sequence Design of Chimeric Carrier Proteins

Universal epitopes were fused to the CRM197A immunogenic carrier protein to construct a new chimeric carrier protein useful for preparation of polysaccharide-protein conjugates. The universal epitope P2, P30 or OVAp was each fused individually to the N-terminus or the C-terminus of the CRM197A carrier protein. Alternatively, each of a combination of two different types of universal epitopes was fused respectively to the N-terminus or the C-terminus of the CRM197A carrier protein. In a third strategy, two copies of the same universal epitope were fused to each other, and then fused to either the N-terminus or the C-terminus of the CRM197A carrier protein. A fourth strategy was to fuse a universal epitope to the C-termus or the N-terminus of the CRM197A carrier protein, and the remaining terminus of CRM197A was linked to two copies of the same or a different type of universal epitope, which were fused to each other.

2-1 Sequence Design of a Chimeric Carrier Protein Comprising P2 and CRM197A 2-1-1 Sequence Design of a P2-N-Terminus-CRM197A Chimeric Carrier Protein (P2CRM197A)

One copy of the amino acid sequence of P2 (SEQ ID NO:1) was fused to the N-terminus of the CRM197A carrier protein (SEQ ID NO:4) via a GSGSG linker (SEQ ID NO:7) disposed therebetween to obtain a new chimeric carrier protein named P2CRM197A. The amino acid sequence of the new chimeric carrier protein is shown below in SEQ ID NO:8. The sequence of the P2 epitope is underlined.

(SEQ ID NO: 8)
QYIKANSKFIGITELGSGSGGADDVVDSSKSFVMENFSSYHGTKPGYVDS

IQKGIQKPKSGTQGNYDDDWKEFYSTDNKYDAAGYSVDNENPLSGKAGGV

VKVTYPGLTKVLALKVDNAETIKKELGLSLTEPLMEQVGTEEFIKRFGDG

ASRVVLSLPFAEGSSSVEYINNWEQAKALSVELEINFETRGKRGQDAMYE

YMAQACAGNRVRR 2-1-2 Sequence Design of a CRM197A-C-Terminus-P2 Chimeric Carrier Protein (CRM197AP2)

One copy of the amino acid sequence of P2 (SEQ ID NO:1) was fused to the C-terminus of the CRM197A carrier protein (SEQ ID NO:4) via a GSGSG linker (SEQ ID NO:7) disposed therebetween to obtain a new chimeric carrier protein named CRM197AP2. The amino acid sequence of the new chimeric carrier protein is shown below in SEQ ID NO:9. The sequence of the P2 epitope is underlined.

(SEQ ID NO: 9)
MGADDVVDSSKSFVMENFSSYHGTKPGYVDSIQKGIQKPKSGTQGNYDDD

WKEFYSTDNKYDAAGYSVDNENPLSGKAGGVVKVTYPGLTKVLALKVDNA

ETIKKELGLSLTEPLMEQVGTEEFIKRFGDGASRVVLSLPFAEGSSSVEY

INNWEQAKALSVELEINFETRGKRGQDAMYEYMAQACAGNRVRRGSGSGQ

YIKANSKFIGITEL 2-1-3 Sequence Design of a P2-N-Terminus-CRM197A-C-Terminus-P2 Chimeric Carrier Protein (P2CRM197AP2)

One copy of the amino acid sequence of P2 (SEQ ID NO:1) was fused to the N-terminus and the C-terminus of the CRM197A carrier protein (SEQ ID NO:4) respectively, each via a GSGSG linker (SEQ ID NO:7) disposed therebetween to obtain a new chimeric carrier protein named P2CRM197AP2. The amino acid sequence of the new chimeric carrier protein is shown below in SEQ ID NO:10. The sequence of the P2 epitope is underlined.

(SEQ ID NO: 10)
QYIKANSKFIGITELGSGSGGADDVVDSSKSFVMENFSSYHGTKPGYVDS

IQKGIQKPKSGTQGNYDDDWKEFYSTDNKYDAAGYSVDNENPLSGKAGGV

VKVTYPGLTKVLALKVDNAETIKKELGLSLTEPLMEQVGTEEFIKRFGDG

ASRVVLSLPFAEGSSSVEYINNWEQAKALSVELEINFETRGKRGQDAMYE

YMAQACAGNRVRRGSGSGQYIKANSKFIGITEL 2-1-4 Sequence Design of a P2P2-N-Terminus-CRM197A Chimeric Carrier Protein (P2P2CRM197A)

Two copies of the amino acid sequence of P2 (SEQ ID NO:1) were fused to each other via a GSGSG linker (SEQ ID NO:7) disposed therebetween, and the fused sequence was then fused to the N-terminus of the CRM197A carrier protein (SEQ ID NO:4) via a GSGSG linker (SEQ ID NO:7) disposed therebetween to obtain a new chimeric carrier protein named P2P2CRM197A. The amino acid sequence of the new chimeric carrier protein is shown below in SEQ ID NO:11. The sequence of the P2 epitope is underlined.

(SEQ ID NO: 11)
QYIKANSKFIGITELGSGSGQYIKANSKFIGITELGSGSGGADDVVDSSK

SFVMENFSSYHGTKPGYVDSIQKGIQKPKSGTQGNYDDDWKEFYSTDNKY

DAAGYSVDNENPLSGKAGGVVKVTYPGLTKVLALKVDNAETIKKELGLSL

TEPLMEQVGTEEFIKRFGDGASRVVLSLPFAEGSSSVEYINNWEQAKALS

VELEINFETRGKRGQDAMYEYMAQACAGNRVRR 2-1-5 Sequence Design of a CRM197A-C-Terminus-P2P2 Chimeric Carrier Protein (CRM197AP2P2)

Two copies of the amino acid sequence of P2 (SEQ ID NO:1) were fused to each other via a GSGSG linker (SEQ ID NO:7) disposed therebetween, and the fused sequence was then fused to the N-terminus of the CRM197A carrier protein (SEQ ID NO:4) via a GSGSG linker (SEQ ID NO:7) disposed therebetween, to obtain a new chimeric carrier protein named P2P2CRM197A. The amino acid sequence of the new chimeric carrier protein is shown below in SEQ ID NO:12. The sequence of the P2 epitope is underlined.

(SEQ ID NO: 12)
GADDVVDSSKSFVMENFSSYHGTKPGYVDSIQKGIQKPKSGTQGNYDDDW

KEFYSTDNKYDAAGYSVDNENPLSGKAGGVVKVTYPGLTKVLALKVDNAE

TIKKELGLSLTEPLMEQVGTEEFIKRFGDGASRVVLSLPFAEGSSSVEYI

NNWEQAKALSVELEINFETRGKRGQDAMYEYMAQACAGNRVRRGSGSGQY

IKANSKFIGITELGSGSGQYIKANSKFIGITEL 2-1-6 Sequence Design of a P2P2-N-Terminus-CRM197A-C-Terminus-P2 Chimeric Carrier Protein (P2P2CRM197AP2)

Two copies of the amino acid sequence of P2 (SEQ ID NO:1) were fused to each other via a GSGSG linker (SEQ ID NO:7) disposed therebetween, and the fused sequence was then fused to the N-terminus of the CRM197A carrier protein (SEQ ID NO:4) via a GSGSG linker (SEQ ID NO:7) disposed therebetween; additionally, one copy of the amino acid sequence of P2 (SEQ ID NO:1) was fused to the C-terminus of the CRM197A carrier protein (SEQ ID NO:4) via a GSGSG linker (SEQ ID NO:7) disposed therebetween, to obtain a new chimeric carrier protein named P2P2CRM197AP2. The amino acid sequence of the new chimeric carrier protein is shown below in SEQ ID NO:13. The sequence of the P2 epitope is underlined.

(SEQ ID NO: 13)

QYIKANSKFIGITELGSGSGQYIKANSKFIGITELGSGSGGADDVVDSSK

SFVMENFSSYHGTKPGYVDSIQKGIQKPKSGTQGNYDDDWKEFYSTDNKY

DAAGYSVDNENPLSGKAGGVVKVTYPGLTKVLALKVDNAETIKKELGLSL

TEPLMEQVGTEEFIKRFGDGASRVVLSLPFAEGSSSVEYINNWEQAKALS

VELEINFETRGKRGQDAMYEYMAQACAGNRVRRGSGSGQYIKANSKFIGI

TEL 2-1-7 Sequence Design of a P2-N-Terminus-CRM197A-C-Terminus-P2P2 Chimeric Carrier Protein (P2CRM197AP2P2)

One copy of the amino acid sequence of P2 (SEQ ID NO:1) was fused to the N-terminus of the CRM197A carrier protein (SEQ ID NO:4) via a GSGSG linker (SEQ ID NO:7) disposed therebetween; additionally, two copies of the amino acid sequence of P2 (SEQ ID NO:1) were fused to each other via a GSGSG linker (SEQ ID NO:7) disposed therebetween, and the fused sequence was then fused to the C-terminus of the CRM197A carrier protein (SEQ ID NO:4) via a GSGSG linker (SEQ ID NO:7) disposed therebetween, to obtain a new chimeric carrier protein named P2CRM197AP2P2. The amino acid sequence of the new chimeric carrier protein is shown below in SEQ ID NO:14. The sequence of the P2 epitope is underlined.

(SEQ ID NO: 14)

QYIKANSKFIGITELGSGSGGADDVVDSSKSFVMENFSSYHGTKPGYVDS

IQKGIQKPKSGTQGNYDDDWKEFYSTDNKYDAAGYSVDNENPLSGKAGGV

VKVTYPGLTKVLALKVDNAETIKKELGLSLTEPLMEQVGTEEFIKRFGDG

ASRVVLSLPFAEGSSSVEYINNWEQAKALSVELEINFETRGKRGQDAMYE

YMAQACAGNRVRRGSGSGQYIKANSKFIGITELGSGSGQYIKANSKFIGI

TEL 2-2 Sequence Design of a Chimeric Carrier Protein Comprising P30 and CRAf197A 2-2-1 Sequence Design of a P30-N-Terminus-CRM197A Chimeric Carrier Protein (P30CRM197A)

One copy of the amino acid sequence of P30 (SEQ ID NO:2) was fused to the N-terminus of the CRM197A carrier protein (SEQ ID NO:4) via a GSGSG linker (SEQ ID NO:7) disposed therebetween, to obtain a new chimeric carrier protein named P30CRM197A. The amino acid sequence of the new chimeric carrier protein is shown below in SEQ ID NO:15. The sequence of the P30 epitope is underlined.

(SEQ ID NO: 15)

FNNFTVSFWLRVPKVSASHLEGSGSGGADDVVDSSKSFVMENFSSYHGTK

PGYVDSIQKGIQKPKSGTQGNYDDDWKEFYSTDNKYDAAGYSVDNENPLS

GKAGGVVKVTYPGLTKVLALKVDNAETIKKELGLSLTEPLMEQVGTEEFI

KRFGDGASRVVLSLPFAEGSSSVEYINNWEQAKALSVELEINFETRGKRG

QDAMYEYMAQACAGNRVRR 2-2-2 Sequence Design of a CRM197A-C-Terminus-P30 Chimeric Carrier Protein (CRM197AP30)

One copy of the amino acid sequence of P30 (SEQ ID NO:2) was fused to the C-terminus of the CRM197A carrier protein (SEQ ID NO:4) via a GSGSG linker (SEQ ID NO:7) disposed therebetween, to obtain a new chimeric carrier protein named CRM197AP30. The amino acid sequence of the new chimeric carrier protein is shown below in SEQ ID NO:16. The sequence of the P30 epitope is underlined.

(SEQ ID NO: 16)

MGADDVVDSSKSFVMENFSSYHGTKPGYVDSIQKGIQKPKSGTQGNYDDD

WKEFYSTDNKYDAAGYSVDNENPLSGKAGGVVKVTYPGLTKVLALKVDNA

ETIKKELGLSLTEPLMEQVGTEEFIKRFGDGASRVVLSLPFAEGSSSVEY

INNWEQAKALSVELEINFETRGKRGQDAMYEYMAQACARNRVRRGSGSGF

NNFTVSFWLRVPKVSASHLE 2-2-3 Sequence Design of a P30-N-Terminus-CRM197A-C-Terminus-P30 Chimeric Carrier Protein (P30CRM197AP30)

One copy of the amino acid sequence of P30 (SEQ ID NO:2) was fused to the N-terminus and the C-terminus of the CRM197A carrier protein (SEQ ID NO:4) respectively, each via a GSGSG linker (SEQ ID NO:7) disposed therebetween, to obtain a new chimeric carrier protein named P30CRM197AP30. The amino acid sequence of the new chimeric carrier protein is shown below in SEQ ID NO:17. The sequence of the P30 epitope is underlined.

(SEQ ID NO: 17)

FNNFTVSFWLRVPKVSASHLEGSGSGGADDVVDSSKSFVMENFSSYHGTK

PGYVDSIQKGIQKPKSGTQGNYDDDWKEFYSTDNKYDAAGYSVDNENPLS

GKAGGVVKVTYPGLTKVLALKVDNAETIKKELGLSLTEPLMEQVGTEEFI

KRFGDGASRVVLSLPFAEGSSSVEYINNWEQAKALSVELEINFETRGKRG

QDAMYEYMAQACAGNRVRRGSGSGFNNFTVSFWLRVPKVSASHLE 2-2-4 Sequence design of a P30P30-N-terminus—CRM197A chimeric carrier protein (P30P30CRM197A)

Two copies of the amino acid sequence of P30 (SEQ ID NO:2) were fused to each other via a GSGSG linker (SEQ ID NO:7) disposed therebetween, and the fused sequence was then fused to the N-terminus of the CRM197A carrier protein (SEQ ID NO:4), via a GSGSG linker (SEQ ID NO:7) disposed therebetween, to obtain a new chimeric carrier protein named P30P30CRM197A. The amino acid sequence of the new chimeric carrier protein is shown below in SEQ ID NO:18. The sequence of the P30 epitope is underlined.

(SEQ ID NO: 18)
FNNFTVSFWKRVPKVSASHLEGSGSGFNNFTVSFWLRVPKVSASHLEGSG

SGGADDVVDSSKSFVMENFSSYHGTKPGYVDSIQKGIQKPKSGTQGNYDD

DWKEFYSTDNKYDAAGYSVDNENPLSGKAGGVVKVTYPGLTKVLALKVDN

AETIKKELGLSLTEPLMEQVGTEEFIKRFGDGASRVVLSLPFAEGSSSVE

YINNWEQAKALSVELEINFETRGKRGQDAMYEYMAQACAGNRVRR 2-2-5 Sequence Design of a CRM197A-C-Terminus—P30P30 Chimeric Carrier Protein (CRM197A P30P30)

Two copies of the amino acid sequence of P30 (SEQ ID NO:2) were fused to each other via a GSGSG linker (SEQ ID NO:7) disposed therebetween, and the fused sequence was then fused to the C-terminus of the CRM197A carrier protein (SEQ ID NO:4), via a GSGSG linker (SEQ ID NO:7) disposed therebetween, to obtain a new chimeric carrier protein named CRM197AP30P30. The amino acid sequence of the new chimeric carrier protein is shown below in SEQ ID NO:19. The sequence of the P30 epitope is underlined.

(SEQ ID NO: 19)
GADDVVDSSKSFVMENFSSYHGTKPGYVDSIQKGIQKPKSGTQGNYDDDW

KEFYSTDNKYDAAGYSVDNENPLSGKAGGVVKVTYPGLTKVLALKVDNAE

TIKKELGLSLTEPLMEQVGTEEFIKRFGDGASRVVLSLPFAEGSSSVEYI

NNWEQAKALSVELEINFETRGKRGQDAMYEYMAQACAGNRVRRGSGSGFN

NFTVSFWLRVPKVSASHLEGSGSGFNNFTVSFWLRVPKVSASHLE 2-2-6 Sequence Design of a P30P30-N-Terminus-CRM197A-C-Terminus—P30 Chimeric Carrier Protein (P30P30CRM197AP30)

Two copies of the amino acid sequence of P30 (SEQ ID NO:2) were fused to each other via a GSGSG linker (SEQ ID NO:7) disposed therebetween, and the fused sequence was then fused to the N-terminus of the CRM197A carrier protein (SEQ ID NO:4), via a GSGSG linker (SEQ ID NO:7) disposed therebetween; additionally, one copy of P30 (SEQ ID NO:2) was fused to the C-terminus of the CRM197A carrier protein (SEQ ID NO:4), via a GSGSG linker (SEQ ID NO:7) disposed therebetween, to obtain a new chimeric carrier protein named P30P30CRM197AP30. The amino acid sequence of the new chimeric carrier protein is shown below in SEQ ID NO:20. The sequence of the P30 epitope is underlined.

(SEQ ID NO: 20)
FNNFTVSFWLRVPKVSASHLEGSGSGFNNFTVSFWLRVPKVSASHLEGSG

SGGADDVVDSSKSFVMENFSSYHGTKPGYVDSIQKGIQKPKSGTQGNYDD

DWKEFYSTDNKYDAAGYSVDNENPLSGKAGGVVKVTYPGLTKVLALKVDN

AETIKKELGLSLTEPLMEQVGTEEFIKRFGDGASRVVLSLPFAEGSSSVE

YINNWEQAKALSVELEINFETRGKRGQDAMYEYMAQACAGNRVRRGSGSG

FNNFTVSFWLRVPKVSASHLE 2-2-7 Sequence Design of a P30-N-Terminus-CRM197A-C-Terminus-P30 P30 Chimeric Carrier Protein (P30CRM197AP30P30)

One copy of the amino acid sequence of P30 (SEQ ID NO:2) was fused to the N-terminus of the CRM197A carrier protein (SEQ ID NO:4), via a GSGSG linker (SEQ ID NO:7) disposed therebetween; additionally, two copies of the amino acid sequence of P30 (SEQ ID NO:2) were fused to each other via a GSGSG linker (SEQ ID NO:7) disposed therebetween, and the fused sequence was then fused to the C-terminus of the CRM197A carrier protein (SEQ ID NO:4), via a GSGSG linker (SEQ ID NO:7) disposed therebetween, to obtain a new chimeric carrier protein named P30CRM197AP30P30. The amino acid sequence of the new chimeric carrier protein is shown below in SEQ ID NO:21. The sequence of the P30 epitope is underlined.

(SEQ ID NO: 21)
FNNFTVSFWLRVPKVSASHLEGSGSGGADDVVDSSKSFVMENFSSYHGTK

PGYVDSIQKGIQKPKSGTQGNYDDDWKEFYSTDNKYDAAGYSVDNENPLS

GKAGGVVKVTYPGLTKVLALKVDNAETIKKELGLSLTEPLMEQVGTEEFI

KRFGDGASRVVLSLPFAEGSSSVEYINNWEQAKALSVELEINFETRGKRG

QDAMYEYMAQACAGNRVRRGSGSGFNNFTVSFWLRVPKVSASHLEGSGSG

FNNFTVSFWLRVPKVSHSHLE 2-3 Sequence Design of a Chimeric Carrier Protein Comprising OVAp and CRM197A 2-3-1 Sequence Design of an OVAp-N-Terminus-CRM197A Chimeric Carrier Protein (OVApCRM197A)

One copy of the amino acid sequence of OVAp (SEQ ID NO:3) was fused to the N-terminus of the CRM197A carrier protein (SEQ ID NO:4) via a GSGSG linker (SEQ ID NO:7) disposed therebetween, to obtain a new chimeric carrier protein named OVApCRM197A. The amino acid sequence of the new chimeric carrier protein is shown below in SEQ ID NO:22. The sequence of the OVAp epitope is underlined.

(SEQ ID NO: 22)
ISQAVHAAHAEINEAGRGSGSGGADDVVDSSKSFVMENFSSYHGTKPGYV

DSIQKGIQKPKSGTQGNYDDDWKEFYSTDNKYDAAGYSVDNENPLSGKAG

GVVKVTYPGLTKVLALKVDNAETIKKELGLSLTEPLMEQVGTEEFIKRFG

DGASRVVLSLPFAEGSSSVEYINNWEQAKALSVELEINFETRGKRGQDAM

YEYMAQACAGNRVRR 2-3-2 Sequence Design of a CRM197A-C-Terminus-OVAp Chimeric Carrier Protein (CRM197AOVAp)

One copy of the amino acid sequence of OVAp (SEQ ID NO:3) was fused to the C-terminus of the CRM197A carrier protein (SEQ ID NO:4) via a GSGSG linker (SEQ ID NO:7) disposed therebetween, to obtain a new chimeric carrier protein named CRM197AOVAp. The amino acid sequence of the new chimeric carrier protein is shown below in SEQ ID NO:23. The sequence of the OVAp epitope is underlined.

```
                                                (SEQ ID NO: 23)
MGADDVVDSSKSFVMENFSSYHGTKPGYVDSIQKGIQKPKSGTQGNYDDD

WKEFYSTDNKYDAAGYSVDNENPLSGKAGGVVKVTYPGLTKVLALKVDNA

ETIKKELGLSLTEPLMEQVGTEEFIKRFGDGASRVVLSLPFAEGSSSVEY

INNWEQAKALSVELEINFETRGKRGQDAMYEYMAQACAGNRVRRGSGSGI

SQAVHAAHAEINEAGR
```

2-3-3 Sequence Design of an OVAp-N-Terminus-CRM197A-C-Terminus-OVAp Chimeric Carrier Protein (OVApCRM197AOVAp)

One copy of the amino acid sequence of OVAp (SEQ ID NO:3) was fused to the N-terminus and the C-terminus of the CRM197A carrier protein (SEQ ID NO:4) respectively, each via a GSGSG linker (SEQ ID NO:7) disposed therebetween, to obtain a new chimeric carrier protein named OVApCRM197AOVAp. The amino acid sequence of the new chimeric carrier protein is shown below in SEQ ID NO:24. The sequence of the OVAp epitope is underlined.

```
                                                (SEQ ID NO: 24)
ISQAVHAAHAEINEAGRGSGSGGADDVVDSSKSFVMENFSSYHGTKPGYV

DSIQKGIQKPKSGTQGNYDDDWKEFYSTDNKYDAAGYSVDNENPLSGKAG

GVVKVTYPGLTKVLALKVDNAETIKKELGLSLTEPLMEQVGTEEFIKRFG

DGASRVVLSLPFAEGSSSVEYINNWEQAKALSVELEINFETRGKRGQDAM

YEYMAQACAGNRVRRGSGSGISQAVHAAHAEINEAGR
```

2-3-4 Sequence Design of an OVApOVAp-N-Terminus-CRM197A Chimeric Carrier Protein (OVApOVApCRM197A)

Two copies of the amino acid sequence of OVAp (SEQ ID NO:3) were fused to each other via a GSGSG linker (SEQ ID NO:7) disposed therebetween, and the fused sequence was then fused to the N-terminus of the CRM197A carrier protein (SEQ ID NO:4) via a GSGSG linker (SEQ ID NO:7) disposed therebetween, to obtain a new chimeric carrier protein named OVApOVApCRM197A. The amino acid sequence of the new chimeric carrier protein is shown below in SEQ ID NO:25. The sequence of the OVAp epitope is underlined.

```
                                                (SEQ ID NO: 25)
ISQAVHAAHAEINEAGRGSGSGISQAVHAAHAEINEAGRGSGSGGADDVV

DSSKSFVMENFSSYHGTKPGYVDSIQKGIQKPKSGTQGNYDDDWKEFYST

DNKYDAAGYSVDNENPLSGKAGGVVKVTYPGLTKVLALKVDNAETIKKEL

GLSLTEPLMEQVGTEEFIKRFGDGASRVVLSLPFAEGSSSVEYINNEEQA

KALSVELEINFETRGKRGQDAMYEYMAQACAGNRVRR
```

2-3-5 Sequence Design of a CRM197A-C-Terminus-OVApOVAp Chimeric Carrier Protein (CRM197AOVApOVAp)

Two copies of the amino acid sequence of OVAp (SEQ ID NO:3) were fused to each other via a GSGSG linker (SEQ ID NO:7) disposed therebetween, and the fused sequence was then fused to the C-terminus of the CRM197A carrier protein (SEQ ID NO:4) via a GSGSG linker (SEQ ID NO:7) disposed therebetween, to obtain a new chimeric carrier protein named CRM197AOVApOVAp. The amino acid sequence of the new chimeric carrier protein is shown below in SEQ ID NO:26. The sequence of the OVAp epitope is underlined.

```
                                                (SEQ ID NO: 26)
GADDVDDSSKSFVMENFSSYGHTKPGYVDSIQKGIQKPKSGTQGNYDDD

WKEFYSTDNKYDAAGYSVDNENPLSGKAGGVVKVTYPGLTKVLALKVDN

AETIKKELGLSLTEPLMEQVGTEEFIKRFGDGASRVVLSLPFAEGSSSV

EYINNWEQAKALSVELEINFETRGKRGQDAMYEYMAQACAGNRVRRGSG

SGISQAVHAAHAEINEAGRGSGSGISQAVHAAHAEINEAGR
```

2-3-6 Sequence Design of an OVApOVAp-N-Terminus-CRM197A-C-Terminus-OVAp Chimeric Carrier Protein (OVApOVApCRM197AOVAp)

Two copies of the amino acid sequence of OVAp (SEQ ID NO:3) were fused to each other via a GSGSG linker (SEQ ID NO:7) disposed therebetween, and the fused sequence was then fused to the N-terminus of the CRM197A carrier protein (SEQ ID NO:4) via a GSGSG linker (SEQ ID NO:7) disposed therebetween; additionally, one copy of the amino acid sequence of OVAp was fused to the C-terminus of the CRM197A carrier protein (SEQ ID NO:4) via a GSGSG linker (SEQ ID NO:7) disposed therebetween, to obtain a new chimeric carrier protein named OVApOVApCRM197AOVAp. The amino acid sequence of the new chimeric carrier protein is shown below in SEQ ID NO:27. The sequence of the OVAp epitope is underlined.

```
                                                (SEQ ID NO: 27)
ISQAVHAAHAEINEAGRGSGSGISQAVHAAHAEINEAGRGSGSGGADDVV

DSSKSFVMENFSSYHGTKPGYVDSIQKGIQKPKSGTQGNYDDDWKEFYST

DNKYDAAGYSVDNENPLSGKAGGVVKVTYPGLTKVLALKVDNAETIKKEL

GLSLTEPLMEQVGTEEFIKRFGDGASRVVLSLPFAEGSSSVEYINNEEQA

KALSVELEINFETRGKRGQDAMYEYMAQACAGNRVRRGSGSGISQAVHAA

HAEINEAGR
```

2-3-7 Sequence Design of an OVAp-N-Terminus-CRM197A-C-Terminus-OVApOVAp Chimeric Carrier Protein (OVApCRM197AOVApOVAp)

One copy of the amino acid sequence of OVAp (SEQ ID NO:3) was fused to the N-terminus of the CRM197A carrier protein (SEQ ID NO:4) via a GSGSG linker (SEQ ID NO:7) disposed therebetween; additionally, two copies of the amino acid sequence of OVAp (SEQ ID NO:3) were fused to each other via a GSGSG linker (SEQ ID NO:7) disposed therebetween, and the fused sequence was then fused to the C-terminus of the CRM197A carrier protein (SEQ ID NO:4) via a GSGSG linker (SEQ ID NO:7) disposed therebetween, to obtain a new chimeric carrier protein named OVApCRM197AOVApOVAp. The amino acid sequence of the new chimeric carrier protein is shown below in SEQ ID NO:28. The sequence of the OVAp epitope is underlined.

```
                                                (SEQ ID NO: 28)
ISQAVHAAHAEINEAGRGSGSGGADDVVDSSKSFVMENFSSYHGTKPGYV

DSIQKGIQKPKSGTQGNYDDDWKEFYSTDNKYDAAGYSVDNENPLSGKAG

GVVKVTYPGLTKVLALKVDNAETIKKELGLSLTEPLMEQVGTEEFIKRFG

DGASRVVLSLPFAEGSSSVEYINNWEQAKALSVELEINFETRGKRGQDAM

YEYMAQACAGNRVRRGSGSGISQAVHAAHAEINEAGRGSGSGISQAVHAA

HAEINEAGR
```

2-4 Sequence Design of a Chimeric Carrier Protein Comprising at Least Two Different Types of Universal Epitopes Combinations of three different universal epitopes, P2, P30 and OVAp were fused to the CRM197A carrier protein respectively to sequence design new chimeric carrier proteins.

2-4-1 Sequence Design of a P2-N-Terminus-CRM197A-C-Terminus-P30 Chimeric Carrier Protein (P2CRM197AP30)

One copy of the amino acid sequence of P2 (SEQ ID NO:1) was fused to the N-terminus of the CRM197A carrier protein (SEQ ID NO:4) via a GSGSG linker (SEQ ID NO:7) disposed therebetween, and one copy of the amino acid sequence of P30 (SEQ ID NO:2) was fused to the C-terminus of the CRM197A carrier protein (SEQ ID NO:4) via a GSGSG linker (SEQ ID NO:7) disposed therebetween, to obtain a new chimeric carrier protein named P2CRM197AP30. The amino acid sequence of the new chimeric carrier protein is shown below in SEQ ID NO:29. The sequences of the P2 and P30 epitopes are underlined.

(SEQ ID NO: 29)
QYIKANSKFIGITELGSGSGGADDVVDSSKSFVMENFSSYHGTKPGYVDS

IQKGIQKPKSGTQGNYDDDWKEFYSTDNKYDAAGYSVDNENPLSGKAGGV

VKVTYPGLTKVLALKVDNAETIKKELGLSLTEPLMEQVGTEEFIKRFGDG

ASRVVLSLPFAEGSSSVEYINNWEQAKALSVELEINFETRGKRGQDAMYE

YMAQACAGNRVRRGSGSGFNNFTVSFWLRVPKVSASHLE 2-4-2 Sequence Design of a P30-N-Terminus-CRM197A-C-Terminus-P2 Chimeric Carrier Protein (P30CRM197AP2)

One copy of the amino acid sequence of P30 (SEQ ID NO:2) was fused to the N-terminus of the CRM197A carrier protein (SEQ ID NO:4) via a GSGSG linker (SEQ ID NO:7) disposed therebetween, and one copy of the amino acid sequence of P2 (SEQ ID NO:1) was fused to the C-terminus of the CRM197A carrier protein (SEQ ID NO:4) via a GSGSG linker (SEQ ID NO:7) disposed therebetween, to obtain a new chimeric carrier protein named P30CRM197AP2. The amino acid sequence of the new chimeric carrier protein is shown below in SEQ ID NO:30. The sequences of the P2 and P30 epitopes are underlined.

(SEQ ID NO: 30)
FNNFTVSFWLRVPKVSASHLEGSGSGGADDVVDSSKSFVMENFSSYHGTK

PGYVDSIQKGIQKPKSGTQGNYDDDWKEFYSTDNKYDAAGYSVDNENPLS

GKAGGVVKVTYPGLTKVLALKVDNAETIKKELGLSLTEPLMEQVGTEEFI

KRFGDGASRVVLSLPFAEGSSSVEYINNWEQAKALSVELEINFETRGKRG

QDAMYEYMAQACAGNRVRRGSGSGQYIKANSKFIGITEL 2-4-3 Sequence Design of a P2P30-N-Terminus-CRM197A-C-Terminus-P2 Chimeric Carrier Protein (P30CRM197AP2)

One copy of the amino acid sequence of P2 (SEQ ID NO:1) and one copy of the amino acid sequence of P30 (SEQ ID NO:2) were fused to each other via a GSGSG linker (SEQ ID NO:7) disposed therebetween, the fused sequence was then fused to the N-terminus of the CRM197A carrier protein (SEQ ID NO:4) via a GSGSG linker (SEQ ID NO:7) disposed therebetween; additionally, and one copy of the amino acid sequence of P2 (SEQ ID NO:1) was fused to the C-terminus of the CRM197A carrier protein (SEQ ID NO:4) via a GSGSG linker (SEQ ID NO:7) disposed therebetween, to obtain a new chimeric carrier protein named P2P30CRM197AP2. The amino acid sequence of the new chimeric carrier protein is shown below in SEQ ID NO:31. The sequences of the P2, P30, and OVAp epitopes are underlined.

(SEQ ID NO: 31)
QYIKANSKFIGITELGSGSGFNNFTVSFWLRVPKVSASHLEGSGSGGADD

VVDSSKSFVMENFSSYHGTKPGYVDSIQKGIQKPKSGTQGNYDDDWKEFY

STDNKYDAAGYSVDNENPLSGKAGGVVKVTYPGLTKVLALKVDNAETIKK

ELGLSLTEPLMEQVGTEEFIKRFGDGASRVVLSLPFAEGSSSVEYINNWE

QAKALSVELEINFETRGKRGQDAMYEYMAQACAGNRVRRGSGSGQYIKAN

SKFIGITEL 2-4-4 Sequence Design of a P2P30-N-Terminus-CRM197A-C-Terminus-OVAp Chimeric Carrier Protein (P2P30CRM197AOVAp)

One copy of the amino acid sequence of P2 (SEQ ID NO:1) and one copy of the amino acid sequence of P30 (SEQ ID NO:2) were fused to each other via a GSGSG linker (SEQ ID NO:7) disposed therebetween, the fused sequence was then fused to the N-terminus of the CRM197A carrier protein (SEQ ID NO:4) via a GSGSG linker (SEQ ID NO:7) disposed therebetween; additionally, and one copy of the amino acid sequence of OVAp (SEQ ID NO:3) was fused to the C-terminus of the CRM197A carrier protein (SEQ ID NO:4) via a GSGSG linker (SEQ ID NO:7) disposed therebetween, to obtain a new chimeric carrier protein named P2P30CRM197AOVAp. The amino acid sequence of the new chimeric carrier protein is shown below in SEQ ID NO:32. The sequences of the P2, P30, and OVAp epitopes are underlined.

(SEQ ID NO: 32)
QYIKANSKFIGITELGSGSGFNNFTVSFWLRVPKVSASHLEGSGSGGADD

VVDSSKSFVMENFSSYHGTKPGYVDSIQKGIQKPKSGTQGNYDDDWKEFY

STDNKYDAAGYSVDNENPLSGKAGGVVKVTYPGLTKVLALKVDNAETIKK

ELGLSLTEPLMEQVGTEEFIKRFGDGASRVVLSLPFAEGSSSVEYINNWE

QAKALSVELEINFETRGKRGQDAMYEYMAQACAGNRVRRGSGSGISQAVH

AAHAEINEAGR

II. Construction of Expression Plasmids for Chimeric Carrier Proteins Comprising CM197A Carrier Protein and Universal Epitope(s)

1. Construction of an Expression Plasmid of the CRM197A Carrier Protein

The amino acid sequence of the complete CRM197 protein, PRF: 224021, was obtained from GenBank, and the sequence of the chain A fragment of CRM197 (hereafter referred to as CRM197A) was determined to be amino acids 1-193 of the CRM197 sequence. Based on the CRM197A sequence, the nucleic acid sequence encoding the CRM197A sequence was optimized to enable high-efficiency expression of the chain A fragment in *Escherichia coli*. A custom expression plasmid was used. Restriction enzyme Nde I was used to recognize sites having a CATATG sequence (SEQ ID NO:78), and restriction enzyme Bam HI was used to recognize sites having a GGATCC sequence (SEQ ID NO:79). The nucleic acid sequence of CRM197A was analyzed and no Nde I or Bam HI recognition sites were found in the CRM197A sequence. The synthesized nucleic acid sequence encoding the CRM197A protein is as shown below in SEQ ID NO:33.

```
                                          (SEQ ID NO: 33)
CATATG GGTGCGGACG ACGTTGTGGA CTCCTCAAA TCGTTTGTCA

TGGAAAACTT CAGCTCTTAT CATGGCACCA AACCGGGTTA

CGTGGACTCC ATTCAGAAGG GCATCCAAAA ACCGAAGTCA

GGCACCCAGG GTAACTACGA TGACGATTGG AAGGAATTCT

ACAGCACGGA CAATAAGTAT GATGCGGCCG GCTACTCTGT

TGACAACGAA AATCCGCTGA GTGGTAAAGC AGGCGGTGTG

GTTAAGGTCA CCTATCCGGG TCTGACGAAA GTTCTGGCGC

TGAAGGTCGA TAACGCCGAA ACCATTAAAA AGGAACTGGG

CCTGTCTCTG ACCGAACCGC TGATGGAACA AGTGGGTACG

GAAGAATTTA TCAAACGTTT CGGCGATGGT GCATCGCGTG

TCGTGCTGAG CCTGCCGTTT GCTGAAGGCA GTTCCTCAGT

GGAATACATT AACAATTGGG AACAAGCAAA AGCTCTGTCA

GTTGAACTGG AAATCAATTT CGAAACGCGT GGCAAACGCG

GTCAAGATGC TATGTATGAA TATATGGCTC AGGCGTGTGC

GGGCAATCGC GTCCGTCGCT AAGGATCC
```

Enzymes NdeI and BamHI were each added to the empty plasmid and the PCR product of the synthesized gene encoding the CRM197A carrier protein to carry out a dual-enzyme restriction digestion. After purification, T4 ligase was added to the ligation mixture to ligate the fragments. After completion of the ligation reaction, the expression plasmid was purified, and verified using PCR verification methods and restriction digestion mapping. Using BL21(DE3) competent cells, the expression plasmid was transformed into the cells, and colonies were screened. After obtaining a positive clone of the engineered expression bacteria, a stock library was established, including master stocks and working stocks. The stock library was stored in the refrigerator at −20° C.

2. Construction of Expression Plasmids for Chimeric Carrier Proteins Comprising CRM197A and Universal Epitopes 2-1. Construction of an Expression Plasmid for P2CRM197A A custom expression plasmid was used. Restriction enzyme Nde I was used to recognize sites having a CATATG sequence (SEQ ID NO:78), and restriction enzyme Bam HI was used to recognize sites having a GGATCC sequence (SEQ ID NO:79). The nucleic acid sequence of P2CRM197A was analyzed, and no Nde I or Bam HI recognition sites were found in the P2CRM197A sequence. The synthesized nucleic acid sequence encoding the P2CRM197A protein is as shown below in SEQ ID NO:34.

```
                                          (SEQ ID NO: 34)
CATATG CAATACATCA AGGCGAACAG CAAATTCATC GGCATCACGG

AACTGGGCTC GGGCTCTGGC GTGCGGACG ACGTTGTGGA

CTCCTCAAAA TCGTTTGTCA TGGAAAACTT CAGCTCTTAT

ATGGCACCA AACCGGGTTA CGTGGACTCC ATTCAGAAGG

GCATCCAAAA ACCGAAGTCA GGCACCCAGG GTAACTACGA

TGACGATTGG AAGGAATTCT ACAGCACGGA CAATAAGTAT

GATGCGGCCG GCTACTCTGT TGACAACGAA AATCCGCTGA

GTGGTAAAGC AGGCGGTGTG GTTAAGGTCA CCTATCCGGG

TCTGACGAAA GTTCTGGCGC TGAAGGTCGA TAACGCCGAA

ACCATTAAAA AGGAACTGGG CCTGTCTCTG ACCGAACCGC

TGATGGAACA AGTGGGTACG GAAGAATTTA TCAAACGTTT

CGGCGATGGT GCATCGCGTG TCGTGCTGAG CCTGCCGTTT

GCTGAAGGCA GTTCCTCAGT GGAATACATT AACAATTGGG

AACAAGCAAA AGCTCTGTCA GTTGAACTGG AAATCAATTT

CGAAACGCGT GGCAAACGCG GTCAAGATGC TATGTATGAA

TATATGGCTC AGGCGTGTGC GGGCAATCGC GTCCGTCGCT

AA GGATCC
```

Enzymes NdeI and BamHI were each added to the empty plasmid and the PCR product of the synthesized gene encoding the P2CRM197A carrier protein to carry out a dual-enzyme restriction digestion. After purification, T4 ligase was added to the ligation mixture to ligate the fragments. After completion of the ligation reaction, the expression plasmid was purified, and verified using PCR verification methods and restriction digestion mapping. Using BL21(DE3) competent cells, the expression plasmid was transformed into the cells, and colonies were screened. After obtaining a positive clone of the engineered expression bacteria, a stock library was established, including master stocks and working stocks. The stock library was stored in the refrigerator at −20° C.

2-2. Construction of an Expression Plasmid for P2CRM197AP2

A custom expression plasmid was used. Restriction enzyme Nde I was used to recognize sites having a CATATG sequence (SEQ ID NO:78), and restriction enzyme Bam HI was used to recognize sites having a GGATCC sequence (SEQ ID NO:79). The nucleic acid sequence of P2CRM197AP2 was analyzed, and no Nde I or Bam HI recognition sites were found in the P2CRM197AP2 sequence. The synthesized nucleic acid sequence encoding the P2CRM197AP2 protein is as shown below in SEQ ID NO:35.

```
                                          (SEQ ID NO: 35)
CATATG CAATACATCA AGGCGAACAG CAAATTCATC GGCATCACGG

AACTGGGCTC GGGCTCTGGC GTGCGGACG ACGTTGTGGA

CTCCTCAAA TCGTTTGTCA TGGAAAACTT CAGCTCTTAT

ATGGCACCA AACCGGGTTA CGTGGACTCC ATTCAGAAGG

GCATCCAAAA ACCGAAGTCA GGCACCCAGG GTAACTACGA

TGACGATTGG AAGGAATTCT ACAGCACGGA CAATAAGTAT

GATGCGGCCG GCTACTCTGT TGACAACGAA AATCCGCTGA

GTGGTAAAGC AGGCGGTGTG GTTAAGGTCA CCTATCCGGG

TCTGACGAAA GTTCTGGCGC TGAAGGTCGA TAACGCCGAA
```

```
ACCATTAAAA AGGAACTGGG CCTGTCTCTG ACCGAACCGC

TGATGGAACA AGTGGGTACG GAAGAATTTA TCAAACGTTT

CGGCGATGGT GCATCGCGTG TCGTGCTGAG CCTGCCGTTT

GCTGAAGGCA GTTCCTCAGT GGAATACATT AACAATTGGG

AACAAGCAAA AGCTCTGTCA GTTGAACTGG AAATCAATTT

CGAAACGCGT GGCAAACGCG GTCAAGATGC TATGTATGAA

TATATGGCTC AGGCGTGTGC GGGCAATCGC GTCCGTCGCT

AAGGCTCGGG CTCTGGCCAA TACATCAAGG CGAACAGCAA

ATTCATCGGC ATCACGGAAC TGGGATCC
```

Enzymes NdeI and BamHI were each added to the empty plasmid and the PCR product of the synthesized gene encoding the P2CRM197AP2 carrier protein to carry out a dual-enzyme restriction digestion. After purification, T4 ligase was added to the ligation mixture to ligate the fragments. After completion of the ligation reaction, the expression plasmid was purified, and verified using PCR verification methods and restriction digestion mapping. Using BL21(DE3) competent cells, the expression plasmid was transformed into the cells, and colonies were screened. After obtaining a positive clone of the engineered expression bacteria, a stock library was established, including master stocks and working stocks. The stock library was stored in the refrigerator at −20° C.

2-3. Construction of Expression Plasmids for CRM197AP2, P2P2CRM197A, CRM197AP2P2, P2P2CRM197AP2, and P2CRM197AP2P2

The method is the same as described above in section "2-1. Construction of an expression plasmid for P2CRM197A".

2-4. Construction of an Expression Plasmid for P30CRM197A

A custom expression plasmid was used. Restriction enzyme Nde I was used to recognize sites having a CATATG sequence (SEQ ID NO:78), and restriction enzyme Bam HI was used to recognize sites having a GGATCC sequence (SEQ ID NO:79). The nucleic acid sequence of P30CRM197A was analyzed, and no Nde I or Bam HI recognition sites were found in the P30CRM197A sequence. The synthesized nucleic acid sequence encoding the P30CRM197A protein is as shown below in SEQ ID NO:36.

```
                                      (SEQ ID NO: 36)
CATATG TTCAATAATT TTACGGTGTC GTTTTGGCTG CGTGTCCCGA

AAGTCTCTGC GAGTCATCTG GAAGGTTCTG GTAGCGGTGG

TGCGGATGAC GTGGTTGATA GCTCTAAATC TTTCGTTATG

GAAAACTTCA GTTCCTATCA TGGCACCAAA CCGGGTTACG

TCGATTCGAT TCAGAAAGGC ATCCAAAAAC CGAAAAGCGG

CACCCAGGGT AACTACGATG ACGATTGGAA AGAATTCTAC

TCAACGGACA ACAAATACGA TGCGGCCGGC TACTCCGTGG

ACAACGAAAA TCCGCTGAGC GGTAAAGCGG GCGGTGTCGT

GAAAGTTACC TATCCGGGTC TGACGAAAGT GCTGGCTCTG

AAAGTTGATA ATGCGGAAAC CATCAAAAAA GAACTGGGCC

TGTCCCTGAC CGAACCGCTG ATGGAACAAG TGGGTACGGA
```

```
                                        -continued
AGAATTTATC AAACGTTTCG GCGACGGTGC CTCTCGCGTT

GTCCTGAGTC TGCCGTTTGC AGAAGGCTCA TCGAGCGTCG

AATACATTAA CAATTGGGAA CAAGCAAAAG CTCTGAGCGT

GGAACTGGAA ATCAACTTCG AAACGCGTGG CAAACGCGGT

CAGGATGCGA TGTATGAATA CATGGCGCAA GCCTGCGCAG

GTAATCGTGT TCGTCGC GGATCC
```

Enzymes NdeI and BamHI were each added to the empty plasmid and the PCR product of the synthesized gene encoding the P30CRM197A carrier protein to carry out a dual-enzyme restriction digestion. After purification, T4 ligase was added to the ligation mixture to ligate the fragments. After completion of the ligation reaction, the expression plasmid was purified, and verified using PCR verification methods and restriction digestion mapping. Using BL21(DE3) competent cells, the expression plasmid was transformed into the cells, and colonies were screened. After obtaining a positive clone of the engineered expression bacteria, a stock library was established, including master stocks and working stocks. The stock library was stored in the refrigerator at −20° C.

2-5. Construction of Expression Plasmids for CRM197AP30, P30CRM197AP30, P30P30CRM197A, CRM197AP30P30, P30P30CRM197AP30, and P30CRM197AP30P30

The method is the same as described above in section "2-4. Construction of an expression plasmid for P30CRM197A".

2-6. Construction of an Expression Plasmid for OVApCRM197A

A custom expression plasmid was used. Restriction enzyme Nde I was used to recognize sites having a CATATG sequence (SEQ ID NO:78), and restriction enzyme Bam HI was used to recognize sites having a GGATCC sequence (SEQ ID NO:79). The nucleic acid sequence of OVApCRM197A was analyzed, and no Nde I or Bam HI recognition sites were found in the OVApCRM197A sequence. The synthesized nucleic acid sequence encoding the OVApCRM197A protein is as shown below in SEQ ID NO:37.

```
                                      (SEQ ID NO: 37)
CATATG ATCAGCCAAG CGGTTCACGC AGCCCACGCC

GAAATTAACG AAGCGGGTCG CGGTAGCGGT TCTGGCGGTG

CAGACGATGT TGTTGACTCC AGCAAATCAT TCGTCATGGA

AAACTTTAGC TCTTATCATG GCACCAAACC GGGTTACGTG

GACTCCATTC AGAAAGGCAT CCAAAAACCG AAATCAGGCA

CCCAGGGTAA CTATGATGAC GATTGGAAAG AATTCTACTC

TACGGACAAC AAATACGATG CGGCCGGCTA CTCTGTTGAC

AACGAAAATC CGCTGAGTGG TAAAGCAGGC GGTGTGGTTA

AAGTCACCTA TCCGGGTCTG ACCAAAGTTC TGGCGCTGAA

AGTCGATAAC GCCGAAACCA TCAAAAAGA ACTGGGCCTG

TCGCTGACCG AACCGCTGAT GGAACAAGTG GGTACGGAAG

AATTTATCAA ACGTTTCGGC GATGGTGCAT CGCGTGTCGT
```

-continued
```
GCTGAGCCTG CCGTTTGCTG AAGGCAGTTC CTCAGTGGAA

TACATTAACA ATTGGGAACA AGCAAAAGCT CTGAGTGTTG

AACTGGAAAT CAATTTCGAA ACGCGTGGTA AACGCGGTCA

GGACGCAATG TATGAATATA TGGCCCAGGC TTGTGCAGGC

AACCGTGTTC GCCGTTAA GGATCC
```

Enzymes NdeI and BamHI were each added to the empty plasmid and the PCR product of the synthesized gene encoding the OVApCRM197A carrier protein to carry out a dual-enzyme restriction digestion. After purification, T4 ligase was added to the ligation mixture to ligate the fragments. After completion of the ligation reaction, the expression plasmid was purified, and verified using PCR verification methods and restriction digestion mapping. Using BL21(DE3) competent cells, the expression plasmid was transformed into the cells, and colonies were screened. After obtaining a positive clone of the engineered expression bacteria, a stock library was established, including master stocks and working stocks. The stock library was stored in the refrigerator at −20° C.

2-7. Construction of Expression Plasmids for CRM197AOVAp, OVApCRM197AOVAp, OVApOVApCRM197A, CRM197AOVApOVAp, OVApOVApCRM197AOVAp, and OVApCRM197AOVApOVAp The method is the same as described above in section "2-6. Construction of an expression plasmid for OVApCRM197A".

2-8. Construction of an Expression Plasmid for P30CRM197AP2

A custom expression plasmid was used. Restriction enzyme Nde I was used to recognize sites having a CATATG sequence (SEQ ID NO:78), and restriction enzyme Bam HI was used to recognize sites having a GGATCC sequence (SEQ ID NO:79). The nucleic acid sequence of P30CRM197AP2 was analyzed, and no Nde I or Bam HI recognition sites were found in the P30CRM197AP2 sequence. The synthesized nucleic acid sequence encoding the P30CRM197AP2 protein is as shown below in SEQ ID NO:38.

```
                                     (SEQ ID NO: 38)
CATATG TTCAACAATT TTACGGTCTC GTTTTGGCTG

CGTGTCCCGA AAGTGTCTGC CTCACATCTG GAAGGTAGCG

GTTCAGGTGG TGCGGATGAC GTGGTTGATA GCTCTAAATC

CTTTGTTATG GAAAACTTCA GTTCCTATCA TGGTACCAAA

CCGGGCTACG TCGATTCTAT TCAGAAAGGT ATCCAAAAAC

CGAAAAGTGG TACCCAGGGC AACTATGATG ACGATTGGAA

AGAATTCTAC TCTACGGACA ACAAATACGA TGCGGCCGGT

TACTCGGTGG ACAACGAAAA TCCGCTGAGC GGTAAAGCCG

GCGGTGTCGT GAAAGTTACC TATCCGGGCC TGACGAAAGT

GCTGGCTCTG AAAGTTGATA ACGCGGAAAC CATCAAAAAA

GAACTGGGTC TGAGCCTGAC CGAACCGCTG ATGGAACAAG

TGGGCACGGA AGAATTTATC AAACGTTTCG GTGACGGTGC

ATCCCGTGTT GTCCTGTCAC TGCCGTTTGC AGAAGGTTCA

TCGAGCGTCG AATACATCAA CAACTGGGAA CAAGCAAAAG

CTCTGAGCGT GGAACTGGAA ATCAATTTCG AAACCCGTGG

TAAACGCGGC CAGGATGCTA TGTATGAATA CATGGCGCAA

GCCTGCGCAG GTAACCGTGT TCGTCGCGGC TCTGGTAGTG

GCCAGTACAT CAAAGCGAAC AGTAAATTCA TCGGCATCAC

GGAACTG GGATCC
```

Enzymes NdeI and BamHI were each added to the empty plasmid and the PCR product of the synthesized gene encoding the P30CRM197AP2 carrier protein to carry out a dual-enzyme restriction digestion. After purification, T4 ligase was added to the ligation mixture to ligate the fragments. After completion of the ligation reaction, the expression plasmid was purified, and verified using PCR verification methods and restriction digestion mapping. Using BL21(DE3) competent cells, the expression plasmid was transformed into the cells, and colonies were screened. After obtaining a positive clone of the engineered expression bacteria, a stock library was established, including master stocks and working stocks. The stock library was stored in the refrigerator at −20° C.

2-9. Construction of Expression Plasmids for P2CRM197AP30, P2P30CRM197AP2, and P2P30CRM197AOVAp The method is the same as described above in section "2-8. Construction of an expression plasmid for P30CRM197AP2".

III. Preparation of CRM197A Chimeric Carrier Proteins Comprising a Universal Epitope Experiments have demonstrated similar properties of the CRM197A carrier protein and chimeric carrier proteins comprising the CRM197A carrier protein and universal epitopes. Therefore, purification methods for all carrier proteins described herein are similar. Described below is an exemplary method for preparing the chimeric carrier protein comprising the CRM197A carrier protein and universal epitopes.

1. Preparation of Engineered Bacteria Expressing CRM197A Chimeric Carrier Proteins Comprising a Universal Epitope Each plasmid for expressing the chimeric carrier protein was transformed into competent cells using standard molecular biology methods, and was examined for protein expression. Clones that had high protein expression levels and passed the antiserum tests were selected to establish a master stock library and a working stock library.

2. Fermentation of Engineered Bacteria Expressing CRM197A Chimeric Carrier Proteins Comprising a Universal Epitope One tube of bacteria that could express a specific CRM197A chimeric carrier protein comprising a universal epitope was taken from the engineered E. coli working stock library in the low-temperature refrigerator, and thawed at room temperature. The suspension of bacteria in the working stock was transferred to a 50 mL media using sterile techniques, and cultured in a shaking incubator at 37° C. at a shaking speed of 180 rpm until $OD_{6M}$ reached about 1.0.

The bacteria culture was then used to inoculate a 1 L culture media, which was cultured in a shaking incubator at 37° C. at a shaking speed of 180 rpm until $OD_{600}$ reached about 1.0. The 1 L bacteria culture was then used to inoculate a 20 L media in a 50 L fermenter, which was then fermented at 240 rpm and 37° C. When $OD_{600}$ reached about 7-8, IPTG was added to the culture to induce protein expression in the bacteria. Fermentation was stopped at 14 hours from the beginning of the fermentation process. The fermented bacteria culture was centrifuged, and the bacteria were collected.

3. Purification of CRM197A Chimeric Carrier Proteins Comprising a Universal Epitope Because CRM197A was used as a core component to construct different chimeric carrier proteins having universal epitopes, experiments showed that despite the addition of the universal epitopes, parameters for protein purification were not significantly affected. The purification procedure of the CRM197A carrier protein could be modified to establish purification methods for the CRM197A chimeric carrier proteins comprising a universal epitope.

50 g of wet bacteria were weighed in a 2 L centrifuge cup. To the cup was added 300 mL 1×PBS pH 7.0 buffer to re-suspend the bacteria. The bacteria suspension was thoroughly mixed on a magnetic stir plate for 30 minutes, and then centrifuged for 20 minutes at 4° C., 4000 rpm. The supernatant was discarded and the bacteria were collected. These steps were repeated for two times. To the centrifuge tube having the bacteria was added 300 mL 1×PBS pH 7.0. The bacteria were lysed in a homogenizer, and centrifuged for 20 minutes at 4° C., 10000 rpm. The pellet was collected and the supernatant was discarded. To the pellet was added 300 mL 1×PBS pH 7.0 buffer, and the mixture was thoroughly mixed on a magnetic stir plate for 30 minutes. The mixture was centrifuged for 20 minutes at 4° C., 4000 rpm. Inclusion body was collected, and the supernatant was discarded. 900 mL denaturing solution was added to the washed inclusion body. The mixture was then centrifuged for 30 minutes at 25° C., 10000 rpm. The supernatant was collected, and the pellet was discarded.

The supernatant was transferred to a 6-8 KDA dialysis bag. The dialysis bag was sealed and placed in 10 L refolding buffer 1, and allowed to equilibrate over night at room temperature on a magnetic stir plate. The next day, the dialysis bag was transferred to 10 L refolding buffer 2, and stirred to equilibrate at room temperature for about 8-10 hours. The dialysis bag was transferred to 10 L dialysis buffer 3, and stirred to equilibrate at room temperature overnight. The next day, the dialysis bag was transferred to 10 L refolding buffer 4, and stirred to equilibrate at room temperature for about 8-10 hours. The dialysis bag was transferred to 10 L refolding buffer 5, and stirred to equilibrate at room temperature overnight. The next day, the dialysis bag was transferred to 2 L storage buffer, and stirred to equilibrate at room temperature for about 8-10 hours. The storage buffer was replaced two times, and dialysis was carried out at room temperature overnight. 1 mL dialysis solution was obtained, and centrifuged for 10 minutes at room temperature and 12000 rpm. The supernatant was collected, and the protein concentration was measured. The protein sample was loaded onto a pre-equilibrated DEAE gel column, and eluted with a gradient mode to collect the target protein peak. The collected sample was then loaded onto phenyl hydrophobic column for further purification, and the eluted peak was collected. Finally, the collected sample was loaded onto an SP gel column, and the eluted peak was collected. The collected purified target protein was transferred to a dialysis bag, and dialyzed against a 0.15 M NaCl buffer. The dialyzed sample was transferred to 4° C. for storage.

IV. Preparation of Bacterial Capsular Polysaccharides

Capsular polysaccharides from three bacterial species, including 13 serotypes of *Streptococcus pneumoniae*, *Haemophilus influenzae* type b, and A, C, Y, and W135 groups of *Neisseria meningitidis*, were purified in order to synthesize the conjugate vaccines. The quality of the purified capsular polysaccharides satisfies the WHO standards for polysaccharides used in the synthesis of polysaccharide-protein conjugate vaccines.

1. Preparation of Capsular Polysaccharides from *Streptococcus pneumoniae*

1-1. Construction of a Stock Library 13 serotype strains of *Streptococcus pneumoniae* were purchased from ATCC, including 1 (item number: 9163), 3 (item number: 10813), 4 (item number: BAA-334), 5 (item number: BAA-341), 6A (item number: BAA-659), 6B (item number: 700675), 7F (item number: 10351), 9V (item number: 700671), 14 (item number: 6314), 18C (item number: 10356), 19A (item number: 700673), 19F (item number: 700905), and 23F (700669). To each of the bacteria strains purchased from ATCC (original stock) was added 0.5 mL *Streptococcus pneumoniae* liquid culture media AHC and mixed thoroughly with the bacteria strain. 0.25 mL of bacteria culture was used to inoculate an AHC culture media containing 5% sheep blood, and incubated in a shaker at 36° C.±1° C., 120 rpm for about 12-20 hours. After $OD_{600}$ reached 1.0, an inoculation loop was used to inoculate the AHC culture containing 5% sheep blood onto an AHC agar plate, and incubated in an incubator at 36° C.±1° C. for 12-20 hours. An inoculation loop was used to inoculate 1 to several bacteria colonies into 10 mL AHC culture solution each, and incubated in a shaker at 36° C.±1° C. for 12 hours with a shaking speed of 150-200 rpm. When $OD_6$ of the bacteria culture reached 1.0, 5 mL of the bacteria AHC culture was used to inoculate a fresh 200 mL AHC culture, and incubated in a shaker at 36° C.±1° C. for 12 hours, with a shaking speed of 150-200 rpm. After $OD_6$ reached 1.0, the bacteria culture was aliquoted into 200 small test tubes with 1 mL bacteria culture each, and centrifuged (4000 rpm, 10 minutes). The supernatant was discarded, and 0.5 mL fresh AHC culture solution and 0.5 mL sterile skim milk was added to the pellet, mixed thoroughly, and flash frozen in ethanol-dry ice bath. The sample was then lyophilized, numbered, and stored in a 4° C. refrigerator as the master stock. The master stock was taken and the method for establishing the master stock was used to establish the working stock: the bacteria culture was used to inoculate a fresh 200 mL AHC culture solution and incubated in a shaker at 36° C.±1° C. for 12 hours, with a shaking speed of 150-200 rpm.

After $OD_{600}$ reached 1.0, the bacteria culture was aliquoted into 200 small test tubes with 1 mL bacteria culture each, and centrifuged (4000 rpm, 10 minutes). The supernatant was discarded, 0.6 mL fresh AHC culture solution and 0.4 mL 40% glycerol solution were added to the sample, mixed thoroughly, flash frozen on dry ice, and stored in a −70° C. low-temperature refrigerator as working stocks.

1-2. Fermentation of *Streptococcus pneumoniae*

A lyophilized working stock was taken from the stock library, and 1 mL AHC rich culture solution was added to dissolve the lyophilized bacteria. Dissolved bacteria solution was used to inoculate a 5 mL AHC rich culture solution in a test tube, and incubated overnight by standing in a $CO_2$ incubator. When bacteria growth was observed, the bacteria culture was used to inoculate a 100 mL AHC rich media in a flask. The flask was placed in a shaker and incubated at 36° C., 200 rpm until $OD_{600}$ reached 1.0. Two aliquots of 100 mL bacteria culture were each used to inoculate a 1 L AHC rich culture media in a culture bottle respectively. The culture bottle was placed in a shaker and incubated at 36° C., 200 rpm until $OD_6$ reached 1.0. 35 L sterile filtered AHC rich culture solution was transferred to a 50 L fermenter. 2 L bacteria culture with an OD of 1 was transferred to the fermenter. When the bacteria growth reached the plateau phase, the bacteria were killed and the supernatant was harvested.

1-3. Purification of Capsular Polysaccharides

A depth filter was used to filter the supernatant to further remove remaining bacteria and debris. The sterile supernatant was concentrated for 10 times (about 600 mL) using a 100 KDa ultrafilter membrane. 6 L 25 mM sodium acetate was used for ultrafiltration wash. HB storage solution was added to obtain a final concentration of 1% (w/v), mixed thoroughly, and stored in a cold room overnight. The solution was centrifuged at 4000 rpm for 1 hour, the polysaccharide/HB precipitate was harvested, and the supernatant was discarded. 25 mM sodium acetate and 1% HB solution was added to the polysaccharide/HB precipitant, which was resuspended by stirring, then the resuspension was centrifuged at 4000 rpm for 1 hour, the polysaccharide/HB precipitant was harvested, and the supernatant was discarded. The centrifugation process was repeated for 3 times. 600 mL 0.25 sodium chloride solution was added to the polysaccharide+HB mixture, mixed thoroughly, and potassium iodide was added to a final concentration of 0.5%. The solution was stored in a cold room overnight. The solution was filtered using a depth filter filter to remove HB/I precipitant, and 0.25M sodium chloride/0.5% potassium iodide solution was used to wash the precipitant on the depth filter filter. The filtrate was collected, and the precipitant was discarded. The crude polysaccharide solution was loop filtered in a depth filter filter with activated carbon for 30 minutes (4% activated filter/0.5 mg/ml crude polysaccharide solution). Sodium phosphate buffer pH6.8 was added to the polysaccharide solution with a final concentration of 25 mM. The above solution was passed through an HA column (50-100 ml) and circulated for 30 minutes. The same phosphate buffer was used to wash the column for 4-5 column volume. A 30 KDa membrane was used to ultrafilter and concentrate the polysaccharide solution for 5 times.

Pyrogen-free water was used to ultrafilter clean the polysaccharide solution. A 0.22 μm membrane was used to filter the polysaccharide solution, which was then lyophilized.

2. Preparation of Capsular Polysaccharides from *Haemophilus influenzae* Type b 2-1. Construction of a Stock Library A *Haemophilus influenzae* type b bacteria strain obtained as a gift was used as the original stock to establish master stock and working stock. The method for establish the stocks is described in the section of construction of a stock library for *Streptococcus pneumoniae.*

2-2. Fermentation of *Haemophilus* Influenza Type b

*Haemophilus* influenza type b (Hib) working stock was used to inoculate media in a plate, and incubated in a 36.5° C. incubator overnight. A Hib colony was taken to inoculate a 5 mL fresh essential culture media, and incubated in a shaker at 36.5° C. and 300 rpm. When the inoculated culture reached the medium log growth phase, with an OD of 0.6-1.0, the inoculated culture was transferred into a 250 mL culture flask with 45 mL of fresh essential culture media, and incubated in a shaker at 36.5° C. and 300 rpm. When the inoculated culture reached the medium log growth phase, with an OD of 0.6-1.0, the inoculated culture was transferred into a 4 L culture flask with 1 L of fresh essential culture media, and incubated in a shaker at 36.5° C. and 300 rpm. When the inoculated culture reached the medium log growth phase (about 16-18 hours), with an OD of 0.6-1.0, the inoculated culture was transferred into a fermenter with 20 L of fresh essential culture media. When the Hib bacteria reached the medium log growth phase, fresh essential culture media and supplemental culture media were added, to provide a final glucose concentration of 23 g/L in the culture media. The added fresh supplemental culture solution had a total volume of 25 L. Fermentation was stopped after 14.5 hours of incubation.

2-3. Purification of Capsular Polysaccharides

The Hib culture was centrifuged and the pelleted Hib bacteria were collected, resuspended in 2 L distilled water, and mixed thoroughly using a magnetic stirrer. 200 mL 12% sodium deoxycholate solution was added to the bacteria suspension, mixed thoroughly for 30 minutes, and transferred to a 10° C.±3° C. cold room and stirred for 8-24 hours in order to lyse bacteria and release the polysaccharides. 50% acetic acid solution was used to adjust the pH of the bacteria lysate to 6.4-6.8 at 20° C.±5° C., and stirring was stopped to allow the solution to stand for 12-24 hours. The solution was centrifuged at 10,000 rpm for 1 hour, the supernatant was collected and the pellet was discarded. A 0.05M phosphate buffer pH7.0 was used to dialyze against the polysaccharide supernatant. An equal volume of 0.2% HB solution was added, mixed using a magnetic stirrer for 30 minutes, and then transferred to a 4° C. cold room to stand overnight. The solution was centrifuged at 10,000 rpm for 1 hour, the pellet was collected and the supernatant was discarded. 100 mL 0.5 M sodium chloride solution was added to dissolve the pellet. 680 mL anhydrous ethanol was added, mixed thoroughly, and then transferred to a 4° C. cold room to stand overnight. The solution was centrifuged at 10,000 rpm for 30 minutes, the supernatant was collected and the pellet was discarded. 5.2 L anhydrous ethanol was added, mixed thoroughly, and then transferred to a 4° C. cold room to stand overnight. The solution was centrifuged at 10,000 rpm for 30 minutes, the pellet was collected and the supernatant was discarded. 500 mL distilled water was added to dissolve the pellet, which was then dialyzed and lyophilized.

3. Preparation of Capsular Polysaccharides from *Neisseria meningitidis*

3-1. Construction of a Stock Library

*Neisseria meningitidis* bacteria strains A, C, Y and W135 obtained as a gift were used as the original strains to establish master stock and working stocks. The method for establish the stocks is described in the section of construction of a stock library for *Streptococcus pneumoniae.*

3-2. Fermentation of *Neisseria meningitidis* and Purification of Capsular Polysaccharides See the corresponding sections for fermentation of Hib and purification of Hib polysaccharides.

V. Preparation of Polysaccharide-Protein Conjugates

The chemical structures of different bacterial polysaccharides contain different functional groups. Therefore, different synthetic methods are needed to covalently link different polysaccharides to the carrier proteins to form the conjugates. The yield and immunogenic properties of conjugates formed by different synthetic methods can be different. Experimental results from the present invention showed that three different synthetic methods, namely reductive amination, CDAP method (using 3-(ethyliminomethyleneamino)-N,N-dimethyl-propan-1-amine), and ADH method (adipic acid dihydrazide), to synthesize specific polysaccharide-protein conjugates. Exemplary polysaccharide-protein conjugates of the present invention include 13-valent *Strepto-* coccus pneumoniae (Pn) polysaccharide conjugates, Haemophilus influenza type b (Hib) polysaccharide conjugates, and 4-valent Neisseria meningitidis (Men) polysaccharide conjugates.

1. Preparation of 13-Valent Streptococcus pneumoniae (Pn) Polysaccharide-P2CRM197A Conjugates 26 types of polysaccharide-protein conjugates comprising CRM197A chimeric carrier proteins were sequence designed and produced. Because the structures of the proteins are similar, the same method selected from reductive amination, ADH method and CDAP method is used to synthesize the polysaccharide-protein conjugates. The example below only shows the synthesis process using the P2CRM197A chimeric carrier protein for illustration purposes. The synthesis methods using other chimeric carrier proteins are similar, and are thus not detailed herein.

1-1. Preparation of Streptococcus pneumoniae Serotype 1 (Pn1) Capsular Polysaccharide-P2CRM197A Conjugate 5 mg Pn1 digested polysaccharide was weighed in a reaction flask, and 0.5 mL of 1 M NaCl was added to the reaction flask. The polysaccharide was completed dissolved by stirring. The initial pH of the polysaccharide solution was recorded, and an appropriate amount of CDAP solution was measured and added to the reaction flask. The mixture was stirred and allowed to react at room temperature for 1.5 minutes, and the pH of the mixture was measured at 30 s. After 1.5 minutes, 0.2M NaOH solution was added to adjust the pH of the solution to 9.5, and the mixture was stirred and allowed to react at room temperature for 3 minutes (0.2 M NaOH was used to maintain the pH of the mixture at 9.5). Immediately after 3 minutes, to the reaction flask was added 5 mg of P2CRM197A chimeric protein, and the mixture was stirred and allowed to react at room temperature (25° C.) for 1 hour. 37.5 μL 2 M lysine solution was added to the reaction flask, and 0.1 N HCl solution was used to adjust the pH of the mixture to 9.0. The mixture was stirred and allowed to react at room temperature for 30 minutes. The reaction flask was transferred to 4° C. to allow reaction overnight. The reaction mixture was transferred to a dialysis bag (MWCO 6-8000), and dialyzed against 0.85% NaCl solution for 3 times (6 Utime) at 4° C. After dialysis, the reaction mixture was centrifuged at 10,000 rpm for 10 minutes, and the supernatant was collected. The supernatant was purified and dialyzed using a Sepharose CL-4B gel column, the conjugate peak was collected, and a sample was taken and sent out for testing.

1-2. Preparation of Streptococcus pneumoniae Serotype 3 (Pn3) Capsular Polysaccharide-P2CRM197A Conjugate 20 mg Pn1 digested polysaccharide was weighed in a reaction flask, and 2 mL of 0.15M NaCl was added to the reaction flask. The polysaccharide was completed dissolved by stirring. An appropriate amount of CDAP solution was measured and added to the reaction flask. The mixture was stirred and allowed to react at room temperature for 1.5 minutes, and the pH of the mixture was measured at 30 s. After 1.5 minutes, 0.2M NaOH solution was added to adjust the pH of the solution to 9.5, and the mixture was stirred and allowed to react at room temperature for 3 minutes (0.2 M NaOH was used to maintain the pH of the mixture at 9.5). ADH was added to the reaction flask to reach a final concentration of 0.8 M, mixed thoroughly, and allowed to react at room temperature for 2 hours. The derived polysaccharide was transferred to a dialysis bag, dialyzed against a 0.15 M NaCl solution, and the NaCl solution was changed three times. The sample was loaded onto a G-50 column, and eluted using 0.15 M NaCl, and the peak outside of the void volume was collected. The collected sample was transferred to a dialysis bag, dialyzed against water, and the water was changed for three times. 5 mg of the derived Pn3 polysaccharide was weighed and dissolved in 0.5 mL of 0.15 M NaCl solution. 5 mg of P2CRM197A chimeric protein was added, and mixed thoroughly. 30 mM EDC was added, and allowed to react at room temperature for 4 hour, and transferred to 4° C. to allow reaction overnight. The reaction mixture was transferred to a dialysis bag (MWCO 6-8000), and dialyzed against 0.85% NaCl solution for 3 times (6 Utime) at 4° C. After dialysis, the reaction mixture was centrifuged at 10,000 rpm for 10 minutes, and the supernatant was collected. The supernatant was purified and dialyzed using a Sepharose CL-4B gel column, the conjugate peak was collected, and a sample was taken and sent out for testing.

1-3. Preparation of Streptococcus pneumoniae Serotype 4 (Pn4) Capsular Polysaccharide-P2CRM197A Conjugate 5 mg activated polysaccharide was weighed in a reaction flask, and 100 μL of 0.5M sodium phosphate buffer was measured and added to the reaction flask. 5 mg of P2CR197A chimeric protein was weighed and added to the reaction flask. The mixture was stirred until the polysaccharide was completed dissolved. 0.5 mL pure water was measured and added to the reaction flask, and mixed thoroughly by stirring. 5.0 mg of sodium cyanoborohydride was weighed and added to the reaction flask. The reaction system was placed in a 40° C. dry bath to allow reaction for 12 hours. After completion of the reaction, 1.5 mL of 0.15 M sodium chloride solution was added to the reaction flask. 2.5 mg of sodium borohydride was weighed and added to the reaction flask. The reaction system was placed at 22° C. to allow reaction for 5 hour. The reaction mixture was transferred to a dialysis bag (MWCO 12-14 kDa), and dialyzed against 0.15M NaCl solution for 3 times (6 Utime) at 4° C. After dialysis, the reaction mixture was centrifuged at 10,000 rpm for 10 minutes, and the supernatant was collected. The supernatant was purified and dialyzed using a Sepharose CL-4B gel column, the conjugate peak was collected, and a sample was taken and sent out for testing.

1-4. Preparation of Streptococcus pneumoniae Serotype 5 (Pn5) Capsular Polysaccharide-P2CRM197A Conjugate 5 mg activated polysaccharide was weighed in a reaction flask, and 100 μL of 0.5M sodium phosphate buffer was measured and added to the reaction flask. 4.0 mg of P2CR197A chimeric protein was weighed and added to the reaction flask. 0.5 mL pure water was measured and added to the reaction flask, mixed by magnetic stirring to dissolve the reactant, and the pH of the reaction mixture was measured. 5.0 mg of sodium cyanoborohydride was weighed and added to the reaction flask. The reaction system was placed at room temperature to allow reaction for 48 hours. 2.5 mg of sodium borohydride was weighed, dissolved in 10 μL pure water using a pipette, and loaded to the reaction flask. The reaction system was placed at 23° C. to allow reaction for 5 hour. The reaction mixture was transferred to a dialysis bag (MWCO 6-8 KDA), and dialyzed against 0.15M NaCl solution for 3 times at 4° C., changing the NaCl solution every 5 hours. After dialysis, the reaction mixture was centrifuged at 10,000 rpm for 10 minutes, and the supernatant was collected. The supernatant was purified and dialyzed using a Sepharose CL-4B gel column, the conjugate peak was collected, and a sample was taken and sent out for testing.

1-5. Preparation of Streptococcus pneumoniae Serotype 6A (Pn6A) Capsular Polysaccharide-P2CRM197A Conjugate 6.0 mg activated polysaccharide Pn6A was weighed in a reaction flask. 1 mL pure water was added to the reaction flask, stirred until the polysaccharide completed dissolved, and the initial pH of the solution was measured. 0.1M NaOH was used to adjust the pH of the solution to 7.0. 4.0 mg of P2CRM197A chimeric protein was added to the reaction flask, and stirred thoroughly. 5.0 mg of sodium cyanoborohydride was weighed and added to the reaction flask, and allowed to react at room temperature for 18 hours. A sample was taken after the reaction and sent out for testing. 2.7 mg of sodium borohydride was weighed, added to the reaction flask, and allowed to react at room temperature for 5 hours. A sample was taken after the reaction and sent out for testing. The reaction mixture was transferred to a dialysis bag, and dialyzed against 0.15M NaCl solution for 3 times (6 Utime) at 4° C. After dialysis, the reaction mixture was centrifuged at 10,000 rpm for 10 minutes, and the supernatant was collected. The supernatant was purified and dialyzed using a Sepharose CL-4B gel column, the conjugate peak was collected, and a sample was taken and sent out for testing.

1-6. Preparation of *Streptococcus pneumoniae* Serotype 6B (Pn6B) Capsular Polysaccharide-P2CRM197A Conjugate 5.0 mg Pn6B polysaccharide was weighed in a reaction flask. 1 mL pure water was added to the reaction flask, stirred until the polysaccharide completed dissolved, and the initial pH of the solution was measured. 0.1M NaOH was used to adjust the pH of the solution to 7.0. 2.5 mg of P2CRM197A chimeric protein was added to the reaction flask, and stirred thoroughly. 5.0 mg of sodium cyanoborohydride was weighed and added to the reaction flask, and allowed to react at room temperature for 20 hours. 2.5 mg of sodium borohydride was weighed, added to the reaction flask, and allowed to react at room temperature for 6 hours. The reaction mixture was transferred to a dialysis bag, and dialyzed against 0.15M NaCl solution for 5 times (6 Utime) at 4° C. After dialysis, the reaction mixture was centrifuged at 10,000 rpm for 10 minutes, and the supernatant was collected. The supernatant was purified and dialyzed using a Sepharose CL-4B gel column, the conjugate peak was collected, and a sample was taken and sent out for testing.

1-7. Preparation of *Streptococcus pneumoniae* Serotype 6F (Pn6B) Capsular Polysaccharide-P2CRM197A Conjugate 10.0 mg Pn6F polysaccharide was weighed in a reaction flask. 1 mL pure water was added to the reaction flask, and stirred until the polysaccharide completed dissolved. 0.1M NaOH was added dropwise to the polysaccharide solution to adjust the pH of the solution to 7.0. 3.5 mg of P2CRM197A chimeric protein was added to the reaction flask, and stirred to mix thoroughly. 5.0 mg of sodium cyanoborohydride was weighed and added to the reaction flask, and allowed to react at room temperature for 20 hours. 990 µL of water was added to the reaction flask and mixed thoroughly. 2.5 mg of sodium borohydride was weighed, added to the reaction flask, and allowed to react at room temperature for 6 hours. The reaction mixture was transferred to a dialysis bag (MWCO 6-8KDA), and dialyzed against 5 mM succinate/0.9% sodium chloride buffer for 5 times (6 Utime) at 4° C. After dialysis, the reaction mixture was centrifuged at 10,000 rpm for 10 minutes, and the supernatant was collected. The supernatant was purified and dialyzed using a Sepharose CL-4B gel column, the conjugate peak was collected, and a sample was taken and sent out for testing.

1-8. Preparation of *Streptococcus pneumoniae* Serotype 9V (Pn9V) Capsular Polysaccharide-P2CRM197A Conjugate 10.0 mg Pn9V activated polysaccharide was weighed in a reaction flask. 125 µL sodium phosphate buffer was added to the reaction flask. 125 µL pure water was added to the reaction flask, and stirred until the polysaccharide completed dissolved. 15 mg of P2CRM197A chimeric protein was added to the reaction flask, and stirred to dissolve completely. 10 mg of NaBH$_3$(CN) was weighed and added to the reaction flask. The reaction system was placed at 22° C. and allowed to react for 48 hours. 2.5 mg of sodium borohydride was weighed, added to the reaction flask, and allowed to react at 22° C. for 5 hours. The reaction mixture was centrifuged at 10,000 rpm for 10 minutes, and the supernatant was collected. The supernatant was purified and dialyzed using a Sepharose CL-4B gel column, the conjugate peak was collected, and a sample was taken and sent out for testing.

1-9. Preparation of *Streptococcus pneumoniae* Serotype 14 (Pn14) Capsular Polysaccharide-P2CRM197A Conjugate 5 mg Pn14 activated polysaccharide was weighed in a reaction flask. 1 ml 3.9 mg of P2CRM197A chimeric protein was added to the reaction flask, and stirred to allow the polysaccharide to dissolve completely. 5 mg of sodium cyanoborohydride was added to the reaction flask, and allowed to react at 22° C. for 48 hours. 2.5 mg of sodium borohydride was added to the reaction flask, and allowed to react at room temperature for 4 hours. The reaction mixture was transferred to a dialysis bag (MWCO 12-14 KDA), including 2 mL of the dialysis solution used to rinse the reaction flask. The reaction mixture was dialyzed against 0.15 M sodium chloride solution for 3 times, 6 Utime, changing the sodium chloride solution every 5 hours. After dialysis, the dialyzed sample was centrifuged at 10,000 rpm for 10 minutes, and the supernatant was collected. The supernatant was purified and dialyzed using a Sepharose CL-4B gel column, the conjugate peak was collected, and a sample was taken and sent out for testing.

1-10. Preparation of *Streptococcus pneumoniae* Serotype 18C (Pn18C) Capsular Polysaccharide-P2CRM197A Conjugate 5 mg Pn18C digested polysaccharide was weighed in a reaction flask, and 1 mL 1M sodium chloride solution was added to dissolve the polysaccharide. An initial pH of the dissolved solution was measured. An appropriate amount of CDAP solution was added, and stirred at room temperature for 1.5 minutes. 0.2 M NaOH solution was added to adjust the pH of the mixture to 9.0. The mixture was then allowed to react at room temperature for 3 minutes. 10 mg of P2CRM197A chimeric protein was added to the reaction flask, and allow to react at 25° C. for 45 minutes. After completion of the reaction, 37.5 µL of 2M lysine solution was added, and allowed to react at 25° C. for 30 minutes. The mixture was then allowed to react at 4° C. overnight. The reaction mixture was transferred to a dialysis bag (MWCO 6-8 KDA), and dialyzed against 0.85% sodium chloride solution, changing the sodium chloride solution for 3 times, 6 Utime, changing the sodium chloride solution every 5 hours. After dialysis, the dialyzed sample was centrifuged at 10,000 rpm for 10 minutes, and the supernatant was collected. The supernatant was purified and dialyzed using a Sepharose CL-4B gel column, the conjugate peak was collected, and a sample was taken and sent out for testing.

1-11. Preparation of *Streptococcus pneumoniae* Serotype 19A (Pn19A) Capsular Polysaccharide-P2CRM197A Conjugate 10 mg Pn19A activated polysaccharide was weighed in a reaction flask. 0.5 mL buffer solution was added to the reaction flaks, and stirred using a magnetic bar until the polysaccharide completely dissolved. 10 mg of P2CRM197A chimeric protein was added to the reaction flask, and stirred to mix thoroughly. 5 mg of sodium cyanoborohydride was added to the reaction flask, and allowed to react at room temperature for 20 hours. 2.5 mg of sodium borohydride was added to the reaction flask, and allowed to react at room temperature for 5 hours. The reaction mixture was transferred to a dialysis bag (MWCO 6-8 KDA), and dialyzed against 0.85% sodium chloride solution for 3 times, 6 Utime, changing the sodium chloride solution every 5 hours. After dialysis, the dialyzed sample was centrifuged at 10,000 rpm for 10 minutes, and the supernatant was collected. The supernatant was purified and dialyzed using a Sepharose CL-4B gel column, the conjugate peak was collected, and a sample was taken and sent out for testing.

1-12. Preparation of *Streptococcus pneumoniae* Serotype 19F (Pn19F) Capsular Polysaccharide-P2CRM197A Conjugate 5.2 mg oxidized Pn19F polysaccharide was weighed and added to a reaction flask. 1 mL of pure water was added to the reaction flask, and stirred using a magnetic bar until the polysaccharide completely dissolved. 3.0 mg of P2CRM197A chimeric protein was added to the reaction flask, and stirred to mix thoroughly. 4.9 mg of sodium cyanoborohydride was added to the reaction flask, stirred on a magnetic stir plate, and allowed to react at 18° C. for 24 hours. 2.5 mg of sodium borohydride was added to the reaction flask, and allowed to react at 18° C. in an incubator for 5 hours. The reaction mixture was transferred to a dialysis bag (MWCO 12-14 KDA), and dialyzed for 5 times, 6 L of dialysis solution/time, changing the dialysis solution every 5 hours. After dialysis, the dialyzed sample was centrifuged at 10,000 rpm for 10 minutes, and the supernatant was collected. The supernatant was purified and dialyzed using a Sepharose CL-4B gel column, the conjugate peak was collected, and a sample was taken and sent out for testing.

1-13. Preparation of *Streptococcus pneumoniae* Serotype 23F (Pn23F) Capsular Polysaccharide-P2CRM197A Conjugate 4.9 mg oxidized Pn23F polysaccharide was weighed and added to a reaction flask. 1 mL of pure water was added to the reaction flask, and stirred using a magnetic bar until the polysaccharide completely dissolved. 5.0 mg of P2CRM197A chimeric protein was added to the reaction flask. 5.1 mg of sodium cyanoborohydride was added to the reaction flask, stirred on a magnetic stir plate, and allowed to react at 18° C. in an incubator for 17 hours. 2.5 mg of sodium borohydride was added to the reaction flask, and allowed to react at 18° C. in an incubator for 5 hours. The reaction mixture was transferred to a dialysis bag (MWCO 12-14 KDA), and dialyzed against 0.15 M sodium chloride solution for 5 times, 6 L of dialysis solution/time, changing the dialysis solution every 5 hours. After dialysis, the dialyzed sample was centrifuged at 10,000 rpm for 10 minutes, and the supernatant was collected. The supernatant was purified and dialyzed using a Sepharose CL-4B gel column, the conjugate peak was collected, and a sample was taken and sent out for testing.

2. Preparation of *Haemophilus* Influenza Type b(Hib) Polysaccharide-P2CRM197A (Hib-P2CRM197A) Conjugates In the examples of synthesizing *Haemophilus* influenza type b (Hib) conjugate vaccines, six chimeric carrier proteins comprising universal epitopes and the CRM197 carrier protein were used, including P2CRM197A, P2CRM197AP2, P30CRM197A, OVApCRM197A, P30CRM197AP2, and P2P30CRM197AOVAp chimeric carrier proteins. Because the methods for synthesizing Hib conjugates having different chimeric carrier proteins are similar, the method using P2CRM197A chimeric carrier protein is used herein as an example in the present invention to describe the conjugate synthesis method.

The ADH method was used to synthesize the Hib conjugates. The synthetic steps of this method can be divided into Hib polysaccharide derivation steps and conjugate synthesis steps.

2-1. Hib Polysaccharide Derivation Steps 5 mg Hib polysaccharide was dissolved in 1 mL of pure water, and activated by adding cyanogen bromide. To the reaction mixture was added 2 mL of ADH solution to reach a final concentration of 0.4 M, and allowed to react over night at 2-8° C. The reaction mixture was dialyzed against 0.2M sodium chloride. The sample was loaded on a G-50 column, and the peak outside the void volume was collected. The conjugate sample was transferred to a dialysis bag, dialyzed against pure water, and lyophilized to obtain the solid polysaccharide derivative. The polysaccharide derivative should be stored under −20° C. or below.

2-2. Synthesis of Hib Polysaccharide-P2CRM197A Conjugate 10 mg of Hib polysaccharide derivative was weighed and added to a reaction flask. 0.5 mL of 0.15 M NaCl was added to the reaction flask, stirred to dissolve the polysaccharide, placed at room temperature followed by 4° C. overnight to ensure complete dissolution of the polysaccharide. The concentration of the polysaccharide in the mixture was 20 mg/mL. The polysaccharide solution was sterile filtered through a 0.45 μm membrane into a reaction flask. 0.1 M NaOH or 0.1N HCl was used to adjust the pH of the filtered solution to 5.5. A solution containing 5 mg of P2CRM197A was added to the reaction flask, and stirred to mix thoroughly. 2.9 mg of EDC was added to the reaction flask, stirred, and allowed to react for 4 hours. The reaction mixture was transferred to a dialysis bag (MWCO 6-8 KDA) against 0.15 M NaCl solution at 4° C., while the NaCl solution was changed for three times. The dialyzed sample was purified through a Sepharose CL-4B column, and the peak outside the void volume was collected. Based on results from analysis, fractions containing the conjugate were pooled, sterile filtered, and stored at 4° C.

2-3. Synthesis of Hib Polysaccharide-CRM197A Conjugates

According to the method described in the above section "synthesis of Hib polysaccharide-P2CRM197A conjugate", the present invention chose six additional chimeric carrier proteins comprising universal epitopes, including CRM197AP2, P2CRM197AP2, P30CRM197A, OVApCRM197A, P30CRM197AP2, P2P30CRM197AOVAp, and the control sample using the CRM197A carrier protein, to prepare a total of 7 conjugates, namely Hib-CRM197AP2, Hib-P2CRM197AP2, Hib-P30CRM197A, Hib-OVApCRM197A, Hib-P30CRM197AP2, Hib-P2P30CRM197AOVAp, and Hib-CRM197A.

3. Preparation of 4-Valent *Neisseria meningitidis* (Men) Polysaccharide-P2CRM197A Conjugates The ADH method was used to synthesize *Neisseria meningitidis* polysaccharide-P2CRM197A conjugates. The method has two steps, namely polysaccharide derivation and conjugate synthesis.

3-1. Synthesis of *Neisseria meningitidis* a Strain Polysaccharide-P2CRM197A Conjugate (MenA-P2CRM197A)

3-1-1. Derivation of *Neisseria meningitidis* Strain A (MenA) Polysaccharides 20 mg of MenA polysaccharides were dissolved in 4 mL of pure water, and activated by adding cyanogen bromide. To the reaction mixture was added 10 mL of ADH solution to reach a final concentration of 0.4 M, and allowed to react over night at 2-8C. The reaction mixture was dialyzed against 0.2M sodium chloride. The sample was loaded on a G-50 column, and the peak outside the void volume was collected. The conjugate sample was transferred to a dialysis bag, dialyzed against pure water, and lyophilized to obtain the solid polysaccharide derivative. The polysaccharide derivative should be stored under −20° C. or below.

3-1-2. Synthesis of MenA Polysaccharide-P2CRM197A Conjugate 5 mg of MenA polysaccharide derivative was weighed and added to a reaction flask. 0.5 mL of 0.15 M NaCl was added to the reaction flask, stirred to dissolve the polysaccharide, and placed at room temperature followed by 4° C. overnight to ensure complete dissolution of the polysaccharide. The concentration of the polysaccharide in the mixture was 20 mg/mL. The polysaccharide solution was sterile filtered through a 0.45 μm membrane into a reaction flask. 0.1 M NaOH or 0.1N HCl was used to adjust the pH of the filtered solution to 5.5. A solution containing 5 mg of P2CRM197A was added to the reaction flask, and stirred to mix thoroughly. 2.9 mg of EDC was added to the reaction flask, stirred, and allowed to react for 4 hours. The reaction mixture was transferred to a dialysis bag (MWCO 6-8 KDA) against 0.15 M NaCl solution at 4° C., while the NaCl solution was changed for three times. The dialyzed sample was purified through a Sepharose CL-4B column, and the peak outside the void volume was collected. Based on results from analysis, fractions containing the conjugate were pooled, sterile filtered, and stored at 4° C.

3-1-3. Synthesis of Other *Neisseria meningitidis* Polysaccharide-CRM197A Conjugates According to the method described in the above section "synthesis of MenA polysaccharide-P2CRM197A conjugate", three additional conjugates were synthesized, including *Neisseria meningitidis* C group polysaccharide-P2CRM197A (referred to as MenC-P2CRM197A), *Neisseria meningitidis* Y group polysaccharide-P2CRM197A (referred to as MenY-P2CRM197A), and *Neisseria meningitidis* W135 group polysaccharide-P2CRM197A (referred to as MenW135-P2CRM197A).

3-2. Preparation of Other 4-Valent *Neisseria meningitidis* Polysaccharide-CRM197A Conjugates According to the method described in the previous section "Preparation of 4-valent *Neisseria meningitidis* (Men) polysaccharide-P2CRM197A conjugates", the present invention chose six chimeric carrier proteins comprising universal epitopes, including CRM197AP2, P2CRM197AP2, P30CRM197A, OVApCRM197A, P30CRM197AP2, P2P30CRM197AOVAp, and the control sample using the CRM197A carrier protein, to prepare a total of 7 types of conjugates, namely 4Men-CRM197AP2, 4Men-P2CRM197AP2, 4Men-P30CRM197A, 4Men-OVApCRM197A, 4Men-P30CRM197AP2, 4Men-P2P30CRM197AOVAp, and 4Men-CRM197A.

VI. Assessment of Immunogenic Properties of Polysaccharide-Protein Conjugates

Vaccines prepared using the corresponding polysaccharide-protein conjugates were injected into mice. Blood samples were collected, and ELISA assays were used to determine the titers of the anti-polysaccharide antibodies in the serum. Opsonophagocytosis assays were used to assess enhancement of immunogenicity.

1. Assessment of Immunogenicity of the 13-Valent *Streptococcus pneumoniae* Polysaccharide-Protein Conjugates 1) Assessment of Immunogenicity of the 13-Valent Pn Polysaccharide-P2CRM197A Conjugates To assess whether polysaccharide-protein conjugates comprising CRM197A chimeric carrier proteins having universal epitopes have superior immunogenicity than polysaccharide-protein conjugates comprising the CRM197A carrier protein without universal epitopes, 13-valent Pn-CRM197A conjugates were synthesized to serve as a control to assess enhancement of immunogenicity of the 13-valent Pn-CRM197A chimeric carrier protein conjugates.

1-1. Preparation of a 13-Valent Pn Polysaccharide-P2CRM197A Protein Conjugate Vaccine and a 13-Valent Pn Polysaccharide-CRM197A Protein Conjugate Vaccine The LABSCALE™ tangential flow filtration (TFF) system (Millipore, USA) was used to concentrate each of solutions of conjugates comprising Pn-1, -3, -4, -5, -6A, -7F, -9V, -14, -18C, -19A, -19F and -23F capsular polysaccharides to a polysaccharide concentration of about 40 μg/mL. The concentration of the solution of the conjugate comprising Pn-6B serotype capsular polysaccharides was concentrated to a polysaccharide concentration of 80 μg/mL. According to final concentrations of polysaccharides listed in Table 1 below, a corresponding calculated volume of each of the single serotype conjugates was added to the preparation bottle.

TABLE 1

Final concentrations of single serotype conjugate solutions

| Serotype of the polysaccharide in the conjugate | Concentration of conjugate solution (mg/ml) | Concentration of polysaccharide (mg/ml) |
|---|---|---|
| 1 | 40 | 1 |
| 3 | 40 | 2 |
| 4 | 40 | 1 |
| 5 | 40 | 1 |
| 6A | 40 | 2 |
| 6B | 80 | 4 |
| 7F | 40 | 1 |
| 9V | 40 | 1 |
| 14 | 40 | 1 |
| 18C | 40 | 1 |
| 19A | 40 | 2 |
| 19F | 40 | 2 |
| 23F | 40 | 2 |

The conjugate mixture was sterile filtered through a 0.22 μm filter. Sterile aluminum phosphate gel was added to reach a final aluminum ion concentration of 125 mg/ml. Buffer was added to the final volume, and packaged into 0.5 ml/bottle.

1-2. Preparation of 13-Valent *Streptococcus pneumoniae* (Pn) Polysaccharide-Protein Conjugates Comprising Other Chimeric Carrier Proteins Having Universal Epitopes According to the method described in the previous sections "Preparation of 13-valent Pn polysaccharide-P2CRM197AP2 protein conjugates", the present invention prepared vaccines corresponding to the following 13-valent Pn polysaccharide-CRM197 chimeric carrier protein conjugates, which were used in immunogenicity assessment assays.

Vaccines prepared using 13-valent Pn polysaccharide conjugates comprising chimeric carrier proteins having a P2 universal epitope: 13Pn-CRM197AP2, 13Pn- P2CRM197AP2, 13Pn-P2P2CRM197A, 13Pn-CRM197AP2P2, 13Pn-P2P2CRM197P2, and 3Pn-P2CRM197AP2P2.

Vaccines prepared using 13-valent Pn polysaccharide conjugates comprising chimeric carrier proteins having a P30 universal epitope: 13Pn-P30CRM197A, 3Pn-CRM197AP30, 13Pn-P30CRM197AP30, 13Pn-P30P30CRM197A, 13Pn-CRM197AP30P30, 13Pn-P30P30CRM197AP30, and 13-P30CRM197AP30P30.

Vaccines prepared using 13-valent Pn polysaccharide conjugates comprising chimeric carrier proteins having an OVAp universal epitope: 13Pn-OVApCRM197A, 3Pn-CRM197AOVAp, 13Pn-OVApCRM197AOVAp, 13Pn-OVApOVApCRM197A, 13Pn-CRM197AOVApOVAp, 13Pn-OVApOVApCRM197AOVAp, and 3Pn-OVApCRM197AOVApOVAp.

Vaccines prepared using 13-valent Pn polysaccharide conjugates comprising chimeric carrier proteins having at least two different types of universal epitopes: 13Pn-P30CRM197AP2, 13Pn-P2CRM197AP30, 13Pn-P2P30CRM197AP2, and 3Pn-P2P30CRM197AOVAp.

1-3. Immunization of Mice and Blood Collection

70 KM57 mice of 5-6 weeks of age were obtained. Each mouse was injected with the prepared 13-valent Pn polysaccharide-P2CRM197A protein conjugate vaccine. Injection volume was 0.1 mL/mouse/time. The mice were divided into two groups: group 1 was injected with the 13-valent Pn polysaccharide-P2CRM197A vaccine; group 2 was injected with the 13-valent Pn polysaccharide-CRM197A vaccine as control. Immunization schedule of the mice was as shown in Table 2 below:

TABLE 2

Immunization schedule.

| Immunization group | Number of mice | Number of injections | Week 1 | Week 2 | Week 3 | Week 4 | Week 5 | Week 6 |
|---|---|---|---|---|---|---|---|---|
| 13Pn-P2CRM197A | 10 | 1 | Inject | Bleed | — | — | — | — |
|  | 10 | 2 | Inject | — | Inject | Bleed | — | — |
|  | 10 | 3 | Inject | — | Inject | — | Inject | Bleed |
| 13Pn-CRM197A | 10 | 1 | Inject | Bleed | — | — | — | — |
|  | 10 | 2 | Inject | — | Inject | Bleed | — | — |
|  | 10 | 3 | Inject | — | Inject | — | Inject | Bleed |

Blood samples were collected in centrifuge tubes, allowed to stand at room temperature for 2 hours, and centrifuged at 10,000 rpm for 10 minutes. A pipette was used to carefully take up the serum from the supernatant, and stored in a 4° C. refrigerator for further testing.

1-4. Determination of Anti-Polysaccharide Antibody Titer in Mice Serum Using EISA 13 solutions, each having 1 mg/ml of one of the 13 Pn serotype-specific polysaccharides (in 1×PBS solution), were prepared and stored in a 4° C. refrigerator. The serotype-specific Pn polysaccharide solutions were diluted to 2-4 µg/mL in coating buffer. 100 µL of coating buffer was added to each well of an ELISA plate to coat the well, and incubated at room temperature overnight. The wells were washed with the washing buffer for 4 times, and 100 µL of blocking buffer was added to each well, incubated at room temperature for 2 hours. The wells were washed with washing buffer for 4 times, and could be stored at 4° C. for 1 week.

Serum samples obtained from mice injected with conjugate vaccines or control sample were diluted 1:10 to obtain working serum samples, which were further diluted by an appropriate number of folds, and added to the first row of wells in the ELISA plate, with a total volume of 200 µL per well. A serial two-fold dilution of the first row of samples was prepared in the following rows, and the plate was incubated at room temperature for 2 hours.

The wells were washed with washing buffer for 4 times. 100 µL alkaline phosphatase-labeled goat-anti-mice antibody (1:2000 dilution) was added to each well, and incubated at room temperature for 4 hours. The wells were washed with washing buffer for 4 times. 100 µL disodium 4-nitrophenylphosphate substrate was added to each well, and OD at a wavelength of 405 nm was recorded. The titers for serotype-specific Pn polysaccharide antibodies in mice serum were as shown in Table 3 below.

TABLE 3

Serotype-specific Pn polysaccharide antibody titers.

Mice serum titer of antibodies against each of the 13 Pn serotype-specific polysaccharides (Eu)

| | 13Pn-P2CRM197A | | | 13Pn-CRM197A | | |
|---|---|---|---|---|---|---|
| Serotype | 1 shot | 2 shots | 3 shots | 1 shot | 2 shots | 3 shots |
| 1 | 0.02 | 1.82 | 5.65 | 0.02 | 0.74 | 1.85 |
| 3 | 0.03 | 1.52 | 4.12 | 0.01 | 0.62 | 1.54 |
| 4 | 0.06 | 2.04 | 8.56 | 0.04 | 1.04 | 1.68 |
| 5 | 0.02 | 2-21 | 5.67 | 0.02 | 0.83 | 1.09 |
| 6A | 0.03 | 1.34 | 5.79 | 0.07 | 0.73 | 1.18 |
| 6B | 0.02 | 0.96 | 4.92 | 0.03 | 0.46 | 0.98 |
| 7F | 0.01 | 1.32 | 5.91 | 0.01 | 0.55 | 1.24 |
| 9V | 0.05 | 0.85 | 5.54 | 0.01 | 0.71 | 1.14 |
| 14 | 0.04 | 2-13 | 5.12 | 0.03 | 0.87 | 1.22 |
| 18C | 0.02 | 1.08 | 4.32 | 0.05 | 0.58 | 1.84 |
| 19A | 0.01 | 0.64 | 3.34 | 0.02 | 0.54 | 1.12 |
| 19F | 0.02 | 1.12 | 4.78 | 0.02 | 0.68 | 1.62 |
| 23F | 0.03 | 0.85 | 4.44 | 0.01 | 0.55 | 1.78 |

The results showed that vaccines of conjugates comprising chimeric carrier proteins having universal epitopes, namely the 13-valent Pn capsular polysaccharide-P2CRM197A conjugates comprising the P2CRM197A chimeric carrier protein, has superior immunogenicity than the 13-valent Pn capsular polysaccharide-CRM197A conjugates. The titers of the specific IgG antibodies against Pn polysaccharides in mice serum after three injections were significantly higher than the titers of the IgG antibodies after one or two injections. Each serotype-specific antibody titer after three injections was higher than more than 4 times the titer after one injection, satisfying the WHO standards for boosting conjugate vaccine titers. Compared to the 13-valent Pn capsular polysaccharide-CRM197A conjugates, the 13-valent Pn PS-P2CRM197A conjugates had higher antibody titers against each serotype-specific CP after three injections in the mice serum.

1-5. Opsonophagocytic Assay (OPA)

Opsonophagocytic assay is a method to assess the bactericidal efficacy of a Pn polysaccharide conjugate-based vaccine. Mice serum samples were tested using the "protocol for multiplexed opsonogphagocytic killing assay for antibodies against Streptococcus pnaeumoniae capsular polysaccharide" by UAB-MOPA. OPA concentrations are shown in Table 4 below.

TABLE 4

| | OPA concentrations. | |
|---|---|---|
| Serotype | 13Pn-CRM197A (Serum after three injections) | 13Pn-P2CRM197A (Serum after three injections) |
| 1 | 1024 | 8192 |
| 3 | 512 | 4096 |
| 4 | 1024 | 8192 |
| 5 | 2048 | 8192 |
| 6A | 1024 | 4096 |
| 6B | 512 | 2048 |
| 7F | 1024 | 8192 |
| 9V | 512 | 4096 |
| 14 | 2048 | 8192 |
| 18C | 512 | 4096 |
| 19A | 512 | 4096 |
| 19F | 1024 | 8192 |
| 23F | 1024 | 8192 |

Results of the experiment showed that the OPA concentrations of the mice serum samples obtained after three injections of the 13-valent Pn PS-P2CRM197A conjugates were significantly enhanced as compared to the OPA concentrations of the mice serum samples obtained after three injections of the 13-valent Pn PS-CRM197A conjugates.

2) Assessmentofimmunogeniciy of Other 13-Valent Pn PS-CRM97A Conjugates

Similar to the methods described in the previous sections "Assessment of immunogenicity of 13-valent Pn PS-P2CRM197A conjugates", the titers of anti-polysaccharide IgG antibodies in response to the other vaccines comprising chimeric carrier proteins having universal epitopes are shown in Table 5 below. Table 5 only lists anti-polysaccharide IgG titers after three injections.

TABLE 5

| Anti-PS IgG titers. | | | | | | | | | | | | | |
|---|---|---|---|---|---|---|---|---|---|---|---|---|---|
| Anti-Pn PS IgG antibody titer in mice serum after 3 injections (Eu) | | | | | | | | | | | | | |
| Name of vaccine | Pn1 | Pn3 | Pn4 | Pn5 | Pn6A | Pn6B | Pn7F | Pn9V | Pn14 | Pn18C | Pn19A | Pn19F | Pn23F |
| 13Pn-P2CRM197A | 4.65 | 4.12 | 8.56 | 5.67 | 4.79 | 4.92 | 5.91 | 4.54 | 5.12 | 4.32 | 4.34 | 5.78 | 4.44 |
| 13Pn-CRM197AP2 | 5.24 | 5.52 | 9.05 | 4.78 | 4.96 | 5.23 | 5.14 | 4.21 | 4.94 | 4.59 | 5.01 | 5.08 | 4.13 |
| 13Pn-P2CRM197AP2 | 6.52 | 6.01 | 12.02 | 6.58 | 7.01 | 5.23 | 5.78 | 5.89 | 7.64 | 5.70 | 5.25 | 6.79 | 5.01 |
| 13Pn-P2P2CRM197A | 4.78 | 4.96 | 11.24 | 5.98 | 6.54 | 5.15 | 6.02 | 3.23 | 6.78 | 6.01 | 4.89 | 5.92 | 4.78 |
| 13Pn-CRM197AP2P2 | 5.02 | 4.54 | 10.45 | 6.13 | 6.95 | 4.79 | 5.81 | 4.01 | 7.29 | 5.83 | 4.55 | 6.11 | 4.86 |
| 13Pn-P2P2CRM197AP2 | 4.12 | 4.33 | 9.79 | 5.10 | 6.09 | 4.30 | 5.24 | 3.89 | 5.98 | 5.01 | 4.66 | 6.01 | 4.58 |
| 13Pn-P2CRM197AP2P2 | 4.46 | 4.06 | 8.86 | 5.78 | 6.12 | 4.78 | 5.63 | 4.14 | 6.34 | 4.98 | 4.59 | 5.96 | 4.12 |
| 13Pn-P30CRM197A | 4.34 | 3.56 | 10.92 | 7.38 | 6.15 | 5.12 | 5.90 | 3.69 | 7.24 | 4.45 | 3.39 | 4.02 | 4.65 |
| 13Pn-CRM197AP30 | 4.76 | 3.01 | 11.05 | 6.89 | 6.54 | 5.08 | 6.32 | 3.19 | 6.54 | 4.38 | 3.01 | 3.98 | 4.16 |
| 13Pn-P30CRM197AP30 | 5.89 | 4.61 | 12.89 | 8.82 | 7.54 | 4.25 | 8.04 | 5.32 | 9.29 | 5.04 | 4.87 | 3.25 | 5.68 |
| 13Pn-P30P30CRM197A | 4.79 | 5.24 | 10.54 | 7.98 | 7.01 | 6.84 | 7.26 | 5.07 | 8.39 | 4.15 | 3.98 | 3.84 | 4.71 |
| 13Pn-CRM197AP30P30 | 4.61 | 4.95 | 11.23 | 7.65 | 6.90 | 4.02 | 6.89 | 4.87 | 8.54 | 3.91 | 4.05 | 3.81 | 4.34 |
| 13Pn-P30P30CRM197P30 | 4.57 | 5.37 | 9.27 | 8.14 | 6.53 | 5.78 | 7.09 | 4.62 | 7.98 | 3.76 | 3.39 | 4.50 | 4.01 |
| 13Pn-P30CRM197P30P30 | 4.32 | 5.78 | 10.32 | 7.98 | 7.49 | 4.17 | 6.99 | 5.16 | 7.75 | 4.08 | 3.74 | 4.01 | 4.25 |
| 13Pn-OVApCRM197A | 4.78 | 4.97 | 8.12 | 6.24 | 4.31 | 2-12 | 4.11 | 3.26 | 4.98 | 4.25 | 3.04 | 4.08 | 3.65 |
| 13Pn-CRM197AOVAp | 4.24 | 5.01 | 9.36 | 6.36 | 5.78 | 3.25 | 4.89 | 4.12 | 5.54 | 5.49 | 2.78 | 5.28 | 4.77 |
| 13Pn-OVApCRM197AOVAp | 5.27 | 6.78 | 11.83 | 7.68 | 7.21 | 4.25 | 6.75 | 5.21 | 7.02 | 6.79 | 3.69 | 6.68 | 4.12 |
| 13Pn-OVApOVApCRM197A | 4.21 | 4.74 | 9.45 | 6.39 | 5.74 | 3.25 | 5.71 | 4.44 | 5.70 | 5.31 | 4.01 | 4.89 | 3.32 |
| 13Pn-CRM197AOVApOVAp | 4.01 | 3.32 | 8.94 | 6.73 | 5.42 | 4.08 | 5.68 | 3.94 | 5.52 | 4.23 | 3.02 | 5.01 | 3.19 |
| 13Pn-OVApOVApCRM197AOVAp | 3.89 | 4.01 | 8.99 | 7.24 | 4.70 | 3.58 | 5.94 | 3.30 | 4.58 | 4.91 | 2.88 | 4.59 | 2.74 |
| 13Pn-OVApCRM197AOVApOVAp | 4.06 | 3.83 | 8.56 | 6.93 | 4.27 | 4.25 | 6.04 | 2.98 | 3.98 | 5.01 | 3.44 | 4.87 | 3.36 |
| 13Pn-P2CRM197AP30 | 6.25 | 7.12 | 11.59 | 8.34 | 6.69 | 6.57 | 7.39 | 5.37 | 6.93 | 6.26 | 5.61 | 6.70 | 5.51 |
| 13Pn-P30CRM197AP2 | 7.12 | 6.58 | 10.89 | 8.11 | 7.03 | 7.64 | 6.88 | 6.06 | 7.11 | 5.89 | 5.43 | 7.05 | 4.88 |
| 13Pn-P2P30CRM197AP2 | 6.94 | 6.44 | 10.32 | 8.54 | 7.58 | 7.62 | 7.73 | 7.41 | 6.73 | 6.39 | 6.46 | 6.49 | 5.11 |

TABLE 5-continued

Anti-PS IgG titers.

Anti-Pn PS IgG antibody titer in mice serum after 3 injections (Eu)

| Name of vaccine | Pn1 | Pn3 | Pn4 | Pn5 | Pn6A | Pn6B | Pn7F | Pn9V | Pn14 | Pn18C | Pn19A | Pn19F | Pn23F |
|---|---|---|---|---|---|---|---|---|---|---|---|---|---|
| 13Pn-P2P30CRM197OVAp | 4.52 | 4.26 | 8.47 | 6.48 | 7.98 | 5.53 | 5.61 | 5.54 | 4.66 | 5.27 | 5.63 | 6.56 | 4.71 |
| 13Pn-CRM197A (Control) | 1.05 | 1.12 | 2.68 | 1.39 | 1.18 | 0.98 | 1.22 | 1.14 | 0.98 | 1.34 | 1.12 | 1.62 | 0.88 |

The results above demonstrated that the immunogenicity of the 13-valent PnPS conjugates comprising the CRM197A chimeric carrier proteins having universal epitopes was significantly enhanced in comparison to the 13-valent Pn PS conjugates comprising the CRM197A carrier protein without universal epitopes. 13-valent Pn PS conjugates comprising a CRM197A chimeric carrier protein having two copies of the same universal epitope had higher immunogenicity than the 13-valent Pn PS conjugates comprising CRM197A chimeric carrier proteins having only one copy of the universal epitope. When the number of copies of a universal epitope in the chimeric carrier protein was increased to three, there was no significant difference in the immunogenicity of the 13-valent Pn PS conjugates prepared thereof, in comparison to the 13-valent Pn PS conjugates comprising a CRM197A chimeric carrier protein having two copies of the universal epitope. Fusion of the universal epitope to the N-terminus or the C-terminus of the chimeric carrier protein resulted in no difference in the immunogenicity of the corresponding 13-valent Pn PS-CRM197A chimeric carrier protein conjugates. Chimeric carrier proteins having at least two different types of universal epitopes further enhanced the immunogenicity of the corresponding 13-valent Pn PS-CRM197A chimeric carrier protein conjugates.

2. Assessment of the Immunogenicity of Hib PS-CRM197A Chimeric Carrier Protein Conjugates 2-1. Preparation of a Vaccine Based on Hib PS-CRM197A Chimeric Protein Conjugates Hib polysaccharides (Hib PS) were used to prepare conjugates comprising the CRM197A carrier protein, or any one of 6 different types of CRM197A chimeric carrier proteins having universal epitopes. The Hib PS-protein conjugates were used to further prepare corresponding vaccines for injection. The method is as described below:

The LABSCALE™ tangential flow filtration (TFF) system (Millipore, USA) was used to concentrate each of solutions of CP-protein conjugates to a polysaccharide concentration of about 25 μg/mL. The concentrated solutions were each sterile filtered through a 0.22 μm filter. Sterile aluminum phosphate adjuvant was added to each solution reach a final aluminum ion concentration of 125 mg/ml. The vaccine solutions were stirred to mix thoroughly, and stored in a 2-8° C. refrigerator.

2-2. Immunization and Assessment of Immunogenicity of the Vaccines.

Similar methods as those described in the previous section "Assessment of immunogenicity of 13-valent Pn PS-CRM197A conjugates" were used to immunize animals, collect blood samples, and determine serum titers of antibodies against Hib polysaccharides using ELISA assays. The results are as shown in Table 6 below.

TABLE 6

Titers of anti-Hib PS antibodies in mice serum.

| | Anti-Hib PS IgG antibody titer in mice serum (Eu) | | |
|---|---|---|---|
| Hib vaccine | 1 injection | 2 injections | 3 injections |
| Hib-P2CRM197A | 0.01 | 1.45 | 5.88 |
| Hib-CRM197AP2 | 0.03 | 1.28 | 6.39 |
| Hib-P2CRM197A VP2 | 0.23 | 2-40 | 7.26 |
| Hib-P30CRM197A | 0.04 | 2.04 | 6.31 |
| Hib-OVApCRM197A | 0.02 | 2.03 | 9.23 |
| Hib-P30CRM197AP2 | 0.16 | 2-26 | 8.11 |
| Hib-P2P30CRM197AOVAp | 0.06 | 2.09 | 6.41 |
| Hib-CRM197A (Control) | 0.02 | 0.78 | 2-41 |

The titers of the anti-Hib PS antibody above showed similar results of the different types of Hib PS-CRM197A chimeric protein conjugates. Compared to the Hib PS-CRM197A protein conjugates without universal epitopes, the other six conjugates comprising CRM197A chimeric carrier proteins having universal epitopes, namely Hib-P2CRM197A, Hib-P2CRM197AP2, Hib-P30CRM197A, Hib-OVApCRM197A, Hib-P30CRM197AP2, and Hib-P2P30CRM197AOVAp, had significantly enhanced IgG titers. The IgG titers of the serum samples after three injections compared to the IgG titers of the serum samples after one injection were also significantly different, with a p<0.05.

3. Assessment of the Immunogenicity of 4-Valent Men PS-CRM197A Chimeric Protein Conjugates 3-1. Preparation of a 4-Valent Men PS-CRM197A Chimeric Protein Conjugate Vaccine (4Men-P2CRM197A)

The LABSCALE™ tangential flow filtration (TFF) system (Millipore, USA) was used to concentrate each solution of MenA-P2CRM197A, MenC-P2CRM197A, MenY-P2CRM197A, and MenW135-P2CRM197A conjugates to a polysaccharide concentration of about 1000 μg/mL, and then diluted with 0.85% NaCl solution and mixed to prepare a 4Men-P2CRM197A conjugate vaccine having a polysaccharide concentration of each group of 100 μg/mL. The vaccine solution was filtered through a 0.22 μm membrane to remove bacteria. Sterile aluminum phosphate adjuvant was added to the vaccine solution to reach a final aluminum ion concentration of 125 mg/ml. The vaccine solutions were stored in a 2-8° C. refrigerator.

3-2. Immunization and Assessment of Immunogenicity of the Vaccine.

Serum samples were obtained using similar methods as those described in the previous section "Assessment of immunogenicity of 13-valent Pn PS-CRM197A conjugates". Each mouse was injected with 0.1 mL of the vaccine solution, with a polysaccharide injection dose of 10

µg/mouse/time. ELISA assays were used to determine serum titers of antibodies against each Men polysaccharide group. The results are as shown in Table 7 below.

TABLE 7

Titers of anti-Men PS antibodies in mice serum.

| Vaccine | PS group | Anti-Men PS IgG antibody titer in mice serum (Eu) | | |
|---|---|---|---|---|
| | | 1 injection | 2 injections | 3 injections |
| 4Men-P2CRM197A | A | 0.03 | 2-32 | 6.78 |
| | C | 0.05 | 1.98 | 5.32 |
| | Y | 0.02 | 1.05 | 4.49 |
| | W135 | 0.08 | 1.75 | 5.44 |
| 4Men-CRM197AP2 | A | 0.02 | 1.65 | 4.98 |
| | C | 0.01 | 1.34 | 5.11 |
| | Y | 0.03 | 1.26 | 6.80 |
| | W135 | 0.03 | 1.07 | 5.50 |
| 4Men-P2CRM197AP2 | A | 0.12 | 3.01 | 7.96 |
| | C | 0.18 | 2-29 | 9.32 |
| | Y | 0.14 | 2.71 | 7.89 |
| | W135 | 0.16 | 2.55 | 7.65 |
| 4Men-P30CRM197A | A | 0.02 | 2-40 | 5.66 |
| | C | 0.04 | 2-18 | 4.64 |
| | Y | 0.03 | 1.14 | 6.15 |
| | W135 | 0.05 | 1.45 | 6.53 |
| 4Men-OVApCRM197A | A | 0.01 | 2-22 | 4.88 |
| | C | 0.03 | 2-41 | 5.01 |
| | Y | 0.02 | 1.20 | 6.84 |
| | W135 | 0.04 | 1.33 | 4.66 |
| 4Men-P30CRM197AP2 | A | 0.15 | 2-34 | 7.06 |
| | C | 0.20 | 2-24 | 9.39 |
| | Y | 0.11 | 2.01 | 8.89 |
| | W135 | 0.13 | 2-40 | 7.45 |
| 4Men-P2P30CRM197AOVAp | A | 0.04 | 1.65 | 5.16 |
| | C | 0.06 | 1.40 | 5.33 |
| | Y | 0.04 | 1.97 | 5.30 |
| | W135 | 0.06 | 1.68 | 4.27 |
| 4Men-CRM197A (Control) | A | 0.03 | 0.75 | 2-23 |
| | C | 0.04 | 0.62 | 1.85 |
| | Y | 0.02 | 0.98 | 1.96 |
| | W135 | 0.06 | 0.82 | 1.77 |

The titers of the anti-Men PS antibody above showed similar results as the 13-valent Pn PS conjugates and the Hib PS conjugates. Compared to the 4-valent Men PS-CRM197A protein conjugates without universal epitopes, the conjugates comprising CRM197A chimeric carrier proteins having universal epitopes had significantly higher specific anti-PS IgG titers. The IgG titers of the serum samples after three injections compared to the IgG titers of the serum samples after one injection were also significantly different, with a p<0.05.

Example 2: Preparation and Assessment of Immunogenicity of Polysaccharide-Protein Conjugates Comprising a Chimeric Carrier Protein Comprising Rotavirus Surface Protein VP8 (CoreVP8) and a Universal Epitope I. Sequence Design of CoreVP8 and CoreVP8 Chimeric Proteins Comprising Universal Epitopes
1. Sequence Design of CoreVP8

Rotavirus can be divided into different types, subtypes and serotypes based on the immunogenic properties of the virus. At the present, 7 serotypes (A-G serotype) have been discovered. Most human pathogenic rotaviruses belong to the A, B and C serotypes. The antigen clusters of the surface capsid proteins VP7 and VP4 of different rotaviruses are different, and each can independently induce corresponding neutralizing antibodies. The serotype of a rotavirus can be determined by the specific immunogenicity of VP4 and VP7 antigens. Rotavirus A can be further categorized as G serotype and P serotype based on the nature of VP7 and VP4. VP4 is a protein that can be cleaved by trypsin into two different viral proteins, namely VP8 and VP5. Research has shown that VP5 has a stable amino acid sequence, but the amino acid sequence of VP8 is associated with a high mutation rate. The sequence of VP8 determines whether the virus belongs to the P serotype. Therefore, the VP8 surface protein can be used as an antigen to immunize animals in order to obtain an antigen with a wide scope of protection. The present invention uses VP8 as an immunogenic carrier protein in polysaccharide-protein conjugates. The antigens derived from the VP8 immunogenic carrier protein in the conjugates can trigger antibody production in immunized human population and provide immunity against infection by rotavirus.

The P serotype of the rotavirus Wa strain belongs to the PlA serotype, and comprises 90% of all endemic pathogenic rotaviral strains in human. The present invention is based on the gene encoding the subunit VP8 in VP4 of the rotavirus Wa strain. The VP8 gene was modified, cloned, expressed and purified to prepare carrier proteins in conjugate vaccines.

The VP8 protein of the human rotavirus Wa strain has 247 amino acids and a molecular weight of 32,000 Dalton. The amino acid sequence is shown below in SEQ ID NO:67.

(SEQ ID NO: 67)
MASLIYRQLLSNSYVTNISDEVNEIGTKKTTNVTVNPGPFAQTGYAPVDW

GHGELPDSTLVQPTLDGPYQPTSLNLPVDYWMLIAPTREGKVAEGTNTTD

RWFACVLVEPNVQNTQRQYVLDGRNVQLNVSNESRTSWKFILFIKLTPDG

TYTQYSTLSTPHKLCAWMKRDNRVYWYQGATPNASESYYLTINNDNSNVS

SDAEFYLIPQSQTAMCTQYINNGLPPIQNTRNIVPVNITSRQIKDAIR

The VP8 viral protein is a capsid protein of rotavirus and it is a structural protein. Full-length VP8 protein has poor water solubility. If full-length VP8 is used as a carrier protein to synthesize conjugates, the purification process would be difficult and the yield of the conjugates would be low. To overcome this issue, the gene encoding the full-length VP8 protein can be selectively cleaved to clone VP8 fragments of varying length, in order to improve the water solubility of the cleaved VP8 protein. Despite the cleavage, the major epitopes of the VP8 protein must be preserved. The cleavage site of the VP8 protein can be at the N-terminus, the C-terminus, or both of the protein. A preferred embodiment of the present invention has cleavage of both the N-terminus and the C-terminus of the VP8 protein, namely cleavage before position 64 from the N-terminus and after position 223 near the C-terminus. The cleaved VP8 protein has 160 amino acids. Experiments have shown that this sequence encompass the receptor region that mediate the attachment of rotavirus to host cells. The sialic acids on the surface of host cells are considered as the ligand for the VP8 attachment. The cleaved VP8 polypeptide is referred to as core VP8, with a molecular weight of 28 kDa. The amino acid sequence of CoreVP8 is shown below in SEQ ID NO:5.

(SEQ ID NO: 5)
LDGPYQPTSLNLPVDYWMLIAPTREGKVAEGTNTTDRWFACVLVEPNVQN

TQRQYVLDGRNVQLNVSNESRTSWKFILFIKLTPDGTYTQYSTLSTPHKL

CAWMKRDNRVYWYQGATPNASESYYLTINNDNSNVSSDAEFYLIPQSQTA

MCTQYINNGL

Experiments have demonstrated that CoreVP8 polypeptide has high water solubility and is easy to purify. Also, as a carrier protein for conjugates, CoreVP8 enables high yield of the synthesized conjugates.

2. Sequence Design of CoreVP8 Chimeric Carrier Proteins Comprising a Universal Epitope Universal epitopes were fused to the CoreVP8 immunogenic carrier protein to construct a new chimeric carrier protein useful for preparation of polysaccharide-protein conjugates. The universal epitope can be fused to the N-terminus or the C-terminus of the CoreVP8 protein. Alternatively, two different universal epitopes can each be fused to the N-terminus or the C-terminus of the CoreVP8 protein respectively. In a third strategy, two copies of the same universal epitope can be fused to each other, and then fused to either the N-terminus or the C-terminus of the CoreVP8 protein.

As the sequence design for chimeric carrier proteins comprising CoreVP8 and universal epitopes is similar to that of chimeric carrier proteins comprising CRM197A and universal epitopes, the present disclosure describes several representative CoreVP8 chimeric carrier proteins comprising universal epitopes. It is to be understood that present invention is not limited to the examples described herein.

2-1 Sequence Design of a Chimeric Carrier Protein Comprising P2 and CoreVP8

2-1-1 Sequence Design of a P2-N-Terminus-CoreVP8 Chimeric Carrier Protein (P2CoreVP8)

One copy of the amino acid sequence of P2 (SEQ ID NO:1) was fused to the N-terminus of the CoreVP8 carrier protein (SEQ ID NO:5) via a GSGSG linker (SEQ ID NO:7) disposed therebetween to obtain a new chimeric carrier protein named P2CoreVP8. The amino acid sequence of the new chimeric carrier protein is shown below in SEQ ID NO:39. The sequence of the P2 epitope is underlined.

(SEQ ID NO: 39)
QYIKANSKFIGITELGSGSGLDGPYQPTSLNLPVDYWMLIAPTREGKVA

EGTNTTDRWFACVLVEPNVQNTQRQYVLDGRNVQLNVSNESRTSWKFIL

FIKLTPDGTYTQYSTLSTPHKLCAWMKRDNRVYWYQGATPNASESYYLT

INNDNSNVSSDAEFYLIPQSQTAMCTQYINNGL 2-1-2 Sequence Design of a P2-N-Terminus-CoreVP8-C-Terminus-P2 Chimeric Carrier Protein (P2CoreVP8P2)

One copy of the amino acid sequence of P2 (SEQ ID NO:1) was fused to the N-terminus and the C-terminus of the CoreVP8 carrier protein (SEQ ID NO:5) respectively, each via a GSGSG linker (SEQ ID NO:7) disposed therebetween to obtain a new chimeric carrier protein named P2CoreVP8P2. The amino acid sequence of the new chimeric carrier protein is shown below in SEQ ID NO:40. The sequence of the P2 epitope is underlined.

(SEQ ID NO: 40)
QYIKANSKFIGITELGSGSGLDGPYQPTSLNLPVDYWMLIAPTREGKVAE

GTNTTDRWFACVLVEPNVQNTQRQYVLDGRNVQLNVSNESRTSWKFILFI

KLTPDGTYTQYSTLSTPHKLCAWMKRDNRVYWYQGATPNASESYYLTINN

DNSNVSSDAEFYLIPQSQTAMCTQYINNGLGSGSGQYIKANSKFIGITEL 2-2 Sequence Design of a Chimeric Carrier Protein Comprising P30 and CoreVP8

2-2-1 Sequence Design of a P30-N-Terminus-CoreVP8 Chimeric Carrier Protein (P30 CoreVP8)

One copy of the amino acid sequence of P30 (SEQ ID NO:2) was fused to the N-terminus of the CoreVP8 carrier protein (SEQ ID NO:5) via a GSGSG linker (SEQ ID NO:7) disposed therebetween, to obtain a new chimeric carrier protein named P30CoreVP8. The amino acid sequence of the new chimeric carrier protein is shown below in SEQ ID NO:41. The sequence of the P30 epitope is underlined.

(SEQ ID NO: 41)
FNNFTVSFWLRVPKVSASHLEGSGSGLDGPYQPTSLNLPVDYWMLIAPTR

EGKVAEGTNTTDRWFACVLVEPNVQNTQRQYVLDGRNVQLNVSNESRTSW

KFILFIKLTPDGTYTQYSTLSTPHKLCAWMKRDNRVYWYQGATPNASESY

YLTINNDNSNVSSDAEFYLIPQSQTAMCTQYINNGL 2-3 Sequence Design of a Chimeric Carrier Protein Comprising OVAp and CoreVP8

2-3-1 Sequence Design of an OVAp-N-Terminus—CoreVP8 Chimeric Carrier Protein (OVAp CoreVP8)

One copy of the amino acid sequence of OVAp (SEQ ID NO:3) was fused to the N-terminus of the CoreVP8 carrier protein (SEQ ID NO:5) via a GSGSG linker (SEQ ID NO:7) disposed therebetween, to obtain a new chimeric carrier protein named OVApCoreVP8. The amino acid sequence of the new chimeric carrier protein is shown below in SEQ ID NO:42. The sequence of the OVAp epitope is underlined.

(SEQ ID NO: 42)
ISQAVHAAHAEINEAGRGSGSGLDGPYQPTSLNLPVDYWMLIAPTREGKV

AEGTNTTDRWFACVLVEPNVQNTQRQYVLDGRNVQLNVSNESRTSWKFIL

FIKLTPDGTYTQYSTLSTPHKLCAWMKRDNRVYWYQGATPNASESYYLTI

NNDNSNVSSDAEFYLIPQSQTAMCTQYINNGL 2-4 Sequence Design of a Chimeric Carrier Protein Comprising at Least Two Different Types of Universal Epitopes 2-4-1 Sequence Design of a P30-N-Terminus-CoreVP8-C-Terminus-P2 Chimeric Carrier Protein (P30CoreVP8P2)

One copy of the amino acid sequence of P30 (SEQ ID NO:2) was fused to the N-terminus of the CoreVP8 carrier protein (SEQ ID NO:5) via a GSGSG linker (SEQ ID NO:7) disposed therebetween, and one copy of the amino acid sequence of P2 (SEQ ID NO:1) was fused to the C-terminus of the CoreVP8 carrier protein (SEQ ID NO:5) via a GSGSG linker (SEQ ID NO:7) disposed therebetween, to obtain a new chimeric carrier protein named P30CoreVP8P2. The amino acid sequence of the new chimeric carrier protein is shown below in SEQ ID NO:43. The sequences of the P2 and P30 epitopes are underlined.

(SEQ ID NO: 43)
<u>FNNFTVSFWLRVPKVSASHLE</u>GSGSGLDGPYQPTSLNLPVDYWMLIAPTRE

GKVAEGTNTTDRWFACVLVEPNVQNTQRQYVLDGRNVQLNVSNESRTSWKF

ILFIKLTPDGTYTQYSTLSTPHKLCAWMKRDNRVYWYQGATPNASESYYLT

INNDNSNVSSDAEFYLIPQSQTAMCTQYINNGLGSGSG<u>QYIKANSKFIGIT</u>

<u>EL</u>

2-4-2 Sequence Design of a P2P30-N-Terminus-CoreVP8-C-Terminus-OVAp Chimeric Carrier Protein (P2P30CoreVP80VAp)

One copy of the amino acid sequence of P2 (SEQ ID NO:1) and one copy of the amino acid sequence of P30 (SEQ ID NO:2) were fused to each other via a GSGSG linker (SEQ ID NO:7) disposed therebetween, the fused sequence was then fused to the N-terminus of the CoreVP8 carrier protein (SEQ ID NO:5) via a GSGSG linker (SEQ ID NO:7) disposed therebetween; additionally, and one copy of the amino acid sequence of OVAp (SEQ ID NO:3) was fused to the C-terminus of the CoreVP8 carrier protein (SEQ ID NO:5) via a GSGSG linker (SEQ ID NO:7) disposed therebetween, to obtain a new chimeric carrier protein named P2P30CoreVP80VAp. The amino acid sequence of the new chimeric carrier protein is shown below in SEQ ID NO:44. The sequences of the P2, P30 and OVAp epitopes are underlined.

(SEQ ID NO: 44)
<u>QYIKANSKFIGITEL</u>GSGSG<u>FNNFTVSFWLRVPKVSASHLE</u>GSGSGLDGP

YQPTSLNLPVDYWMLIAPTREGKVAEGTNTTDRWFACVLVEPNVQNTQRQ

YVLDGRNVQLNVSNESRTSWKFILFIKLTPDGTYTQYSTLSTPHKLCAWM

KRDNRVYWYQGATPNASESYYLTINNDNSNVSSDAEFYLIPQSQTAMCTQ

YINNGLGSGSG<u>ISQAVHAAHAEINEAGR</u>

1. Construction of Expression Plasmids for Chimeric Carrier Proteins Comprising CoreVP8 Carrier Protein and Universal Epitope(s)

1. Construction of an Expression Plasmid of the CoreVP8 Carrier Protein

The amino acid sequence of the human rotavirus Wa strain, GenBank:AGI04377, was obtained from GenBank, and the sequence of the VP8 protein fragment was determined. Based on the VP8 sequence, segments from the N-terminus and the C-terminus of the amino acid sequence were removed respectively to obtain the CoreVP8 amino acid sequence. The nucleic acid sequence encoding the CoreVP8 amino acid sequence was optimized to enable high-efficiency expression of the CoreVP8 protein in *Escherichia coli*.

A custom expression plasmid was used. Restriction enzyme Nde I was used to recognize sites having a CATATG sequence (SEQ ID NO:78), and restriction enzyme Bam HI was used to recognize sites having a GGATCC sequence (SEQ ID NO:79). The nucleic acid sequence of CoreVP8 was analyzed and no Nde I or Bam HI recognition sites were found in the CoreVP8 sequence. The synthesized nucleic acid sequence encoding the CoreVP8 protein is as shown below in SEQ ID NO:45.

(SEQ ID NO: 45)
CATATG TGGATGGTCC GTATCAACCG ACGACGTTTA

CCCCGCCGAA CGATTATTGG ATTCTGATCA ACTCAAATAC

GAACGGCGTG GTTTACGAAA GTACCAACAA TTCCGATTTC

TGGACGGCGG TCGTGGCCAT CGAACCGCAT GTTAATCCGG

CGACCGCCA GTATACCATT TTTGGTGAAAT GCAAACAATT

CAATGTCAGC AACGACTCTA ATAAATGGAA GTTTCTGGAA

ATGTTCCGTA GCTCTAGTCA GAACGAATTT TATAATCGTC

GCACCCTGAC GTCTGATACC CGTCTGGTGG GCATCCTGAA

GTACGGCGGT CGCGTTTGGA CCTTCCATGG TGAAACGCCG

CGTGCAACCA CGGACTCCTC ATCGACCGCG AACCTGAACA

ATATTTCAAT CACGATTCAC CACGATTCAC CACGATTCAC

TCGGAATTTT ACATCATCCC GCGTAGCCAG GAAAGCAAAT

GCAACGAATA CATCAATAAT GGTCTGTGAT AAGCATCC

Enzymes NdeI and BamHI were each added to the empty plasmid and the PCR product of the synthesized gene encoding the CRM197A carrier protein to carry out a dual-enzyme restriction digestion. After purification, T4 ligase was added to the ligation mixture to ligate the fragments. After completion of the ligation reaction, the expression plasmid was purified, and verified using PCR verification methods and restriction digestion mapping. Using BL21(DE3) competent cells, the expression plasmid was transformed into the cells, and colonies were screened. After obtaining a positive clone of the engineered expression bacteria, a stock library was established, including master stocks and working stocks. The stock library was stored in the refrigerator at −20° C.

2. Construction of Expression Plasmids for Chimeric Carrier Proteins Comprising CoreVP8 and Universal Epitopes In order to assess the immunogenicity of PS-protein conjugates comprising a CoreVP8 chimeric carrier protein having a universal epitope, six different types of CoreVP8 chimeric carrier proteins were designed as an example.

2-1. Construction of an Expression Plasmid for P2CoreVP8

A custom expression plasmid was used. Restriction enzyme Nde I was used to recognize sites having a CATATG sequence (SEQ ID NO:78), and restriction enzyme Bam HI was used to recognize sites having a GGATCC sequence (SEQ ID NO:79). The nucleic acid sequence of P2CoreVP8 was analyzed, and no Nde I or Bam HI recognition sites were found in the P2CoreVP8 sequence. The synthesized nucleic acid sequence encoding the P2CoreVP8 protein is as shown below in SEQ ID NO:46.

(SEQ ID NO: 46)
CATATG CAGTACATTA AAGCAAACTC AAAATTCATT

GGCATTACCG AACTGGGCTC AGGCTCAGGT TGGATGGTC

CGTATCAACC GACGACGTTT ACCCCGCCGA ACGATTATTG

GATTCTGATC ACTCAAATA CGAACGGCGT GGTTTACGAA

AGTACCAACA ATTCCGATTT CTGGACGGCG GTCGTGGCCA

TCGAACCGCA TGTTAATCCG GTCGACCGCC AGTATACCAT

TTTTGGTGAA AGCAAACAAT TCAATGTCAG CAACGACTCT

```
AATAAATGGA AGTTTCTGGA AATGTTCCGT AGCTCTAGTC

AGAACGAATT TTATAATCGT CGCACCCTGA CGTCTGATAC

CCGTCTGGTG GGCATCCTGA AGTACGGCGG TCGCGTTTGG

ACCTTCCATG GTGAAACGCC GCGTGCAACC ACGGACTCCT

CATCGACCGC GAACCTGAAC AATATTTCAA TCACGATTCA

CTCGGAATTT TACATCATCC CGCGTAGCCA GGAAAGCAAA

TGCAACGAAT ACATCAATAA TGGTCTGTGA GGATCC
```

Enzymes NdeI and BamHI were each added to the empty plasmid and the PCR product of the synthesized gene encoding the P2CoreVP8 carrier protein to carry out a dual-enzyme restriction digestion. After purification, T4 ligase was added to the ligation mixture to ligate the fragments. After completion of the ligation reaction, the expression plasmid was purified, and verified using PCR verification methods and restriction digestion mapping. Using BL21(DE3) competent cells, the expression plasmid was transformed into the cells, and colonies were screened. After obtaining a positive clone of the engineered expression bacteria, a stock library was established, including master stocks and working stocks. The stock library was stored in the refrigerator at −20° C.

2-2. Construction of an Expression Plasmid for P2CoreVP8P2

The method is similar to the method described in the previous section "2-1. Construction of an expression plasmid for P2CoreVP8.

2-3. Construction of Expression Plasmids for P30CoreVP8

A custom expression plasmid was used. Restriction enzyme Nde I was used to recognize sites having a CATATG sequence (SEQ ID NO:78), and restriction enzyme Bam HI was used to recognize sites having a GGATCC sequence (SEQ ID NO:79). The nucleic acid sequence of P30CoreVP8 was analyzed, and no Nde I or Bam HI recognition sites were found in the P30CoreVP8 sequence. The synthesized nucleic acid sequence encoding the P30CoreVP8 protein is as shown below in SEQ ID NO:47.

```
                                    (SEQ ID NO: 47)
CATATG TTCAATAATT TTACGGTGTC GTTTTGGCTG

CGTGTGCCGA AAGTGTCTGC CTCCCATCTG GAAGGTTCTG

GTTCAGGTCT GGACGGTCCG TATCAGCCGA CCACGTTTAC

CCCGCCGAAC GATTACTGGA TTCTGATCAA CAGCAATACG

AACGGCGTGG TTTATGAATC AACCAACAAT TCGGATTTCT

GGACGGCGGT CGTGGCCATC GAACCGCATG TTAATCCGGT

CGACCGCCAG TACACCATCT TCGGTGAATC AAAACAATTC

AACGTCAGCA ACGACTCTAA CAAATGGAAA TTCCTGGAAA

TGTTCCGTAG CTCTAGTCAG AACGAATTTT ATAATCGTCG

CACCCTGACG TCCGATACCC GTCTGGTGGG CATCCTGAAA

TACGGCGGTC GCGTTTGGAC CTTCCATGGT GAAACGCCGC

GTGCAACCAC GGACTCCTCA TCGACCGCGA ACCTCAACAA

TATTAGCATC ACGATCCACT CTGAATTCTA CATCATCCCG
```

-continued

```
CGCAGTCAAG AATCCAAATG CAACGAATAC ATCAACAATG

GCCTGTAA GGATCC
```

Enzymes NdeI and BamHI were each added to the empty plasmid and the PCR product of the synthesized gene encoding the P30CoreVP8 carrier protein to carry out a dual-enzyme restriction digestion. After purification, T4 ligase was added to the ligation mixture to ligate the fragments. After completion of the ligation reaction, the expression plasmid was purified, and verified using PCR verification methods and restriction digestion mapping. Using BL21(DE3) competent cells, the expression plasmid was transformed into the cells, and colonies were screened. After obtaining a positive clone of the engineered expression bacteria, a stock library was established, including master stocks and working stocks. The stock library was stored in the refrigerator at −20° C.

2-4. Construction of an Expression Plasmid for OVApCoreVP8

A custom expression plasmid was used. Restriction enzyme Nde I was used to recognize sites having a CATATG sequence (SEQ ID NO:78), and restriction enzyme Bam HI was used to recognize sites having a GGATCC sequence (SEQ ID NO:79). The nucleic acid sequence of OVApCoreVP8 was analyzed, and no Nde I or Bam HI recognition sites were found in the OVApCoreVP8 sequence. The synthesized nucleic acid sequence encoding the OVApCoreVP8 protein is as shown below in SEQ ID NO:48.

```
                                    (SEQ ID NO: 48)
CATATG ATCAGCCAAG CGGTTCACGC AGCCCACGCC

GAAATTAACG AAGCGGGTCG CGGTAGCGGT TCTGGCCTGG

ATGGTCCGTA TCAACCGACG ACGTTTACCC CGCCGAACGA

TTATTGGATT CTGATCAACT CAAATACGAA CGGCGTGGTT

TACGAAAGTA CCAACAATTC CGATTTCTGG ACGGCGGTCG

TGGCCATCGA ACCGCATGTT AATCCGGTCG ACCGCCAGTA

TACCATTTTT GGTGAAAGCA AACAATTCAA TGTCAGCAAC

GACTCTAATA AATGGAAGTT TCTGCAAATG TTCCGTAGCT

CTAGTCAGAA CGAATTTTAT AATCGTCGCA CCCTGACGTC

TGATACCCGT CTGGTGGGCA TCCTGAAGTA CGGCGGTCGC

GTTTGGACCT TCCATGGTGA AACGCCGCGT GCAACC ACG

GACTCCTCAT CGACCGCGAA CCTGAACAAT ATTTCAATCA

CGATTCACTC GGAATTTTAC ATCATCCCGC GTAGCCAGGA

AAGCAAATGC AACGAATACA TCAATAATGG TCTGTGATAA GGATCC
```

Enzymes NdeI and BamHI were each added to the empty plasmid and the PCR product of the synthesized gene encoding the OVApCoreVP8 carrier protein to carry out a dual-enzyme restriction digestion. After purification, T4 ligase was added to the ligation mixture to ligate the fragments. After completion of the ligation reaction, the expression plasmid was purified, and verified using PCR verification methods and restriction digestion mapping. Using BL21(DE3) competent cells, the expression plasmid was transformed into the cells, and colonies were screened. After obtaining a positive clone of the engineered expression bacteria, a stock library was established, including master stocks and working stocks. The stock library was stored in the refrigerator at −20° C.

2-5. Construction of Expression Plasmids for P30CoreVP8P2

A custom expression plasmid was used. Restriction enzyme Nde I was used to recognize sites having a CATATG sequence (SEQ ID NO:78), and restriction enzyme Bam HI was used to recognize sites having a GGATCC sequence (SEQ ID NO:79). The nucleic acid sequence of P30CoreVP8P2 was analyzed, and no Nde I or Bam HI recognition sites were found in the P30CoreVP8P2 sequence. The synthesized nucleic acid sequence encoding the P30CoreVP8P2 protein is as shown below in SEQ ID NO:49.

```
                                              (SEQ ID NO: 49)
CATATG ATCAGCCAAG CGGTTCACGC AGCCCACGCC GAAATTAACG

AAGCGGGTCG CGGTAGCGGT TCTGGCCTGG ATGGTCCGTA

TCAACCGACG ACGTTTACCC CGCCGAACGA TTATTGGATT

CTGATCAACT CAAATACGAA CGGGTGGTT TACGAAAGTA

CCAACAATTC CGATTTCTGG ACGGCGGTCG TGGCCATCGA

ACCGCATGTT AATCCGGTCG ACCGCCAGTA TACCATTTTT

GGTGAAAGCA AACAATTCAA TGTCAGCAAC GACTCTAATA

AATGGAAGTT TCTGGAAATG TTCCGTAGCT CTAGTCAGAA

CGAATTTTAT AATCGTCGCA CCCTGACGTC TGATACCCGT

CTGGTGGGCA TCCTGAAGTA CGGCGGTCGC GTTTGGACCT

TCCATGGTGA AACGCCGCGT GCAACC ACG GACTCCTCAT

CGACCGCGAA CCTGAACAAT ATTTCAATCA CGATTCACTC

GGAATTTTAC ATCATCCCGC GTAGCCAGGA AAGCAAATGC

AACGAATACA TCAATAATGG TCTGTGATAA GGCTCAGGCT

CAGGTCAGTA CATTAAAGCA AACTCAAAAT TCATTGGCAT

TACCGAACTG GGATCC
```

Enzymes NdeI and BamHI were each added to the empty plasmid and the PCR product of the synthesized gene encoding the P30CoreVP8P2 carrier protein to carry out a dual-enzyme restriction digestion. After purification, T4 ligase was added to the ligation mixture to ligate the fragments. After completion of the ligation reaction, the expression plasmid was purified, and verified using PCR verification methods and restriction digestion mapping. Using BL21(DE3) competent cells, the expression plasmid was transformed into the cells, and colonies were screened. After obtaining a positive clone of the engineered expression bacteria, a stock library was established, including master stocks and working stocks. The stock library was stored in the refrigerator at −20° C.

2-6. Construction of an Expression Plasmid for P2P30CoreVP80VAp

A custom expression plasmid was used. Restriction enzyme Nde I was used to recognize sites having a CATATG sequence (SEQ ID NO:78), and restriction enzyme Bam HI was used to recognize sites having a GGATCC sequence (SEQ ID NO:79). The nucleic acid sequence of P2P30CoreVP80VAp was analyzed, and no Nde I or Bam HI recognition sites were found in the P2P30CoreVP80VAp sequence. The synthesized nucleic acid sequence encoding the P2P30CoreVP80VAp protein is as shown below in SEQ ID NO:50.

```
                                                        (SEQ ID NO: 50)
CATATG CAGTACATTA AAGCAAACTC AAAAT TCAT TGGCATTACC

GAACTGGGTA GCGGTTCTGG CATCAGCCAA GCGGTTCACG

CAGCCCACGC CGAAATTAAC GAAGCGCGTC GCGCTAGCGG

TTCTGGCCTG GATGGTCCGT ATCAACCGAC GACGTTTACC

CCGCCGAACG ATTATTGGAT TCTGATCAAC TCAAATACGA

ACGGCGTGGT TTACGAAAGT ACCAACAATT CCGATTTCTG

GACGGCGGTC GTGGCCATCG AACCGCATGT TAATCCGGTC

GACCGCCAGT ATACCATTTT TGGTGAAAGC AAACAATTCA

ATGTCACCAA CGACTCTAAT AAATGGAAGT TTCTCCAAAT

GTTCCGTAGC TCTAGTCAGA ACGAATTTTA TAATCGTCGC

ACCCTGACGT CTGATACCCG TCTGGTGGGC ATCCTGAAGT

ACGGCGGTCG CGTTTGGACC TTCCATGGTG AAACGCCGCG

TGCAACCACG GACTCCTCAT CGACCGCGAA CCTGAACAAT

ATTTCAATCA CGATTCACTC GGAATTTTAC ATCATCCCGC

GTAGCCAGGA AAGCAAATGC AACGAATACA TCAATAATGG

TCTGTGATAA GGCTCAGGCT CAGGTATCAG CCAAGCGGTT

CACGCAGCCC ACGCCGAAAT TAACGAAGCG GGTCGC GGATCC
```

Enzymes NdeI and BamHI were each added to the empty plasmid and the PCR product of the synthesized gene encoding the P2P30CoreVP80VAp carrier protein to carry out a dual-enzyme restriction digestion. After purification, T4 ligase was added to the ligation mixture to ligate the fragments. After completion of the ligation reaction, the expression plasmid was purified, and verified using PCR verification methods and restriction digestion mapping. Using BL21(DE3) competent cells, the expression plasmid was transformed into the cells, and colonies were screened. After obtaining a positive clone of the engineered expression bacteria, a stock library was established, including master stocks and working stocks. The stock library was stored in the refrigerator at −20° C.

III. Preparation of CoreVP8 Carrier Protein and CoreVP8 Chimeric Carrier Proteins Comprising a Universal Epitope Experiments have demonstrated similar properties of the CoreVP8 carrier protein and chimeric carrier proteins comprising the CoreVP8 carrier protein and universal epitopes. Therefore, purification methods for all carrier proteins described herein are similar. Described below is an exemplary method for preparing the CoreVP8 chimeric carrier protein comprising a universal epitope. 1. Preparation of Engineered Bacteria Expressing CoreVP8 Chimeric Carrier Proteins Comprising a Universal Epitope Each plasmid for expressing the chimeric carrier protein was transformed into competent cells using standard molecular biology methods, and was examined for protein expression. Clones that had high protein expression levels and passed the antisera tests were selected to establish a master stock library and a working stock library.

2. Fermentation of Engineered Bacteria Expressing CoreVP8 Chimeric Carrier Proteins Comprising a Universal Epitope One tube of bacteria that could express a specific CoreVP8 chimeric carrier protein comprising a universal epitope was taken from the engineered *E. coli* working stock library in the low-temperature refrigerator, and thawed at room temperature. The suspension of bacteria in the working stock was transferred to a 50 mL media using sterile techniques, and cultured in a shaking incubator at 37° C. at a shaking speed of 180 rpm until $OD_{600}$ reached about 1.0. The bacteria culture was then used to inoculate a 1 L culture media, which was cultured in a shaking incubator at 37° C. at a shaking speed of 180 rpm until $OD_{600}$ reached about 1.0. The 1 L bacteria culture was then used to inoculate a 20 L media in a 50 L fermenter, which was then fermented at 240 rpm and 37° C. When $OD_{600}$ reached about 7-8, ITG was added to the culture to induce protein expression in the bacteria. Fermentation was stopped at 14 hours from the beginning of the fermentation process. The fermented bacteria culture was centrifuged, and the bacteria were collected.

3. Purification of CoreVP8 Chimeric Carrier Proteins Comprising a Universal Epitope Because CoreVP8 was used as a core component to construct different chimeric carrier proteins having universal epitopes, experiments showed that despite the addition of the universal epitopes, parameters for protein purification were not significantly affected. The purification procedure of the CoreVP8 carrier protein could be modified to establish purification methods for the CoreVP8 chimeric carrier proteins comprising a universal epitope.

50 g of wet bacteria were weighed in a 2 L centrifuge cup. To the cup was added 300 mL 1×PBS pH 7.0 buffer to re-suspend the bacteria. The bacteria suspension was thoroughly mixed on a magnetic stir plate for 30 minutes, and then centrifuged for 20 minutes at 4° C., 4000 rpm. The supernatant was discarded and the bacteria were collected. These steps were repeated for two times. To the centrifuge tube having the bacteria was added 300 mL 1×PBS pH 7.0. The bacteria were lysed in a homogenizer, and centrifuged for 20 minutes at 4° C., 10000 rpm. The pellet was collected and the supernatant was discarded. To the pellet was added 300 mL 1×PBS pH 7.0 buffer, and the mixture was thoroughly mixed on a magnetic stir plate for 30 minutes. The mixture was centrifuged for 20 minutes at 4° C., 4000 rpm. Inclusion body was collected, and the supernatant was discarded. 900 mL denaturing solution was added to the washed inclusion body. The mixture was then centrifuged for 30 minutes at 25° C., 10000 rpm. The supernatant was collected, and the pellet was discarded. The supernatant was transferred to a 6-8 KDA dialysis bag. The dialysis bag was sealed and placed in 10 L refolding buffer 1, and allowed to equilibrate over night at room temperature on a magnetic stir plate. The next day, the dialysis bag was transferred to 10 L refolding buffer 2, and stirred to equilibrate at room temperature for about 8-10 hours. The dialysis bag was transferred to 10 L dialysis buffer 3, and stirred to equilibrate at room temperature overnight. The next day, the dialysis bag was transferred to 10 L refolding buffer 4, and stirred to equilibrate at room temperature for about 8-10 hours. The dialysis bag was transferred to 10 L refolding buffer 5, and stirred to equilibrate at room temperature overnight. The next day, the dialysis bag was transferred to 2 L storage buffer, and stirred to equilibrate at room temperature for about 8-10 hours. The storage buffer was replaced two times, and dialysis was carried out at room temperature overnight. 1 mL dialysis solution was obtained, and centrifuged for 10 minutes at room temperature and 12000 rpm. The supernatant was collected, and the protein concentration was measured. The protein sample was loaded onto a pre-equilibrated DEAE gel column, and eluted with a gradient mode to collect the target protein peak. The collected sample was then loaded onto a Q Sepharose column for further purification, and the eluted peak was collected. Finally, the collected sample was loaded onto an SP gel column, and the eluted peak was collected. The collected purified target protein was transferred to a dialysis bag, and dialyzed against a 0.15 M NaCl buffer. The dialyzed sample was transferred to 4° C. for storage.

IV. Preparation of Polysaccharide-CoreVP8 Conjugates

Three different synthetic methods, namely reductive amination, CDAP method (using 3-(ethyliminomethyleneamino)-N,N-dimethyl-propan-1-amine), and ADH method (using adipic acid dihydrazide), were used to synthesize specific polysaccharide-CoreVP8 conjugates. The yield and immunogenic properties of conjugates formed by different synthetic methods can be different. In order to investigate the effect of different chimeric carrier proteins having universal epitopes on the immunogenicity of different bacterial polysaccharide (PS) conjugates, the present disclosure describes 13-valent *Streptococcus pneumoniae* (Pn) PS-CoreVP8 conjugates, *Haemophilus* influenza type b (Hib) PS-CoreVP8 conjugates, and 4-valent *Neisseria meningitidis* (Men) PS-CoreVP8 conjugates.

1. Preparation of 13-Valent Pn PS-CoreVP8 Protein (with or without Universal Epitopes) Conjugates 6 CoreVP8 chimeric carrier proteins having universal epitopes, including P2CoreVp8, P2CoreVP8P2, P30CoreVP8, OVApCoreVP8, P30CoreVP8P2, and P2P30CoreVP80VAp, were used to each synthesize a 13-valent Pn PS conjugate vaccine: 13Pn-P2CoreVp8, 13Pn-P2CoreVP8P2, 13Pn-P30CoreVP8, 13Pn-OVApCoreVP8, 13Pn-P30CoreVP8P2, and 13Pn-P2P30CoreVP80VAp. The methods for preparing these conjugates are similar to the methods for preparing the 13-valent Pn PS-CRM197A conjugate vaccines described above.

2. Preparation of Hib PS-CoreVP8 Protein (with or without Universal Epitopes) Conjugates 6 CoreVP8 chimeric carrier proteins having universal epitopes, including P2CoreVp8, P2CoreVP8P2, P30CoreVP8, OVApCoreVP8, P30CoreVP8P2, and P2P30CoreVP80VAp, were used to each synthesize a Hib PS conjugate vaccine: Hib-P2CoreVp8, Hib-P2CoreVP8P2, Hib-P30CoreVP8, Hib-OVApCoreVP8, Hib-P30CoreVP8P2, and 13Pn-P2P30CoreVP80VAp. The methods for preparing these conjugates are similar to the methods for preparing the Hib PS-CRM197A conjugate vaccines described above.

3. Preparation of 4-Valent Men PS-CoreVP8 Protein (with or without Universal Epitopes) Conjugates 6 CoreVP8 chimeric carrier proteins having universal epitopes, including P2CoreVp8, P2CoreVP8P2, P30CoreVP8, OVApCoreVP8, P30CoreVP8P2, and P2P30CoreVP80VAp, were used to each synthesize a 4-valent Men PS conjugate vaccine: 4Men-P2CoreVp8, 4Men-P2CoreVP8P2, 4Men-P30CoreVP8, 4Men-OVApCoreVP8, 4Men-P30CoreVP8P2, and 4Men-P2P30CoreVP80VAp. The methods for preparing these conjugates are similar to the methods for preparing the 4-valent Men PS-CRM197A conjugate vaccines described above.

V. Assessment of Immunogenicity of Polysaccharide-CoreVP8 Conjugate Vaccines

1. Assessment of Immunogenicity of 13-Valent Pn PS-CoreVP8 Conjugate Vaccines

Methods similar to those described in the previous sections "Assessment of immunogenicity of 13-valent Pn PS-P2CRM197A conjugate vaccines" were used to determine the titers of anti-PS IgG antibodies, the results are shown in Table 9 below. Table 9 only lists anti-PS IgG titers after three injections.

TABLE 9

Anti-PS IgG titers in mice serum after three injections of 13-valent Pn PS-CoreVP8 conjugate vaccines.

Anti-Pn PS IgG antibody titer in mice serum after 3 injections (Eu)

| Name of vaccine | Pn1 | Pn3 | Pn4 | Pn5 | Pn6A | Pn6B | Pn7F | Pn9V | Pn14 | Pn18C | Pn19A | Pn19F | Pn23F |
|---|---|---|---|---|---|---|---|---|---|---|---|---|---|
| 13Pn-P2CoreVP8 | 4.23 | 2.83 | 7.98 | 6.15 | 5.30 | 2.54 | 4.65 | 3.78 | 6.71 | 4.32 | 3.16 | 4.09 | 5.98 |
| 13Pn-P2CoreVP8P2 | 3.98 | 3.15 | 8.54 | 6.69 | 5.01 | 3.31 | 5.24 | 3.20 | 6.80 | 4.45 | 3.86 | 3.97 | 4.78 |
| 13Pn-P30CoreVP8 | 3.78 | 1.95 | 8.02 | 5.90 | 4.57 | 2.40 | 4.27 | 3.01 | 5.96 | 3.88 | 3.54 | 4.12 | 5.31 |
| 13Pn-OVApCoreVP8 | 2.99 | 3.20 | 7.50 | 5.69 | 4.13 | 2.91 | 4.78 | 3.51 | 5.64 | 4.50 | 3.05 | 3.19 | 6.89 |
| 13Pn-P30CoreVP8P2 | 6.14 | 3.23 | 8.15 | 6.96 | 5.27 | 5.06 | 6.14 | 4.40 | 6.80 | 6.41 | 4.95 | 5.87 | 8.95 |
| 13Pn-P2P30CoreVP8OVAp | 2.78 | 3.88 | 6.89 | 6.60 | 4.28 | 3.69 | 4.46 | 3.79 | 5.38 | 4.73 | 4.01 | 4.78 | 5.69 |
| 13Pn-CoreVP8 (Control) | 1.21 | 1.01 | 1.54 | 1.18 | 0.85 | 0.79 | 1.60 | 1.02 | 1.25 | 1.68 | 0.98 | 1.28 | 1.87 |

Data from Table 9 showed that the immunogenicity of the 13-valent Pn PS-CoreVP8 conjugates comprising chimeric carrier proteins having universal epitopes were significantly enhanced compared to the 13-valent Pn PS-CoreVP8 conjugates comprising the CoreVP8 carrier protein without a universal epitope. 13-valent Pn PS conjugates comprising a CoreVP8 chimeric carrier protein having two copies of the same universal epitope had higher immunogenicity than the 13-valent Pn PS conjugates comprising a CoreVP8 chimeric carrier protein having only one copy of the universal epitope. Chimeric carrier proteins having at least two different types of universal epitopes further enhanced the immunogenicity of the corresponding 13-valent Pn PS-CoreVP8 conjugates.

2. Assessment of the Immunogenicity of Hib PS-CoreVP8 Conjugate Vaccines

Methods similar to those described in the previous sections "Assessment of immunogenicity of Hib PS-P2CRM197A conjugate vaccines" were used to determine the titers of anti-PS IgG antibodies using ELISA assays. The results are shown in Table 10 below.

TABLE 10

Anti-PS IgG titers in mice serum in response to Hib PS-CoreVP8 conjugate vaccines.

| Hib vaccine | Anti-Hib PS IgG antibody titer in mice serum (Eu) | | |
|---|---|---|---|
| | 1 injection | 2 injections | 3 injections |
| Hib-P2CoreVP8 | 0.01 | 1.45 | 5.88 |
| Hib-P2CoreVP8P2 | 0.23 | 2.40 | 7.26 |
| Hib-P30CoreVP8 | 0.04 | 2.04 | 5.31 |
| Hib-OVApCoreVP8 | 0.02 | 2.33 | 5.23 |
| Hib-P2CoreVP8P30 | 0.16 | 2.26 | 8.11 |
| Hib-P2P30CoreVP8OVAp | 0.06 | 2.09 | 6.41 |
| Hib-CoreVP8 (Control) | 0.02 | 1.22 | 2.41 |

The titers of the anti-Hib PS antibody above showed similar results of the different types of Hib PS-CoreVP8 chimeric protein conjugates. Compared to the Hib PS-CoreVP8 protein conjugates without universal epitopes, the other six conjugates comprising CoreVP8 chimeric carrier proteins having universal epitopes, namely Hib-P2CoreVP8, Hib-P2CoreVP8P2, Hib-P30CoreVP8, Hib-OVApCoreVP8, Hib-P30CoreVP8P2, and Hib-P2P30CoreVP8OVAp, had significantly enhanced IgG titers. The IgG titers of the serum samples after three injections compared to the IgG titers of the serum samples after one injection were also significantly different, with a $p<0.05$.

3. Assessment of the Immunogenicity of 4-Valent Men PS-CoreVP8 Conjugate Vaccines Serum samples were obtained using similar methods as those described in the previous section "Assessment of immunogenicity of 13-valent Pn PS-P2CRM197A conjugate vaccines". Each mouse was injected with 0.1 mL of the vaccine solution, with a polysaccharide injection dose of 10 μg/mouse/time. ELISA assays were used to determine serum titers of antibodies against each polysaccharide group. The results are as shown in Table 11 below.

TABLE 11

Titers of anti-Men PS antibodies in mice serum.

| Vaccine | PS group | Anti-Men PS IgG antibody titer in mice serum (Eu) | | |
|---|---|---|---|---|
| | | 1 injection | 2 injections | 3 injections |
| 4Men-P2CoreVP8 | A | 0.04 | 1.80 | 4.68 |
| | C | 0.01 | 2.32 | 5.52 |
| | Y | 0.05 | 1.95 | 4.19 |
| | W135 | 0.07 | 1.80 | 4.04 |
| 4Men-P2CoreVP8P2 | A | 0.20 | 2.51 | 6.06 |
| | C | 0.14 | 1.69 | 5.12 |
| | Y | 0.18 | 2.01 | 6.49 |
| | W135 | 0.07 | 2.40 | 7.25 |
| 4Men-P30CoreVP8 | A | 0.03 | 1.55 | 3.35 |
| | C | 0.02 | 1.12 | 3.80 |
| | Y | 0.01 | 1.24 | 3.81 |
| | W135 | 0.04 | 1.39 | 4.13 |
| 4Men-OVApCoreVP8 | A | 0.02 | 1.22 | 3.43 |
| | C | 0.04 | 1.81 | 4.52 |
| | Y | 0.01 | 1.50 | 3.14 |
| | W135 | 0.05 | 1.44 | 3.96 |
| 4Men-P30CoreVP8P2 | A | 0.20 | 2.34 | 7.11 |
| | C | 0.16 | 1.98 | 5.44 |
| | Y | 0.11 | 2.11 | 5.09 |
| | W135 | 0.13 | 1.80 | 5.80 |
| 4Men-P2P30CoreVP8OVAp | A | 0.08 | 1.60 | 4.46 |
| | C | 0.11 | 1.55 | 5.22 |
| | Y | 0.07 | 1.90 | 4.54 |
| | W135 | 0.12 | 1.78 | 4.01 |
| 4Men-CoreVP8 (Control) | A | 0.02 | 0.66 | 1.43 |
| | C | 0.01 | 0.70 | 1.58 |
| | Y | 0.04 | 0.84 | 1.16 |
| | W135 | 0.03 | 1.03 | 1.22 |

The titers of the anti-Men PS antibody above showed similar results as the 13-valent Pn PS conjugates and the Hib PS conjugates. Compared to the 4-valent Men PS-CoreVP8 protein conjugates without universal epitopes, the conjugates comprising CoreVP8 chimeric carrier proteins having universal epitopes had significantly higher specific anti-PS IgG titers. The IgG titers of the serum samples after three injections compared to the IgG titers of the serum samples after one injection were also significantly different, with a p<0.05.

Example 3: Preparation and Assessment of Immunogenicity of Polysaccharide-Protein Conjugates Comprising a Chimeric Carrier Protein Comprising Diphtheria H21G Protein Chain A (Referred Hereafter as H21G) and a Universal Epitope I. Sequence Design of H21G and H21G Chimeric Carrier Proteins Comprising Universal Epitopes 1. Sequence Design of H21G The H21G carrier protein is a recombinant protein based on the diphtheria toxin chain A, in which histidine (H) 21 of the diphtheria toxin chain A is replaced by a glycine (G). Similar to the diphtheria toxin mutant CRM197, the modified diphtheria toxin mutant chain A preserves the specific immunogenicity of the diphtheria toxin. The anti-H21G sera cross-react with diphtheria toxin or toxoid. As H21G is similar to the diphtheria toxin, from a safety point of view, H21G can serve as a suitable carrier protein for synthesizing conjugate vaccines. The amino acid sequence of the diphtheria toxin mutant H21G is shown below in SEQ ID NO: 6.

(SEQ ID NO: 6)
GADDVVDSSKSFVMENFSSYGGTKPGYVDSIQKGIQKPKSGTQGNYDDDW

KGFYSTDNKYDAAGYSVDNENPLSGKAGGVVKVTYPGLTKVLALKVDNAE

TIKKELGLSLTEPLMEQVGTEEFIKRFGDGASRVVLSLPFAEGSSSVEYI

NNWEQAKALSVELEINFETRGKRGQDAMYEYMAQACAGNRVRR

2. Sequence Design of H21G Chimeric Carrier Proteins Comprising a Universal Epitope Universal epitopes were fused to the H21G immunogenic carrier protein to construct a new chimeric carrier protein useful for preparation of polysaccharide-protein conjugates. The universal epitope can be fused to the N-terminus or the C-terminus of the H21G protein. Alternatively, two different universal epitopes can each be fused to the N-terminus or the C-terminus of the H21G protein respective. In a third strategy, two copies of the same universal epitope can be fused to each other, and then fused to either the N-terminus or the C-terminus of the H21G protein.

Because of the similar mechanisms of polysaccharide-protein conjugates comprising chimeric carrier proteins having universal epitopes, the present disclosure describes 6 representative CoreVP8 chimeric carrier proteins comprising universal epitopes. It is to be understood that present invention is not limited to the examples described herein.

2-1 Sequence Design of a Chimeric Carrier Protein Comprising P30 and H21G 2-1-1 Sequence Design of a P30-N-Terminus-H21G Chimeric Carrier Protein (P30H21G)

One copy of the amino acid sequence of P30 (SEQ ID NO:2) was fused to the N-terminus of the H21G carrier protein (SEQ ID NO:6) via a GSGSG linker (SEQ ID NO:7) disposed therebetween to obtain a new chimeric carrier protein named P30H21G. The amino acid sequence of the new chimeric carrier protein is shown below in SEQ ID NO:51. The sequence of the P30 epitope is underlined.

(SEQ ID NO: 51)
FNNFTVSFWLRVPKVSASHLEGSGSGGADDVVDSSKSFVMENFSSYGGTK

PGYVDSIQKGIQKPKSGTQGNYDDDWKGFYSTDNKYDAAGYSVDNENPLS

GKAGGVVKVTYPGLTKVLALKVDNAETIKKELGLSLTEPLMEQVGTEEFI

KRFGDGASRVVLSLPFAEGSSSVEYINNWEQAKALSVELEINFETRGKRG

QDAMYEYMAQACAGNRVRR 2-1-2 Sequence Design of a P30-N-Terminus-H21G-C-Terminus-P30 Chimeric Carrier Protein (P2CoreVP8P2)

One copy of the amino acid sequence of P30 (SEQ ID NO:2) was fused to the N-terminus and the C-terminus of the H21G carrier protein (SEQ ID NO:6) respectively, each via a GSGSG linker (SEQ ID NO:7) disposed therebetween to obtain a new chimeric carrier protein named P30H21GP30. The amino acid sequence of the new chimeric carrier protein is shown below in SEQ ID NO:52. The sequence of the P30 epitope (SEQ ID NO:2) is underlined.

(SEQ ID NO: 52)
FNNFTVSFWLRVPKVSASHLEGSGSGGADDVVDSSKSFVMENFSSYGGTK

PGYVDSIQKGIQKPKSGTQGNYDDDWKGFYSTDNKYDAAGYSVDNENPLS

GKAGGVVKVTYPGLTKVLALKVDNAETIKKELGLSLTEPLMEQVGTEEFI

KRFGDGASRVVLSLPFAEGSSSVEYINNWEQAKALSVELEINFETRGKRG

QDAMYEYMAQACAGNRVRRGSGSGFNNFTVSFWLRVPKVSASHLE 2-2 Sequence Design of a Chimeric Carrier Protein Comprising P3 and H21G 2-2-1 Sequence Design of a P2-N-Terminus-H2G Chimeric Carrier Protein (P2H21G)

One copy of the amino acid sequence of P2 (SEQ ID NO:1) was fused to the N-terminus of the H21G carrier protein (SEQ ID NO:6) via a GSGSG linker (SEQ ID NO:7) disposed therebetween, to obtain a new chimeric carrier protein named P2H21G. The amino acid sequence of the new chimeric carrier protein is shown below in SEQ ID NO:53. The sequence of the P2 epitope (SEQ ID NO:1) is underlined.

(SEQ ID NO: 53)
QYIKANSKFIGITELGSGSGGADDVVDSSKSFVMENFSSYGGTKPGYVDSI

QKGIQKPKSGTQGNYDDDWKGFYSTDNKYDAAGYSVDNENPLSGKAGGVVK

VTYPGLTKVLALKVDNAETIKKELGLSLTEPLMFQVGTEEFIKRFGDGASR

VVLSLPFAEGSSSVEYINNWEQAKALSVELEINFETRGKRGQDAMYEYMAQ

ACAGNRVRR 2-3 Sequence Design of a Chimeric Carrier Protein Comprising OVAp and H21G 2-3-1 Sequence Design of an OVAp-N-Terminus—H21G Chimeric Carrier Protein (OVApH21G)

One copy of the amino acid sequence of OVAp (SEQ ID NO:3) was fused to the N-terminus of the H21G carrier protein (SEQ ID NO:6) via a GSGSG linker (SEQ ID NO:7) disposed therebetween, to obtain a new chimeric carrier protein named OVApCoreVP8. The amino acid sequence of the new chimeric carrier protein is shown below in SEQ ID NO:54. The sequence of the OVAp epitope (SEQ ID NO:3) is underlined.

(SEQ ID NO: 54)
ISQAVHAAHAEINEAGRGSGSGGADDVVDSSKSFVMENFSSYGGTKPGYV

DSIQKGIQKPKSGTQGNYDDDWKGFYSTDNKYDAAGYSVDNENPLSGKAG

GVVKVTYPGLTKVLALKVDNAETIKKELGLSLTEPLMEQVGTEEFIKRFG

DGASRVVLSLPFAEGSSSVEYINNWEQAKALSVELEINFETRGKRGQDAM

YEYMAQACAGNRVRR 2-4 Sequence Design of a Chimeric Carrier Protein Comprising at Least Two Different Types of Universal Epitopes 2-4-1 Sequence Design of a P30-N-Terminus-H21G-C-Terminus-P2 Chimeric Carrier Protein (P30H21GP2)

One copy of the amino acid sequence of P30 (SEQ ID NO:2) was fused to the N-terminus of the H21G carrier protein (SEQ ID NO:6) via a GSGSG linker (SEQ ID NO:7) disposed therebetween, and one copy of the amino acid sequence of P2 (SEQ ID NO:1) was fused to the C-terminus of the H21G carrier protein (SEQ ID NO:6) via a GSGSG linker (SEQ ID NO:7) disposed therebetween, to obtain a new chimeric carrier protein named P30H21GP2. The amino acid sequence of the new chimeric carrier protein is shown below in SEQ ID NO:55. The sequences of the P2 (SEQ ID NO:1) and P30 (SEQ ID NO:2) epitopes are underlined.

(SEQ ID NO: 55)
FNNFTVSFWLRVPKVSASHLEGSGSGGADDVVDSSKSFVMENFSSYGGTK

PGYVDSIQKGIQKPKSGTQGNYDDDWKGFYSTDNKYDAAGYSVDNENPLS

GKAGGVVKVTYPGLTKVLALKVDNAETIKKELGLSLTEPLMEQVGTEEFI

KRFGDGASRVVLSLPFAEGSSSVEYINNWEQAKALSVELEINFETRGKRG

QDAMYEYMAQACAGNRVRRGSGSGQYIKANSKFIGITEL 2-4-2 Sequence Design of a P2OVAp-N-Terminus-H21G-C-Terminus—P30 Chimeric Carrier Protein (P2OVApH21GP30)

One copy of the amino acid sequence of P2 (SEQ ID NO:1) and one copy of the amino acid sequence of OVAp (SEQ ID NO:3) were fused to each other via a GSGSG linker (SEQ ID NO:7) disposed therebetween, the fused sequence was then fused to the N-terminus of the H21G carrier protein (SEQ ID NO:6) via a GSGSG linker (SEQ ID NO:7) disposed therebetween; additionally, and one copy of the amino acid sequence of P30 (SEQ ID NO:2) was fused to the C-terminus of the H21G carrier protein (SEQ ID NO:6) via a GSGSG linker (SEQ ID NO:7) disposed therebetween, to obtain a new chimeric carrier protein named P2OVApH21GP30. The amino acid sequence of the new chimeric carrier protein is shown below in SEQ ID NO:56. The sequences of the P2 (SEQ ID NO:1), P30 (SEQ ID NO:2) and OVAp (SEQ ID NO:3) epitopes are underlined.

(SEQ ID NO: 56)
QYIKANSKFIGITELGSGSGISQAVHAAHAEINEAGRGSGSGGADDVVDS

SKSFVMENFSSYGGTKPGYVDSIQKGIQKPKSGTQGNYDDDWKGFYSTDN

KYDAAGYSVDNENPLSGKAGGVVKVTYPGLTKVLAIKVDNAETIKKELGL

SLTEPLMEQVGTEEFIKRFGDGASRVVLSLPFAEGSSSVEYINNWEQAKA

LSVELEINFETRGKRGQDAMYEYMAQACAGNRVRRGSGSGFNNFTVSFWL

RVPKVSASHLE

II. Construction of Expression Plasmids for Chimeric Carrier Proteins Comprising H21G Carrier Protein and Universal Epitope(s)

1. Construction of an Expression Plasmid of the H21G Carrier Protein

The amino acid sequence of full length diphtheria toxin, Reference Sequence: NP_928615, was obtained from GenBank, and the sequence of the diphtheria toxin chain A fragment was determined. Histidine 21 of the sequence was replaced by a glycine. Based on the modified sequence, the nucleic acid sequence encoding the H21G amino acid sequence was optimized to enable high-efficiency expression of the H21G protein in *Escherichia coli.* A custom expression plasmid was used. Restriction enzyme Nde I was used to recognize sites having a CATATG sequence (SEQ ID NO:78), and restriction enzyme Bam HI was used to recognize sites having a GGATCC sequence (SEQ ID NO:79). The nucleic acid sequence of H21G was analyzed and no Nde I or Bam HI recognition sites were found in the H21G sequence. The synthesized nucleic acid sequence encoding the H21G protein is as shown below in SEQ ID NO:57.

(SEQ ID NO: 57)
CATATG GGTGCCGACG ACGTGGTTGA TAGCTCTAAA TCTTTCGTTA

TGGAAAACTT CAGTTCCTAT GGCGGTACCA AACCGGGCTA

CGTCGATTCG ATTCAGAAAG GTATCCAAAA ACCGAAAAGC

GGCACCCAGG GTAACTATGA TGACGATTGG AAAGGCTTTT

ACTCAACGGA CAATAAATAT GATGCGGCCG GCTACTCCGT

GGACAACGAA AATCCGCTGA GCGGTAAAGC GGGCGGTGTC

GTGAAAGTTA CCTATCCGGG TCTGACGAAA GTGCTGGCTC

TGAAAGTTGA TAATGCGGAA ACCATCAAAA AAGAACTGGG

CCTGTCCCTG ACCGAACCGC TGATGGAACA AGTGGGTACG

GAAGAATTTA TCAAACGTTT CGGCGACGGT GCCTCTCGCG

TTGTCCTGAG TCTGCCGTTT GCAGAAGGCT CATCGAGCGT

CGAATACATT AACAATTGGG AACAAGCAAA AGCTCTGAGC

GTGGAACTGG AAATCAACTT CGAAACGCGT GGCAAACGCG

GTCAGGATGC GATGTATGAA TACATGGCGC AAGCCTGCGC

AGGTAATCGT GTTCGTCGC GGATCC

Enzymes NdeI and BamHI were each added to the empty plasmid and the PCR product of the synthesized gene encoding the H21G carrier protein to carry out a dual-enzyme restriction digestion. After purification, T4 ligase was added to the ligation mixture to ligate the fragments. After completion of the ligation reaction, the expression plasmid was purified, and verified using PCR verification methods and restriction digestion mapping. Using BL21 (DE3) competent cells, the expression plasmid was transformed into the cells, and colonies were screened. After obtaining a positive clone of the engineered expression bacteria, a stock library was established, including master stocks and working stocks. The stock library was stored in the refrigerator at −20° C.

2. Construction of Expression Plasmids for Chimeric Carrier Proteins Comprising H21G and Universal Epitopes 2-1. Construction of an Expression Plasmid for P30H21G A custom expression plasmid was used. Restriction enzyme Nde I was used to recognize sites having a CATATG sequence (SEQ ID NO:78), and restriction enzyme Bam HI was used to recognize sites having a GGATCC sequence (SEQ ID NO:79). The nucleic acid sequence of P30H21G was analyzed, and no Nde I or Bam HI recognition sites were found in the P30H21G sequence. The synthesized nucleic acid sequence encoding the P30H21G protein is as shown below in SEQ ID NO:58.

(SEQ ID NO: 58)
CATATG TTCAACAATT TTACGGTGTC TTTTTGGCTG CGTGTGCCGA

AAGTGTCTGC GAGTCATCTG GAAGGTAGTG GTTCTGGTGG

TGCCGACGAC GTCGTTCATA GCTCTAAATC TTTCCTTATG

GAAAACTTCA GTTCCTATGG CGGTACCAAA CCGGGCTACG

TCGATTCGAT TCAGAAAGGT ATCCAAAAAC CGAAAAGCGG

CACCCAGGGT AACTATGATG ACGATTGGAA AGGCTTTTAC

TCAACGGACA ATAAATATGA TGCGGCCGGC TACTCCGTGG

ACAACGAAAA TCCGCTGAGC GGTAAAGCGG GCGGTGTCGT

GAAAGTTACC TATCCGGGTC TGACGAAAGT GCTGGCTCTG

AAAGTTGATA ATGCGGAAAC CATCAAAAAA GAACTGGGCC

TGTCCCTGAC CGAACCGCTG ATGGAACAAG TGGGTACGGA

AGAATTTATC AAACGTTTCG GCGACGGTGC CTCTCGCGTT

GTCCTGAGTC TGCCGTTTGC AGAAGGCTCA TCGAGCGTCG

AATACATTAA CAATTGGGAA CAAGCAAAAG CTCTGAGCGT

GGAACTGGAA ATCAACTTCG AAACGCGTGG CAAACGCGGT

CAGGATGCGA TGTATGAATA CATGGCGCAA GCCTGCGCAG

GTAATCGTGT TCGTCGCTAA GGATCC

Enzymes NdeI and BamHI were each added to the empty plasmid and the PCR product of the synthesized gene encoding the P30H21G carrier protein to carry out a dual-enzyme restriction digestion. After purification, T4 ligase was added to the ligation mixture to ligate the fragments. After completion of the ligation reaction, the expression plasmid was purified, and verified using PCR verification methods and restriction digestion mapping. Using BL21 (DE3) competent cells, the expression plasmid was transformed into the cells, and colonies were screened. After obtaining a positive clone of the engineered expression bacteria, a stock library was established, including master stocks and working stocks. The stock library was stored in the refrigerator at −20° C.

2-2. Construction of an Expression Plasmid for P30H21GP30

A custom expression plasmid was used. Restriction enzyme Nde I was used to recognize sites having a CATATG sequence (SEQ ID NO:78), and restriction enzyme Bam HI was used to recognize sites having a GGATCC sequence (SEQ ID NO:79). The nucleic acid sequence of P30H21GP30 was analyzed, and no Nde I or Bam HI recognition sites were found in the P30H21GP30 sequence. The synthesized nucleic acid sequence encoding the P30H21GP30 protein is as shown below in SEQ ID NO:59.

(SEQ ID NO: 59)
CATATG TTCAACAATT TTACGGTGTC TTTTTGGCTG CGTGTGCCGA

AAGTGTCTGC GAGTCATCTG GAAGGTAGTG GTTCTGGTGG

TGCCGACGAC GTGGTTGATA GCTCTAAATC TTTCGTTATG

GAAAACTTCA GTTCCTATGG CGGTACCAAA CCGGGCTACG

TCGATTCGAT TCAGAAAGGT ATCCAAAAAC CGAAAAGCGG

CACCCAGGGT AACTATGATG ACGATTGGAA AGGCTTTTAC

TCAACGGACA ATAAATATGA TGCGGCCGGC TACTCCGTGG

ACAACGAAAA TCCGCTGAGC GGTAAAGCGG GCGGTGTCGT

GAAAGTTACC TATCCGGGTC TGACGAAAGT GCTGGCTCTG

AAAGTTGATA ATGCGGAAAC CATCAAAAAA GAACTGGGCC

TGTCCCTGAC CGAACCGCTG ATGGAACAAG TGGGTACGGA

AGAATTTATC AAACGTTTCG GCGACGGTGC CTCTCGCGTT

GTCCTGAGTC TGCCGTTTGC AGAAGGCTCA TCGAGCGTCG

AATACATTAA CAATTGGGAA CAAGCAAAAG CTCTGAGCGT

GGAACTGGAA ATCAACTTCG AAACGCGTGG CAAACGCGGT

CAGGATGCGA TGTATGAATA CATGGCGCAA GCCTGCGCAG

GTAATCGTGT TCGTCGCTAA GGTAGTGGTT CTGGTTTCAA

CAATTTTACG GTGTCTTTTT GGCTGCGTGT GCCGAAAGTG

TCTGCGAGTC ATCTGGAA GGATCC

Enzymes NdeI and BamHI were each added to the empty plasmid and the PCR product of the synthesized gene encoding the P30H21GP30 carrier protein to carry out a dual-enzyme restriction digestion. After purification, T4 ligase was added to the ligation mixture to ligate the fragments. After completion of the ligation reaction, the expression plasmid was purified, and verified using PCR verification methods and restriction digestion mapping. Using BL21(DE3) competent cells, the expression plasmid was transformed into the cells, and colonies were screened. After obtaining a positive clone of the engineered expression bacteria, a stock library was established, including master stocks and working stocks. The stock library was stored in the refrigerator at −20° C.

2-3. Construction of Expression Plasmids for P2H21G

A custom expression plasmid was used. Restriction enzyme Nde I was used to recognize sites having a CATATG sequence (SEQ ID NO:78), and restriction enzyme Bam HI was used to recognize sites having a GGATCC sequence (SEQ ID NO:79). The nucleic acid sequence of P2H21G was analyzed, and no Nde I or Bam HI recognition sites were found in the P2H21G sequence. The synthesized nucleic acid sequence encoding the P2H21G protein is as shown below in SEQ ID NO:60.

(SEQ ID NO: 60)
CATATG CAGTACATTA AACCAAACTC AAAAT TCAT TGGCATTACC

GAACTGGGTA GTGGTTCTGG TGGTGCCGAC GACGTGGTTG

ATAGCTCTAA ATCTTTCGTT ATGGAAAACT TCAGTTCCTA TGG

CGGTAC CAAACCGGGCT ACGTCGATTC GATTCAGAAA

GGTATCCAAA AACCGAAAAG CGGCACCCAG GGTAACTATG

```
ATGACGATTG GAAAGGCTTT TACTCAACGC ACAATAAATA

TGATGCGGCC GGCTACTCCG TGGACAACGA AAATCCGCTG

AGCGGTAAAG CGGGCGGTGT CGTGAAAGTT ACCTATCCGG

GTCTGACGAA AGTGCTGGCT CTGAAAGTTA ATAATGCGGA

AACCATCAAA AAGAACTGG GCCTGTCCCT

GACCGAACCG CTGATGGAAC AAGTGGGTAC GGAAGAATTT

ATCAAACGTT TCGGCGACGG TGCCTCTCGC GTTGTCCTGA

GTCTGCCGTT TGCAGAAGGC TCATCGAGCG TCGAATACAT

TAACAATTGG GAACAAGCAA AAGCTCTGAG CGTGGAACTG

GAAATCAACT TCGAAACGCG TGGCAAACGC GGTCAGGATG

CGATGTATGA ATACATGGCG CAAGCCTGCG CAGGTAATCG

TGTTCGTCGC TAA GGATCC
```

Enzymes NdeI and BamHI were each added to the empty plasmid and the PCR product of the synthesized gene encoding the P2H21G carrier protein to carry out a dual-enzyme restriction digestion. After purification, T4 ligase was added to the ligation mixture to ligate the fragments. After completion of the ligation reaction, the expression plasmid was purified, and verified using PCR verification methods and restriction digestion mapping. Using BL21 (DE3) competent cells, the expression plasmid was transformed into the cells, and colonies were screened. After obtaining a positive clone of the engineered expression bacteria, a stock library was established, including master stocks and working stocks. The stock library was stored in the refrigerator at −20° C.

2-4. Construction of an Expression Plasmid for OVApH21G

A custom expression plasmid was used. Restriction enzyme Nde I was used to recognize sites having a CATATG sequence (SEQ ID NO:78), and restriction enzyme Bam HI was used to recognize sites having a GGATCC sequence (SEQ ID NO:79). The nucleic acid sequence of OVApH21G was analyzed, and no Nde I or Bam HI recognition sites were found in the OVApH21G sequence. The synthesized nucleic acid sequence encoding the OVApH21G protein is as shown below in SEQ ID NO:61.

```
                                              (SEQ ID NO: 61)
CATATG ATCAGCCAAG CGGTTCACGC AGCCCACGCC GAAATTAACG

AAGCGGGTCG CGGTAGCGGT TCTGGCGGTG CCGACGACGT

GGTTGATAGC TCTAAATCTT TCGTTATGGA AAACTTCAGT

TCCTATGGCG GTACCAAACC GGGCTACGTC GATTCGATTC

AGAAAGGTAT CCAAAAACCG AAAAGCGGCA CCCAGGGTAA

CTATGATGAC GATTGGAAAG CTTTTACTC AACGGACAAT

AAATATGATG CGGCCGGCTA CTCCGTGGAC AACGAAAATC

CGCTGAGCGG TAAAGCGGGC GGTGTCGTGA AAGTTACCTA

TCCGGGTCTG ACGAAAGTGC TGGCTCTGAA AGTTGATAAT

GCGGAAACCA TCAAAAAAGA ACTGGGCCTG TCCCTGACCG

AACCGCTGAT GGAACAAGTG GGTACGGAAG AATTTATCAA

ACGTTTCGGC GACGGTGCCT CTCGCGTTGT CCTGAGTCTG

CCGTTTGCAG AAGGCTCATC GAGCGTCGAA TACATTAACA

ATTGGGAACA AGCAAAAGCT CTGAGCGTGG AACTGGAAAT

CAACTTCGAA ACGCGTGGCA AACGCGGTCA GGATGCGATG

TATGAATACA TGGCGCAAGC CTGCGCAGGT AATCGTGTTC

GTCGCTAA GGATCC
```

Enzymes NdeI and BamHI were each added to the empty plasmid and the PCR product of the synthesized gene encoding the OVApH21G carrier protein to carry out a dual-enzyme restriction digestion. After purification, T4 ligase was added to the ligation mixture to ligate the fragments. After completion of the ligation reaction, the expression plasmid was purified, and verified using PCR verification methods and restriction digestion mapping. Using BL21(DE3) competent cells, the expression plasmid was transformed into the cells, and colonies were screened. After obtaining a positive clone of the engineered expression bacteria, a stock library was established, including master stocks and working stocks. The stock library was stored in the refrigerator at −20° C.

2-5. Construction of Expression Plasmids for P30H21GP2

A custom expression plasmid was used. Restriction enzyme Nde I was used to recognize sites having a CATATG sequence (SEQ ID NO:78), and restriction enzyme Bam HI was used to recognize sites having a GGATCC sequence (SEQ ID NO:79). The nucleic acid sequence of P30H21GP2 was analyzed, and no Nde I or Bam HI recognition sites were found in the P30H21GP2 sequence. The synthesized nucleic acid sequence encoding the P30H21GP2 protein is as shown below in SEQ ID NO:62.

```
                                              (SEQ ID NO: 62)
CATATG TTCAACAATT TTACGGTGTC TTTTTGGCTG CGTGTGCCGA

AAGTGTCTGC GAGTCATCTG GAAGGTAGTG GTTCTGGTGG

TGCCGACGAC GTGGTTGATA GCTCTAAATC TTTCGTTATG

GAAAACT TC AGTTCCTATG GCGGTACCAA ACCGGGCTAC

GTCGATTCGA TTCAGAAAGG TATCCAAA A ACCGAAAAGC

GGCACCCAGG GTAACTATGA TGACGATTGG AAAGGCTTTT

ACTCAACGGA CAATAAATAT GATGCGGCCG GCTACTCCGT

GGACAACGAA AATCCGCTGA GCGGTAAAGC GGGCGGTGTC

GTGAAAGTTA CCTATCCGGG TCTGACGAAA GTGCTGGCTC

TGAAAGTTGA TAATGCGGAA ACCATCAAAA AGAACTGGG

CCTGTCCCTG ACCGAACCGC TGATGGAACA AGTGGGTACG

GAAGAATTTA TCAAACGTTT CGGCGACGGT GCCTCTCGCG

TTGTCCTGAG TCTGCCGTTT GCAGAAGGCT CATCGAGCGT

CGAATACATT AACAATTGGG AACAAGCAAA AGCTCTGAGC

GTGGAACTGG AAATCAACTT CGAAACGCGT GGCAAACGCG

GTCAGGATGC GATGTATGAA TACATGGCGC AAGCCTGCGC
```

-continued

```
AGGTAATCGT GTTCGTCGCT AAGGCTCAGG CTCAGGTCAG

TACATTAAAG CAAACTCAAA ATTCATTGGC ATTACCGAAC

TGGGATCC
```

Enzymes NdeI and BamHI were each added to the empty plasmid and the PCR product of the synthesized gene encoding the P30H21GP2 carrier protein to carry out a dual-enzyme restriction digestion. After purification, T4 ligase was added to the ligation mixture to ligate the fragments. After completion of the ligation reaction, the expression plasmid was purified, and verified using PCR verification methods and restriction digestion mapping. Using BL21(DE3) competent cells, the expression plasmid was transformed into the cells, and colonies were screened. After obtaining a positive clone of the engineered expression bacteria, a stock library was established, including master stocks and working stocks. The stock library was stored in the refrigerator at −20° C.

2-6. Construction of an Expression Plasmid for P2OVApH21GP30

A custom expression plasmid was used. Restriction enzyme Nde I was used to recognize sites having a CATATG sequence (SEQ ID NO:78), and restriction enzyme Bam HI was used to recognize sites having a GGATCC sequence (SEQ ID NO:79). The nucleic acid sequence of P2OVApH21GP30 was analyzed, and no Nde I or Bam HI recognition sites were found in the P2OVApH21GP30 sequence. The synthesized nucleic acid sequence encoding the P2OVApH21GP30 protein is as shown below in SEQ ID NO:63.

```
                                        (SEQ ID NO: 63)
CATATG CAGTACATTA AAGCAAACTC AAAAT TCAT TGGCATTACC

GAACTGGGTA GTGGTTCTGG TATCAGCCAA GCGGTTCACG

CAGCCCACGC CGAAATTAAC GAAGCGGGTC GCGGTAGCGG

TTCTGGCGGT GCCGACGACG TGGTTGATAG CTCTAAATCT

TTCGTTATGG AAAACTTCAG TTCCTATGGC GGTACCAAAC

CGGGCTACGT CGATTCGATT CAGAAAGGTA TCCAAAAACC

GAAAAGCGGC ACCCAGGGTA ACTATGATGA CGATTGGAAA

GGCTTTTACT CAACGGACAA TAAATATGAT GCGGCCGGCT

ACTCCGTGGA CAACGAAAAT CCGCTGAGCG GTAAAGCGGG

CGGTGTCGTG AAAGTTACCT ATCCGGGTCT GACGAAAGTG

CTGGCTCTGA AAGTTGATAA TGCGGAAACC ATCAAAAAAG

AACTGGGCCT GTCCCTGACC GAACCGCTGA TGGAACAAGT

GGGTACGGAA GAATTTATCA AACGTTTCGG CGACGGTGCC

TCTCGCGTTG TCCTGAGTCT GCCGTTTGCA GAAGGCTCAT

CGAGCGTCGA ATACATTAAC AATTGGGAAC AAGCAAAAGC

TCTGAGCGTG GAACTGGAAA TCAACTTCGA AACGCGTGGC

AAACGCGGTC AGGATGCGAT GTATGAATAC ATGGCGCAAG

CCTGCGCAGG TAATCGTGTT CGTCGCTAAG GTAGTGGTTC

TGGTTTCAAC AATTTTACGG TGTCTTTTTG GCTGCGTGTG

CCGAAAGTGT CTGCGAGTCA TCTGGAA GGATCC
```

Enzymes NdeI and BamHI were each added to the empty plasmid and the PCR product of the synthesized gene encoding the P2OVApH21GP30 carrier protein to carry out a dual-enzyme restriction digestion. After purification, T4 ligase was added to the ligation mixture to ligate the fragments. After completion of the ligation reaction, the expression plasmid was purified, and verified using PCR verification methods and restriction digestion mapping. Using BL21(DE3) competent cells, the expression plasmid was transformed into the cells, and colonies were screened. After obtaining a positive clone of the engineered expression bacteria, a stock library was established, including master stocks and working stocks. The stock library was stored in the refrigerator at −20° C.

III. Preparation of CoreVP8 Carrier Protein and H21G Chimeric Carrier Proteins Comprising a Universal Epitope Experiments have demonstrated similar properties of the H21G carrier protein and chimeric carrier proteins comprising the H21P carrier protein and universal epitopes. Therefore, purification methods for all carrier proteins described herein are similar. Described below is an exemplary method for preparing the H21P chimeric carrier protein comprising a universal epitope.

1. Preparation of Engineered Bacteria Expressing H21G Chimeric Carrier Proteins Comprising a Universal Epitope Each plasmid for expressing the chimeric carrier protein was transformed into competent cells using standard molecular biology methods, and was examined for protein expression. Clones that had high protein expression levels and passed the antisera tests were selected to establish a master stock library and a working stock library.

2. Fermentation of Engineered Bacteria Expressing H21G Chimeric Carrier Proteins Comprising a Universal Epitope See the methods described in the section “Fermentation of engineered bacteria expressing CRM197A chimeric carrier proteins comprising a universal epitope”.

3. Purification of H21G Chimeric Carrier Proteins Comprising a Universal Epitope Because H21G was used as a core component to construct different chimeric carrier proteins having universal epitopes, experiments showed that despite the addition of the universal epitopes, parameters for protein purification were not significantly affected. The purification procedure of the H21G carrier protein could be modified to establish purification methods for the H21G chimeric carrier proteins comprising a universal epitope.

50 g of wet bacteria were weighed in a 2 L centrifuge cup. To the cup was added 300 mL 1×PBS pH 7.0 buffer to re-suspend the bacteria. The bacteria suspension was thoroughly mixed on a magnetic stir plate for 30 minutes, and then centrifuged for 20 minutes at 4° C., 4000 rpm. The supernatant was discarded and the bacteria were collected. These steps were repeated for two times. To the centrifuge tube having the bacteria was added 300 mL 1×PBS pH 7.0. The bacteria were lysed in a homogenizer, and centrifuged for 20 minutes at 4° C., 10000 rpm. The pellet was collected and the supernatant was discarded. To the pellet was added 300 mL 1×PBS pH 7.0 buffer, and the mixture was thoroughly mixed on a magnetic stir plate for 30 minutes. The mixture was centrifuged for 20 minutes at 4° C., 4000 rpm. Inclusion body was collected, and the supernatant was discarded. 900 mL denaturing solution was added to the washed inclusion body. The mixture was then centrifuged for 30 minutes at 25° C., 10000 rpm. The supernatant was collected, and the pellet was discarded. The supernatant was transferred to a 6-8 KDA dialysis bag. The dialysis bag was sealed and placed in 10 L refolding buffer 1, and allowed to equilibrate over night at room temperature on a magnetic stir plate. The next day, the dialysis bag was transferred to 10 L refolding buffer 2, and stirred to equilibrate at room temperature for about 8-10 hours. The dialysis bag was transferred to 10 L dialysis buffer 3, and stirred to equilibrate at room temperature overnight. The next day, the dialysis bag was transferred to 10 L refolding buffer 4, and stirred to equilibrate at room temperature for about 8-10 hours. The dialysis bag was transferred to 10 L refolding buffer 5, and stirred to equilibrate at room temperature overnight. The next day, the dialysis bag was transferred to 2 L storage buffer, and stirred to equilibrate at room temperature for about 8-10 hours. The storage buffer was replaced two times, and dialysis was carried out at room temperature overnight. 1 mL dialysis solution was obtained, and centrifuged for 10 minutes at room temperature and 12000 rpm. The supernatant was collected, and the protein concentration was measured. The protein sample was loaded onto a pre-equilibrated DEAE gel column, and eluted with a gradient mode to collect the target protein peak. The collected sample was then loaded onto a Phenyl Sepharose column for further purification, and the eluted peak was collected. Finally, the collected sample was loaded onto a Q Sepharose gel column, and the eluted peak was collected. The collected purified target protein was transferred to a dialysis bag, and dialyzed against a 0.15 M NaCl buffer. The dialyzed sample was transferred to 4° C. for storage.

IV. Preparation of Polysaccharide-H21G Conjugates

Three different synthetic methods, namely reductive amination, CDAP method (using 3-(ethyliminomethyleneamino)-N,N-dimethyl-propan-1-amine), and ADH method (using adipic acid dihydrazide), were used to synthesize specific polysaccharide-H21G conjugates. The yield and immunogenic properties of conjugates formed by different synthetic methods can be different. In order to investigate the effect of different chimeric carrier proteins having universal epitopes on the immunogenicity of different bacterial polysaccharide (PS) conjugates, the present disclosure describes 13-valent Streptococcus pneumoniae (Pn) PS-H21G conjugates, Haemophilus influenza type b (Hib) PS-H21G conjugates, and 4-valent Neisseria meningitidis (Men) PS-H21G conjugates.

1. Preparation of 13-Valent Pn PS-H21G Protein (with or without Universal Epitopes) Conjugates 6 H21G chimeric carrier proteins having universal epitopes, including P30H21G, P30H21GP30, P2H21G, OVApH21G, P30H21GP2, and P2OVApH21GP30, were used to each synthesize a 13-valent Pn PS conjugate vaccine: 13Pn-P30H21G, 13Pn-P30H21GP30, 13Pn-P2H21G, 13Pn-OVApH21G, 13Pn-P30H21GP2, and 13Pn-P2OVApH21GP30. The methods for preparing these conjugates are similar to the methods for preparing the 13-valent Pn PS-CRM197A conjugate vaccines described above.

2. Preparation of Hib PS-H21G Protein (with or without Universal Epitopes) Conjugates 6 H21B chimeric carrier proteins having universal epitopes, including P30H21G, P30H21GP30, P2H21G, OVApH21G, P30H21GP2, and P2OVApH21GP30, were used to each synthesize a Hib PS conjugate vaccine: Hib-P30H21G, Hib-P30H21GP30, Hib-P2H21G, Hib-OVApH21G, Hib-P30H21GP2, and Hib-P2OVApH21GP30. The methods for preparing these conjugates are similar to the methods for preparing the Hib PS-CRM197A conjugate vaccines described above.

3. Preparation of 4-Valent Men PS-H21G Protein (with or without Universal Epitopes) Conjugates 6 H21G chimeric carrier proteins having universal epitopes, including P30H21G, P30H21GP30, P2H21G, OVApH21G, P30H21GP2, and P2OVApH21GP30, were used to each synthesize a 4-valent Men PS conjugate vaccine: 4Men-P30H21G, 4Men-P30H21GP30, 4Men-P2H21G, 4Men-OVApH21G, 4Men-P30H21GP2, and 4Men-P2OVApH21GP30. The methods for preparing these conjugates are similar to the methods for preparing the 4-valent Men PS-CRM197A conjugate vaccines described above.

V. Assessment of Immunogenicity of Polysaccharide-H2G Conjugate Vaccines

1. Assessment of Immunogenicity of 13-Valent Pn PS-H21G Conjugate Vaccines

Methods similar to those described in the previous sections "Assessment of immunogenicity of 13-valent Pn PS-P2CRM197A conjugate vaccines" were used to determine the titers of anti-PS IgG antibodies, the results are shown in Table 12 below. Table 12 only lists anti-PS IgG titers after three injections. The prepared 13-valent Pn PS-H21G conjugate vaccine was used to immunize mice and serum samples were obtained from the mice. Each mouse was injected with 0.1 mL of the vaccine solution, and the polysaccharide dosage is 10 µg/mouse/time.

TABLE 12

Anti-PS IgG titers in mice serum after three injections of 13-valent Pn PS-H21G conjugate vaccines.

| | Anti-Pn PS IgG antibody titer in mice serum after 3 injections (Eu) | | | | | | | | | | | | |
|---|---|---|---|---|---|---|---|---|---|---|---|---|---|
| Name of vaccine | Pn1 | Pn3 | Pn4 | Pn5 | Pn6A | Pn6B | Pn7F | Pn9V | Pn14 | Pn18C | Pn19A | Pn19F | Pn23F |
| 13Pn-P30H21G | 3.60 | 3.79 | 8.61 | 6.28 | 5.91 | 2.44 | 4.48 | 3.42 | 5.94 | 4.28 | 3.09 | 4.51 | 5.09 |
| 13Pn-P30H21GP30 | 3.54 | 4.15 | 7.74 | 6.48 | 5.32 | 2.65 | 4.83 | 4.05 | 5.85 | 4.78 | 2.81 | 4.65 | 4.69 |
| 13Pn-P2H21G | 4.76 | 5.01 | 10.25 | 7.39 | 6.74 | 4.25 | 6.43 | 4.89 | 6.60 | 6.74 | 4.11 | 5.18 | 4.36 |
| 13Pn-OVApH21G | 3.44 | 4.05 | 7.29 | 6.41 | 5.80 | 3.01 | 4.89 | 3.92 | 5.21 | 4.64 | 3.07 | 4.35 | 4.78 |
| 13Pn-P30H21GP2 | 4.66 | 5.84 | 11.25 | 8.08 | 6.58 | 4.44 | 7.02 | 4.91 | 7.19 | 6.69 | 4.55 | 5.21 | 4.88 |
| 13Pn-P2P30H21GOVAp | 3.78 | 4.11 | 6.83 | 5.84 | 5.37 | 2.98 | 4.56 | 4.02 | 5.55 | 4.78 | 2.79 | 4.54 | 3.82 |
| 13Pn-H21G (Control) | 1.96 | 0.98 | 1.45 | 1.77 | 0.92 | 1.01 | 1.59 | 0.79 | 1.21 | 1.47 | 1.05 | 1.56 | 0.90 |

Data from Table 12 showed that the immunogenicity of the 13-valent n PS-H2G conjugates comprising chimeric carrier proteins having universal epitopes were significantly enhanced compared to the 13-valent Pn PS-H21G conjugates comprising the CoreVP8 carrier protein without a universal epitope.

2. Assessment of the immunogenicity of Hib PS-H2G conjugate vaccines

Methods similar to those described in the previous sections "Assessment of immunogenicity of Hib PS-P2CRM197A conjugate vaccines" were used to determine the titers of anti-PS IgG antibodies using ELISA assays. The results are shown in Table 13 below.

TABLE 13

Anti-PS IgG titers in mice serum in response to Hib PS-H21G conjugate vaccines.

| Hib vaccine | Anti-Hib PS IgG antibody titer in mice serum (Eu) | | |
|---|---|---|---|
| | 1 injection | 2 injections | 3 injections |
| Hib-P30H21G | 0.04 | 2.33 | 4.57 |
| Hib-P30H21GP30 | 0.32 | 3.14 | 6.33 |
| Hib-P2H21G | 0.02 | 2.05 | 4.66 |
| Hib-OVApH21G | 0.03 | 2.39 | 5.77 |
| Hib-P30H21GP2 | 0.26 | 3.44 | 7.43 |
| Hib-P2OVApH21GP30 | 0.05 | 2.44 | 4.15 |
| Hib-H21G (Control) | 0.01 | 0.78 | 2.38 |

The titers of the anti-Hib PS antibody above showed similar results of the different types of Hib PS-H21G chimeric protein conjugates. Compared to the Hib PS-H21G protein conjugates without universal epitopes, the other six conjugates comprising H21G chimeric carrier proteins having universal epitopes, namely Hib-P30H21G, Hib-P30H21GP30, Hib-P2H21G, Hib-OVApH21G, Hib-P30H21GP2, and Hib-P2OVApH21GP30, had significantly enhanced IgG titers. The IgG titers of the serum samples after three injections compared to the IgG titers of the serum samples after one injection were also significantly different, with a $p<0.05$.

3. Assessment of the Immunogenicity of 4-Valent Men PS-H21G Conjugate Vaccines

Serum samples were obtained using similar methods as those described in the previous section "Assessment of immunogenicity of 13-valent Pn PS-P2CRM197A conjugate vaccines". Each mouse was injected with 0.1 mL of the vaccine solution, with a polysaccharide injection dose of 10 μg/mouse/time. ELISA assays were used to determine serum titers of antibodies against each polysaccharide group. The results are as shown in Table 14 below.

TABLE 14

Titers of anti-Men PS antibodies in mice serum.

| Vaccine | PS group | Anti-Men PS IgG antibody titer in mice serum (Eu) 1 injection | 2 injections | 3 injections |
|---|---|---|---|---|
| 4Men-P30H21G | A | 0.06 | 1.79 | 4.90 |
| | C | 0.03 | 1.54 | 4.50 |
| | Y | 0.02 | 1.78 | 5.22 |
| | W135 | 0.05 | 1.60 | 4.33 |
| 4Men-P30H21GP30 | A | 0.04 | 2.53 | 6.16 |
| | C | 0.04 | 2.44 | 5.52 |
| | Y | 0.02 | 1.89 | 7.19 |
| | W135 | 0.03 | 1.68 | 6.55 |
| 4Men-P2H21G | A | 0.23 | 1.65 | 5.44 |
| | C | 0.12 | 1.82 | 4.82 |
| | Y | 0.11 | 1.39 | 4.33 |
| | W135 | 0.14 | 1.47 | 4.06 |
| 4Men-OVApH21G | A | 0.03 | 1.42 | 3.55 |
| | C | 0.05 | 1.51 | 4.80 |
| | Y | 0.02 | 2.01 | 3.22 |
| | W135 | 0.04 | 1.39 | 3.80 |
| 4Men-P30H21GP2 | A | 0.18 | 2.34 | 7.11 |
| | C | 0.20 | 1.77 | 6.74 |
| | Y | 0.10 | 1.51 | 6.44 |
| | W135 | 0.15 | 1.92 | 8.10 |
| 4Men-P2OVApH21GP30 | A | 0.09 | 1.20 | 3.46 |
| | C | 0.10 | 1.35 | 2.82 |
| | Y | 0.09 | 1.40 | 3.64 |
| | W135 | 0.11 | 1.38 | 4.41 |
| 4Mne-H21G (control) | A | 0.03 | 0.65 | 1.46 |
| | C | 0.02 | 0.81 | 1.08 |
| | Y | 0.01 | 0.74 | 1.62 |
| | W135 | 0.01 | 0.73 | 1.11 |

The titers of the anti-Men PS antibody above showed similar results as the 13-valent Pn PS conjugates and the Hib PS conjugates. Compared to the 4-valent Men PS-H21G protein conjugates without universal epitopes, the conjugates comprising H21G chimeric carrier proteins having universal epitopes had significantly higher specific anti-PS IgG titers. The IgG titers of the serum samples after three injections compared to the IgG titers of the serum samples after one injection were also significantly different, with a $p<0.05$.

SEQUENCE LISTING

```
<160> NUMBER OF SEQ ID NOS: 79

<210> SEQ ID NO 1
<211> LENGTH: 15
<212> TYPE: PRT
<213> ORGANISM: Artificial Sequence
<220> FEATURE:
<223> OTHER INFORMATION: Tetanus toxoid P2 epitope

<400> SEQUENCE: 1

Gln Tyr Ile Lys Ala Asn Ser Lys Phe Ile Gly Ile Thr Glu Leu
1               5                   10                  15

<210> SEQ ID NO 2
<211> LENGTH: 21
<212> TYPE: PRT
<213> ORGANISM: Artificial Sequence
<220> FEATURE:
<223> OTHER INFORMATION: Tetanus toxoid P30 epitope
```

<400> SEQUENCE: 2

Phe Asn Asn Phe Thr Val Ser Phe Trp Leu Arg Val Pro Lys Val Ser
1               5                   10                  15

Ala Ser His Leu Glu
            20

<210> SEQ ID NO 3
<211> LENGTH: 17
<212> TYPE: PRT
<213> ORGANISM: Artificial Sequence
<220> FEATURE:
<223> OTHER INFORMATION: Tetanus toxoid OVAp epitope

<400> SEQUENCE: 3

Ile Ser Gln Ala Val His Ala Ala His Ala Glu Ile Asn Glu Ala Gly
1               5                   10                  15

Arg

<210> SEQ ID NO 4
<211> LENGTH: 193
<212> TYPE: PRT
<213> ORGANISM: Artificial Sequence
<220> FEATURE:
<223> OTHER INFORMATION: Diphtheria toxin CRM197A

<400> SEQUENCE: 4

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg

<210> SEQ ID NO 5
<211> LENGTH: 160
<212> TYPE: PRT
<213> ORGANISM: Artificial Sequence
<220> FEATURE:
<223> OTHER INFORMATION: Rotavirus CoreVP8

```
<400> SEQUENCE: 5

Leu Asp Gly Pro Tyr Gln Pro Thr Ser Leu Asn Leu Pro Val Asp Tyr
1               5                   10                  15

Trp Met Leu Ile Ala Pro Thr Arg Glu Gly Lys Val Ala Glu Gly Thr
            20                  25                  30

Asn Thr Thr Asp Arg Trp Phe Ala Cys Val Leu Val Glu Pro Asn Val
        35                  40                  45

Gln Asn Thr Gln Arg Gln Tyr Val Leu Asp Gly Arg Asn Val Gln Leu
    50                  55                  60

Asn Val Ser Asn Glu Ser Arg Thr Ser Trp Lys Phe Ile Leu Phe Ile
65                  70                  75                  80

Lys Leu Thr Pro Asp Gly Thr Tyr Thr Gln Tyr Ser Thr Leu Ser Thr
                85                  90                  95

Pro His Lys Leu Cys Ala Trp Met Lys Arg Asp Asn Arg Val Tyr Trp
            100                 105                 110

Tyr Gln Gly Ala Thr Pro Asn Ala Ser Glu Ser Tyr Tyr Leu Thr Ile
            115                 120                 125

Asn Asn Asp Asn Ser Asn Val Ser Ser Asp Ala Glu Phe Tyr Leu Ile
        130                 135                 140

Pro Gln Ser Gln Thr Ala Met Cys Thr Gln Tyr Ile Asn Asn Gly Leu
145                 150                 155                 160

<210> SEQ ID NO 6
<211> LENGTH: 193
<212> TYPE: PRT
<213> ORGANISM: Artificial Sequence
<220> FEATURE:
<223> OTHER INFORMATION: Diphtheria toxin H21G

<400> SEQUENCE: 6

Gly Ala Asp Asp Val Val Asp Ser Ser Lys Ser Phe Val Met Glu Asn
1               5                   10                  15

Phe Ser Ser Tyr Gly Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
            115                 120                 125

Asp Gly Ala Ser Arg Val Val Leu Ser Leu Pro Phe Ala Glu Gly Ser
        130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190
```

Arg

<210> SEQ ID NO 7
<211> LENGTH: 5
<212> TYPE: PRT
<213> ORGANISM: Artificial Sequence
<220> FEATURE:
<223> OTHER INFORMATION: linker

<400> SEQUENCE: 7

Gly Ser Gly Ser Gly
1               5

<210> SEQ ID NO 8
<211> LENGTH: 213
<212> TYPE: PRT
<213> ORGANISM: Artificial Sequence
<220> FEATURE:
<223> OTHER INFORMATION: P2CRM197A

<400> SEQUENCE: 8

Gln Tyr Ile Lys Ala Asn Ser Lys Phe Ile Gly Ile Thr Glu Leu Gly
1               5                   10                  15

Ser Gly Ser Gly Gly Ala Asp Asp Val Val Asp Ser Ser Lys Ser Phe
            20                  25                  30

Val Met Glu Asn Phe Ser Ser Tyr His Gly Thr Lys Pro Gly Tyr Val
        35                  40                  45

Asp Ser Ile Gln Lys Gly Ile Gln Lys Pro Lys Ser Gly Thr Gln Gly
    50                  55                  60

Asn Tyr Asp Asp Asp Trp Lys Glu Phe Tyr Ser Thr Asp Asn Lys Tyr
65                  70                  75                  80

Asp Ala Ala Gly Tyr Ser Val Asp Asn Glu Asn Pro Leu Ser Gly Lys
                85                  90                  95

Ala Gly Gly Val Val Lys Val Thr Tyr Pro Gly Leu Thr Lys Val Leu
            100                 105                 110

Ala Leu Lys Val Asp Asn Ala Glu Thr Ile Lys Lys Glu Leu Gly Leu
        115                 120                 125

Ser Leu Thr Glu Pro Leu Met Glu Gln Val Gly Thr Glu Glu Phe Ile
    130                 135                 140

Lys Arg Phe Gly Asp Gly Ala Ser Arg Val Val Leu Ser Leu Pro Phe
145                 150                 155                 160

Ala Glu Gly Ser Ser Ser Val Glu Tyr Ile Asn Asn Trp Glu Gln Ala
                165                 170                 175

Lys Ala Leu Ser Val Glu Leu Glu Ile Asn Phe Glu Thr Arg Gly Lys
            180                 185                 190

Arg Gly Gln Asp Ala Met Tyr Glu Tyr Met Ala Gln Ala Cys Ala Gly
        195                 200                 205

Asn Arg Val Arg Arg
    210

<210> SEQ ID NO 9
<211> LENGTH: 214
<212> TYPE: PRT
<213> ORGANISM: Artificial Sequence
<220> FEATURE:
<223> OTHER INFORMATION: CRM197AP2

<400> SEQUENCE: 9

Met Gly Ala Asp Asp Val Val Asp Ser Ser Lys Ser Phe Val Met Glu
1               5                   10                  15

-continued

```
Asn Phe Ser Ser Tyr His Gly Thr Lys Pro Gly Tyr Val Asp Ser Ile
         20                  25                  30

Gln Lys Gly Ile Gln Lys Pro Lys Ser Gly Thr Gln Gly Asn Tyr Asp
     35                  40                  45

Asp Asp Trp Lys Glu Phe Tyr Ser Thr Asp Asn Lys Tyr Asp Ala Ala
 50                  55                  60

Gly Tyr Ser Val Asp Asn Glu Asn Pro Leu Ser Gly Lys Ala Gly Gly
 65                  70                  75                  80

Val Val Lys Val Thr Tyr Pro Gly Leu Thr Lys Val Leu Ala Leu Lys
                 85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
130                 135                 140

Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Gly Ser Gly Ser Gly Gln Tyr Ile Lys Ala Asn Ser Lys Phe
        195                 200                 205

Ile Gly Ile Thr Glu Leu
    210
```

<210> SEQ ID NO 10
<211> LENGTH: 233
<212> TYPE: PRT
<213> ORGANISM: Artificial Sequence
<220> FEATURE:
<223> OTHER INFORMATION: P2CRM197AP2

<400> SEQUENCE: 10

```
Gln Tyr Ile Lys Ala Asn Ser Lys Phe Ile Gly Ile Thr Glu Leu Gly
 1               5                  10                  15

Ser Gly Ser Gly Gly Ala Asp Asp Val Val Asp Ser Ser Lys Ser Phe
             20                  25                  30

Val Met Glu Asn Phe Ser Ser Tyr His Gly Thr Lys Pro Gly Tyr Val
         35                  40                  45

Asp Ser Ile Gln Lys Gly Ile Gln Lys Pro Lys Ser Gly Thr Gln Gly
 50                  55                  60

Asn Tyr Asp Asp Asp Trp Lys Glu Phe Tyr Ser Thr Asp Asn Lys Tyr
 65                  70                  75                  80

Asp Ala Ala Gly Tyr Ser Val Asp Asn Glu Asn Pro Leu Ser Gly Lys
                 85                  90                  95

Ala Gly Gly Val Val Lys Val Thr Tyr Pro Gly Leu Thr Lys Val Leu
            100                 105                 110

Ala Leu Lys Val Asp Asn Ala Glu Thr Ile Lys Lys Glu Leu Gly Leu
        115                 120                 125

Ser Leu Thr Glu Pro Leu Met Glu Gln Val Gly Thr Glu Glu Phe Ile
130                 135                 140

Lys Arg Phe Gly Asp Gly Ala Ser Arg Val Val Leu Ser Leu Pro Phe
145                 150                 155                 160
```

Ala Glu Gly Ser Ser Val Glu Tyr Ile Asn Asn Trp Glu Gln Ala
            165                 170                 175

Lys Ala Leu Ser Val Glu Leu Glu Ile Asn Phe Glu Thr Arg Gly Lys
            180                 185                 190

Arg Gly Gln Asp Ala Met Tyr Glu Tyr Met Ala Gln Ala Cys Ala Gly
            195                 200                 205

Asn Arg Val Arg Arg Gly Ser Gly Ser Gly Gln Tyr Ile Lys Ala Asn
210                 215                 220

Ser Lys Phe Ile Gly Ile Thr Glu Leu
225                 230

<210> SEQ ID NO 11
<211> LENGTH: 233
<212> TYPE: PRT
<213> ORGANISM: Artificial Sequence
<220> FEATURE:
<223> OTHER INFORMATION: P2P2CRM197A

<400> SEQUENCE: 11

Gln Tyr Ile Lys Ala Asn Ser Lys Phe Ile Gly Ile Thr Glu Leu Gly
1               5                   10                  15

Ser Gly Ser Gly Gln Tyr Ile Lys Ala Asn Ser Lys Phe Ile Gly Ile
            20                  25                  30

Thr Glu Leu Gly Ser Gly Ser Gly Gly Ala Asp Asp Val Val Asp Ser
        35                  40                  45

Ser Lys Ser Phe Val Met Glu Asn Phe Ser Ser Tyr His Gly Thr Lys
50                  55                  60

Pro Gly Tyr Val Asp Ser Ile Gln Lys Gly Ile Gln Lys Pro Lys Ser
65                  70                  75                  80

Gly Thr Gln Gly Asn Tyr Asp Asp Asp Trp Lys Glu Phe Tyr Ser Thr
                85                  90                  95

Asp Asn Lys Tyr Asp Ala Ala Gly Tyr Ser Val Asp Asn Glu Asn Pro
            100                 105                 110

Leu Ser Gly Lys Ala Gly Gly Val Val Lys Val Thr Tyr Pro Gly Leu
        115                 120                 125

Thr Lys Val Leu Ala Leu Lys Val Asp Asn Ala Glu Thr Ile Lys Lys
130                 135                 140

Glu Leu Gly Leu Ser Leu Thr Glu Pro Leu Met Glu Gln Val Gly Thr
145                 150                 155                 160

Glu Glu Phe Ile Lys Arg Phe Gly Asp Gly Ala Ser Arg Val Val Leu
                165                 170                 175

Ser Leu Pro Phe Ala Glu Gly Ser Ser Ser Val Glu Tyr Ile Asn Asn
            180                 185                 190

Trp Glu Gln Ala Lys Ala Leu Ser Val Glu Leu Glu Ile Asn Phe Glu
        195                 200                 205

Thr Arg Gly Lys Arg Gly Gln Asp Ala Met Tyr Glu Tyr Met Ala Gln
    210                 215                 220

Ala Cys Ala Gly Asn Arg Val Arg Arg
225                 230

<210> SEQ ID NO 12
<211> LENGTH: 233
<212> TYPE: PRT
<213> ORGANISM: Artificial Sequence
<220> FEATURE:
<223> OTHER INFORMATION: CRM197AP2P2

<400> SEQUENCE: 12

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Gly Ser Gly Ser Gly Gln Tyr Ile Lys Ala Asn Ser Lys Phe Ile
        195                 200                 205

Gly Ile Thr Glu Leu Gly Ser Gly Ser Gly Gln Tyr Ile Lys Ala Asn
    210                 215                 220

Ser Lys Phe Ile Gly Ile Thr Glu Leu
225                 230

<210> SEQ ID NO 13
<211> LENGTH: 253
<212> TYPE: PRT
<213> ORGANISM: Artificial Sequence
<220> FEATURE:
<223> OTHER INFORMATION: P2P2CRM197AP2

<400> SEQUENCE: 13

Gln Tyr Ile Lys Ala Asn Ser Lys Phe Ile Gly Ile Thr Glu Leu Gly
1               5                   10                  15

Ser Gly Ser Gly Gln Tyr Ile Lys Ala Asn Ser Lys Phe Ile Gly Ile
            20                  25                  30

Thr Glu Leu Gly Ser Gly Ser Gly Ala Asp Asp Val Val Asp Ser Ser
        35                  40                  45

Ser Lys Ser Phe Val Met Glu Asn Phe Ser Ser Tyr His Gly Thr Lys
    50                  55                  60

Pro Gly Tyr Val Asp Ser Ile Gln Lys Gly Ile Gln Lys Pro Lys Ser
65                  70                  75                  80

Gly Thr Gln Gly Asn Tyr Asp Asp Asp Trp Lys Glu Phe Tyr Ser Thr
                85                  90                  95

Asp Asn Lys Tyr Asp Ala Ala Gly Tyr Ser Val Asp Asn Glu Asn Pro
            100                 105                 110

Leu Ser Gly Lys Ala Gly Gly Val Val Lys Val Thr Tyr Pro Gly Leu

```
            115                 120                 125
Thr Lys Val Leu Ala Leu Lys Val Asp Asn Ala Glu Thr Ile Lys Lys
    130                 135                 140

Glu Leu Gly Leu Ser Leu Thr Glu Pro Leu Met Glu Gln Val Gly Thr
145                 150                 155                 160

Glu Glu Phe Ile Lys Arg Phe Gly Asp Gly Ala Ser Arg Val Val Leu
                165                 170                 175

Ser Leu Pro Phe Ala Glu Gly Ser Ser Val Glu Tyr Ile Asn Asn
            180                 185                 190

Trp Glu Gln Ala Lys Ala Leu Ser Val Glu Leu Glu Ile Asn Phe Glu
                195                 200                 205

Thr Arg Gly Lys Arg Gly Gln Asp Ala Met Tyr Glu Tyr Met Ala Gln
    210                 215                 220

Ala Cys Ala Gly Asn Arg Val Arg Arg Gly Ser Gly Ser Gly Gln Tyr
225                 230                 235                 240

Ile Lys Ala Asn Ser Lys Phe Ile Gly Ile Thr Glu Leu
                245                 250
```

<210> SEQ ID NO 14
<211> LENGTH: 253
<212> TYPE: PRT
<213> ORGANISM: Artificial Sequence
<220> FEATURE:
<223> OTHER INFORMATION: P2CRM197AP2P2

<400> SEQUENCE: 14

```
Gln Tyr Ile Lys Ala Asn Ser Lys Phe Ile Gly Ile Thr Glu Leu Gly
1               5                   10                  15

Ser Gly Ser Gly Gly Ala Asp Asp Val Val Asp Ser Ser Lys Ser Phe
                20                  25                  30

Val Met Glu Asn Phe Ser Ser Tyr His Gly Thr Lys Pro Gly Tyr Val
            35                  40                  45

Asp Ser Ile Gln Lys Gly Ile Gln Lys Pro Lys Ser Gly Thr Gln Gly
50                  55                  60

Asn Tyr Asp Asp Asp Trp Lys Glu Phe Tyr Ser Thr Asp Asn Lys Tyr
65                  70                  75                  80

Asp Ala Ala Gly Tyr Ser Val Asp Asn Glu Asn Pro Leu Ser Gly Lys
                85                  90                  95

Ala Gly Gly Val Val Lys Val Thr Tyr Pro Gly Leu Thr Lys Val Leu
                100                 105                 110

Ala Leu Lys Val Asp Asn Ala Glu Thr Ile Lys Lys Glu Leu Gly Leu
            115                 120                 125

Ser Leu Thr Glu Pro Leu Met Glu Gln Val Gly Thr Glu Glu Phe Ile
130                 135                 140

Lys Arg Phe Gly Asp Gly Ala Ser Arg Val Val Leu Ser Leu Pro Phe
145                 150                 155                 160

Ala Glu Gly Ser Ser Ser Val Glu Tyr Ile Asn Asn Trp Glu Gln Ala
                165                 170                 175

Lys Ala Leu Ser Val Glu Leu Glu Ile Asn Phe Glu Thr Arg Gly Lys
            180                 185                 190

Arg Gly Gln Asp Ala Met Tyr Glu Tyr Met Ala Gln Ala Cys Ala Gly
                195                 200                 205

Asn Arg Val Arg Arg Gly Ser Gly Ser Gly Gln Tyr Ile Lys Ala Asn
            210                 215                 220

Ser Lys Phe Ile Gly Ile Thr Glu Leu Gly Ser Gly Ser Gly Gln Tyr
```

```
225                 230                 235                 240

Ile Lys Ala Asn Ser Lys Phe Ile Gly Ile Thr Glu Leu
                245                 250

<210> SEQ ID NO 15
<211> LENGTH: 219
<212> TYPE: PRT
<213> ORGANISM: Artificial Sequence
<220> FEATURE:
<223> OTHER INFORMATION: P30CRM197A

<400> SEQUENCE: 15

Phe Asn Asn Phe Thr Val Ser Phe Trp Leu Arg Val Pro Lys Val Ser
1               5                   10                  15

Ala Ser His Leu Glu Gly Ser Gly Ser Gly Gly Ala Asp Asp Val Val
            20                  25                  30

Asp Ser Ser Lys Ser Phe Val Met Glu Asn Phe Ser Ser Tyr His Gly
        35                  40                  45

Thr Lys Pro Gly Tyr Val Asp Ser Ile Gln Lys Gly Ile Gln Lys Pro
    50                  55                  60

Lys Ser Gly Thr Gln Gly Asn Tyr Asp Asp Asp Trp Lys Glu Phe Tyr
65                  70                  75                  80

Ser Thr Asp Asn Lys Tyr Asp Ala Ala Gly Tyr Ser Val Asp Asn Glu
                85                  90                  95

Asn Pro Leu Ser Gly Lys Ala Gly Gly Val Val Lys Val Thr Tyr Pro
            100                 105                 110

Gly Leu Thr Lys Val Leu Ala Leu Lys Val Asp Asn Ala Glu Thr Ile
        115                 120                 125

Lys Lys Glu Leu Gly Leu Ser Leu Thr Glu Pro Leu Met Glu Gln Val
    130                 135                 140

Gly Thr Glu Glu Phe Ile Lys Arg Phe Gly Asp Gly Ala Ser Arg Val
145                 150                 155                 160

Val Leu Ser Leu Pro Phe Ala Glu Gly Ser Ser Val Glu Tyr Ile
                165                 170                 175

Asn Asn Trp Glu Gln Ala Lys Ala Leu Ser Val Glu Leu Glu Ile Asn
            180                 185                 190

Phe Glu Thr Arg Gly Lys Arg Gly Gln Asp Ala Met Tyr Glu Tyr Met
        195                 200                 205

Ala Gln Ala Cys Ala Gly Asn Arg Val Arg Arg
    210                 215

<210> SEQ ID NO 16
<211> LENGTH: 220
<212> TYPE: PRT
<213> ORGANISM: Artificial Sequence
<220> FEATURE:
<223> OTHER INFORMATION: CRM197AP30

<400> SEQUENCE: 16

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Glu Phe Tyr Ser Thr Asp Asn Lys Tyr Asp Ala Ala
    50                  55                  60
```

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Gly Ser Gly Ser Gly Phe Asn Asn Phe Thr Val Ser Phe Trp
        195                 200                 205

Leu Arg Val Pro Lys Val Ser Ala Ser His Leu Glu
    210                 215                 220

<210> SEQ ID NO 17
<211> LENGTH: 245
<212> TYPE: PRT
<213> ORGANISM: Artificial Sequence
<220> FEATURE:
<223> OTHER INFORMATION: P30CRM197AP30

<400> SEQUENCE: 17

Phe Asn Asn Phe Thr Val Ser Phe Trp Leu Arg Val Pro Lys Val Ser
1               5                   10                  15

Ala Ser His Leu Glu Gly Ser Gly Ser Gly Gly Ala Asp Asp Val Val
                20                  25                  30

Asp Ser Ser Lys Ser Phe Val Met Glu Asn Phe Ser Ser Tyr His Gly
            35                  40                  45

Thr Lys Pro Gly Tyr Val Asp Ser Ile Gln Lys Gly Ile Gln Lys Pro
        50                  55                  60

Lys Ser Gly Thr Gln Gly Asn Tyr Asp Asp Asp Trp Lys Glu Phe Tyr
65                  70                  75                  80

Ser Thr Asp Asn Lys Tyr Asp Ala Ala Gly Tyr Ser Val Asp Asn Glu
                85                  90                  95

Asn Pro Leu Ser Gly Lys Ala Gly Gly Val Val Lys Val Thr Tyr Pro
            100                 105                 110

Gly Leu Thr Lys Val Leu Ala Leu Lys Val Asp Asn Ala Glu Thr Ile
        115                 120                 125

Lys Lys Glu Leu Gly Leu Ser Leu Thr Glu Pro Leu Met Glu Gln Val
    130                 135                 140

Gly Thr Glu Glu Phe Ile Lys Arg Phe Gly Asp Gly Ala Ser Arg Val
145                 150                 155                 160

Val Leu Ser Leu Pro Phe Ala Glu Gly Ser Ser Ser Val Glu Tyr Ile
                165                 170                 175

Asn Asn Trp Glu Gln Ala Lys Ala Leu Ser Val Glu Leu Glu Ile Asn
            180                 185                 190

Phe Glu Thr Arg Gly Lys Arg Gly Gln Asp Ala Met Tyr Glu Tyr Met
        195                 200                 205

```
Ala Gln Ala Cys Ala Gly Asn Arg Val Arg Arg Gly Ser Gly Ser Gly
    210                 215                 220

Phe Asn Asn Phe Thr Val Ser Phe Trp Leu Arg Val Pro Lys Val Ser
225                 230                 235                 240

Ala Ser His Leu Glu
            245

<210> SEQ ID NO 18
<211> LENGTH: 245
<212> TYPE: PRT
<213> ORGANISM: Artificial Sequence
<220> FEATURE:
<223> OTHER INFORMATION: P30P30CRM197A

<400> SEQUENCE: 18

Phe Asn Asn Phe Thr Val Ser Phe Trp Leu Arg Val Pro Lys Val Ser
1               5                   10                  15

Ala Ser His Leu Glu Gly Ser Gly Ser Gly Phe Asn Asn Phe Thr Val
            20                  25                  30

Ser Phe Trp Leu Arg Val Pro Lys Val Ser Ala Ser His Leu Glu Gly
        35                  40                  45

Ser Gly Ser Gly Gly Ala Asp Asp Val Val Asp Ser Ser Lys Ser Phe
50                  55                  60

Val Met Glu Asn Phe Ser Ser Tyr His Gly Thr Lys Pro Gly Tyr Val
65                  70                  75                  80

Asp Ser Ile Gln Lys Gly Ile Gln Lys Pro Lys Ser Gly Thr Gln Gly
                85                  90                  95

Asn Tyr Asp Asp Asp Trp Lys Glu Phe Tyr Ser Thr Asp Asn Lys Tyr
            100                 105                 110

Asp Ala Ala Gly Tyr Ser Val Asp Asn Glu Asn Pro Leu Ser Gly Lys
        115                 120                 125

Ala Gly Gly Val Val Lys Val Thr Tyr Pro Gly Leu Thr Lys Val Leu
    130                 135                 140

Ala Leu Lys Val Asp Asn Ala Glu Thr Ile Lys Lys Glu Leu Gly Leu
145                 150                 155                 160

Ser Leu Thr Glu Pro Leu Met Glu Gln Val Gly Thr Glu Glu Phe Ile
                165                 170                 175

Lys Arg Phe Gly Asp Gly Ala Ser Arg Val Val Leu Ser Leu Pro Phe
            180                 185                 190

Ala Glu Gly Ser Ser Ser Val Glu Tyr Ile Asn Asn Trp Glu Gln Ala
        195                 200                 205

Lys Ala Leu Ser Val Glu Leu Glu Ile Asn Phe Glu Thr Arg Gly Lys
    210                 215                 220

Arg Gly Gln Asp Ala Met Tyr Glu Tyr Met Ala Gln Ala Cys Ala Gly
225                 230                 235                 240

Asn Arg Val Arg Arg
            245

<210> SEQ ID NO 19
<211> LENGTH: 245
<212> TYPE: PRT
<213> ORGANISM: Artificial Sequence
<220> FEATURE:
<223> OTHER INFORMATION: CRM197AP30P30

<400> SEQUENCE: 19

Gly Ala Asp Asp Val Val Asp Ser Ser Lys Ser Phe Val Met Glu Asn
1               5                   10                  15
```

Phe Ser Ser Tyr His Gly Thr Lys Pro Gly Tyr Val Asp Ser Ile Gln
                 20                  25                  30

Lys Gly Ile Gln Lys Pro Lys Ser Gly Thr Gln Gly Asn Tyr Asp Asp
             35                  40                  45

Asp Trp Lys Glu Phe Tyr Ser Thr Asp Asn Lys Tyr Asp Ala Ala Gly
 50                  55                  60

Tyr Ser Val Asp Asn Glu Asn Pro Leu Ser Gly Lys Ala Gly Gly Val
 65                  70                  75                  80

Val Lys Val Thr Tyr Pro Gly Leu Thr Lys Val Leu Ala Leu Lys Val
                 85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
            115                 120                 125

Asp Gly Ala Ser Arg Val Val Leu Ser Leu Pro Phe Ala Glu Gly Ser
130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Gly Ser Gly Ser Gly Phe Asn Asn Phe Thr Val Ser Phe Trp Leu
            195                 200                 205

Arg Val Pro Lys Val Ser Ala Ser His Leu Glu Gly Ser Gly Ser Gly
            210                 215                 220

Phe Asn Asn Phe Thr Val Ser Phe Trp Leu Arg Val Pro Lys Val Ser
225                 230                 235                 240

Ala Ser His Leu Glu
            245

<210> SEQ ID NO 20
<211> LENGTH: 271
<212> TYPE: PRT
<213> ORGANISM: Artificial Sequence
<220> FEATURE:
<223> OTHER INFORMATION: P30P30CRM197AP30

<400> SEQUENCE: 20

Phe Asn Asn Phe Thr Val Ser Phe Trp Leu Arg Val Pro Lys Val Ser
 1               5                  10                  15

Ala Ser His Leu Glu Gly Ser Gly Ser Gly Phe Asn Asn Phe Thr Val
                 20                  25                  30

Ser Phe Trp Leu Arg Val Pro Lys Val Ser Ala Ser His Leu Glu Gly
             35                  40                  45

Ser Gly Ser Gly Gly Ala Asp Asp Val Val Asp Ser Ser Lys Ser Phe
 50                  55                  60

Val Met Glu Asn Phe Ser Ser Tyr His Gly Thr Lys Pro Gly Tyr Val
 65                  70                  75                  80

Asp Ser Ile Gln Lys Gly Ile Gln Lys Pro Lys Ser Gly Thr Gln Gly
                 85                  90                  95

Asn Tyr Asp Asp Asp Trp Lys Glu Phe Tyr Ser Thr Asp Asn Lys Tyr
            100                 105                 110

Asp Ala Ala Gly Tyr Ser Val Asp Asn Glu Asn Pro Leu Ser Gly Lys
            115                 120                 125

```
Ala Gly Gly Val Val Lys Val Thr Tyr Pro Gly Leu Thr Lys Val Leu
            130                 135                 140
Ala Leu Lys Val Asp Asn Ala Glu Thr Ile Lys Lys Glu Leu Gly Leu
145                 150                 155                 160
Ser Leu Thr Glu Pro Leu Met Glu Gln Val Gly Thr Glu Glu Phe Ile
                165                 170                 175
Lys Arg Phe Gly Asp Gly Ala Ser Arg Val Val Leu Ser Leu Pro Phe
            180                 185                 190
Ala Glu Gly Ser Ser Ser Val Glu Tyr Ile Asn Asn Trp Glu Gln Ala
        195                 200                 205
Lys Ala Leu Ser Val Glu Leu Glu Ile Asn Phe Glu Thr Arg Gly Lys
    210                 215                 220
Arg Gly Gln Asp Ala Met Tyr Glu Tyr Met Ala Gln Ala Cys Ala Gly
225                 230                 235                 240
Asn Arg Val Arg Arg Gly Ser Gly Ser Gly Phe Asn Asn Phe Thr Val
            245                 250                 255
Ser Phe Trp Leu Arg Val Pro Lys Val Ser Ala Ser His Leu Glu
            260                 265                 270

<210> SEQ ID NO 21
<211> LENGTH: 271
<212> TYPE: PRT
<213> ORGANISM: Artificial Sequence
<220> FEATURE:
<223> OTHER INFORMATION: P30CRM197AP30P30

<400> SEQUENCE: 21

Phe Asn Asn Phe Thr Val Ser Phe Trp Leu Arg Val Pro Lys Val Ser
1               5                   10                  15
Ala Ser His Leu Glu Gly Ser Gly Ser Gly Gly Ala Asp Asp Val Val
            20                  25                  30
Asp Ser Ser Lys Ser Phe Val Met Glu Asn Phe Ser Ser Tyr His Gly
        35                  40                  45
Thr Lys Pro Gly Tyr Val Asp Ser Ile Gln Lys Gly Ile Gln Lys Pro
    50                  55                  60
Lys Ser Gly Thr Gln Gly Asn Tyr Asp Asp Asp Trp Lys Glu Phe Tyr
65                  70                  75                  80
Ser Thr Asp Asn Lys Tyr Asp Ala Ala Gly Tyr Ser Val Asp Asn Glu
                85                  90                  95
Asn Pro Leu Ser Gly Lys Ala Gly Gly Val Val Lys Val Thr Tyr Pro
            100                 105                 110
Gly Leu Thr Lys Val Leu Ala Leu Lys Val Asp Asn Ala Glu Thr Ile
        115                 120                 125
Lys Lys Glu Leu Gly Leu Ser Leu Thr Glu Pro Leu Met Glu Gln Val
    130                 135                 140
Gly Thr Glu Glu Phe Ile Lys Arg Phe Gly Asp Gly Ala Ser Arg Val
145                 150                 155                 160
Val Leu Ser Leu Pro Phe Ala Glu Gly Ser Ser Ser Val Glu Tyr Ile
                165                 170                 175
Asn Asn Trp Glu Gln Ala Lys Ala Leu Ser Val Glu Leu Glu Ile Asn
            180                 185                 190
Phe Glu Thr Arg Gly Lys Arg Gly Gln Asp Ala Met Tyr Glu Tyr Met
        195                 200                 205
Ala Gln Ala Cys Ala Gly Asn Arg Val Arg Arg Gly Ser Gly Ser Gly
    210                 215                 220
```

```
Phe Asn Asn Phe Thr Val Ser Phe Trp Leu Arg Val Pro Lys Val Ser
225                 230                 235                 240

Ala Ser His Leu Glu Gly Ser Gly Ser Gly Phe Asn Asn Phe Thr Val
            245                 250                 255

Ser Phe Trp Leu Arg Val Pro Lys Val Ser Ala Ser His Leu Glu
        260                 265                 270
```

<210> SEQ ID NO 22
<211> LENGTH: 215
<212> TYPE: PRT
<213> ORGANISM: Artificial Sequence
<220> FEATURE:
<223> OTHER INFORMATION: OVApCRM197A

<400> SEQUENCE: 22

```
Ile Ser Gln Ala Val His Ala Ala His Ala Glu Ile Asn Glu Ala Gly
1               5                   10                  15

Arg Gly Ser Gly Ser Gly Gly Ala Asp Asp Val Val Asp Ser Ser Lys
            20                  25                  30

Ser Phe Val Met Glu Asn Phe Ser Ser Tyr His Gly Thr Lys Pro Gly
        35                  40                  45

Tyr Val Asp Ser Ile Gln Lys Gly Ile Gln Lys Pro Lys Ser Gly Thr
50                  55                  60

Gln Gly Asn Tyr Asp Asp Asp Trp Lys Glu Phe Tyr Ser Thr Asp Asn
65                  70                  75                  80

Lys Tyr Asp Ala Ala Gly Tyr Ser Val Asp Asn Glu Asn Pro Leu Ser
                85                  90                  95

Gly Lys Ala Gly Gly Val Val Lys Val Thr Tyr Pro Gly Leu Thr Lys
            100                 105                 110

Val Leu Ala Leu Lys Val Asp Asn Ala Glu Thr Ile Lys Lys Glu Leu
        115                 120                 125

Gly Leu Ser Leu Thr Glu Pro Leu Met Glu Gln Val Gly Thr Glu Glu
130                 135                 140

Phe Ile Lys Arg Phe Gly Asp Gly Ala Ser Arg Val Val Leu Ser Leu
145                 150                 155                 160

Pro Phe Ala Glu Gly Ser Ser Val Glu Tyr Ile Asn Asn Trp Glu
                165                 170                 175

Gln Ala Lys Ala Leu Ser Val Glu Leu Glu Ile Asn Phe Glu Thr Arg
            180                 185                 190

Gly Lys Arg Gly Gln Asp Ala Met Tyr Glu Tyr Met Ala Gln Ala Cys
        195                 200                 205

Ala Gly Asn Arg Val Arg Arg
210                 215
```

<210> SEQ ID NO 23
<211> LENGTH: 216
<212> TYPE: PRT
<213> ORGANISM: Artificial Sequence
<220> FEATURE:
<223> OTHER INFORMATION: CRM197AOVAp

<400> SEQUENCE: 23

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
```

```
            35                  40                  45
Asp Asp Trp Lys Glu Phe Tyr Ser Thr Asp Asn Lys Tyr Asp Ala Ala
 50                  55                  60

Gly Tyr Ser Val Asp Asn Glu Asn Pro Leu Ser Gly Lys Ala Gly Gly
 65                  70                  75                  80

Val Val Lys Val Thr Tyr Pro Gly Leu Thr Lys Val Leu Ala Leu Lys
                 85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Gly Ser Gly Ser Gly Ile Ser Gln Ala Val His Ala Ala His
        195                 200                 205

Ala Glu Ile Asn Glu Ala Gly Arg
    210                 215

<210> SEQ ID NO 24
<211> LENGTH: 237
<212> TYPE: PRT
<213> ORGANISM: Artificial Sequence
<220> FEATURE:
<223> OTHER INFORMATION: OVApCRM197AOVAp

<400> SEQUENCE: 24

Ile Ser Gln Ala Val His Ala Ala His Ala Glu Ile Asn Glu Ala Gly
 1               5                  10                  15

Arg Gly Ser Gly Ser Gly Gly Ala Asp Asp Val Val Asp Ser Ser Lys
                20                  25                  30

Ser Phe Val Met Glu Asn Phe Ser Ser Tyr His Gly Thr Lys Pro Gly
            35                  40                  45

Tyr Val Asp Ser Ile Gln Lys Gly Ile Gln Lys Pro Lys Ser Gly Thr
 50                  55                  60

Gln Gly Asn Tyr Asp Asp Asp Trp Lys Glu Phe Tyr Ser Thr Asp Asn
 65                  70                  75                  80

Lys Tyr Asp Ala Ala Gly Tyr Ser Val Asp Asn Glu Asn Pro Leu Ser
                 85                  90                  95

Gly Lys Ala Gly Gly Val Val Lys Val Thr Tyr Pro Gly Leu Thr Lys
            100                 105                 110

Val Leu Ala Leu Lys Val Asp Asn Ala Glu Thr Ile Lys Lys Glu Leu
        115                 120                 125

Gly Leu Ser Leu Thr Glu Pro Leu Met Glu Gln Val Gly Thr Glu Glu
    130                 135                 140

Phe Ile Lys Arg Phe Gly Asp Gly Ala Ser Arg Val Val Leu Ser Leu
145                 150                 155                 160

Pro Phe Ala Glu Gly Ser Ser Ser Val Glu Tyr Ile Asn Asn Trp Glu
                165                 170                 175

Gln Ala Lys Ala Leu Ser Val Glu Leu Glu Ile Asn Phe Glu Thr Arg
```

```
                180                 185                 190
Gly Lys Arg Gly Gln Asp Ala Met Tyr Glu Tyr Met Ala Gln Ala Cys
            195                 200                 205

Ala Gly Asn Arg Val Arg Gly Ser Gly Ser Gly Ile Ser Gln Ala
            210                 215                 220

Val His Ala Ala His Ala Glu Ile Asn Glu Ala Gly Arg
225                 230                 235
```

<210> SEQ ID NO 25
<211> LENGTH: 237
<212> TYPE: PRT
<213> ORGANISM: Artificial Sequence
<220> FEATURE:
<223> OTHER INFORMATION: OVApOVApCRM197A

<400> SEQUENCE: 25

```
Ile Ser Gln Ala Val His Ala Ala His Ala Glu Ile Asn Glu Ala Gly
1               5                   10                  15

Arg Gly Ser Gly Ser Gly Ile Ser Gln Ala Val His Ala His Ala
            20                  25                  30

Glu Ile Asn Glu Ala Gly Arg Gly Ser Gly Ser Gly Gly Ala Asp Asp
            35                  40                  45

Val Val Asp Ser Ser Lys Ser Phe Val Met Glu Asn Phe Ser Ser Tyr
50                  55                  60

His Gly Thr Lys Pro Gly Tyr Val Asp Ser Ile Gln Lys Gly Ile Gln
65                  70                  75                  80

Lys Pro Lys Ser Gly Thr Gln Gly Asn Tyr Asp Asp Asp Trp Lys Glu
            85                  90                  95

Phe Tyr Ser Thr Asp Asn Lys Tyr Asp Ala Ala Gly Tyr Ser Val Asp
            100                 105                 110

Asn Glu Asn Pro Leu Ser Gly Lys Ala Gly Gly Val Val Lys Val Thr
            115                 120                 125

Tyr Pro Gly Leu Thr Lys Val Leu Ala Leu Lys Val Asp Asn Ala Glu
            130                 135                 140

Thr Ile Lys Lys Glu Leu Gly Leu Ser Leu Thr Glu Pro Leu Met Glu
145                 150                 155                 160

Gln Val Gly Thr Glu Glu Phe Ile Lys Arg Phe Gly Asp Gly Ala Ser
            165                 170                 175

Arg Val Val Leu Ser Leu Pro Phe Ala Glu Gly Ser Ser Ser Val Glu
            180                 185                 190

Tyr Ile Asn Asn Trp Glu Gln Ala Lys Ala Leu Ser Val Glu Leu Glu
            195                 200                 205

Ile Asn Phe Glu Thr Arg Gly Lys Arg Gly Gln Asp Ala Met Tyr Glu
            210                 215                 220

Tyr Met Ala Gln Ala Cys Ala Gly Asn Arg Val Arg Arg
225                 230                 235
```

<210> SEQ ID NO 26
<211> LENGTH: 237
<212> TYPE: PRT
<213> ORGANISM: Artificial Sequence
<220> FEATURE:
<223> OTHER INFORMATION: CRM197AOVApOVAp

<400> SEQUENCE: 26

```
Gly Ala Asp Asp Val Val Asp Ser Ser Lys Ser Phe Val Met Glu Asn
1               5                   10                  15
```

```
Phe Ser Ser Tyr His Gly Thr Lys Pro Gly Tyr Val Asp Ser Ile Gln
                20                  25                  30

Lys Gly Ile Gln Lys Pro Lys Ser Gly Thr Gln Gly Asn Tyr Asp Asp
            35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Gly Ser Gly Ser Gly Ile Ser Gln Ala Val His Ala Ala His Ala
        195                 200                 205

Glu Ile Asn Glu Ala Gly Arg Gly Ser Gly Ser Gly Ile Ser Gln Ala
    210                 215                 220

Val His Ala Ala His Ala Glu Ile Asn Glu Ala Gly Arg
225                 230                 235

<210> SEQ ID NO 27
<211> LENGTH: 259
<212> TYPE: PRT
<213> ORGANISM: Artificial Sequence
<220> FEATURE:
<223> OTHER INFORMATION: OVApOVApCRM197AOVAp

<400> SEQUENCE: 27

Ile Ser Gln Ala Val His Ala Ala His Ala Glu Ile Asn Glu Ala Gly
1               5                   10                  15

Arg Gly Ser Gly Ser Gly Ile Ser Gln Ala Val His Ala Ala His Ala
            20                  25                  30

Glu Ile Asn Glu Ala Gly Arg Gly Ser Gly Ser Gly Ala Asp Asp
        35                  40                  45

Val Val Asp Ser Ser Lys Ser Phe Val Met Glu Asn Phe Ser Ser Tyr
    50                  55                  60

His Gly Thr Lys Pro Gly Tyr Val Asp Ser Ile Gln Lys Gly Ile Gln
65                  70                  75                  80

Lys Pro Lys Ser Gly Thr Gln Gly Asn Tyr Asp Asp Trp Lys Glu
                85                  90                  95

Phe Tyr Ser Thr Asp Asn Lys Tyr Asp Ala Ala Gly Tyr Ser Val Asp
            100                 105                 110

Asn Glu Asn Pro Leu Ser Gly Lys Ala Gly Gly Val Val Lys Val Thr
        115                 120                 125

Tyr Pro Gly Leu Thr Lys Val Leu Ala Leu Lys Val Asp Asn Ala Glu
    130                 135                 140
```

```
Thr Ile Lys Lys Glu Leu Gly Leu Ser Leu Thr Glu Pro Leu Met Glu
145                 150                 155                 160

Gln Val Gly Thr Glu Glu Phe Ile Lys Arg Phe Gly Asp Gly Ala Ser
                165                 170                 175

Arg Val Val Leu Ser Leu Pro Phe Ala Glu Gly Ser Ser Ser Val Glu
            180                 185                 190

Tyr Ile Asn Asn Trp Glu Gln Ala Lys Ala Leu Ser Val Glu Leu Glu
        195                 200                 205

Ile Asn Phe Glu Thr Arg Gly Lys Arg Gly Gln Asp Ala Met Tyr Glu
    210                 215                 220

Tyr Met Ala Gln Ala Cys Ala Gly Asn Arg Val Arg Arg Gly Ser Gly
225                 230                 235                 240

Ser Gly Ile Ser Gln Ala Val His Ala Ala His Ala Glu Ile Asn Glu
                245                 250                 255

Ala Gly Arg

<210> SEQ ID NO 28
<211> LENGTH: 259
<212> TYPE: PRT
<213> ORGANISM: Artificial Sequence
<220> FEATURE:
<223> OTHER INFORMATION: OVApCRM197AOVApOVAp

<400> S

<210> SEQ ID NO 29
<211> LENGTH: 239
<212> TYPE: PRT
<213> ORGANISM: Artificial Sequence
<220> FEATURE:
<223> OTHER INFORMATION: P2CRM197AP30

<400> SEQUENCE: 29

```
Gln Tyr Ile Lys Ala Asn Ser Lys Phe Ile Gly Ile Thr Glu Leu Gly
1               5                   10                  15
Ser Gly Ser Gly Gly Ala Asp Asp Val Val Asp Ser Ser Lys Ser Phe
            20                  25                  30
Val Met Glu Asn Phe Ser Ser Tyr His Gly Thr Lys Pro Gly Tyr Val
        35                  40                  45
Asp Ser Ile Gln Lys Gly Ile Gln Lys Pro Lys Ser Gly Thr Gln Gly
    50                  55                  60
Asn Tyr Asp Asp Asp Trp Lys Glu Phe Tyr Ser Thr Asp Asn Lys Tyr
65                  70                  75                  80
Asp Ala Ala Gly Tyr Ser Val Asp Asn Glu Asn Pro Leu Ser Gly Lys
                85                  90                  95
Ala Gly Gly Val Val Lys Val Thr Tyr Pro Gly Leu Thr Lys Val Leu
            100                 105                 110
Ala Leu Lys Val Asp Asn Ala Glu Thr Ile Lys Lys Glu Leu Gly Leu
        115                 120                 125
Ser Leu Thr Glu Pro Leu Met Glu Gln Val Gly Thr Glu Glu Phe Ile
    130                 135                 140
Lys Arg Phe Gly Asp Gly Ala Ser Arg Val Val Leu Ser Leu Pro Phe
145                 150                 155                 160
Ala Glu Gly Ser Ser Ser Val Glu Tyr Ile Asn Asn Trp Glu Gln Ala
                165                 170                 175
Lys Ala Leu Ser Val Glu Leu Glu Ile Asn Phe Glu Thr Arg Gly Lys
            180                 185                 190
Arg Gly Gln Asp Ala Met Tyr Glu Tyr Met Ala Gln Ala Cys Ala Gly
        195                 200                 205
Asn Arg Val Arg Arg Gly Ser Gly Ser Gly Phe Asn Asn Phe Thr Val
    210                 215                 220
Ser Phe Trp Leu Arg Val Pro Lys Val Ser Ala Ser His Leu Glu
225                 230                 235
```

<210> SEQ ID NO 30
<211> LENGTH: 239
<212> TYPE: PRT
<213> ORGANISM: Artificial Sequence
<220> FEATURE:
<223> OTHER INFORMATION: P30CRM197AP2

<400> SEQUENCE: 30

```
Phe Asn Asn Phe Thr Val Ser Phe Trp Leu Arg Val Pro Lys Val Ser
1               5                   10                  15
Ala Ser His Leu Glu Gly Ser Gly Ser Gly Gly Ala Asp Asp Val Val
            20                  25                  30
Asp Ser Ser Lys Ser Phe Val Met Glu Asn Phe Ser Ser Tyr His Gly
        35                  40                  45
Thr Lys Pro Gly Tyr Val Asp Ser Ile Gln Lys Gly Ile Gln Lys Pro
```

```
        50                  55                  60
Lys Ser Gly Thr Gln Gly Asn Tyr Asp Asp Trp Lys Glu Phe Tyr
 65                  70                  75                  80

Ser Thr Asp Asn Lys Tyr Asp Ala Ala Gly Tyr Ser Val Asp Asn Glu
                 85                  90                  95

Asn Pro Leu Ser Gly Lys Ala Gly Val Val Lys Val Thr Tyr Pro
            100                 105                 110

Gly Leu Thr Lys Val Leu Ala Leu Lys Val Asp Asn Ala Glu Thr Ile
            115                 120                 125

Lys Lys Glu Leu Gly Leu Ser Leu Thr Glu Pro Leu Met Glu Gln Val
130                 135                 140

Gly Thr Glu Glu Phe Ile Lys Arg Phe Gly Asp Gly Ala Ser Arg Val
145                 150                 155                 160

Val Leu Ser Leu Pro Phe Ala Glu Gly Ser Ser Val Glu Tyr Ile
            165                 170                 175

Asn Asn Trp Glu Gln Ala Lys Ala Leu Ser Val Glu Leu Glu Ile Asn
            180                 185                 190

Phe Glu Thr Arg Gly Lys Arg Gly Gln Asp Ala Met Tyr Glu Tyr Met
            195                 200                 205

Ala Gln Ala Cys Ala Gly Asn Arg Val Arg Arg Gly Ser Gly Ser Gly
            210                 215                 220

Gln Tyr Ile Lys Ala Asn Ser Lys Phe Ile Gly Ile Thr Glu Leu
225                 230                 235

<210> SEQ ID NO 31
<211> LENGTH: 259
<212> TYPE: PRT
<213> ORGANISM: Artificial Sequence
<220> FEATURE:
<223> OTHER INFORMATION: P30CRM197AP2

<400> SEQUENCE: 31

Gln Tyr Ile Lys Ala Asn Ser Lys Phe Ile Gly Ile Thr Glu Leu Gly
 1               5                  10                  15

Ser Gly Ser Gly Phe Asn Asn Phe Thr Val Ser Phe Trp Leu Arg Val
            20                  25                  30

Pro Lys Val Ser Ala Ser His Leu Glu Gly Ser Gly Ser Gly Gly Ala
            35                  40                  45

Asp Asp Val Val Asp Ser Ser Lys Ser Phe Val Met Glu Asn Phe Ser
 50                  55                  60

Ser Tyr His Gly Thr Lys Pro Gly Tyr Val Asp Ser Ile Gln Lys Gly
 65                  70                  75                  80

Ile Gln Lys Pro Lys Ser Gly Thr Gln Gly Asn Tyr Asp Asp Trp
                85                  90                  95

Lys Glu Phe Tyr Ser Thr Asp Asn Lys Tyr Asp Ala Ala Gly Tyr Ser
            100                 105                 110

Val Asp Asn Glu Asn Pro Leu Ser Gly Lys Ala Gly Val Val Lys
            115                 120                 125

Val Thr Tyr Pro Gly Leu Thr Lys Val Leu Ala Leu Lys Val Asp Asn
            130                 135                 140

Ala Glu Thr Ile Lys Lys Glu Leu Gly Leu Ser Leu Thr Glu Pro Leu
145                 150                 155                 160

Met Glu Gln Val Gly Thr Glu Glu Phe Ile Lys Arg Phe Gly Asp Gly
                165                 170                 175

Ala Ser Arg Val Val Leu Ser Leu Pro Phe Ala Glu Gly Ser Ser Ser
```

```
                180                 185                 190
Val Glu Tyr Ile Asn Asn Trp Glu Gln Ala Lys Ala Leu Ser Val Glu
            195                 200                 205

Leu Glu Ile Asn Phe Glu Thr Arg Gly Lys Arg Gly Gln Asp Ala Met
        210                 215                 220

Tyr Glu Tyr Met Ala Gln Ala Cys Ala Gly Asn Arg Val Arg Arg Gly
225                 230                 235                 240

Ser Gly Ser Gly Gln Tyr Ile Lys Ala Asn Ser Lys Phe Ile Gly Ile
            245                 250                 255

Thr Glu Leu

<210> SEQ ID NO 32
<211> LENGTH: 261
<212> TYPE: PRT
<213> ORGANISM: Artificial Sequence
<220> FEATURE:
<223> OTHER INFORMATION: P2P30CRM197AOVAp

<400> SEQUENCE: 32

Gln Tyr Ile Lys Ala Asn Ser Lys Phe Ile Gly Ile Thr Glu Leu Gly
1               5                   10                  15

Ser Gly Ser Gly Phe Asn Asn Phe Thr Val Ser Phe Trp Leu Arg Val
            20                  25                  30

Pro Lys Val Ser Ala Ser His Leu Glu Gly Ser Gly Ser Gly Gly Ala
        35                  40                  45

Asp Asp Val Val Asp Ser Ser Lys Ser Phe Val Met Glu Asn Phe Ser
50                  55                  60

Ser Tyr His Gly Thr Lys Pro Gly Tyr Val Asp Ser Ile Gln Lys Gly
65                  70                  75                  80

Ile Gln Lys Pro Lys Ser Gly Thr Gln Gly Asn Tyr Asp Asp Asp Trp
                85                  90                  95

Lys Glu Phe Tyr Ser Thr Asp Asn Lys Tyr Asp Ala Ala Gly Tyr Ser
            100                 105                 110

Val Asp Asn Glu Asn Pro Leu Ser Gly Lys Ala Gly Gly Val Val Lys
        115                 120                 125

Val Thr Tyr Pro Gly Leu Thr Lys Val Leu Ala Leu Lys Val Asp Asn
130                 135                 140

Ala Glu Thr Ile Lys Lys Glu Leu Gly Leu Ser Leu Thr Glu Pro Leu
145                 150                 155                 160

Met Glu Gln Val Gly Thr Glu Glu Phe Ile Lys Arg Phe Gly Asp Gly
                165                 170                 175

Ala Ser Arg Val Val Leu Ser Leu Pro Phe Ala Glu Gly Ser Ser Ser
            180                 185                 190

Val Glu Tyr Ile Asn Asn Trp Glu Gln Ala Lys Ala Leu Ser Val Glu
        195                 200                 205

Leu Glu Ile Asn Phe Glu Thr Arg Gly Lys Arg Gly Gln Asp Ala Met
    210                 215                 220

Tyr Glu Tyr Met Ala Gln Ala Cys Ala Gly Asn Arg Val Arg Arg Gly
225                 230                 235                 240

Ser Gly Ser Gly Ile Ser Gln Ala Val His Ala Ala His Ala Glu Ile
                245                 250                 255

Asn Glu Ala Gly Arg
            260

<210> SEQ ID NO 33
```

<211> LENGTH: 594
<212> TYPE: DNA
<213> ORGANISM: Artificial Sequence
<220> FEATURE:
<223> OTHER INFORMATION: CRM197A

<400> SEQUENCE: 33

```
catatgggtg cggacgacgt tgtggactcc tcaaaatcgt tgtcatgga aaacttcagc    60
tcttatcatg gcaccaaacc gggttacgtg gactccattc agaagggcat ccaaaaaccg   120
aagtcaggca cccagggtaa ctacgatgac gattggaagg aattctacag cacggacaat   180
aagtatgatg cggccggcta ctctgttgac aacgaaaatc cgctgagtgg taaagcaggc   240
ggtgtggtta aggtcaccta tccgggtctg acgaaagttc tggcgctgaa ggtcgataac   300
gccgaaacca ttaaaaagga actgggcctg tctctgaccg aaccgctgat ggaacaagtg   360
ggtacggaag aatttatcaa acgtttcggc gatggtgcat cgcgtgtcgt gctgagcctg   420
ccgtttgctg aaggcagttc ctcagtggaa tacattaaca attgggaaca agcaaaagct   480
ctgtcagttg aactggaaat caatttcgaa acgcgtggca acgcggtca agatgctatg   540
tatgaatata tggctcaggc gtgtgcgggc aatcgcgtcc gtcgctaagg atcc          594
```

<210> SEQ ID NO 34
<211> LENGTH: 652
<212> TYPE: DNA
<213> ORGANISM: Artificial Sequence
<220> FEATURE:
<223> OTHER INFORMATION: P2CRM197A

<400> SEQUENCE: 34

```
catatgcaat acatcaaggc gaacagcaaa ttcatcggca tcacggaact gggctcgggc    60
tctggcgtgc ggacgacgtt gtggactcct caaaatcgtt gtcatggaa aacttcagct   120
cttatatggc accaaaccgg ttacgtgga ctccattcag aagggcatcc aaaaaccgaa   180
gtcaggcacc cagggtaact acgatgacga ttggaaggaa ttctacagca cggacaataa   240
gtatgatgcg gccggctact ctgttgacaa cgaaaatccg ctgagtggta agcaggcgg   300
tgtggttaag gtcacctatc cgggtctgac gaaagttctg gcgctgaagg tcgataacgc   360
cgaaaccatt aaaaaggaac tgggcctgtc tctgaccgaa ccgctgatgg aacaagtggg   420
tacggaagaa tttatcaaac gtttcggcga tggtgcatcg cgtgtcgtgc tgagcctgcc   480
gtttgctgaa ggcagttcct cagtggaata cattaacaat tgggaacaag caaaagctct   540
gtcagttgaa ctggaaatca atttcgaaac gcgtggcaaa cgcggtcaag atgctatgta   600
tgaatatatg gctcaggcgt gtgcgggcaa tcgcgtccgt cgctaaggat cc            652
```

<210> SEQ ID NO 35
<211> LENGTH: 712
<212> TYPE: DNA
<213> ORGANISM: Artificial Sequence
<220> FEATURE:
<223> OTHER INFORMATION: P2CRM197AP2

<400> SEQUENCE: 35

```
catatgcaat acatcaaggc gaacagcaaa ttcatcggca tcacggaact gggctcgggc    60
tctggcgtgc ggacgacgtt gtggactcct caaaatcgtt gtcatggaa aacttcagct   120
cttatatggc accaaaccgg ttacgtgga ctccattcag aagggcatcc aaaaaccgaa   180
gtcaggcacc cagggtaact acgatgacga ttggaaggaa ttctacagca cggacaataa   240
gtatgatgcg gccggctact ctgttgacaa cgaaaatccg ctgagtggta agcaggcgg   300
```

| | | |
|---|---|---|
| tgtggttaag gtcacctatc cgggtctgac gaaagttctg gcgctgaagg tcgataacgc | 360 |
| cgaaaccatt aaaaaggaac tgggcctgtc tctgaccgaa ccgctgatgg aacaagtggg | 420 |
| tacggaagaa tttatcaaac gtttcggcga tggtgcatcg cgtgtcgtgc tgagcctgcc | 480 |
| gtttgctgaa ggcagttcct cagtggaata cattaacaat tgggaacaag caaaagctct | 540 |
| gtcagttgaa ctggaaatca atttcgaaac gcgtggcaaa cgcggtcaag atgctatgta | 600 |
| tgaatatatg gctcaggcgt gtgcgggcaa tcgcgtccgt cgctaaggct cgggtctgg | 660 |
| ccaatacatc aaggcgaaca gcaaattcat cggcatcacg gaactgggat cc | 712 |

<210> SEQ ID NO 36
<211> LENGTH: 669
<212> TYPE: DNA
<213> ORGANISM: Artificial Sequence
<220> FEATURE:
<223> OTHER INFORMATION: P30CRM197A

<400> SEQUENCE: 36

| | | |
|---|---|---|
| catatgttca ataattttac ggtgtcgttt tggctgcgtg tcccgaaagt ctctgcgagt | 60 |
| catctggaag ttctggtag cggtggtgcg gatgacgtgg ttgatagctc taaatctttc | 120 |
| gttatggaaa acttcagttc ctatcatggc accaaaccgg gttacgtcga ttcgattcag | 180 |
| aaaggcatcc aaaaaccgaa aagcggcacc cagggtaact acgatgacga ttggaaagaa | 240 |
| ttctactcaa cggacaacaa atacgatgcg ccggctact ccgtggacaa cgaaaatccg | 300 |
| ctgagcggta agcgggcgg tgtcgtgaaa gttacctatc cgggtctgac gaaagtgctg | 360 |
| gctctgaaag ttgataatgc ggaaaccatc aaaaaagaac tgggcctgtc cctgaccgaa | 420 |
| ccgctgatgg aacaagtggg tacggaagaa tttatcaaac gtttcggcga cggtgcctct | 480 |
| cgcgttgtcc tgagtctgcc gtttgcagaa ggctcatcga gcgtcgaata cattaacaat | 540 |
| tgggaacaag caaaagctct gagcgttgaa ctggaaatca acttcgaaac gcgtggcaaa | 600 |
| cgcggtcagg atgcgatgta tgaatacatg gcgcaagcct gcgcaggtaa tcgtgttcgt | 660 |
| cgcggatcc | 669 |

<210> SEQ ID NO 37
<211> LENGTH: 660
<212> TYPE: DNA
<213> ORGANISM: Artificial Sequence
<220> FEATURE:
<223> OTHER INFORMATION: OVApCRM197A

<400> SEQUENCE: 37

| | | |
|---|---|---|
| catatgatca gccaagcggt tcacgcagcc cacgccgaaa ttaacgaagc gggtcgcggt | 60 |
| agcggttctg gcgtgcaga cgatgttgtt gactccagca atcattcgt catggaaaac | 120 |
| tttagctctt atcatggcac caaaccgggt tacgtggact ccattcagaa aggcatccaa | 180 |
| aaaccgaaat caggcacccca gggtaactat gatgacgatt ggaagaatt ctactctacg | 240 |
| gacaacaaat acgatgcggc cggctactct gttgacaacg aaaatccgct gagtggtaaa | 300 |
| gcaggcggtg tggttaaagt cacctatccg ggtctgacga agttctggc gctgaaagtc | 360 |
| gataacgccg aaaccatcaa aaaagaactg ggcctgtcgc tgaccgaacc gctgatggaa | 420 |
| caagtgggta cggaagaatt tatcaaacgt ttcggcgatg gtgcatcgcg tgtcgtgctg | 480 |
| agcctgccgt ttgctgaagg cagttcctca gtggaataca ttaacaattg ggaacaagca | 540 |
| aaagctctga gtgttgaact ggaaatcaat ttcgaaacgc gtggtaaacg cggtcaggac | 600 |

```
gcaatgtatg aatatatggc ccaggcttgt gcaggcaacc gtgttcgccg ttaaggatcc      660
```

<210> SEQ ID NO 38
<211> LENGTH: 729
<212> TYPE: DNA
<213> ORGANISM: Artificial Sequence
<220> FEATURE:
<223> OTHER INFORMATION: P30CRM197AP2

<400> SEQUENCE: 38

```
catatgttca acaattttac ggtctcgttt tggctgcgtg tcccgaaagt gtctgcctca       60
catctggaag gtagcggttc aggtggtgcg gatgacgtgg ttgatagctc taaatccttt      120
gttatggaaa acttcagttc ctatcatggt accaaaccgg gctacgtcga ttctattcag      180
aaaggtatcc aaaaaccgaa aagtggtacc cagggcaact atgatgacga ttggaaagaa      240
ttctactcta cggacaacaa atacgatgcg gccggttact cggtggacaa cgaaaatccg      300
ctgagcggta agccggcgg tgtcgtgaaa gttacctatc cgggcctgac gaaagtgctg      360
gctctgaaag ttgataacgc ggaaaccatc aaaaaagaac tgggtctgag cctgaccgaa      420
ccgctgatgg aacaagtggg cacggaagaa tttatcaaac gtttcggtga cggtgcatcc      480
cgtgttgtcc tgtcactgcc gtttgcagaa ggttcatcga cgtcgaata tcatcaacaac      540
tgggaacaag caaaagctct gagcgtggac tggaaatca atttcgaaac ccgtggtaaa      600
cgcggccagg atgctatgta tgaatacatg gcgcaagcct gcgcaggtaa ccgtgttcgt      660
cgcggctctg gtagtggcca gtacatcaaa gcgaacagta aattcatcgg catcacggaa      720
ctgggatcc                                                              729
```

<210> SEQ ID NO 39
<211> LENGTH: 180
<212> TYPE: PRT
<213> ORGANISM: Artificial Sequence
<220> FEATURE:
<223> OTHER INFORMATION: P2CoreVP8

<400> SEQUENCE: 39

```
Gln Tyr Ile Lys Ala Asn Ser Lys Phe Ile Gly Ile Thr Glu Leu Gly
1               5                   10                  15

Ser Gly Ser Gly Leu Asp Gly Pro Tyr Gln Pro Thr Ser Leu Asn Leu
            20                  25                  30

Pro Val Asp Tyr Trp Met Leu Ile Ala Pro Thr Arg Glu Gly Lys Val
        35                  40                  45

Ala Glu Gly Thr Asn Thr Thr Asp Arg Trp Phe Ala Cys Val Leu Val
    50                  55                  60

Glu Pro Asn Val Gln Asn Thr Gln Arg Gln Tyr Val Leu Asp Gly Arg
65                  70                  75                  80

Asn Val Gln Leu Asn Val Ser Asn Glu Ser Arg Thr Ser Trp Lys Phe
                85                  90                  95

Ile Leu Phe Ile Lys Leu Thr Pro Asp Gly Thr Tyr Thr Gln Tyr Ser
            100                 105                 110

Thr Leu Ser Thr Pro His Lys Leu Cys Ala Trp Met Lys Arg Asp Asn
        115                 120                 125

Arg Val Tyr Trp Tyr Gln Gly Ala Thr Pro Asn Ala Ser Glu Ser Tyr
    130                 135                 140

Tyr Leu Thr Ile Asn Asn Asp Asn Ser Asn Val Ser Ser Asp Ala Glu
145                 150                 155                 160

Phe Tyr Leu Ile Pro Gln Ser Gln Thr Ala Met Cys Thr Gln Tyr Ile
```

165                 170                 175

Asn Asn Gly Leu
            180

<210> SEQ ID NO 40
<211> LENGTH: 200
<212> TYPE: PRT
<213> ORGANISM: Artificial Sequence
<220> FEATURE:
<223> OTHER INFORMATION: P2CoreVP8P2

<400> SEQUENCE: 40

Gln Tyr Ile Lys Ala Asn Ser Lys Phe Ile Gly Ile Thr Glu Leu Gly
1               5                   10                  15

Ser Gly Ser Gly Leu Asp Gly Pro Tyr Gln Pro Thr Ser Leu Asn Leu
            20                  25                  30

Pro Val Asp Tyr Trp Met Leu Ile Ala Pro Thr Arg Glu Gly Lys Val
        35                  40                  45

Ala Glu Gly Thr Asn Thr Thr Asp Arg Trp Phe Ala Cys Val Leu Val
    50                  55                  60

Glu Pro Asn Val Gln Asn Thr Gln Arg Gln Tyr Val Leu Asp Gly Arg
65                  70                  75                  80

Asn Val Gln Leu Asn Val Ser Asn Glu Ser Arg Thr Ser Trp Lys Phe
                85                  90                  95

Ile Leu Phe Ile Lys Leu Thr Pro Asp Gly Thr Tyr Thr Gln Tyr Ser
            100                 105                 110

Thr Leu Ser Thr Pro His Lys Leu Cys Ala Trp Met Lys Arg Asp Asn
        115                 120                 125

Arg Val Tyr Trp Tyr Gln Gly Ala Thr Pro Asn Ala Ser Glu Ser Tyr
    130                 135                 140

Tyr Leu Thr Ile Asn Asn Asp Asn Ser Asn Val Ser Ser Asp Ala Glu
145                 150                 155                 160

Phe Tyr Leu Ile Pro Gln Ser Gln Thr Ala Met Cys Thr Gln Tyr Ile
                165                 170                 175

Asn Asn Gly Leu Gly Ser Gly Ser Gly Gln Tyr Ile Lys Ala Asn Ser
            180                 185                 190

Lys Phe Ile Gly Ile Thr Glu Leu
        195                 200

<210> SEQ ID NO 41
<211> LENGTH: 186
<212> TYPE: PRT
<213> ORGANISM: Artificial Sequence
<220> FEATURE:
<223> OTHER INFORMATION: P30CoreVP8

<400> SEQUENCE: 41

Phe Asn Asn Phe Thr Val Ser Phe Trp Leu Arg Val Pro Lys Val Ser
1               5                   10                  15

Ala Ser His Leu Glu Gly Ser Gly Ser Gly Leu Asp Gly Pro Tyr Gln
            20                  25                  30

Pro Thr Ser Leu Asn Leu Pro Val Asp Tyr Trp Met Leu Ile Ala Pro
        35                  40                  45

Thr Arg Glu Gly Lys Val Ala Glu Gly Thr Asn Thr Thr Asp Arg Trp
    50                  55                  60

Phe Ala Cys Val Leu Val Glu Pro Asn Val Gln Asn Thr Gln Arg Gln
65                  70                  75                  80

Tyr Val Leu Asp Gly Arg Asn Val Gln Leu Asn Val Ser Asn Glu Ser
            85                  90                  95

Arg Thr Ser Trp Lys Phe Ile Leu Phe Ile Lys Leu Thr Pro Asp Gly
            100                 105                 110

Thr Tyr Thr Gln Tyr Ser Thr Leu Ser Thr Pro His Lys Leu Cys Ala
            115                 120                 125

Trp Met Lys Arg Asp Asn Arg Val Tyr Trp Tyr Gln Gly Ala Thr Pro
            130                 135                 140

Asn Ala Ser Glu Ser Tyr Tyr Leu Thr Ile Asn Asn Asp Asn Ser Asn
145                 150                 155                 160

Val Ser Ser Asp Ala Glu Phe Tyr Leu Ile Pro Gln Ser Gln Thr Ala
                165                 170                 175

Met Cys Thr Gln Tyr Ile Asn Asn Gly Leu
            180                 185

<210> SEQ ID NO 42
<211> LENGTH: 182
<212> TYPE: PRT
<213> ORGANISM: Artificial Sequence
<220> FEATURE:
<223> OTHER INFORMATION: OVApCoreVP8

<400> SEQUENCE: 42

Ile Ser Gln Ala Val His Ala Ala His Ala Glu Ile Asn Glu Ala Gly
1               5                   10                  15

Arg Gly Ser Gly Ser Gly Leu Asp Gly Pro Tyr Gln Pro Thr Ser Leu
            20                  25                  30

Asn Leu Pro Val Asp Tyr Trp Met Leu Ile Ala Pro Thr Arg Glu Gly
            35                  40                  45

Lys Val Ala Glu Gly Thr Asn Thr Thr Asp Arg Trp Phe Ala Cys Val
        50                  55                  60

Leu Val Glu Pro Asn Val Gln Asn Thr Gln Arg Gln Tyr Val Leu Asp
65                  70                  75                  80

Gly Arg Asn Val Gln Leu Asn Val Ser Asn Glu Ser Arg Thr Ser Trp
                85                  90                  95

Lys Phe Ile Leu Phe Ile Lys Leu Thr Pro Asp Gly Thr Tyr Thr Gln
            100                 105                 110

Tyr Ser Thr Leu Ser Thr Pro His Lys Leu Cys Ala Trp Met Lys Arg
            115                 120                 125

Asp Asn Arg Val Tyr Trp Tyr Gln Gly Ala Thr Pro Asn Ala Ser Glu
            130                 135                 140

Ser Tyr Tyr Leu Thr Ile Asn Asn Asp Asn Ser Asn Val Ser Ser Asp
145                 150                 155                 160

Ala Glu Phe Tyr Leu Ile Pro Gln Ser Gln Thr Ala Met Cys Thr Gln
                165                 170                 175

Tyr Ile Asn Asn Gly Leu
            180

<210> SEQ ID NO 43
<211> LENGTH: 206
<212> TYPE: PRT
<213> ORGANISM: Artificial Sequence
<220> FEATURE:
<223> OTHER INFORMATION: P30CoreVP8P2

<400> SEQUENCE: 43

Phe Asn As

```
Ala Ser His Leu Glu Gly Ser Gly Ser Gly Leu Asp Gly Pro Tyr Gln
            20                  25                  30

Pro Thr Ser Leu Asn Leu Pro Val Asp Tyr Trp Met Leu Ile Ala Pro
        35                  40                  45

Thr Arg Glu Gly Lys Val Ala Glu Gly Thr Asn Thr Thr Asp Arg Trp
    50                  55                  60

Phe Ala Cys Val Leu Val Glu Pro Asn Val Gln Asn Thr Gln Arg Gln
65                  70                  75                  80

Tyr Val Leu Asp Gly Arg Asn Val Gln Leu Asn Val Ser Asn Glu Ser
                85                  90                  95

Arg Thr Ser Trp Lys Phe Ile Leu Phe Ile Lys Leu Thr Pro Asp Gly
            100                 105                 110

Thr Tyr Thr Gln Tyr Ser Thr Leu Ser Thr Pro His Lys Leu Cys Ala
        115                 120                 125

Trp Met Lys Arg Asp Asn Arg Val Tyr Trp Tyr Gln Gly Ala Thr Pro
    130                 135                 140

Asn Ala Ser Glu Ser Tyr Tyr Leu Thr Ile Asn Asn Asp Asn Ser Asn
145                 150                 155                 160

Val Ser Ser Asp Ala Glu Phe Tyr Leu Ile Pro Gln Ser Gln Thr Ala
                165                 170                 175

Met Cys Thr Gln Tyr Ile Asn Asn Gly Leu Gly Ser Gly Ser Gly Gln
            180                 185                 190

Tyr Ile Lys Ala Asn Ser Lys Phe Ile Gly Ile Thr Glu Leu
        195                 200                 205

<210> SEQ ID NO 44
<211> LENGTH: 228
<212> TYPE: PRT
<213> ORGANISM: Artificial Sequence
<220> FEATURE:
<223> OTHER INFORMATION: P2P30CoreVP8OVAp

<400> SEQUENCE: 44

Gln Tyr Ile Lys Ala Asn Ser Lys Phe Ile Gly Ile Thr Glu Leu Gly
1               5                   10                  15

Ser Gly Ser Gly Phe Asn Asn Phe Thr Val Ser Phe Trp Leu Arg Val
            20                  25                  30

Pro Lys Val Ser Ala Ser His Leu Glu Gly Ser Gly Ser Gly Leu Asp
        35                  40                  45

Gly Pro Tyr Gln Pro Thr Ser Leu Asn Leu Pro Val Asp Tyr Trp Met
    50                  55                  60

Leu Ile Ala Pro Thr Arg Glu Gly Lys Val Ala Glu Gly Thr Asn Thr
65                  70                  75                  80

Thr Asp Arg Trp Phe Ala Cys Val Leu Val Glu Pro Asn Val Gln Asn
                85                  90                  95

Thr Gln Arg Gln Tyr Val Leu Asp Gly Arg Asn Val Gln Leu Asn Val
            100                 105                 110

Ser Asn Glu Ser Arg Thr Ser Trp Lys Phe Ile Leu Phe Ile Lys Leu
        115                 120                 125

Thr Pro Asp Gly Thr Tyr Thr Gln Tyr Ser Thr Leu Ser Thr Pro His
    130                 135                 140

Lys Leu Cys Ala Trp Met Lys Arg Asp Asn Arg Val Tyr Trp Tyr Gln
145                 150                 155                 160

Gly Ala Thr Pro Asn Ala Ser Glu Ser Tyr Tyr Leu Thr Ile Asn Asn
                165                 170                 175
```

Asp Asn Ser Asn Val Ser Ser Asp Ala Glu Phe Tyr Leu Ile Pro Gln
            180                 185                 190

Ser Gln Thr Ala Met Cys Thr Gln Tyr Ile Asn Asn Gly Leu Gly Ser
        195                 200                 205

Gly Ser Gly Ile Ser Gln Ala Val His Ala Ala His Ala Glu Ile Asn
    210                 215                 220

Glu Ala Gly Arg
225

<210> SEQ ID NO 45
<211> LENGTH: 514
<212> TYPE: DNA
<213> ORGANISM: Artificial Sequence
<220> FEATURE:
<223> OTHER INFORMATION: CoreVP8

<400> SEQUENCE: 45

```
catatgtgga tggtccgtat caaccgacga cgtttacccc gccgaacgat tattggattc      60
tgatcaactc aaatacgaac ggcgtggttt acgaaagtac caacaattcc gatttctgga     120
cggcggtcgt ggccatcgaa ccgcatgtta tccggcgac cgccagtata ccattttggg     180
tgaaatgcaa acaattcaat gtcagcaacg actctaataa atggaagttt ctggaaatgt    240
tccgtagctc tagtcagaac gaattttata atcgtcgcac cctgacgtct gatacccgtc    300
tggtgggcat cctgaagtac ggcggtcgcg tttggaccctt ccatggtgaa acgccgcgtg    360
caaccacgga ctcctcatcg accgcgaacc tgaacaatat tcaatcacg attcaccacg     420
attcaccacg attcactcgg aatttacat catcccgcgt agccaggaaa gcaaatgcaa      480
cgaatacatc aataatggtc tgtgataagg atcc                                514
```

<210> SEQ ID NO 46
<211> LENGTH: 550
<212> TYPE: DNA
<213> ORGANISM: Artificial Sequence
<220> FEATURE:
<223> OTHER INFORMATION: P2CoreVP8

<400> SEQUENCE: 46

```
catatgcagt acattaaagc aaactcaaaa ttcattggca ttaccgaact gggctcaggc      60
tcaggttgga tggtccgtat caaccgacga cgtttacccc gccgaacgat tattggattc    120
tgatcactca aatacgaacg gcgtggttta cgaaagtacc aacaattccg atttctggac    180
ggcggtcgtg gccatcgaac cgcatgttaa tccggtcgac cgccagtata ccattttggg    240
tgaaagcaaa caattcaatg tcagcaacga ctctaataaa tggaagtttc tggaaatgtt    300
ccgtagctct agtcagaacg aattttataa tcgtcgcacc ctgacgtctg atacccgtct    360
ggtgggcatc ctgaagtacg gcggtcgcgt ttggaccttc catggtgaaa cgccgcgtgc    420
aaccacggac tcctcatcga ccgcgaacct gaacaatatt tcaatcacga ttcactcgga    480
attttacatc atcccgcgta gccaggaaag caaatgcaac gaatacatca ataatggtct    540
gtgaggatcc                                                          550
```

<210> SEQ ID NO 47
<211> LENGTH: 570
<212> TYPE: DNA
<213> ORGANISM: Artificial Sequence
<220> FEATURE:
<223> OTHER INFORMATION: P30CoreVP8

<400> SEQUENCE: 47

```
catatgttca ataattttac ggtgtcgttt tggctgcgtg tgccgaaagt gtctgcctcc    60
catctggaag gttctggttc aggtctggac ggtccgtatc agccgaccac gtttaccccg   120
ccgaacgatt actggattct gatcaacagc aatacgaacg gcgtggttta tgaatcaacc   180
aacaattcgg atttctggac ggcggtcgtg gccatcgaac cgcatgttaa tccggtcgac   240
cgccagtaca ccatcttcgg tgaatcaaaa caattcaacg tcagcaacga ctctaacaaa   300
tggaaattcc tggaaatgtt ccgtagctct agtcagaacg aatttttataa tcgtcgcacc   360
ctgacgtccg ataccgtctc ggtgggcatc ctgaaatacg gcggtcgcgt ttggaccttc   420
catggtgaaa cgccgcgtgc aaccacggac tcctcatcga ccgcgaacct gaacaatatt   480
agcatcacga tccactctga attctacatc atcccgcgca gtcaagaatc aaatgcaac    540
gaatacatca acaatggcct gtaaggatcc                                    570
```

<210> SEQ ID NO 48
<211> LENGTH: 561
<212> TYPE: DNA
<213> ORGANISM: Artificial Sequence
<220> FEATURE:
<223> OTHER INFORMATION: OVApCoreVP8

<400> SEQUENCE: 48

```
catatgatca gccaagcggt tcacgcagcc cacgccgaaa ttaacgaagc gggtcgcggt    60
agcggttctg gcctggatgg tccgtatcaa ccgacgacgt ttaccccgcc gaacgattat   120
tggattctga tcaactcaaa tacgaacggc gtggtttacg aaagtaccaa caattccgat   180
ttctggacgg cggtcgtggc catcgaaccg catgttaatc cggtcgaccg ccagtatacc   240
atttttggtg aaagcaaaca attcaatgtc agcaacgact ctaataaatg gaagtttctg   300
gaaatgttcc gtagctctag tcagaacgaa tttttataatc gtcgcaccct gacgtctgat   360
acccgtctgg tgggcatcct gaagtacggc ggtcgcgttt ggaccttcca tggtgaaacg   420
ccgcgtgcaa ccacggactc ctcatcgacc gcgaacctga acaatatttc aatcacgatt   480
cactcggaat tttacatcat cccgcgtagc caggaaagca atgcaacga atacatcaat   540
aatggtctgt gataaggatc c                                             561
```

<210> SEQ ID NO 49
<211> LENGTH: 621
<212> TYPE: DNA
<213> ORGANISM: Artificial Sequence
<220> FEATURE:
<223> OTHER INFORMATION: P30CoreVP8P2

<400> SEQUENCE: 49

```
catatgatca gccaagcggt tcacgcagcc cacgccgaaa ttaacgaagc gggtcgcggt    60
agcggttctg gcctggatgg tccgtatcaa ccgacgacgt ttaccccgcc gaacgattat   120
tggattctga tcaactcaaa tacgaacggc gtggtttacg aaagtaccaa caattccgat   180
ttctggacgg cggtcgtggc catcgaaccg catgttaatc cggtcgaccg ccagtatacc   240
atttttggtg aaagcaaaca attcaatgtc agcaacgact ctaataaatg gaagtttctg   300
gaaatgttcc gtagctctag tcagaacgaa tttttataatc gtcgcaccct gacgtctgat   360
acccgtctgg tgggcatcct gaagtacggc ggtcgcgttt ggaccttcca tggtgaaacg   420
ccgcgtgcaa ccacggactc ctcatcgacc gcgaacctga acaatatttc aatcacgatt   480
cactcggaat tttacatcat cccgcgtagc caggaaagca atgcaacga atacatcaat   540
```

```
aatggtctgt gataaggctc aggctcaggt cagtacatta aagcaaactc aaaattcatt      600
ggcattaccg aactgggatc c                                                621
```

<210> SEQ ID NO 50
<211> LENGTH: 687
<212> TYPE: DNA
<213> ORGANISM: Artificial Sequence
<220> FEATURE:
<223> OTHER INFORMATION: P2P30CoreVP8OVAp

<400> SEQUENCE: 50

```
catatgcagt acattaaagc aaactcaaaa ttcattggca ttaccgaact gggtagcggt       60
tctggcatca gccaagcggt tcacgcagcc cacgccgaaa ttaacgaagc gggtcgcggt      120
agcggttctg gcctggatgg tccgtatcaa ccgacgacgt ttaccccgcc gaacgattat      180
tggattctga tcaactcaaa tacgaacggc gtggtttacg aaagtaccaa caattccgat      240
ttctggacgg cggtcgtggc catcgaaccg catgttaatc cggtcgaccg ccagtatacc      300 attttggtg aaagcaaaca attcaatgtc agcaacgact ctaataaatg aagtttctg       360 gaaatgttcc gtagctctag tcagaacgaa ttttataatc gtcgcaccct gacgtctgat      420
acccgtctgg tgggcatcct gaagtacggc ggtcgcgttt ggaccttcca tggtgaaacg      480
ccgcgtgcaa ccacggactc ctcatcgacc gcgaacctga acaatatttc aatcacgatt      540
cactcggaat tttacatcat cccgcgtagc caggaaagca aatgcaacga atacatcaat      600
aatggtctgt gataaggctc aggctcaggt atcagccaag cggttcacgc agcccacgcc      660
gaaattaacg aagcgggtcg cggatcc                                          687
```

<210> SEQ ID NO 51
<211> LENGTH: 219
<212> TYPE: PRT
<213> ORGANISM: Artificial Sequence
<220> FEATURE:
<223> OTHER INFORMATION: P30H21G

<400> SEQUENCE: 51

```
Phe Asn Asn Phe Thr Val Ser Phe Trp Leu Arg Val Pro Lys Val Ser
1               5                   10                  15

Ala Ser His Leu Glu Gly Ser Gly Ser Gly Gly Ala Asp Asp Val Val
            20                  25                  30

Asp Ser Ser Lys Ser Phe Val Met Glu Asn Phe Ser Ser Tyr Gly Gly
        35                  40                  45

Thr Lys Pro Gly Tyr Val Asp Ser Ile Gln Lys Gly Ile Gln Lys Pro
    50                  55                  60

Lys Ser Gly Thr Gln Gly Asn Tyr Asp Asp Trp Lys Gly Phe Tyr
65                  70                  75                  80

Ser Thr Asp Asn Lys Tyr Asp Ala Ala Gly Tyr Ser Val Asp Asn Glu
                85                  90                  95

Asn Pro Leu Ser Gly Lys Ala Gly Gly Val Val Lys Val Thr Tyr Pro
            100                 105                 110

Gly Leu Thr Lys Val Leu Ala Leu Lys Val Asp Asn Ala Glu Thr Ile
        115                 120                 125

Lys Lys Glu Leu Gly Leu Ser Leu Thr Glu Pro Leu Met Glu Gln Val
    130                 135                 140

Gly Thr Glu Glu Phe Ile Lys Arg Phe Gly Asp Gly Ala Ser Arg Val
145                 150                 155                 160
```

-continued

```
Val Leu Ser Leu Pro Phe Ala Glu Gly Ser Ser Val Glu Tyr Ile
                165                 170                 175

Asn Asn Trp Glu Gln Ala Lys Ala Leu Ser Val Glu Leu Glu Ile Asn
            180                 185                 190

Phe Glu Thr Arg Gly Lys Arg Gly Gln Asp Ala Met Tyr Glu Tyr Met
        195                 200                 205

Ala Gln Ala Cys Ala Gly Asn Arg Val Arg Arg
    210                 215

<210> SEQ ID NO 52
<211> LENGTH: 245
<212> TYPE: PRT
<213> ORGANISM: Artificial Sequence
<220> FEATURE:
<223> OTHER INFORMATION: P30H21GP30

<400> SEQUENCE: 52

Phe Asn Asn Phe Thr Val Ser Phe Trp Leu Arg Val Pro Lys Val Ser
1               5                   10                  15

Ala Ser His Leu Glu Gly Ser Gly Gly Ala Asp Val Val
            20                  25                  30

Asp Ser Ser Lys Ser Phe Val Met Glu Asn Phe Ser Ser Tyr Gly Gly
        35                  40                  45

Thr Lys Pro Gly Tyr Val Asp Ser Ile Gln Lys Gly Ile Gln Lys Pro
    50                  55                  60

Lys Ser Gly Thr Gln Gly Asn Tyr Asp Asp Trp Lys Gly Phe Tyr
65              70                  75                  80

Ser Thr Asp Asn Lys Tyr Asp Ala Ala Gly Tyr Ser Val Asp Asn Glu
                85                  90                  95

Asn Pro Leu Ser Gly Lys Ala Gly Gly Val Val Lys Val Thr Tyr Pro
            100                 105                 110

Gly Leu Thr Lys Val Leu Ala Leu Lys Val Asp Asn Ala Glu Thr Ile
        115                 120                 125

Lys Lys Glu Leu Gly Leu Ser Leu Thr Glu Pro Leu Met Glu Gln Val
130                 135                 140

Gly Thr Glu Glu Phe Ile Lys Arg Phe Gly Asp Gly Ala Ser Arg Val
145                 150                 155                 160

Val Leu Ser Leu Pro Phe Ala Glu Gly Ser Ser Val Glu Tyr Ile
                165                 170                 175

Asn Asn Trp Glu Gln Ala Lys Ala Leu Ser Val Glu Leu Glu Ile Asn
            180                 185                 190

Phe Glu Thr Arg Gly Lys Arg Gly Gln Asp Ala Met Tyr Glu Tyr Met
        195                 200                 205

Ala Gln Ala Cys Ala Gly Asn Arg Val Arg Arg Gly Ser Gly Ser Gly
    210                 215                 220

Phe Asn Asn Phe Thr Val Ser Phe Trp Leu Arg Val Pro Lys Val Ser
225                 230                 235                 240

Ala Ser His Leu Glu
                245

<210> SEQ ID NO 53
<211> LENGTH: 213
<212> TYPE: PRT
<213> ORGANISM: Artificial Sequence
<220> FEATURE:
<223> OTHER INFORMATION: P2H21G

<400> SEQUENCE: 53
```

```
Gln Tyr Ile Lys Ala Asn Ser Lys Phe Ile Gly Ile Thr Glu Leu Gly
1               5                   10                  15

Ser Gly Ser Gly Gly Ala Asp Asp Val Val Asp Ser Ser Lys Ser Phe
            20                  25                  30

Val Met Glu Asn Phe Ser Ser Tyr Gly Gly Thr Lys Pro Gly Tyr Val
        35                  40                  45

Asp Ser Ile Gln Lys Gly Ile Gln Lys Pro Lys Ser Gly Thr Gln Gly
    50                  55                  60

Asn Tyr Asp Asp Asp Trp Lys Gly Phe Tyr Ser Thr Asp Asn Lys Tyr
65                  70                  75                  80

Asp Ala Ala Gly Tyr Ser Val Asp Asn Glu Asn Pro Leu Ser Gly Lys
                85                  90                  95

Ala Gly Gly Val Val Lys Val Thr Tyr Pro Gly Leu Thr Lys Val Leu
            100                 105                 110

Ala Leu Lys Val Asp Asn Ala Glu Thr Ile Lys Lys Glu Leu Gly Leu
        115                 120                 125

Ser Leu Thr Glu Pro Leu Met Glu Gln Val Gly Thr Glu Glu Phe Ile
    130                 135                 140

Lys Arg Phe Gly Asp Gly Ala Ser Arg Val Val Leu Ser Leu Pro Phe
145                 150                 155                 160

Ala Glu Gly Ser Ser Ser Val Glu Tyr Ile Asn Asn Trp Glu Gln Ala
                165                 170                 175

Lys Ala Leu Ser Val Glu Leu Glu Ile Asn Phe Glu Thr Arg Gly Lys
            180                 185                 190

Arg Gly Gln Asp Ala Met Tyr Glu Tyr Met Ala Gln Ala Cys Ala Gly
        195                 200                 205

Asn Arg Val Arg Arg
    210

<210> SEQ ID NO 54
<211> LENGTH: 215
<212> TYPE: PRT
<213> ORGANISM: Artificial Sequence
<220> FEATURE:
<223> OTHER INFORMATION: OVApH21G

<400> SEQUENCE: 54

Ile Ser Gln Ala Val His Ala Ala His Ala Glu Ile Asn Glu Ala Gly
1               5                   10                  15

Arg Gly Ser Gly Ser Gly Gly Ala Asp Asp Val Val Asp Ser Ser Lys
            20                  25                  30

Ser Phe Val Met Glu Asn Phe Ser Ser Tyr Gly Gly Thr Lys Pro Gly
        35                  40                  45

Tyr Val Asp Ser Ile Gln Lys Gly Ile Gln Lys Pro Lys Ser Gly Thr
    50                  55                  60

Gln Gly Asn Tyr Asp Asp Asp Trp Lys Gly Phe Tyr Ser Thr Asp Asn
65                  70                  75                  80

Lys Tyr Asp Ala Ala Gly Tyr Ser Val Asp Asn Glu Asn Pro Leu Ser
                85                  90                  95

Gly Lys Ala Gly Gly Val Val Lys Val Thr Tyr Pro Gly Leu Thr Lys
            100                 105                 110

Val Leu Ala Leu Lys Val Asp Asn Ala Glu Thr Ile Lys Lys Glu Leu
        115                 120                 125

Gly Leu Ser Leu Thr Glu Pro Leu Met Glu Gln Val Gly Thr Glu Glu
    130                 135                 140
```

```
Phe Ile Lys Arg Phe Gly Asp Gly Ala Ser Arg Val Val Leu Ser Leu
145                 150                 155                 160

Pro Phe Ala Glu Gly Ser Ser Val Glu Tyr Ile Asn Asn Trp Glu
                165                 170                 175

Gln Ala Lys Ala Leu Ser Val Glu Leu Glu Ile Asn Phe Glu Thr Arg
            180                 185                 190

Gly Lys Arg Gly Gln Asp Ala Met Tyr Glu Tyr Met Ala Gln Ala Cys
            195                 200                 205

Ala Gly Asn Arg Val Arg Arg
        210                 215

<210> SEQ ID NO 55
<211> LENGTH: 239
<212> TYPE: PRT
<213> ORGANISM: Artificial Sequence
<220> FEATURE:
<223> OTHER INFORMATION: P30H21GP2

<400> SEQUENCE: 55

Phe Asn Asn Phe Thr Val Ser Phe Trp Leu Arg Val Pro Lys Val Ser
1               5                   10                  15

Ala Ser His Leu Glu Gly Ser Gly Ser Gly Ala Asp Asp Val Val
            20                  25                  30

Asp Ser Ser Lys Ser Phe Val Met Glu Asn Phe Ser Ser Tyr Gly Gly
        35                  40                  45

Thr Lys Pro Gly Tyr Val Asp Ser Ile Gln Lys Gly Ile Gln Lys Pro
    50                  55                  60

Lys Ser Gly Thr Gln Gly Asn Tyr Asp Asp Trp Lys Gly Phe Tyr
65                  70                  75                  80

Ser Thr Asp Asn Lys Tyr Asp Ala Ala Gly Tyr Ser Val Asp Asn Glu
                85                  90                  95

Asn Pro Leu Ser Gly Lys Ala Gly Gly Val Val Lys Val Thr Tyr Pro
            100                 105                 110

Gly Leu Thr Lys Val Leu Ala Leu Lys Val Asp Asn Ala Glu Thr Ile
        115                 120                 125

Lys Lys Glu Leu Gly Leu Ser Leu Thr Glu Pro Leu Met Glu Gln Val
    130                 135                 140

Gly Thr Glu Glu Phe Ile Lys Arg Phe Gly Asp Gly Ala Ser Arg Val
145                 150                 155                 160

Val Leu Ser Leu Pro Phe Ala Glu Gly Ser Ser Val Glu Tyr Ile
                165                 170                 175

Asn Asn Trp Glu Gln Ala Lys Ala Leu Ser Val Glu Leu Glu Ile Asn
            180                 185                 190

Phe Glu Thr Arg Gly Lys Arg Gly Gln Asp Ala Met Tyr Glu Tyr Met
        195                 200                 205

Ala Gln Ala Cys Ala Gly Asn Arg Val Arg Arg Gly Ser Gly Ser Gly
    210                 215                 220

Gln Tyr Ile Lys Ala Asn Ser Lys Phe Ile Gly Ile Thr Glu Leu
225                 230                 235

<210> SEQ ID NO 56
<211> LENGTH: 261
<212> TYPE: PRT
<213> ORGANISM: Artificial Sequence
<220> FEATURE:
<223> OTHER INFORMATION: P2OVApH21GP30
```

<400> SEQUENCE: 56

Gln Tyr Ile Lys Ala Asn Ser Lys Phe Ile Gly Ile Thr Glu Leu Gly
1               5                   10                  15

Ser Gly Ser Gly Ile Ser Gln Ala Val His Ala Ala His Ala Glu Ile
            20                  25                  30

Asn Glu Ala Gly Arg Gly Ser Gly Ser Gly Gly Ala Asp Asp Val Val
        35                  40                  45

Asp Ser Ser Lys Ser Phe Val Met Glu Asn Phe Ser Ser Tyr Gly Gly
50                  55                  60

Thr Lys Pro Gly Tyr Val Asp Ser Ile Gln Lys Gly Ile Gln Lys Pro
65                  70                  75                  80

Lys Ser Gly Thr Gln Gly Asn Tyr Asp Asp Asp Trp Lys Gly Phe Tyr
                85                  90                  95

Ser Thr Asp Asn Lys Tyr Asp Ala Ala Gly Tyr Ser Val Asp Asn Glu
            100                 105                 110

Asn Pro Leu Ser Gly Lys Ala Gly Gly Val Val Lys Val Thr Tyr Pro
        115                 120                 125

Gly Leu Thr Lys Val Leu Ala Leu Lys Val Asp Asn Ala Glu Thr Ile
130                 135                 140

Lys Lys Glu Leu Gly Leu Ser Leu Thr Glu Pro Leu Met Glu Gln Val
145                 150                 155                 160

Gly Thr Glu Glu Phe Ile Lys Arg Phe Gly Asp Gly Ala Ser Arg Val
                165                 170                 175

Val Leu Ser Leu Pro Phe Ala Glu Gly Ser Ser Val Glu Tyr Ile
            180                 185                 190

Asn Asn Trp Glu Gln Ala Lys Ala Leu Ser Val Glu Leu Glu Ile Asn
        195                 200                 205

Phe Glu Thr Arg Gly Lys Arg Gly Gln Asp Ala Met Tyr Glu Tyr Met
210                 215                 220

Ala Gln Ala Cys Ala Gly Asn Arg Val Arg Arg Gly Ser Gly Ser Gly
225                 230                 235                 240

Phe Asn Asn Phe Thr Val Ser Phe Trp Leu Arg Val Pro Lys Val Ser
                245                 250                 255

Ala Ser His Leu Glu
            260

<210> SEQ ID NO 57
<211> LENGTH: 591
<212> TYPE: DNA
<213> ORGANISM: Artificial Sequence
<220> FEATURE:
<223> OTHER INFORMATION: H21G

<400> SEQUENCE: 57
catatgggtg ccgacgacgt ggttgatagc tctaaatctt tcgttatgga aaacttcagt      60
tcctatggcg gtaccaaacc gggctacgtc gattcgattc agaaaggtat ccaaaaaccg     120
aaaagcggca cccagggtaa ctatgatgac gattggaaag gcttttactc aacggacaat     180
aaatatgatg cggccggcta ctccgtggac aacgaaaatc cgctgagcgg taaagcgggc     240
ggtgtcgtga agttaccta tccgggtctg acgaaagtgc tggctctgaa agttgataat     300
gcggaaacca tcaaaaaaga actgggcctg tccctgaccg aaccgctgat ggaacaagtg     360
ggtacggaag aatttatcaa acgtttcggc gacggtgcct ctcgcgttgt cctgagtctg     420
ccgtttgcag aaggctcatc gagcgtcgaa tacattaaca attgggaaca agcaaaagct     480

```
ctgagcgtgg aactggaaat caacttcgaa acgcgtggca acgcggtcag gatgcgatg      540 tatgaataca tggcgcaagc ctgcgcaggt aatcgtgttc gtcgcggatc c              591
```

<210> SEQ ID NO 58
<211> LENGTH: 672
<212> TYPE: DNA
<213> ORGANISM: Artificial Sequence
<220> FEATURE:
<223> OTHER INFORMATION: P30H21G

<400> SEQUENCE: 58

```
catatgttca acaattttac ggtgtctttt tggctgcgtg tgccgaaagt gtctgcgagt       60
catctggaag gtagtggttc tggtggtgcc gacgacgtgg ttgatagctc taaatctttc      120
gttatggaaa acttcagttc ctatggcggt accaaaccgg gctacgtcga ttcgattcag      180
aaaggtatcc aaaaaccgaa aagcggcacc cagggtaact atgatgacga ttggaaaggc      240
ttttactcaa cggacaataa atatgatgcg gccggctact ccgtggacaa cgaaaatccg      300
ctgagcggta agcgggcgg tgtcgtgaaa gttacctatc cgggtctgac gaaagtgctg       360
gctctgaaag ttgataatgc ggaaaccatc aaaaaagaac tgggcctgtc cctgaccgaa      420
ccgctgatgg aacaagtggg tacggaagaa tttatcaaac gtttcggcga cggtgcctct      480
cgcgttgtcc tgagtctgcc gtttgcagaa ggctcatcga gcgtcgaata cattaacaat      540
tgggaacaag caaaagctct gagcgtgaa ctggaaatca acttcgaaac gcgtggcaaa       600
cgcggtcagg atgcgatgta tgaatacatg gcgcaagcct gcgcaggtaa tcgtgttcgt      660
cgctaaggat cc                                                          672
```

<210> SEQ ID NO 59
<211> LENGTH: 750
<212> TYPE: DNA
<213> ORGANISM: Artificial Sequence
<220> FEATURE:
<223> OTHER INFORMATION: P30H21GP30

<400> SEQUENCE: 59

```
catatgttca acaattttac ggtgtctttt tggctgcgtg tgccgaaagt gtctgcgagt       60
catctggaag gtagtggttc tggtggtgcc gacgacgtgg ttgatagctc taaatctttc      120
gttatggaaa acttcagttc ctatggcggt accaaaccgg gctacgtcga ttcgattcag      180
aaaggtatcc aaaaaccgaa aagcggcacc cagggtaact atgatgacga ttggaaaggc      240
ttttactcaa cggacaataa atatgatgcg gccggctact ccgtggacaa cgaaaatccg      300
ctgagcggta agcgggcgg tgtcgtgaaa gttacctatc cgggtctgac gaaagtgctg       360
gctctgaaag ttgataatgc ggaaaccatc aaaaaagaac tgggcctgtc cctgaccgaa      420
ccgctgatgg aacaagtggg tacggaagaa tttatcaaac gtttcggcga cggtgcctct      480
cgcgttgtcc tgagtctgcc gtttgcagaa ggctcatcga gcgtcgaata cattaacaat      540
tgggaacaag caaaagctct gagcgtgaa ctggaaatca acttcgaaac gcgtggcaaa       600
cgcggtcagg atgcgatgta tgaatacatg gcgcaagcct gcgcaggtaa tcgtgttcgt      660
cgctaaggta gtggttctgg tttcaacaat tttacggtgt cttttttggct gcgtgtgccg    720 aaagtgtctg cgagtcatct ggaaggatcc                                       750
```

<210> SEQ ID NO 60
<211> LENGTH: 654
<212> TYPE: DNA
<213> ORGANISM: Artificial Sequence

<220> FEATURE:
<223> OTHER INFORMATION: P2H21G

<400> SEQUENCE: 60

| | | | | | |
|---|---|---|---|---|---|
| catatgcagt | acattaaagc | aaactcaaaa | ttcattggca | ttaccgaact | gggtagtggt | 60 |
| tctggtggtg | ccgacgacgt | ggttgatagc | tctaaatctt | tcgttatgga | aaacttcagt | 120 |
| tcctatggcg | gtaccaaacc | gggctacgtc | gattcgattc | agaaaggtat | ccaaaaaccg | 180 |
| aaagcggca | cccagggtaa | ctatgatgac | gattggaaag | cttttactc | aacgacaat | 240 |
| aaatatgatg | cggccggcta | ctccgtggac | aacgaaaatc | cgctgagcgg | taaagcgggc | 300 |
| ggtgtcgtga | agttaccta | tccgggtctg | acgaaagtgc | tggctctgaa | agttgataat | 360 |
| gcggaaacca | tcaaaaaaga | actgggcctg | tccctgaccg | aaccgctgat | ggaacaagtg | 420 |
| ggtacgaag | aatttatcaa | acgtttcggc | gacggtgcct | ctcgcgttgt | cctgagtctg | 480 |
| ccgtttgcag | aaggctcatc | gagcgtcgaa | tacattaaca | attgggaaca | agcaaaagct | 540 |
| ctgagcgtgg | aactgaaat | caacttcgaa | acgcgtggca | aacgcggtca | ggatgcgatg | 600 |
| tatgaataca | tggcgcaagc | ctgcgcaggt | aatcgtgttc | gtcgctaagg | atcc | 654 |

<210> SEQ ID NO 61
<211> LENGTH: 660
<212> TYPE: DNA
<213> ORGANISM: Artificial Sequence
<220> FEATURE:
<223> OTHER INFORMATION: OVApH21G

<400> SEQUENCE: 61

| | | | | | |
|---|---|---|---|---|---|
| catatgatca | gccaagcggt | tcacgcagcc | cacgccgaaa | ttaacgaagc | gggtcgcggt | 60 |
| agcggttctg | gcggtgccga | cgacgtggtt | gatagctcta | atctttcgt | tatggaaaac | 120 |
| ttcagttcct | atggcggtac | caaaccgggc | tacgtcgatt | cgattcagaa | aggtatccaa | 180 |
| aaaccgaaaa | gcggcaccca | gggtaactat | gatgacgatt | ggaaaggctt | ttactcaacg | 240 |
| gacaataaat | atgatgcggc | cggctactcc | gtggacaacg | aaaatccgct | gagcggtaaa | 300 |
| gcgggcggtg | tcgtgaaagt | tacctatccg | ggtctgacga | aagtgctggc | tctgaaagtt | 360 |
| gataatgcgg | aaaccatcaa | aaaagaactg | ggcctgtccc | tgaccgaacc | gctgatggaa | 420 |
| caagtgggta | cggaagaatt | tatcaaacgt | ttcggcgacg | gtgcctctcg | cgttgtcctg | 480 |
| agtctgccgt | ttgcagaagg | ctcatcgagc | gtcgaataca | ttaacaattg | ggaacaagca | 540 |
| aaagctctga | gcgtggaact | ggaaatcaac | ttcgaaacgc | gtggcaaacg | cggtcaggat | 600 |
| gcgatgtatg | aatacatggc | gcaagcctgc | gcaggtaatc | gtgttcgtcg | ctaaggatcc | 660 |

<210> SEQ ID NO 62
<211> LENGTH: 732
<212> TYPE: DNA
<213> ORGANISM: Artificial Sequence
<220> FEATURE:
<223> OTHER INFORMATION: P30H21GP2

<400> SEQUENCE: 62

| | | | | | |
|---|---|---|---|---|---|
| catatgttca | acaattttac | ggtgtctttt | tggctgcgtg | tgccgaaagt | gtctgcgagt | 60 |
| catctggaag | gtagtggttc | tggtggtgcc | gacgacgtgg | ttgatagctc | taaatctttc | 120 |
| gttatggaaa | acttcagttc | ctatggcggt | accaaaccgg | gctacgtcga | ttcgattcag | 180 |
| aaaggtatcc | aaaaaccgaa | aagcggcacc | cagggtaact | atgatgacga | ttggaaaggc | 240 |
| ttttactcaa | cggacaataa | atatgatgcg | gccggctact | ccgtggacaa | cgaaaatccg | 300 |

-continued

```
ctgagcggta aagcgggcgg tgtcgtgaaa gttacctatc cgggtctgac gaaagtgctg    360
gctctgaaag ttgataatgc ggaaaccatc aaaaaagaac tgggcctgtc cctgaccgaa    420
ccgctgatgg aacaagtggg tacggaagaa tttatcaaac gtttcggcga cggtgcctct    480
cgcgttgtcc tgagtctgcc gtttgcagaa ggctcatcga gcgtcgaata cattaacaat    540
tgggaacaag caaaagctct gagcgtggaa ctggaaatca acttcgaaac gcgtggcaaa    600
cgcggtcagg atgcgatgta tgaatacatg gcgcaagcct gcgcaggtaa tcgtgttcgt    660
cgctaaggct caggctcagg tcagtacatt aaagcaaact caaaattcat tggcattacc    720
gaactgggat cc                                                        732
```

<210> SEQ ID NO 63
<211> LENGTH: 798
<212> TYPE: DNA
<213> ORGANISM: Artificial Sequence
<220> FEATURE:
<223> OTHER INFORMATION: P2OVApH21GP30

<400> SEQUENCE: 63

```
catatgcagt acattaaagc aaactcaaaa ttcattggca ttaccgaact gggtagtggt     60
tctggtatca gccaagcggt tcacgcagcc cacgccgaaa ttaacgaagc gggtcgcggt    120
agcggttctg gcggtgccga cgacgtggtt gatagctcta aatctttcgt tatggaaaac    180
ttcagttcct atggcggtac caaaccgggc tacgtcgatt cgattcagaa aggtatccaa    240
aaaccgaaaa gcggcaccca gggtaactat gatgacgatt ggaaaggctt ttactcaacg    300
gacaataaat atgatgcggc cggctactcc gtggacaacg aaaatccgct gagcggtaaa    360
gcgggcggtg tcgtgaaagt tacctatccg ggtctgacga aagtgctggc tctgaaagtt    420
gataatgcgg aaaccatcaa aaaagaactg ggcctgtccc tgaccgaacc gctgatggaa    480
caagtgggta cggaagaatt tatcaaacgt ttcggcgacg gtgcctctcg cgttgtcctg    540
agtctgccgt ttgcagaagg ctcatcgagc gtcgaataca ttaacaattg ggaacaagca    600
aaagctctga gcgtggaact ggaaatcaac ttcgaaacgc gtggcaaacg cggtcaggat    660
gcgatgtatg aatacatggc gcaagcctgc gcaggtaatc gtgttcgtcg ctaaggtagt    720
ggttctggtt tcaacaattt tacggtgtct tttggctgc gtgtgccgaa agtgtctgcg    780
agtcatctgg aaggatcc                                                  798
```

<210> SEQ ID NO 64
<211> LENGTH: 560
<212> TYPE: PRT
<213> ORGANISM: Artificial Sequence
<220> FEATURE:
<223> OTHER INFORMATION: Diphtheria toxin full length

<400> SEQUENCE: 64

```
Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Val Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile Gln Lys Gly Ile Gln Lys Pro Lys
    50                  55                  60

Ser Gly Thr Gln Gly Asn Tyr Asp Asp Asp Trp Lys Gly Phe Tyr Ser
65                  70                  75                  80
```

-continued

```
Thr Asp Asn Lys Tyr Asp Ala Ala Gly Tyr Ser Val Asp Asn Glu Asn
                 85                  90                  95
Pro Leu Ser Gly Lys Ala Gly Val Val Lys Val Thr Tyr Pro Gly
            100                 105                 110
Leu Thr Lys Val Leu Ala Leu Lys Val Asp Asn Ala Glu Thr Ile Lys
            115                 120                 125
Lys Glu Leu Gly Leu Ser Leu Thr Glu Pro Leu Met Glu Gln Val Gly
130                 135                 140
Thr Glu Glu Phe Ile Lys Arg Phe Gly Asp Gly Ala Ser Arg Val Val
145                 150                 155                 160
Leu Ser Leu Pro Phe Ala Glu Gly Ser Ser Val Glu Tyr Ile Asn
                165                 170                 175
Asn Trp Glu Gln Ala Lys Ala Leu Ser Val Glu Leu Glu Ile Asn Phe
                180                 185                 190
Glu Thr Arg Gly Lys Arg Gly Gln Asp Ala Met Tyr Glu Tyr Met Ala
                195                 200                 205
Gln Ala Cys Ala Gly Asn Arg Val Arg Arg Ser Val Gly Ser Ser Leu
            210                 215                 220
Ser Cys Ile Asn Leu Asp Trp Asp Val Ile Arg Asp Lys Thr Lys Thr
225                 230                 235                 240
Lys Ile Glu Ser Leu Lys Glu His Gly Pro Ile Lys Asn Lys Met Ser
                245                 250                 255
Glu Ser Pro Asn Lys Thr Val Ser Glu Lys Ala Lys Gln Tyr Leu
                260                 265                 270
Glu Glu Phe His Gln Thr Ala Leu Glu His Pro Glu Leu Ser Glu Leu
            275                 280                 285
Lys Thr Val Thr Gly Thr Asn Pro Val Phe Ala Gly Ala Asn Tyr Ala
290                 295                 300
Ala Trp Ala Val Asn Val Ala Gln Val Ile Asp Ser Glu Thr Ala Asp
305                 310                 315                 320
Asn Leu Glu Lys Thr Thr Ala Ala Leu Ser Ile Leu Pro Gly Ile Gly
                325                 330                 335
Ser Val Met Gly Ile Ala Asp Gly Ala Val His His Asn Thr Glu Glu
            340                 345                 350
Ile Val Ala Gln Ser Ile Ala Leu Ser Ser Leu Met Val Ala Gln Ala
            355                 360                 365
Ile Pro Leu Val Gly Glu Leu Val Asp Ile Gly Phe Ala Ala Tyr Asn
370                 375                 380
Phe Val Glu Ser Ile Ile Asn Leu Phe Gln Val Val His Asn Ser Tyr
385                 390                 395                 400
Asn Arg Pro Ala Tyr Ser Pro Gly His Lys Thr Gln Pro Phe Leu His
                405                 410                 415
Asp Gly Tyr Ala Val Ser Trp Asn Thr Val Glu Asp Ser Ile Ile Arg
            420                 425                 430
Thr Gly Phe Gln Gly Glu Ser Gly His Asp Ile Lys Ile Thr Ala Glu
            435                 440                 445
Asn Thr Pro Leu Pro Ile Ala Gly Val Leu Leu Pro Thr Ile Pro Gly
450                 455                 460
Lys Leu Asp Val Asn Lys Ser Lys Thr His Ile Ser Val Asn Gly Arg
465                 470                 475                 480
Lys Ile Arg Met Arg Cys Arg Ala Ile Asp Gly Asp Val Thr Phe Cys
                485                 490                 495
Arg Pro Lys Ser Pro Val Tyr Val Gly Asn Gly Val His Ala Asn Leu
```

```
                    500                 505                 510
His Val Ala Phe His Arg Ser Ser Glu Lys Ile His Ser Asn Glu
            515                 520                 525

Ile Ser Ser Asp Ser Ile Gly Val Leu Gly Tyr Gln Lys Thr Val Asp
            530                 535                 540

His Thr Lys Val Asn Ser Lys Leu Ser Leu Phe Phe Glu Ile Lys Ser
545                 550                 555                 560

<210> SEQ ID NO 65
<211> LENGTH: 535
<212> TYPE: PRT
<213> ORGANISM: Artificial Sequence
<220> FEATURE:
<223> OTHER INFORMATION: Diphtheria toxin full length secreted

<400> SEQUENCE: 65

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
```

```
                305                 310                 315                 320

Val His His Asn Thr Glu Glu Ile Val Ala Gln Ser Ile Ala Leu Ser
                    325                 330                 335

Ser Leu Met Val Ala Gln Ala Ile Pro Leu Val Gly Glu Leu Val Asp
                    340                 345                 350

Ile Gly Phe Ala Ala Tyr Asn Phe Val Glu Ser Ile Asn Leu Phe
                355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
                420                 425                 430

Leu Leu Pro Thr Ile Pro Gly Lys Leu Asp Val Asn Lys Ser Lys Thr
                435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
                500                 505                 510

Gly Tyr Gln Lys Thr Val Asp His Thr Lys Val Asn Ser Lys Leu Ser
                515                 520                 525

Leu Phe Phe Glu Ile Lys Ser
                530                 535

<210> SEQ ID NO 66
<211> LENGTH: 193
<212> TYPE: PRT
<213> ORGANISM: Artificial Sequence
<220> FEATURE:
<223> OTHER INFORMATION: Diphtheria toxin, chain A

<400> SEQUENCE: 66

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
                20                  25                  30

Lys Gly Ile Gln Lys Pro Lys Ser Gly Thr Gln Gly Asn Tyr Asp Asp
            35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
```

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg

<210> SEQ ID NO 67
<211> LENGTH: 247
<212> TYPE: PRT
<213> ORGANISM: Artificial Sequence
<220> FEATURE:
<223> OTHER INFORMATION: VP8 full length

<400> SEQUENCE: 67

Met Ala Ser Leu Ile Tyr Arg Gln Leu Leu Ser Asn Ser Tyr Val Thr
1               5                   10                  15

Asn Ile Ser Asp Glu Val Asn Glu Ile Gly Thr Lys Lys Thr Thr Asn
                20                  25                  30

Val Thr Val Asn Pro Gly Pro Phe Ala Gln Thr Gly Tyr Ala Pro Val
            35                  40                  45

Asp Trp Gly His Gly Glu Leu Pro Asp Ser Thr Leu Val Gln Pro Thr
50                  55                  60

Leu Asp Gly Pro Tyr Gln Pro Thr Ser Leu Asn Leu Pro Val Asp Tyr
65                  70                  75                  80

Trp Met Leu Ile Ala Pro Thr Arg Glu Gly Lys Val Ala Glu Gly Thr
                85                  90                  95

Asn Thr Thr Asp Arg Trp Phe Ala Cys Val Leu Val Glu Pro Asn Val
            100                 105                 110

Gln Asn Thr Gln Arg Gln Tyr Val Leu Asp Gly Arg Asn Val Gln Leu
        115                 120                 125

Asn Val Ser Asn Glu Ser Arg Thr Ser Trp Lys Phe Ile Leu Phe Ile
130                 135                 140

Lys Leu Thr Pro Asp Gly Thr Tyr Thr Gln Tyr Ser Thr Leu Ser Thr
145                 150                 155                 160

Pro His Lys Leu Cys Ala Trp Met Lys Arg Asp Asn Arg Val Tyr Trp
                165                 170                 175

Tyr Gln Gly Ala Thr Pro Asn Ala Ser Glu Ser Tyr Tyr Leu Thr Ile
            180                 185                 190

Asn Asn Asp Asn Ser Asn Val Ser Ser Asp Ala Glu Phe Tyr Leu Ile
        195                 200                 205

Pro Gln Ser Gln Thr Ala Met Cys Thr Gln Tyr Ile Asn Asn Gly Leu
    210                 215                 220

Pro Pro Ile Gln Asn Thr Arg Asn Ile Val Pro Val Asn Ile Thr Ser
225                 230                 235                 240

Arg Gln Ile Lys Asp Ile Arg
                245

<210> SEQ ID NO 68
<211> LENGTH: 2
<212> TYPE: PRT
<213> ORGANISM: Artificial Sequence
<220> FEATURE:
<223> OTHER INFORMATION: Synthetic Construct
<220> FEATURE:

```
<221> NAME/KEY: VARIANT
<222> LOCATION: 1, 2
<223> OTHER INFORMATION: can be present in repeat of at least 1

<400> SEQUENCE: 68

Gly Ser
1

<210> SEQ ID NO 69
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5
<223> OTHER INFORMATION: can be present in repeat of at least 1

<400> SEQUENCE: 69

Gly Ser Gly Gly Ser
1               5

<210> SEQ ID NO 70
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4
<223> OTHER INFORMATION: can be present in repeat of at least 1

<400> SEQUENCE: 70

Gly Gly Gly Ser
1

<210> SEQ ID NO 71
<211> LENGTH: 4
<212> TYPE: PRT
<213> ORGANISM: Artificial Sequence
<220> FEATURE:
<223> OTHER INFORMATION: Synthetic Construct

<400> SEQUENCE: 71

Gly Gly Ser Gly
1

<210> SEQ ID NO 72
<211> LENGTH: 15
<212> TYPE: PRT
<213> ORGANISM: Artificial Sequence
<220> FEATURE:
<223> OTHER INFORMATION: Synthetic Construct

<400> SEQUENCE: 72

Gly Gly Gly Gly Ser Gly Gly Gly Ser Gly Gly Gly Gly Ser
1               5                   10                  15

<210> SEQ ID NO 73
<211> LENGTH: 6
<212> TYPE: PRT
<213> ORGANISM: Artificial Sequence
<220> FEATURE:
<223> OTHER INFORMATION: Synthetic Construct

<400> SEQUENCE: 73
```

Gly Gly Gly Gly Ser Gly
1               5

<210> SEQ ID NO 74
<211> LENGTH: 5
<212> TYPE: PRT
<213> ORGANISM: Artificial Sequence
<220> FEATURE:
<223> OTHER INFORMATION: Synthetic Construct

<400> SEQUENCE: 74

Gly Gly Ser Gly Gly
1               5

<210> SEQ ID NO 75
<211> LENGTH: 5
<212> TYPE: PRT
<213> ORGANISM: Artificial Sequence
<220> FEATURE:
<223> OTHER INFORMATION: Synthetic Construct

<400> SEQUENCE: 75

Gly Ser Gly Gly Gly
1               5

<210> SEQ ID NO 76
<211> LENGTH: 5
<212> TYPE: PRT
<213> ORGANISM: Artificial Sequence
<220> FEATURE:
<223> OTHER INFORMATION: Synthetic Construct

<400> SEQUENCE: 76

Gly Gly Gly Ser Gly
1               5

<210> SEQ ID NO 77
<211> LENGTH: 5
<212> TYPE: PRT
<213> ORGANISM: Artificial Sequence
<220> FEATURE:
<223> OTHER INFORMATION: Synthetic Construct

<400> SEQUENCE: 77

Gly Ser Ser Ser Gly
1               5

<210> SEQ ID NO 78
<211> LENGTH: 6
<212> TYPE: DNA
<213> ORGANISM: Artificial Sequence
<220> FEATURE:
<223> OTHER INFORMATION: Synthetic Construct

<400> SEQUENCE: 78 catatg                                                                  6

<210> SEQ ID NO 79
<211> LENGTH: 6
<212> TYPE: DNA
<213> ORGANISM: Artificial Sequence
<220> FEATURE:
<223> OTHER INFORMATION: Synthetic Construct

<400> SEQUENCE: 79 ggatcc                                                                  6

What is claimed is:

1. A polysaccharide-protein conjugate comprising a) a chimeric carrier protein comprising i) a carrier protein and ii) a universal epitope, and b) a polysaccharide antigen, wherein:
the carrier protein is derived from cross reacting materials (CRM) of diphtheria toxin,
the universal epitope comprises the amino acid sequence of SEQ ID NO:2, and
the polysaccharide antigen is derived from *Streptococcus pneumoniae* (Pn),
wherein the universal epitope is covalently fused to the N- and/or C-terminus of the carrier protein, wherein the chimeric carrier protein comprises no more than three universal epitopes, and wherein the polysaccharide antigen is covalently conjugated to the chimeric carrier protein.

2. The polysaccharide-protein conjugate of claim 1, wherein the chimeric carrier protein comprises one, two or three copies of the universal epitope having the amino acid sequence of SEQ ID NO: 2.

3. The polysaccharide-protein conjugate of claim 1, wherein the chimeric carrier protein further comprises an additional universal epitope of a different amino acid sequence.

4. The polysaccharide-protein conjugate of claim 1, wherein the carrier protein comprises the amino acid sequence of SEQ ID NO:4.

5. The polysaccharide-protein conjugate of claim 1, wherein the universal epitope is covalently fused to the carrier protein by a peptide linker disposed therebetween.

6. The polysaccharide-protein conjugate of claim 5, wherein the peptide linker is a flexible linker selected from the group consisting of a glycine polymer, a glycine-serine polymer, a glycine-alanine polymer, or an alanine-serine polymer.

7. The polysaccharide-protein conjugate of claim 1, wherein the weight to weight ratio of the polysaccharide antigen to the chimeric carrier protein is about 0.8 to about 1.2.

8. The polysaccharide-protein conjugate of claim 1, wherein the polysaccharide antigen has an average molecular weight between about 10 kDa to about 1000 kDa.

9. The polysaccharide-protein conjugate of claim 1, wherein the polysaccharide antigen is derived from a capsular polysaccharide.

10. An immunogenic composition comprising one or more polysaccharide-protein conjugate of claim 1.

11. The immunogenic composition of claim 10, comprising a plurality of the polysaccharide-protein conjugates, wherein at least two of the polysaccharide-protein conjugates comprise a carrier protein that is different from each other.

12. The immunogenic composition of claim 10, comprising a plurality of the polysaccharide-protein conjugates, wherein at least two of the polysaccharide-protein conjugates comprise a polysaccharide antigen that is derived from a bacterial species that is different from each other.

13. The immunogenic composition of claim 10, comprising a plurality of the polysaccharide-protein conjugates, wherein each polysaccharide-protein conjugate comprises a polysaccharide antigen derived from a bacterium of a distinct serotype of the same species.

14. A method of preparing the polysaccharide-protein conjugate of claim 1, comprising conjugating the polysaccharide antigen to the chimeric carrier protein.

15. The polysaccharide-protein conjugate of claim 1, wherein the chimeric carrier protein comprises the amino acid sequence of any one selected from the group consisting of SEQ ID NOs: 15-21.

16. The polysaccharide-protein conjugate of claim 1, wherein the polysaccharide-protein conjugate is 13-valent, 20-valent, or 24-valent.

17. The polysaccharide-protein conjugate of claim 16, wherein the polysaccharide-protein conjugate is 13-valent, and wherein the polysaccharide-protein conjugate comprises one, two or three copies of the universal epitope peptide having the amino acid sequence of SEQ ID NO:2.

18. The polysaccharide-protein conjugate of claim 16, wherein the polysaccharide-protein conjugate is 20-valent, and wherein the polysaccharide-protein conjugate comprises one, two or three copies of the universal epitope peptide having the amino acid sequence of SEQ ID NO:2.

19. The polysaccharide-protein conjugate of claim 16, wherein the polysaccharide-protein conjugate is 24-valent, and wherein the polysaccharide-protein conjugate comprises one, two or three copies of the universal epitope peptide having the amino acid sequence of SEQ ID NO:2.

* * * * *